United States Patent
Kurz et al.

(10) Patent No.: US 11,453,660 B2
(45) Date of Patent: Sep. 27, 2022

(54) ANDROGEN RECEPTOR AND GLUCOCORTICOID RECEPTOR MODULATORS

(71) Applicant: ONCOSTELLAE, S.L., A Coruña (ES)

(72) Inventors: Guido Kurz, Barcelona (ES); Juan Camacho Gómez, Navarra (ES)

(73) Assignee: ONCOSTELLAE, S.L.

( * ) Notice: Subject to any disclaimer, the term of this patent is extended or adjusted under 35 U.S.C. 154(b) by 0 days.

(21) Appl. No.: 16/761,921

(22) PCT Filed: Nov. 6, 2018

(86) PCT No.: PCT/EP2018/080367
§ 371 (c)(1),
(2) Date: May 6, 2020

(87) PCT Pub. No.: WO2019/086720
PCT Pub. Date: May 9, 2019

(65) Prior Publication Data
US 2020/0325123 A1  Oct. 15, 2020

(30) Foreign Application Priority Data
Nov. 6, 2017 (EP) .................................. 17382741

(51) Int. Cl.
| C07D 409/04 | (2006.01) |
| C07D 409/14 | (2006.01) |
| C07D 495/04 | (2006.01) |
| A61K 45/06 | (2006.01) |

(52) U.S. Cl.
CPC ......... *C07D 409/04* (2013.01); *C07D 409/14* (2013.01); *C07D 495/04* (2013.01); *A61K 45/06* (2013.01)

(58) Field of Classification Search
CPC .. C07D 409/04; C07D 409/14; C07D 495/04; A61K 45/06
See application file for complete search history.

(56) References Cited

U.S. PATENT DOCUMENTS

| 4,659,717 | A | * | 4/1987 | Wikel .................... A61P 11/08 514/301 |
| 4,902,694 | A | * | 2/1990 | Holland ............... C07D 495/04 514/301 |
| 8,030,302 | B2 | | 10/2011 | Li et al. |
| 2006/0116369 | A1 | | 6/2006 | Ramchandani et al. |
| 2016/0151388 | A1 | | 6/2016 | Szmulewitz et al. |
| 2018/0303807 | A1 | | 10/2018 | Katzenellenbogen et al. |

FOREIGN PATENT DOCUMENTS

| EP | 217530 A1 | 4/1987 |
| WO | 2005016885 A2 | 2/2005 |
| WO | 2006047537 A1 | 5/2006 |
| WO | WO-2008070875 A2 * | 6/2008 ............. A61K 31/47 |
| WO | 2017059401 A2 | 4/2017 |

OTHER PUBLICATIONS

International Search Report, dated Jan. 21, 2019 for International Application No. PCT/EP2018/080367.
Mangelsdorf DJ. et al, The nuclear receptor superfamily: the second decade, Cell 1995, 83, 835-839.
Huang P. et al, Structural overview of the nuclear receptor superfamily: Insights into physiology and therapeutics, Annu Rev Physiol. 2010, 72, 247-272.
Watson PA. et al, Emerging mechanisms of resistance to AR inhibitors in prostate cancer, Nat Rev Cancer 2015, 15, 701-711.
Thoreson GR. et al, Emerging therapies in castration resistant prostate cancer, Can J Urol 2014, 21, 98-105.
Elancheran R. et al, Recent discoveries and developments of androgen receptor based therapy for prostate cancer, Med Chem Commun 2015, 6, 746-768.
Hickey TE et al, Expression of androgen receptor splice variants in clinical breast cancer, Oncotarget 2015, 6 (42), 44728-44744.
Jie, Jack L, et al, Rational design and synthesis of 4-((1R,2R)-2-hydroxycyclohexyl)-2(trifluoromethyl)benzonitrile (PF-998425), a novel, nonsteroidal androgen receptor antagonist devoid of phototoxicity for dermatological indications, J Med Chem 2008, 51, 7010-7014.

(Continued)

*Primary Examiner* — Theodore R. Howell
*Assistant Examiner* — George W Kosturko
(74) *Attorney, Agent, or Firm* — Tristan A. Fuierer; Casimir Jones, S.C.

(57) ABSTRACT

The present invention relates to novel dihydropyridine derivatives of formula (I):

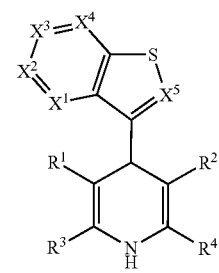

as modulators of nuclear receptors selected from androgen receptor and glucocorticoid receptor, to processes for their preparation, to pharmaceutical compositions comprising said compounds and to the use of said for manufacturing a medicament for the treatment of pathological conditions or diseases that can improve by modulation of androgen receptor and/or glucocorticoid receptor, selected from cancer, metastasizing cancers, benign prostate hyperplasia, polycystic ovary syndrome (PCOS), hair loss, hirsutism, acne, hypogonadism, muscle wasting diseases, cachexia, Cushing's syndrome, anti-psychotic drug induced weight gain, obesity, post-traumatic stress disorder and alcoholism.

20 Claims, No Drawings

(56) References Cited

OTHER PUBLICATIONS

Narayanan S, et al, Androgen-glucocorticoid interactions in the era of novel prostate cancer therapy, Nature Reviews | UROLOGY, 2015, doi:10.1038/nrurol.2015.254.

K. Xing et al., Dexamethasone enhances programmed cell death 1 (PD-1) expression during T cell activation: an insight into the optimum application of glucocorticoids in anti-cancer therapy, BMC Immunology 2015, 16, 39.

M. Xia et al., Dexamethasone enhances CTLA-4 expression during T cell activation, Cell Mol Life Sci 1999, 55, 1649-1659.

H.M. Kim et al., Random serum cortisol as a predictor for survival of terminally ill patients with cancer, Am J Hosp Pall Med 2016, 33, 281-285.

A. Schrepf et al., Diurnal cortisol and survival in epithelial ovarian cancer, Psychoneuroendocrinology 2015, 53, 256-267.

N. Cirillo et al., Characterisation of the cancer-associated glucocorticoid system: key role of 11b-hydroxysteroid dehydrogenase type 2, Br J. Cancer 2017, advanced online publication 1-10, doi: 10 1038/bjc. 2017.243.

Schteingart D.E., Drugs in the medical treatment of Cushing's syndrome, Expert Opin. Emerging Drugs (2009) 14(4):661-671.

Kach J. et al., Selective glucocorticoid receptor modulators (SGRMs) delay castrate-resistant prostate cancer growth, 2017, DOI: 10.1158/1535-7163.MCT-16-0923.

Hunt H.J. et al, The Identification of the Clinical Candidate (R)-(1-(4-fluorophenyl)-6-((1-methyl-1Hpyrazol-4-yl)sulfonyl)-4,4a,5,6,7,8-hexahydro-1H-pyrazolo[3,4-g]isoquinolin-4ayl)(4-(trifluoromethyl)pyridin-2-yl)methanone(CORT125134):A Selective Glucocorticoid Receptor (GR) Antagonist, J Med Chem, 2017, DOI: 10.1021/acs. imedchem.7b00162.

P. Ioan et al., 1,4-Dihydropyridine scaffold in medicinal chemistry,The story so far and perspectives. (Part 1): Action in Ion Channelsand GPCRs. Curr. Med Chem. 2011, 18, 4901-4922.

E. Carosati et al., 1,4-Dihydropyridine Scaffold in Medicinal Chemistry, The story so far and perspectives (Part 2): Action in Other Targets and Antitargets, Curr. Med. Chem. 2012,19, 4306-4323.

Liu, et al., Selectivity Control in Lewis Acid Catalyzed Regiodivergent Tandem Cationic Cyclization/Ring Expansion Terminated by Pinacol Rearrangement, Angew Chem. Int. Ed. 2009, 48, 6093-6096.

Haibin Mao et al., Construction of Enantiomerically Enriched Diazo Compounds Using Diazo Esters as Nucleophiles: Chiral Lewis Base Catalysis, Angew. Chem. Int. Ed. 2013, 52, 6288-6291; DOI: 10.1002/anie.201301509.

M. A. Walker et al., Triketoacid inhibitors of HIV-integrase: A new chemotype of useful for probing the integrase pharmacophore, Bioorg. Med. Chem. Lett. 2006, 16, 2920-2924.

Rampa, A et al, Fluorenone and benzophenone 1,4-dihydropyridine derivatives with cardiodepressant activity, Arzneim.-Forsch./Drug Res. 1992, 42, 1284-1287.

Y. Satoh et al., Studies on Nilvadipine. I. Synthesis and Structure-Activity Relationships of 1,4-Dihydropyridines Containing Novel Substituents at the 2-Position, Chem. Pharm. Bull. 1991, 39, 3189-3201.

\* cited by examiner

ANDROGEN RECEPTOR AND GLUCOCORTICOID RECEPTOR MODULATORS

CROSS-REFERENCE TO RELATED APPLICATIONS

This application is filed under the provisions of 35 U.S.C. § 371 and claims the priority of International Patent Application No. PCT/EP2018/080367 filed on Nov. 6, 2018 entitled "NEW ANALOGS AS ANDROGEN RECEPTOR AND GLUCOCORTICOID RECEPTOR MODULATORS" in the name of Guido KURZ, et al., which claims priority to European Patent Application No. 17382741.1, filed on Nov. 6, 2017, both of which are hereby incorporated by reference herein in their entirety.

FIELD OF THE INVENTION

This invention relates to novel pharmaceutically-useful, optionally substituted dihydropyridines derivatives which are useful as modulators of nuclear receptors, such as receptors selected from androgen receptor and glucocorticoid receptor. The compounds are of potential utility in the treatment of diseases and conditions mediated by the nuclear receptors selected from androgen receptor and glucocorticoid receptor, such as cancer. The invention also relates to the use of such compounds as medicaments, to pharmaceutical compositions containing them, and to synthetic routes for their production.

BACKGROUND OF THE INVENTION

Nuclear receptors constitute a large superfamily of ligand-dependent transcription factors that are involved in many physiologic and developmental processes and are linked to a wide range of human diseases. That makes them attractive targets for drug discovery. In fact, approximately 13% of all FDA-approved drugs act on nuclear receptors. (Mangelsdorf D J. et al, *The nuclear receptor superfamily: the second decade*, Cell 1995, 83, 835-839).

Nuclear receptors bind specific DNA elements in the regulatory regions of genes via a highly-conserved DNA-binding domain (DBD) and specific ligands via another highly conserved domain, the ligand binding domain (LBD), which consists of a series of approximately 12 helices that form a hydrophobic pocket. The binding of ligands in the pocket induces conformational changes in the receptor that affect the recruitment of coregulatory molecules (cofactors) that stimulate (co-activators) or repress (corepressors) transcription. (Huang P. et al, *Structural overview of the nuclear receptor superfamily: Insights into physiology and therapeutics*, Annu Rev Physiol 2010, 72, 247-272).

The androgen receptor (AR) belongs to the subfamily of steroid hormone-activated nuclear receptors which include also the estrogen, glucocorticoid, minerocorticoid and progesterone receptors (ER, GR, MR and PR). In the cytoplasm, unliganded AR is stabilized by heat shock proteins. Upon ligand binding of testosterone or dihydrotestosterone (DHT), a conformational change arises in the AR causing dissociation of specific chaperones, dimerization and phosphorylation of AR, and AR translocation to the nucleus. The DNA-binding domain (DBD) in AR binds to androgen response elements (AREs) inside the nucleus, causing recruitment of DNA transcriptional machinery and gene transcription. AR is found in a variety of tissues throughout the human body including prostate, scalp, skin and muscle.

Androgen receptor is the primary therapeutic target in prostate cancer which is a major health problem in industrialized countries, as it represents the second main cause of death from cancer in men. In newly diagnosed patients, the tumor is frequently confined to the prostate where it can be removed surgically or treated by radiotherapy. When metastases are detected or rising prostate-specific antigen (PSA) biomarker levels indicate disease progression, the first course of treatment is lowering the supply of androgens to the tumor (androgen deprivation therapy, ADT) because, in the primary stage, prostate tumor growth is androgen-dependent. Androgen levels can be decreased by surgical castration (elimination of testosterone production in the testis) or by medical treatment with antiandrogens (deactivation of AR), LHRH (luteinizing hormone-releasing hormone) agonists or antagonists (suppression of testosterone production in the testis) and CYP17 or 5alpha-reductase inhibitors (inhibition of androgen biosynthesis).

Initially ADT is effective in controlling the disease, but within a few years tumor cells usually evolve mechanisms for continued growth under conditions of androgen depletion and the cancer becomes what is known as recurrent or castration-resistant prostate cancer (CRPC). Most of the mechanisms promoting CRPC are still AR-dependent and include intratumoral androgen synthesis, increased expression of AR through gene amplification or overexpression, upregulation of coactivator proteins that augment AR activity, acquisition of mutations within the AR protein that increase its activity in response to antagonists or other steroid hormones, constitutively active AR splice variants, and signaling through alternative pathways (e.g. induced by glucocorticoid receptor overexpression). (Watson P A. et al, *Emerging mechanisms of resistance to AR inhibitors in prostate cancer*, Nat Rev Cancer 2015, 15, 701-711).

There is no cure for CRPC and current medication provides only a modest overall survival benefit of 4 to 5 months. The median survival of patients with advanced metastatic prostate cancer, who have failed androgen deprivation therapy, was typically 16 to 20 months in 2009. (Thoreson G R. et al, *Emerging therapies in castration resistant prostate cancer*, Can J Urol 2014, 21, 98-105).

Nonsteroidal antiandrogens have been preferred over steroidal compounds for prostate cancer because they are more selective and have fewer side effects. (Elancheran R, *Recent discoveries and developments of androgen receptor based therapy for prostate cancer*, Med Chem Commun 2015, 6, 746-768).

Therefore, there is still a great need for new treatment options including improved, non-steroidal AR antagonists that could be useful for the treatment of both primary and especially castrate-resistant prostate cancer.

AR antagonists may also be useful for the treatment of other conditions, disorders and diseases which are regulated by the androgen receptor including but not limited to breast cancer (Hickey T E et al, *Expression of androgen receptor splice variants in clinical breast cancer*, Oncotarget 2015, advanced publication November 5), epithelial ovarian cancer, benign prostate hyperplasia, alopecia and acne (Jie J L, et al, *Rational design and synthesis of 4-((1R,2R)-2-hydroxycyclohexyl)-2(trifluoromethyl)benzonitrile (PF-998425), a novel, nonsteroidal androgen receptor antagonist devoid of phototoxicity for dermatological indications*, J Med Chem 2008, 51, 7010-7014), hirsutism and polycystic ovary syndrome.

As has been pointed out previously, glucocorticoid receptor might play a role in one of the mechanisms promoting CRPC. At first, the hypothesis that GR can confer resistance may seem inconsistent with clinical evidence that glucocorticoid administration can be beneficial to some patients with CRPC. This apparent contradiction is explained by the fact that glucocorticoids inhibit adrenocorticotropic hormone (ACTH) production by the pituitary gland, which results in reduced androgen levels. This androgen-lowering activity explains the decline in serum PSA levels that is observed in men taking prednisone alone, which was documented in the comparator arm of the Phase III clinical trial that led to approval of abiraterone for chemotherapy-naive CRPC. However, in men with prostate cancers that express high levels of GR, this androgen-lowering benefit would be counteracted by GR activation in tumour cells. In this setting, a more effective treatment strategy could be combined inhibition of AR and GR, as is currently being explored in an early-phase clinical trial of enzalutamide in combination with the GR antagonist mifepristone/RU486 (ClinicalTrials.gov identifier: NCT02012296). One potential confounder of this study is the fact that mifepristone also has a high binding affinity for AR and can function as an AR agonist. Therefore, mifepristone treatment could unintentionally result in AR activation through agonism by displacing the potent antagonism of enzalutamide. (Watson P A. et al, *Emerging mechanisms of resistance to androgen receptor inhibitors in prostate cancer*, Nature Reviews Cancer|AOP, published online 13 Nov. 2015, and references therein).

There are studies showing that GR agonists, such as dexamethasone, are sufficient to induce enzalutamide resistance, whereas a GR antagonist could restore sensitivity. Currently, with the widespread use of enzalutamide, resistance is increasing as a clinical problem, in which activation of the glucocorticoid signalling pathway seems to have an important role. These findings suggest the role that glucocorticoids might have in promoting tumour growth. A major implication of these studies is that glucocorticoids might promote tumour growth and progression in men whose cancers express the GR. Thus, new strategies that block both AR signalling and GR signalling might be necessary and efforts to develop GR-specific antagonists that do not have off-target effects on the AR would be useful to prevent or overcome enzalutamide resistance. As opposed to AR inhibition, which can cause unpleasant but tolerable adverse effects, total GR inhibition can be lethal. (Narayanan S, et al, *Androgen-glucocorticoid interactions in the era of novel prostate cancer therapy*, NATURE REVIEWS|UROLOGY, doi:10.1038/nrurol.2015.254, Published online 8 Dec. 2015, and references therein).

Glucocorticoids (GR agonists) are strong immunosuppressive and anti-inflammatory agents that are widely used as co-medication in cancer therapy of solid tumors to alleviate adverse effects, reduce toxicity and protect normal tissue. However, glucocorticoids may interfere with therapeutic efficacy of anti-cancer medication, e.g. by inhibiting apoptosis and promoting proliferation. Therefore, there have been suggestions to minimize the use of glucocorticoids in anti-cancer therapy. Mechanistically, dexamethasone (an important glucocorticoid drug) has been found to suppress immune response by enhancing expression of the T cell checkpoint proteins PD-1 and CTLA-4. GR antagonist mifepristone has been shown to reverse this effect (K. Xing et al., *Dexamethasone enhances programmed cell death 1 (PD-1) expression during T cell activation: an insight into the optimum application of glucocorticoids in anti-cancer therapy*, BMC Immunology 2015, 16, 39; M. Xia et al., *Dexamethasone enhances CTLA-4 expression during T cell activation*, Cell Mol Life Sci 1999, 55, 1649-1659).

GR antagonists that have the opposite effect to glucocorticoids might therefore be useful as activators of the immune system for the treatment of solid tumors as a single agent and in combination with checkpoint inhibitors. Currently, Mifepristone is being studied in cancer patients, wherein stress-response mechanisms including the hypothalamic-pituitary-adrenal (HPA) axis are frequently activated and dysregulated.

High levels and altered diurnal rhythms of cortisol, a glucocorticoid hormone involved in stress signaling, inflammation and metabolism, have been correlated with poor prognosis of terminal cancer patients, e.g. lung, breast, colorectal and ovarian cancer (H. M. Kim et al., *Random serum cortisol as a predictor for survival of terminally ill patients with cancer*, Am J Hosp Pall Med 2016, 33, 281-285; A. Schrepf et al., *Diurnal cortisol and survival in epithelial ovarian cancer*, Psychoneuroendocrinology 2015, 53, 256-267).

Recently it was shown that cortisol production is a common feature of a broad spectrum of malignant cells and that cancer-derived cortisol inhibits tumor-specific CD8+ T cell proliferation in a GR-specific fashion. The effect was inhibited in the presence of GR antagonist mifepristone/RU486. These data suggest that the production of cortisol by tumor cells may have an important immunoregulatory function and that GR antagonists may have a therapeutic potential as reactivators of the immune system (N. Cirillo et al., *Characterisation of the cancer-associated glucocorticoid system: key role of 11b-hydroxysteroid dehydrogenase type 2*, Br. J. Cancer 2017, advanced online publication 1-10, doi: 10.1038/bjc.2017.243).

Currently, there are few glucocorticoid receptor antagonists marketed and in clinical assays. Among them is mifepristone, a synthetic steroid compound which has been investigated as an antiglucocorticoid drug in the treatment of persistent or recurrent Cushing's disease. Its affinity to the progesterone receptor is a main drawback. (Schteingart D. E., *Drugs in the medical treatment of Cushing's syndrome*, Expert Opin. Emerging Drugs (2009) 14(4):661-671). Other glucocorticoid receptor antagonists are in (pre)clinical development (Kach J. et al, *Selective glucocorticoid receptor modulators (SGRMs) delay castrate-resistant prostate cancer growth*, mct.aacrjournals.org on Apr. 21, 2017; Hunt H. J. et al, *The Identification of the Clinical Candidate (R)-(1-(4-fluorophenyl)-6-((1-methyl-1Hpyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor (GR) Antagonist*, J. Med. Chem, DOI: 10.1021/acs.jmedchem.7b00162•Publication Date (Web): 3 Apr. 2017).

The listing or discussion of an apparently prior-published document in this specification should not necessarily be taken as an acknowledgement that the document is part of the state of the art or is common general knowledge.

1,4-dihydropyridines are an important class of cardiovascular drugs such as nifedipine, nitrendipine, amlodipine and many other analogs which exert their antihypertensive and antianginal actions by blocking L-type calcium channels. The 1,4-dihydropyridine nucleus is also a privileged scaffold that can, when appropriately substituted, interact at diverse receptors and ion channels, providing a wide range of biological activities (P. Ioan et al., *1,4-Dihydropyridine scaffold in medicinal chemistry, The story so far and perspectives. (Part 1): Action in Ion Channels and GPCRs*. Curr. Med. Chem. 2011, 18, 4901-4922; E. Carosati et al., *1,4-Dihydropyridine Scaffold in Medicinal Chemistry, The* story so far and perspectives (Part 2): Action in Other Targets and Antitargets, Curr. Med. Chem. 2012, 19, 4306-4323).

International patent application WO 2005/016885 A2 discloses various dihydropyridines with inhibitory activity against beta-adrenergic receptors and L-type calcium channels that may be useful for the treatment of heart disease. However, there is no mention that these compounds may be useful for the treatment of cancer.

European patent application EP 0 217 530 A1 discloses dihydropyridines derivatives as vasodilators useful in the treatment of stroke, angina and migraine. In addition, the compounds are useful as antiasthma agents. Among the disclosed compounds there are 4-benzothiophene-1,4-dihydropyridine-3,5-diester derivatives which are not active as modulators of androgen receptor, therefore are not included in the scope of the present invention.

Patent application US 2016/0151388 A1 discloses a method and compositions related to glucocorticoid receptor antagonist in prostate cancer, alone or in combination with an androgen receptor antagonist. The prostate cancer may be one that has become resistant to androgen deprivation therapy, for example, by increase in glucocorticoid receptor expression and/or activity.

The problem to be solved by the present invention is to provide compounds as modulators of nuclear receptors selected from androgen receptor and glucocorticoid receptor.

SUMMARY OF THE INVENTION

In one of its aspects (aspect 1), the present invention refers to dihydropyridine derivative of formula (I):

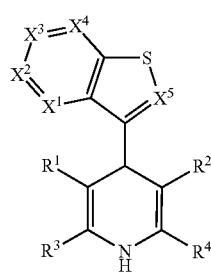

(I)

wherein:
R$^1$ is a group selected from:
  a) —COR$^5$,
  b) —COOR$^5$,
  c) —CN,
  d) —C(O)NH$_2$,
R$^5$ is a group selected from:
  a) linear or branched C$_1$-C$_6$ alkyl optionally substituted by 1, 2 or 3 substituents selected from —N(R$^6$)R$^7$ and —OR$^6$, halogen atom, C$_3$-C$_6$ cycloalkyl and alkynyl,
  b) C$_3$-C$_6$ cycloalkyl,
R$^2$ is a group selected from:
  a) —COOR$^8$,
  b) —COR$^8$,
  c) —C(O)N(R$^8$)R$^9$,
  d) —CN,
  e) —S(O)$_n$R$^8$, wherein n is an integer from 1 to 2, R$^8$ and R$^9$ are independently selected from:
  a) linear or branched C$_1$-C$_6$ alkyl optionally substituted by 1, 2 or 3 substituents selected from A$^1$ or B$^2$,
  b) A$^1$ group,
  c) hydrogen atom,
  or
R$^8$ and R$^9$ together with the nitrogen atom to which they are attached form a 5-6 membered heterocycle which optionally comprises 1 heteroatom selected from O and N, and said heterocycle being optionally substituted by 1 or 2 groups independently selected from linear or branched C$_1$-C$_4$ alkyl,
R$^3$ is a group selected from:
  a) linear or branched C$_1$-C$_6$ alkyl optionally substituted by 1, 2 or 3 substituents selected from halogen atom, —N(R$^6$)R$^7$, and —OR$^6$,
  b) C$_3$-C$_6$ cycloalkyl optionally substituted by 1, 2 or 3 halogen atoms,
  c) hydrogen atom,
  d) —NH$_2$,
  e) —CN,
R$^4$ is a group selected from:
  a) A$^1$ group,
  b) linear or branched C$_1$-C$_6$ alkyl optionally substituted by 1, 2 or 3 substituents selected from A$^1$ or B$^2$,
  c) —N(R$^6$)R$^7$,
  d) —CN,
  e) —CO—H,
  f) —CO-Me,
  g) —CO—OMe,
  h) hydrogen atom,
X$^1$, X$^2$, X$^3$, X$^4$, and X$^5$ are independently selected from C—B$^1$, N and C—H,
A$^1$ is selected from:
  a) C$_3$-C$_6$ cycloalkyl which ring is optionally substituted by 1, 2, 3 or 4 substituents selected from =O and B$^3$;
  b) a 3 to 6 membered saturated heterocyclyl ring comprising 1, 2 or 3 heteroatoms selected from O, S and N, and which ring is optionally substituted by 1, 2 or 3 substituents selected from =O and B$^3$;
  c) phenyl or 5 to 6 membered heteroaryl group, either ones are optionally substituted by 1, 2 or 3 substituents selected from B$^1$;
each B$^1$ is independently selected from halogen atom, —CF$_3$ group, 5 to 6 membered heteroaryl, linear or branched C$_1$-C$_6$ alkyl, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$ and —S(O)$_2$R$^6$,
each B$^2$ is independently selected from halogen atom, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$, —S(O)$_2$R$^6$, and alkynyl group,
each B$^3$ is independently selected from halogen atom, linear or branched C$_1$-C$_6$ alkyl, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$, —S(O)$_2$R$^6$,
each R$^6$ and R$^7$ independently represents:
  hydrogen atom,
  linear or branched C$_1$-C$_{12}$ alkyl, C$_3$-C$_6$ cycloalkyl and C$_4$-C$_6$ heterocycloalkyl, which are optionally substituted by 1, 2 or 3 substituents selected from =O (oxo), halogen atom, hydroxy, phenyl, C$_3$-C$_6$ cycloalkyl, linear or branched C$_1$-C$_6$ alkoxy, amino, alkylamino, dialkylamino, linear or branched C$_1$-C$_6$ alkylcarbonyl, phenyl or 5 to 6 membered heteroaryl group, which are optionally substituted by 1, 2 or 3 substituents selected from halogen atom, cyano group, linear or branched $C_1$-$C_6$ alkyl, linear or branched $C_1$-$C_6$ haloalkyl, hydroxy, linear or branched $C_1$-$C_6$ alkoxy, amino, alkylamino, dialkylamino;

$R^6$ and $R^7$ form together with the nitrogen atom to which they are attached, a 3- to 8 membered ring which optionally contains a further heteroatom selected from O, N and S, and which ring is optionally substituted by 1, 2 or 3 substituents selected from =O (oxo), linear or branched $C_1$-$C_6$ alkyl, linear or branched $C_1$-$C_6$ haloalkyl, linear or branched $C_1$-$C_6$ alkylcarbonyl;

with the proviso that when $R^1$ is —COOR$^5$ and $R^2$ is —COOR$^8$ then $R^4$ is not a methyl group, and pharmaceutically acceptable salts thereof.

Other aspects of the present invention are:

In a second aspect, the present invention refers to processes for the preparation of the compounds defined in the first aspect.

In a third aspect, the present invention refers to pharmaceutical compositions comprising an effective amount of a compound defined in the first aspect.

In a fourth, the present invention refers to a combination product comprising a compound as defined in the first aspect and another therapeutic agent selected from agents for treating prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases, cachexia and Cushing's syndrome, anti-psychotic drug induced weight gain, obesity, post-traumatic stress disorder and alcoholism.

In a fifth aspect, the present invention relates to the use of the compounds of the first aspect for the manufacture of a medicament, in particular for treating diseases that can be ameliorated by modulation of nuclear receptors, in particular by antagonism of androgen receptor and/or glucocorticoid receptor; the disease or pathological condition susceptible of improvement by antagonism of androgen receptor and/or glucocorticoid receptor is selected from prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

In a sixth aspect, the present invention relates to methods for the treatment of diseases that can be ameliorated by modulation of nuclear receptors, in particular by antagonism of androgen receptor and/or glucocorticoid receptor, by administration of the compounds defined in the first aspect or the pharmaceutical compositions of the third aspect or the combination product of the fourth aspect to a subject in need of said treatment.

In a seventh aspect, the present invention relates to a compound as defined in the first aspect for use as a medicament.

In an eight aspect the present invention relates to a compound as defined in the first aspect for use in the treatment of a disease or pathological condition selected from the group consisting of cancer, prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

As it is said before, the dihydropyridine derivatives of the invention are useful in the treatment or prevention of diseases known to be susceptible to amelioration by treating with modulators of nuclear receptors, in particular by modulators of nuclear receptors selected from androgen receptor and glucocorticoid receptor. Such diseases are, for example cancer, prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

Accordingly, the derivatives of the present invention and pharmaceutically acceptable salts thereof, and pharmaceutical compositions comprising such compounds and/or salts thereof, may be used in a method of treatment of pathological conditions or disease of human body which comprises administering to a subject in need of said treatment, an effective amount of the dihydropyridine derivatives of the invention or a pharmaceutically acceptable salt thereof.

As used herein, the term halogen atom is used to designate an atom selected from the group consisting of chlorine, fluorine, bromine or iodine atom, preferably bromine, fluorine or chlorine atom.

As used herein the term alkyl is used to designate linear or branched hydrocarbon radicals ($C_nH_{2n+1}$) having 1 to 12 carbon atoms. Examples include methyl, ethyl, n-propyl, i-propyl, n-butyl, sec-butyl, tert-butyl, n-pentyl, 1-methylbutyl, 2-methyl-butyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3dimethylbutyl, 2,2-dimethylbutyl, 2,3-dimethylbutyl, 2-methylpentyl and 3-methylpentyl, n-heptyl, 3-methylheptyl, n-octyl, 2,2-dimethyloctyl radicals. In a preferred embodiment said alkyl groups have 1 to 6 carbon atoms.

As used herein, the term haloalkyl is used to designate $C_1$-$C_6$ alkyl substituted by one or more halogen atoms, preferably one, two or three halogen atoms. The haloalkyl groups may be linear or branched. Preferably, the halogen atoms are selected from the group consisting of fluorine or chlorine atoms. In a preferred embodiment, the haloalkyl group is a linear or branched $C_1$-$C_4$ alkyl substituted by one, two or three fluorine or chlorine atoms.

As used herein, the term cycloalkyl is used to designate hydrocarbon cyclic groups ($C_nH_{2n-1}$) having 3 to 6 carbon atoms. Such cycloalkyl groups include, by way of example, single ring structures such as cyclopropyl, cyclobutyl, cyclopentyl, cyclooctyl, and the like.

As used herein, the term heterocyclyl is used to designate saturated rings comprising 3 to 6 carbon atoms and 1, 2 or 3 heteroatoms selected from O, S and N as part of the ring. The heterocyclyl groups include, for example, azetidinyl, pyrrolidinyl, piperidinyl, morpholinyl and piperazinyl.

As used herein, the term $C_1$-$C_6$ alkoxy is used to designate radicals which contain a linear or branched $C_1$-$C_6$ alkyl group linked to an oxygen atom ($C_nH_{2n+1}$—O—). Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy or 2-hydroxypropoxy.

As used herein, the term carbonyl group is used to designate a group C=O. As used herein, when the term oxo (=O) is used to designate a substituent in a ring, it means that a carbon atom of said ring is present in the form of a carbonyl (C=O) group.

As used herein, the term heteroaryl group is used to designate a 5 or 6-membered heteroaromatic ring containing carbon, hydrogen and one or more atoms selected from O, N and S. Said groups may optionally be substituted by 1, 2 or 3 substituents selected from the group consisting of halogen atom, cyano group, linear or branched $C_1$-$C_6$ haloalkyl, linear or branched $C_1$-$C_6$ alkyl, hydroxy, linear or branched $C_1$-$C_6$ alkoxy, amino, alkylamino and dialkylamino. The heteroaryl groups may optionally be substituted by substituents such as those defined under $R^6$ and $B^1$. The preferred groups are optionally substituted pyridyl and pyrimidinyl. When a heteroaryl radical carries 2 or more substituents, the substituents may be the same or different.

As used herein, the term alkylamino is used to designate radicals which contain a linear or branched $C_1$-$C_6$ alkyl group linked to a group —NH—. Preferred alkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyetylamino or 2-hydroxypropylamino.

As used herein, the term dialkylamino is used to designate radicals which contain two linear or branched $C_1$-$C_6$ alkyl groups linked to a group nitrogen atom which alkyl groups may be identical or different. Preferred dialkylamino radicals include di(methyl)amino, di(ethyl)amino, di-(n-propyl)amino, di-(i-propyl)amino, di-(n-butyl)amino, di-(sec-butyl)amino, di-(t-butyl)amino, di-(trifluoromethyl)amino, di(hydroxymethyl)amino, di(2-hydroxyetyl)amino, di(2-hydroxypropyl)amino, methylethylamino, methyl-i-propylamino and ethyl-n-propylamino.

As used herein, some of the atoms, radicals, chains or cycles present in the general structures of the invention are "optionally substituted". This means that these atoms, radicals, chains or cycles can be either unsubstituted or substituted in any position by one or more, for example 1, 2, 3 or 4, substituents, whereby the hydrogen atoms bound to the unsubstituted atoms, radicals, chains or cycles are replaced by chemically acceptable atoms, radicals, chains or cycles. When two or more substituents are present, each substituent may be the same or different.

As used herein, the term pharmaceutically acceptable salt is used to designate salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium), alkali earth metal (e.g. calcium or magnesium) hydroxides, and organic bases, for example alkyl amines, phenylalkyl amines and heterocyclic amines.

Other preferred salts according to the invention are quaternary ammonium compounds wherein an equivalent of an anion ($X^{-n}$), wherein "-n" indicates the negative charge of the anion and is typically −1, −2 or −3, is associated with the positive charge of the N atom. $X^{-n}$ may be an anion of various mineral acids such as, for example, chloride, bromide, iodide, sulphate, nitrate, phosphate, or an anion of an organic acid such as, for example, acetate, maleate, fumarate, citrate, oxalate, succinate, tartrate, malate, mandelate, trifluoroacetate, methanesulphonate and ptoluenesulphonate. $X^{-n}$ is preferably an anion selected from chloride, bromide, iodide, sulphate, nitrate, acetate, maleate, oxalate, succinate or trifluoroacetate. More preferably, X— is chloride, bromide, trifluoroacetate or methanesulphonate.

According to one embodiment of the present invention in the compounds of formula (I), $X^1$, $X^2$, $X^3$ and $X^5$ represent C—H or C—B group. In a preferred embodiment $B^1$ represents a halogen atom. In a more preferred embodiment $X^1$, $X^3$ and $X^5$ represent C—H and $X^2$ is C—$B^1$, wherein $B^1$ represents a halogen atom.

According to another embodiment of the present invention in the compounds of formula (I), $X^4$ represents a group selected from C—$B^1$ and N atom. In a preferred embodiment $X^4$ represents C—$B^1$. In a more preferred embodiment $B^1$ is selected from —CN group and halogen atom.

According to another embodiment of the present invention in the compounds of formula (I), $R^1$ is a group selected from —$COR^5$, —$COOR^5$ and —CN group. In a preferred embodiment, $R^5$ is independently selected from $C_3$-$C_6$ cycloalkyl, —$C_1$-$C_3$ alkyl wherein the terminal methyl is unsubstituted or substituted by three fluorine atoms (—$CF_3$) and $C_1$-$C_3$ alkyl optionally substituted at any position by an alkynyl group. In a more preferred embodiment, each $R^5$ is independently selected from —$C_1$-$C_3$ alkyl and —$C_3$-$C_5$ cycloalkyl.

According to one embodiment of the present invention in the compounds of formula (I), $R^2$ is a group selected from —$COR^8$ and —$COOR^8$ preferably —$COOR^8$. In a preferred embodiment, $R^8$ is independently selected from:
  linear or branched $C_1$-$C_6$ alkyl optionally substituted by 1, 2 or 3 substituents selected from $A^1$ or $B^2$, preferably $A^1$ wherein $A^1$ represents a group selected from phenyl, $C_3$-$C_6$ cycloalkyl, which is optionally substituted by 1, 2 or 3 $C_1$-$C_3$ alkyl and 3 to 6 membered saturated heterocyclyl rings comprising 1, 2 or 3 heteroatoms selected from O, S and N, and which ring is optionally substituted by 1, 2 or 3 $C_1$-$C_3$ alkyl groups; and $B^2$ represents a halogen atom.

In a more preferred embodiment $R^2$ represents —$COOR^8$, wherein $R^8$ represents independently:
  linear or branched $C_1$-$C_6$ alkyl optionally substituted by 1, 2 or 3 substituents selected from fluorine atoms and $C_3$-$C_5$ cycloalkyl optionally substituted by 1, 2 or 3 fluorine atoms, or
  $A^1$ group, which represents $C_3$-$C_6$ cycloalkyl which is optionally substituted by 1, 2 or 3 substituents selected from the group consisting of fluorine atoms and $C_1$-$C_3$ alkyl groups.

According to another embodiment of the present invention in the compounds of formula (I), $R^2$ represents a —CN group.

According to another embodiment of the present invention in the compounds of formula (I), $R^3$ is a group selected from $C_3$-$C_6$ cycloalkyl optionally substituted by 1, 2 or 3 halogen atoms; and linear or branched $C_1$-$C_4$ alkyl optionally substituted by 1, 2 or 3 substituents selected from halogen atom, —$N(R^6)R^7$, and —$OR^6$. In a preferred embodiment, $R^6$ and $R^7$ are selected from hydrogen atom and a linear or branched $C_1$-$C_6$ alkyl.

In a more preferred embodiment $R^3$ is selected from linear or branched $C_1$-$C_4$ alkyl and $C_3$-$C_6$ cycloalkyl. In a more preferred embodiment $R^3$ is selected from methyl or cyclopropyl group, said groups being optionally substituted by 1, 2 or 3 fluorine atoms.

According to another embodiment of the present invention in the compounds of formula (I), $R^4$ represents a linear or branched $C_1$-$C_6$ alkyl optionally substituted by 1, 2 or 3 substituents selected from $A^1$ or $B^2$. In a more preferred embodiment $A^1$ represents $C_3$-$C_6$ cycloalkyl and $B^2$ represents a group selected from halogen atom, —N($R^6$)$R^7$, and —$OR^6$. In a more preferred embodiment, $R^6$ and $R^7$ are selected from hydrogen atom and a linear or branched $C_1$-$C_6$ alkyl. In a more preferred embodiment $R^4$ represents a linear or branched $C_1$-$C_3$ alkyl optionally substituted by 1, 2 or 3 substituents selected from 1, 2 or 3 fluorine atoms and hydroxyl group.

According to another embodiment of the present invention in the compounds of formula (I), $R^4$ represents an A group. In a more preferred embodiment, A represents $C_3$-$C_6$ cycloalkyl which optionally contains 1, 2 or 3 heteroatoms selected from O, S and N, and which ring is optionally substituted by $C_1$-$C_3$ alkyl. In a more preferred embodiment $R^4$ represents an A group, which represents $C_3$-$C_6$ cycloalkyl.

According to one embodiment of the present invention in the compounds of formula (I), $R^4$ represents a —N($R^6$)$R^7$ group. In a more preferred embodiment, $R^6$ and $R^7$ are selected from a hydrogen atom and a linear or branched $C_1$-$C_4$ alkyl.

In a more preferred embodiment $R^4$ is a group selected from:
N($R^6$)$R^7$, wherein $R^6$ and $R^7$ are independently selected from a hydrogen atom and a linear or branched $C_1$-$C_3$ alkyl,
$A^1$ group, which represents $C_3$-$C_6$ cycloalkyl,
linear or branched $C_1$-$C_6$ alkyl optionally substituted by 1, 2 or 3 substituents selected from 1, 2 or 3 fluorine atoms or 1 hydroxyl group, According to one embodiment of the present invention in the compounds of formula (I), $X^1$, $X^2$, $X^3$ and $X^5$ represent —CH, $X^4$ represents C—$B^1$, wherein $B^1$ represents —CN group or bromine atom, $R^1$ is a group selected from —C(O)CH$_3$, —C(O)OCH$_3$, —C(O)OCH$_2$-alkynyl and CN, $R^2$ is a group selected from —C(O)OCH-lineal or branched $C_1$-$C_6$ alkyl group optionally substituted by 1, 2 or 3 fluorine atoms and C(O)OCH$_2$-cyclopropyl optionally substituted by 1, 2 or 3 fluorine atoms, $R^3$ is a group selected from linear or branched $C_1$-$C_3$ alkyl and $C_3$-$C_4$ cycloalkyl and $R^4$ is a group selected from a linear or branched $C_1$-$C_3$ alkyl, $C_3$-$C_4$ cycloalkyl and —NH$_2$.

Compound according to claim 1 wherein $X^1$, $X^2$, $X^3$ and $X^5$ represent a —CH, $X^4$ represents a C—$B^1$, wherein $B^1$ represents —CN group, $R^1$ is a group selected from —C(O)CH$_3$, —C(O)OCH$_3$, $R^2$ is a group selected from —C(O)OCH$_2$-cyclopropyl optionally substituted by 1, 2 or 3 fluorine atoms, and —C(O)OCH$_2$—CF$_3$, $R^3$ is a group selected from methyl and cyclopropyl and $R^4$ is a group selected from cyclopropyl and —NH$_2$.

According to another embodiment of the present invention in the compounds of formula (I), $X^1$, $X^3$, $X^4$ and $X^5$ represent a —CH and $X^2$ represents a C—$B^1$ group. In a more preferred embodiment $B^1$ represents a halogen atom.

According to another embodiment of the present invention in the compounds of formula (I), $X^1$, $X^2$, $X^3$, $X^4$ and $X^5$ represent a —CH.

Individual compounds of the present invention include:
Methyl 5-acetyl-4-(benzo[b]thiophen-3-yl)-2,6-dimethyl-1,4-dihydro-pyridine-3-carboxylate
Methyl 5-acetyl-4-(benzo[b]thiophen-3-yl)-2,6-dimethyl-1,4-dihydro-pyridine-3-carboxylate (Enantiomer 1)
Methyl 5-acetyl-4-(benzo[b]thiophen-3-yl)-2,6-dimethyl-1,4-dihydro-pyridine-3-carboxylate (Enantiomer 2)
5-acetyl-4-(benzo[b]thiophen-3-yl)-2,6-dimethyl-1,4-dihydropyridine-3-carboxamide
1-(4-(benzo[b]thiophen-3-yl)-5-benzoyl-2,6-dimethyl-1,4-dihydropyridin-3-yl)ethan-1-one
Methyl 5-acetyl-4-(benzo[b]thiophen-3-yl)-6-methyl-2-phenyl-1,4-dihydropyridine-3-carboxylate
1-(4-(benzo[b]thiophen-3-yl)-2,6-dimethyl-5-nicotinoyl-1,4-dihydro pyridin-3-yl)ethan-1-one
Methyl 5-acetyl-4-(benzo[b]thiophen-3-yl)-6-methyl-1,4-dihydro-[2,3'-bipyridine]-3-carboxylate
2,2,2-trifluoroethyl 5-acetyl-4-(benzo[b]thiophen-3-yl)-2,6-dimethyl-1,4-dihydropyridine-3-carboxylate
5-Acetyl-4-(benzo[b]thiophen-3-yl)-2,6-dimethyl-1,4-dihydropyridine-3-carboxylic acid
1-(4-(Benzo[b]thiophen-3-yl)-2,6-dimethyl-5-(4-methylpiperazine-1-carbonyl)-1,4-dihydropyridin-3-yl)ethan-1-one
5-Acetyl-4-(benzo[b]thiophen-3-yl)-N,N-diethyl-2,6-dimethyl-1,4-dihydropyridine-3-carboxamide
1-(4-(Benzo[b]thiophen-3-yl)-2,6-dimethyl-5-(morpholine-4-carbonyl)-1,4-dihydropyridin-3-yl)ethan-1-one
2-Methoxyethyl 5-acetyl-4-(benzo[b]thiophen-3-yl)-2,6-dimethyl-1,4-dihydropyridine-3-carboxylate
3-Acetamidopropyl 5-acetyl-4-(benzo[b]thiophen-3-yl)-2,6-dimethyl-1,4-dihydropyridine-3-carboxylate
Benzyl 5-acetyl-4-(benzo[b]thiophen-3-yl)-2,6-dimethyl-1,4-dihydro-pyridine-3-carboxylate
2-Morpholinoethyl 5-acetyl-4-(benzo[b]thiophen-3-yl)-2,6-dimethyl-1,4-dihydropyridine-3-carboxylate
2-(Dimethylamino)ethyl 5-acetyl-4-(benzo[b]thiophen-3-yl)-2,6-dimethyl-1,4-dihydropyridine-3-carboxylate
2-Acetamidoethyl 5-acetyl-4-(benzo[b]thiophen-3-yl)-2,6-dimethyl-1,4-dihydropyridine-3-carboxylate
Methyl 5-acetyl-4-(benzo[b]thiophen-3-yl)-2-(methoxymethyl)-6-methyl-1,4-dihydropyridine-3-carboxylate
Methyl 5-acetyl-4-(benzo[b]thiophen-3-yl)-2-((dimethylamino)methyl)-6-methyl-1,4-dihydropyridine-3-carboxylate
Pyridin-4-ylmethyl 5-acetyl-4-(benzo[b]thiophen-3-yl)-2,6-dimethyl-1,4-dihydropyridine-3-carboxylate
4-Methoxybenzyl 5-acetyl-4-(benzo[b]thiophen-3-yl)-2,6-dimethyl-1,4-dihydropyridine-3-carboxylate
Pyridin-2-ylmethyl 5-acetyl-4-(benzo[b]thiophen-3-yl)-2,6-dimethyl-1,4-dihydropyridine-3-carboxylate
Methyl 5-acetyl-4-(benzo[b]thiophen-3-yl)-6-methyl-2-(morpholino-methyl)-1,4-dihydropyridine-3-carboxylate
Dimethyl 4-(benzo[b]thiophen-3-yl)-2,6-bis(morpholinomethyl)-1,4-dihydropyridine-3,5-dicarboxylate
2-Hydroxyethyl 5-acetyl-4-(benzo[b]thiophen-3-yl)-2,6-dimethyl-1,4-dihydropyridine-3-carboxylate
1-(4-(Benzo[b]thiophen-3-yl)-5-(cyclopropanecarbonyl)-6-cyclopropyl-2-methyl-1,4-dihydropyridin-3-yl)ethan-1-one
Methyl 5-acetyl-4-(benzo[b]thiophen-3-yl)-2-(1-(tert-butoxycarbonyl) azetidin-3-yl)-6-methyl-1,4-dihydropyridine-3-carboxylate
(1-(tert-Butoxycarbonyl)piperidin-4-yl)methyl 5-acetyl-4-(benzo[b] thiophen-3-yl)-2,6-dimethyl-1,4-dihydropyridine-3-carboxylate
Cyclohexylmethyl 5-acetyl-4-(benzo[b]thiophen-3-yl)-2,6-dimethyl-1,4-dihydropyridine-3-carboxylate Methyl 4-(benzo[b]thiophen-3-yl)-5-(cyclopropanecarbonyl)-2,6-dicyclopropyl-1,4-dihydropyridine-3-carboxylate 5-acetyl-4-(benzo[b]thiophen-3-yl)-2,6-dimethyl-N-phenyl-1,4-dihydropyridine-3-carboxamide Tetrahydro-2H-pyran-4-yl 5-acetyl-4-(benzo[b]thiophen-3-yl)-2,6-dimethyl-1,4-dihydropyridine-3-carboxylate (Tetrahydro-2H-pyran-4-yl)methyl 5-acetyl-4-(benzo[b]thiophen-3-yl)-2,6-dimethyl-1,4-dihydropyridine-3-carboxylate Cyclohexyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-2-(2-methoxy-2-oxoethyl)-6-methyl-1,4-dihydropyridine-3-carboxylate Methyl 5-acetyl-2,6-dimethyl-4-(2-methylbenzo[b]thiophen-3-yl)-1,4-dihydropyridine-3-carboxylate Cyclopropylmethyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-2-(2-methoxyethyl)-6-methyl-1,4-dihydropyridine-3-carboxylate Methyl 5-acetyl-4-(benzo[b]thiophen-3-yl)-2-((benzyloxy)methyl)-6-methyl-1,4-dihydropyridine-3-carboxylate Methyl 5-acetyl-4-(benzo[b]thiophen-3-yl)-6-methyl-2-(phenoxymethyl)-1,4-dihydropyridine-3-carboxylate Phenethyl 5-acetyl-4-(benzo[b]thiophen-3-yl)-2,6-dimethyl-1,4-dihydropyridine-3-carboxylate Methyl 4-(benzo[b]thiophen-3-yl)-5-(cyclopropanecarbonyl)-6-cyclopropyl-2-methyl-1,4-dihydropyridine-3-carboxylate Methyl 5-acetyl-4-(benzo[b]thiophen-3-yl)-6-methyl-2-(trifluoromethyl)-1,4-dihydropyridine-3-carboxylate Methyl 5-acetyl-4-(benzo[b]thiophen-3-yl)-6-benzyl-2-methyl-1,4-dihydropyridine-3-carboxylate Methyl 4-(benzo[b]thiophen-3-yl)-2,6-dimethyl-5-(2-phenylacetyl)-1,4-dihydropyridine-3-carboxylate Methyl 4-(benzo[b]thiophen-3-yl)-5-(2-methoxyacetyl)-2,6-dimethyl-1,4-dihydropyridine-3-carboxylate Methyl 5-acetyl-4-(benzo[b]thiophen-3-yl)-6-(methoxymethyl)-2-methyl-1,4-dihydropyridine-3-carboxylate Methyl 5-acetyl-4-(benzo[b]thiophen-3-yl)-2-(fluoromethyl)-6-methyl-1,4-dihydropyridine-3-carboxylate Cyclopropylmethyl 5-acetyl-4-(5-fluorobenzo[b]thiophen-3-yl)-2,6-dimethyl-1,4-dihydropyridine-3-carboxylate 1-(tert-Butoxycarbonyl)piperidin-4-yl 5-acetyl-4-(benzo[b]thiophen-3-yl)-2,6-dimethyl-1,4-dihydropyridine-3-carboxylate Cyclopentylmethyl 5-acetyl-4-(benzo[b]thiophen-3-yl)-2,6-dimethyl-1,4-dihydropyridine-3-carboxylate Cyclopropylmethyl 5-acetyl-2,6-dimethyl-4-(thieno[2,3-b]pyridin-3-yl)-1,4-dihydropyridine-3-carboxylate 1-methylpiperidin-4-yl 5-acetyl-4-(benzo[b]thiophen-3-yl)-2,6-dimethyl-1,4-dihydropyridine-3-carboxylate Cyclopentyl 5-acetyl-4-(benzo[b]thiophen-3-yl)-2,6-dimethyl-1,4-dihydropyridine-3-carboxylate 4,4-dimethylcyclohexyl 5-acetyl-4-(benzo[b]thiophen-3-yl)-2,6-dimethyl-1,4-dihydropyridine-3-carboxylate Cyclobutyl 5-acetyl-4-(benzo[b]thiophen-3-yl)-2,6-dimethyl-1,4-dihydropyridine-3-carboxylate Methyl 5-acetyl-4-(5-fluorobenzo[b]thiophen-3-yl)-6-methyl-2-(trifluoromethyl)-1,4-dihydropyridine-3-carboxylate Methyl 5-acetyl-2,6-dimethyl-4-(thieno[3,2-b]pyridin-3-yl)-1,4-dihydropyridine-3-carboxylate Methyl 5-acetyl-4-(benzo[b]thiophen-3-yl)-2-methyl-6-(trifluoromethyl)-1,4-dihydropyridine-3-carboxylate Cyclopropylmethyl 5-acetyl-4-(5-chlorobenzo[b]thiophen-3-yl)-2,6-dimethyl-1,4-dihydropyridine-3-carboxylate Cyclohexylmethyl 5-acetyl-4-(5-chlorobenzo[b]thiophen-3-yl)-2,6-dimethyl-1,4-dihydropyridine-3-carboxylate Cyclohexylmethyl 5-acetyl-2,6-dimethyl-4-(thieno[2,3-b]pyridin-3-yl)-1,4-dihydropyridine-3-carboxylate Cyclopentylmethyl 5-acetyl-2,6-dimethyl-4-(thieno[2,3-b]pyridin-3-yl)-1,4-dihydropyridine-3-carboxylate Cyclohexyl 5-acetyl-2,6-dimethyl-4-(thieno[2,3-b]pyridin-3-yl)-1,4-dihydropyridine-3-carboxylate Cyclopentyl 5-acetyl-2,6-dimethyl-4-(thieno[2,3-b]pyridin-3-yl)-1,4-dihydropyridine-3-carboxylate Methyl 5-acetyl-4-(5-chlorobenzo[b]thiophen-3-yl)-6-methyl-2-(trifluoromethyl)-1,4-dihydropyridine-3-carboxylate Benzyl 5-acetyl-2,6-dimethyl-4-(thieno[2,3-b]pyridin-3-yl)-1,4-dihydropyridine-3-carboxylate (Tetrahydro-2H-pyran-4-yl)methyl 5-acetyl-2,6-dimethyl-4-(thieno[2,3-b]pyridin-3-yl)-1,4-dihydropyridine-3-carboxylate Benzyl 5-acetyl-4-(5-fluorobenzo[b]thiophen-3-yl)-2,6-dimethyl-1,4-dihydropyridine-3-carboxylate Benzyl 5-acetyl-4-(5-chlorobenzo[b]thiophen-3-yl)-2,6-dimethyl-1,4-dihydropyridine-3-carboxylate (Tetrahydro-2H-pyran-4-yl)methyl 5-acetyl-4-(5-chlorobenzo[b]thiophen-3-yl)-2,6-dimethyl-1,4-dihydropyridine-3-carboxylate (Tetrahydro-2H-pyran-4-yl)methyl 5-acetyl-4-(5-fluorobenzo[b]thiophen-3-yl)-2,6-dimethyl-1,4-dihydropyridine-3-carboxylate Benzyl 5-acetyl-4-(benzo[b]thiophen-3-yl)-6-methyl-2-(trifluoromethyl)-1,4-dihydropyridine-3-carboxylate Pyridin-4-ylmethyl 5-acetyl-4-(5-fluorobenzo[b]thiophen-3-yl)-2,6-dimethyl-1,4-dihydropyridine-3-carboxylate 4-Fluorobenzyl 5-acetyl-2,6-dimethyl-4-(thieno[2,3-b]pyridin-3-yl)-1,4-dihydropyridine-3-carboxylate Pyridin-3-ylmethyl 5-acetyl-4-(benzo[b]thiophen-3-yl)-2,6-dimethyl-1,4-dihydropyridine-3-carboxylate 1,1'-(4-(benzo[b]thiophen-3-yl)-2-benzyl-6-methyl-1,4-dihydropyridine-3,5-diyl)bis(ethan-1-one)

1-(5-acetyl-4-(benzo[b]thiophen-3-yl)-2,6-dimethyl-1,4-dihydropyridin-3-yl)-2-phenylethan-1-one Methyl 5-acetyl-6-methyl-4-(thieno[2,3-b]pyridin-3-yl)-2-(trifluoromethyl)-1,4-dihydropyridine-3-carboxylate 1-(2-methyl-5-(piperidine-1-carbonyl)-4-(thieno[2,3-b]pyridin-3-yl)-6-(trifluoromethyl)-1,4-dihydropyridin-3-yl)ethan-1-one 4-(((5-acetyl-4-(benzo[b]thiophen-3-yl)-2,6-dimethyl-1,4-dihydro-pyridine-3-carbonyl)oxy)methyl)benzoic acid Benzyl 5-acetyl-6-methyl-4-(thieno[2,3-b]pyridin-3-yl)-2-(trifluoromethyl)-1,4-dihydropyridine-3-carboxylate Pyridin-3-ylmethyl 5-acetyl-4-(5-fluorobenzo[b]thiophen-3-yl)-2,6-dimethyl-1,4-dihydropyridine-3-carboxylate Pyridin-3-ylmethyl 5-acetyl-4-(7-bromobenzo[b]thiophen-3-yl)-2,6-dimethyl-1,4-dihydropyridine-3-carboxylate Pyridin-3-ylmethyl 5-acetyl-4-(7-cyanobenzo[b]thiophen-3-yl)-2,6-dimethyl-1,4-dihydropyridine-3-carboxylate Pyridin-3-ylmethyl 5-acetyl-4-(5-chlorobenzo[b]thiophen-3-yl)-2,6-dimethyl-1,4-dihydropyridine-3-carboxylate Pyridin-3-ylmethyl 5-acetyl-2,6-dimethyl-4-(thieno[2,3-b]pyridin-3-yl)-1,4-dihydropyridine-3-carboxylate Pyridin-4-ylmethyl 5-acetyl-4-(5-chlorobenzo[b]thiophen-3-yl)-2,6-dimethyl-1,4-dihydropyridine-3-carboxylate 4-(Cyclopropylcarbamoyl)benzyl 5-acetyl-4-(benzo[b]thiophen-3-yl)-2,6-dimethyl-1,4-dihydropyridine-3-carboxylate Pyridin-4-ylmethyl 5-acetyl-2,6-dimethyl-4-(thieno[2,3-b]pyridin-3-yl)-1,4dihydropyridine-3-carboxylate 4-Bromobenzyl 5-acetyl-2,6-dimethyl-4-(thieno[2,3-b]pyridin-3-yl)-1,4-dihydropyridine-3-carboxylate 3-Bromobenzyl 5-acetyl-2,6-dimethyl-4-(thieno[2,3-b]pyridin-3-yl)-1,4-dihydropyridine-3-carboxylate 2-Bromobenzyl 5-acetyl-2,6-dimethyl-4-(thieno[2,3-b]pyridin-3-yl)-1,4-dihydropyridine-3-carboxylate (3-Fluoropyridin-4-yl)methyl 5-acetyl-2,6-dimethyl-4-(thieno[2,3-b]pyridin-3-yl)-1,4-dihydropyridine-3-carboxylate Pyrimidin-5-ylmethyl 5-acetyl-2,6-dimethyl-4-(thieno[2,3-b]pyridin-3-yl)-1,4-dihydropyridine-3-carboxylate (5-Bromopyridin-3-yl)methyl 5-acetyl-2,6-dimethyl-4-(thieno[2,3-b]pyridin-3-yl)-1,4-dihydropyridine-3-carboxylate 2-Phenylpropan-2-yl 5-acetyl-2,6-dimethyl-4-(thieno[2,3-b]pyridin-3-yl)-1,4-dihydropyridine-3-carboxylate 3-cyanobenzyl 5-acetyl-2,6-dimethyl-4-(thieno[2,3-b]pyridin-3-yl)-1,4-dihydropyridine-3-carboxylate 4-cyanobenzyl 5-acetyl-2,6-dimethyl-4-(thieno[2,3-b]pyridin-3-yl)-1,4-dihydropyridine-3-carboxylate (6-Chloropyridin-3-yl)methyl 5-acetyl-2,6-dimethyl-4-(thieno[2,3-b]pyridin-3-yl)-1,4-dihydropyridine-3-carboxylate 3-Morpholinobenzyl 5-acetyl-2,6-dimethyl-4-(thieno[2,3-b]pyridin-3-yl)-1,4-dihydropyridine-3-carboxylate 4,4-Dimethylcyclohexyl 5-acetyl-2,6-dimethyl-4-(thieno[2,3-b]pyridin-3-yl)-1,4-dihydropyridine-3-carboxylate (2-Chloropyridin-4-yl)methyl 5-acetyl-2,6-dimethyl-4-(thieno[2,3-b]pyridin-3-yl)-1,4-dihydropyridine-3-carboxylate Tetrahydro-2H-pyran-4-yl 5-acetyl-2,6-dimethyl-4-(thieno[2,3-b]pyridin-3-yl)-1,4-dihydropyridine-3-carboxylate 4,4-Difluorocyclohexyl 5-acetyl-2,6-dimethyl-4-(thieno[2,3-b]pyridin-3-yl)-1,4-dihydropyridine-3-carboxylate 5-Acetyl-N-benzyl-N,2,6-trimethyl-4-(thieno[2,3-b]pyridin-3-yl)-1,4-dihydropyridine-3-carboxamide Oxetan-3-yl 5-acetyl-4-(7-bromobenzo[b]thiophen-3-yl)-2-cyclopropyl-6-methyl-1,4-dihydropyridine-3-carboxylate Isopropyl 5-acetyl-4-(7-bromobenzo[b]thiophen-3-yl)-2-cyclopropyl-6-methyl-1,4-dihydropyridine-3-carboxylate Methyl 5-acetyl-4-(7-bromobenzo[b]thiophen-3-yl)-6-methyl-2-(trifluoromethyl)-1,4-dihydropyridine-3-carboxylate Cyclopropylmethyl 5-acetyl-4-(7-bromobenzo[b]thiophen-3-yl)-2-cyclopropyl-6-methyl-1,4-dihydropyridine-3-carboxylate Methyl 5-acetyl-2-cyclopropyl-6-methyl-4-(7-(2,2,2-trifluoroacetyl)benzo[b]thiophen-3-yl)-1,4-dihydropyridine-3-carboxylate 2-Phenylpropan-2-yl 5-acetyl-4-(7-bromobenzo[b]thiophen-3-yl)-2,6-dimethyl-1,4-dihydropyridine-3-carboxylate Methyl 5-acetyl-2-amino-4-(benzo[b]thiophen-3-yl)-6-methyl-1,4-dihydropyridine-3-carboxylate Methyl 2-amino-4-(benzo[b]thiophen-3-yl)-5-(cyclopropanecarbonyl)-6-methyl-1,4-dihydropyridine-3-carboxylate Methyl 5-acetyl-2-amino-4-(5-fluorobenzo[b]thiophen-3-yl)-6-methyl-1,4-dihydropyridine-3-carboxylate Methyl 5-acetyl-2-amino-4-(7-bromobenzo[b]thiophen-3-yl)-6-methyl-1,4-dihydropyridine-3-carboxylate Methyl 5-acetyl-2-amino-4-(7-cyanobenzo[b]thiophen-3-yl)-6-methyl-1,4-dihydropyridine-3-carboxylate Cyclopentyl 5-acetyl-2-amino-4-(7-bromobenzo[b]thiophen-3-yl)-6-methyl-1,4-dihydropyridine-3-carboxylate Dimethyl 2-amino-4-(7-cyanobenzo[b]thiophen-3-yl)-6-methyl-1,4-dihydropyridine-3,5-dicarboxylate Cyclopentyl 5-acetyl-2-amino-4-(7-cyanobenzo[b]thiophen-3-yl)-6-methyl-1,4-dihydropyridine-3-carboxylate Dimethyl 2,6-diamino-4-(benzo[b]thiophen-3-yl)-1,4-dihydropyridine-3,5-dicarboxylate cyclopropylmethyl 5-acetyl-2-amino-4-(7-cyanobenzo[b]thiophen-3-yl)-6-methyl-1,4-dihydropyridine-3-carboxylate 4,4-difluorocyclohexyl 5-acetyl-2-amino-4-(7-cyanobenzo[b]thiophen-3-yl)-6-methyl-1,4-dihydropyridine-3-carboxylate methyl 2-amino-5-cyano-4-(7-cyanobenzo[b]thiophen-3-yl)-6-methyl-1,4-dihydropyridine-3-carboxylate 4-fluorobenzyl 5-acetyl-2-amino-4-(7-cyanobenzo[b]thiophen-3-yl)-6-methyl-1,4-dihydropyridine-3-carboxylate methyl 5-acetyl-2-amino-4-(5-fluorothieno[2,3-b]pyridin-3-yl)-6-methyl-1,4-dihydropyridine-3-carboxylate methyl 2-acetamido-5-acetyl-4-(5-fluorothieno[2,3-b]pyridin-3-yl)-6-methyl-1,4-dihydropyridine-3-carboxylate cyclopentylmethyl 5-acetyl-2-amino-4-(7-cyanobenzo[b]thiophen-3-yl)-6-methyl-1,4-dihydropyridine-3-carboxylate 3-(cyclopropylmethyl) 5-methyl 2-amino-4-(7-cyanobenzo[b]thiophen-3-yl)-6-methyl-1,4-dihydropyridine-3,5-dicarboxylate dimethyl 2-amino-4-(7-cyanobenzo[b]thiophen-3-yl)-6-cyclopropyl-1,4-dihydropyridine-3,5-dicarboxylate 3-(cyclopropylmethyl) 5-methyl 2-amino-4-(7-cyanobenzo[b]thiophen-3-yl)-6-cyclopropyl-1,4-dihydropyridine-3,5-dicarboxylate dimethyl 2,6-diamino-4-(7-cyanobenzo[b]thiophen-3-yl)-1,4-dihydropyridine-3,5-dicarboxylate 5-(cyclopropylmethyl) 3-methyl 2-amino-4-(7-cyanobenzo[b]thiophen-3-yl)-6-cyclopropyl-1,4-dihydropyridine-3,5-dicarboxylate 3-(4-fluorobenzyl) 5-methyl 2-amino-4-(7-cyanobenzo[b]thiophen-3-yl)-6-methyl-1,4-dihydropyridine-3,5-dicarboxylate 3-(4-fluorobenzyl) 5-methyl 2-amino-4-(7-cyanobenzo[b]thiophen-3-yl)-6-cyclopropyl-1,4-dihydropyridine-3,5-dicarboxylate Cyclopropylmethyl 2-amino-5-cyano-4-(7-cyanobenzo[b]thiophen-3-yl)-6-methyl-1,4-dihydropyridine-3-carboxylate 4-Fluorobenzyl 2-amino-5-cyano-4-(7-cyanobenzo[b]thiophen-3-yl)-6-methyl-1,4-dihydropyridine-3-carboxylate Cyclopropylmethyl 6-amino-5-cyano-4-(7-cyanobenzo[b]thiophen-3-yl)-2-cyclopropyl-1,4-dihydropyridine-3-carboxylate 3-Cyclopentyl 5-methyl 2-amino-4-(7-cyanobenzo[b]thiophen-3-yl)-6-methyl-1,4-dihydropyridine-3,5-dicarboxylate Cyclopropylmethyl 5-acetyl-2-amino-4-(6-cyanobenzo[b]thiophen-3-yl)-6-methyl-1,4-dihydropyridine-3-carboxylate Cyclohexyl 5-acetyl-2-amino-4-(7-cyanobenzo[b]thiophen-3-yl)-6-methyl-1,4-dihydropyridine-3-carboxylate Cyclohexylmethyl 5-acetyl-2-amino-4-(7-cyanobenzo[b]thiophen-3-yl)-6-methyl-1,4-dihydropyridine-3-carboxylate Cyclopropylmethyl 2-amino-4-(7-cyanobenzo[b]thiophen-3-yl)-5-(cyclopropanecarbonyl)-6-methyl-1,4-dihydropyridine-3-carboxylate 3-Fluorobenzyl 5-acetyl-2-amino-4-(7-cyanobenzo[b]thiophen-3-yl)-6-methyl-1,4-dihydropyridine-3-carboxylate 3-(Cyclobutylmethyl) 5-methyl 2-amino-4-(7-cyanobenzo[b]thiophen-3-yl)-6-methyl-1,4-dihydropyridine-3,5-dicarboxylate 3-((3,3-Difluorocyclobutyl)methyl) 5-methyl 2-amino-4-(7-cyanobenzo[b]thiophen-3-yl)-6-methyl-1,4-dihydropyridine-3,5-dicarboxylate Cyclopropylmethyl 2-amino-5-carbamoyl-4-(7-cyanobenzo[b]thiophen-3-yl)-6-methyl-1,4-dihydropyridine-3-carboxylate 3-((2,2-Difluorocyclopropyl)methyl) 5-methyl 2-amino-4-(7-cyanobenzo[b]thiophen-3-yl)-6-methyl-1,4-dihydropyridine-3,5-dicarboxylate 5-Cyclopropyl 3-(cyclopropylmethyl) 2-amino-4-(7-cyanobenzo[b]thiophen-3-yl)-6-methyl-1,4-dihydropyridine-3,5-dicarboxylate 3-((2,2-Difluorocyclopropyl)methyl) 5-methyl 2-amino-4-(7-cyanobenzo[b]thiophen-3-yl)-6-cyclopropyl-1,4-dihydropyridine-3,5-dicarboxylate 3-(Cyclopropylmethyl) 5-methyl 2-amino-4-(7-cyano-5-fluorobenzo[b]thiophen-3-yl)-6-methyl-1,4-dihydropyridine-3,5-dicarboxylate 3-(cyclopropylmethyl) 5-methyl 2-amino-4-(7-cyano-4-fluorobenzo[b]thiophen-3-yl)-6-methyl-1,4-dihydropyridine-3,5-dicarboxylate 3-Isopropyl 5-methyl 2-amino-4-(7-cyanobenzo[b]thiophen-3-yl)-6-methyl-1,4-dihydropyridine-3,5-dicarboxylate 3-((2,2-Difluoro-3,3-dimethylcyclopropyl)methyl) 5-methyl 2-amino-4-(7-cyanobenzo[b]thiophen-3-yl)-6-methyl-1,4-dihydropyridine-3,5-dicarboxylate 5-Methyl 3-neopentyl 2-amino-4-(7-cyanobenzo[b]thiophen-3-yl)-6-methyl-1,4-dihydropyridine-3,5-dicarboxylate 3-(Cyclopropylmethyl) 5-methyl 2-amino-4-(7-cyanothieno[3,2-b]pyridin-3-yl)-6-methyl-1,4-dihydropyridine-3,5-dicarboxylate 5-Methyl 3-neopentyl 2-amino-4-(7-cyanobenzo[b]thiophen-3-yl)-6-cyclopropyl-1,4-dihydropyridine-3,5-dicarboxylate Bis(cyclopropylmethyl) 2-amino-4-(7-cyanobenzo[b]thiophen-3-yl)-6-methyl-1,4-dihydropyridine-3,5-dicarboxylate 3-(Cyclopropylmethyl) 5-(prop-2-yn-1-yl) 2-amino-4-(7-cyanobenzo[b]thiophen-3-yl)-6-methyl-1,4-dihydropyridine-3,5-dicarboxylate 3-(Cyclopropylmethyl) 5-methyl 2-amino-4-(5,7-dicyanobenzo[b]thiophen-3-yl)-6-methyl-1,4-dihydropyridine-3,5-dicarboxylate 5-(But-2-yn-1-yl) 3-(cyclopropylmethyl) 2-amino-4-(7-cyanobenzo[b]thiophen-3-yl)-6-methyl-1,4-dihydropyridine-3,5-dicarboxylate 5-Methyl 3-(2,2,2-trifluoroethyl) 2-amino-4-(7-cyanobenzo[b]thiophen-3-yl)-6-methyl-1,4-dihydropyridine-3,5-dicarboxylate 3-(Cyclopropylmethyl) 5-(2,2,2-trifluoroethyl) 2-amino-4-(7-cyanobenzo[b]thiophen-3-yl)-6-methyl-1,4-dihydropyridine-3,5-dicarboxylate 3-(Cyclopropylmethyl) 5-methyl 2-amino-4-(6-chloro-7-cyanobenzo[b]thiophen-3-yl)-6-methyl-1,4-dihydropyridine-3,5-dicarboxylate 3-(2-Fluoro-2-methylpropyl) 5-methyl 2-amino-4-(7-cyanobenzo[b]thiophen-3-yl)-6-methyl-1,4-dihydropyridine-3,5-dicarboxylate 3-(Cyclopropylmethyl) 5-methyl 2-amino-4-(7-cyano-6-(trifluoromethyl)benzo[b]thiophen-3-yl)-6-methyl-1,4-dihydropyridine-3,5-dicarboxylate 5-Methyl 3-prop-2-yn-1-yl 2-amino-4-(7-cyanobenzo[b]thiophen-3-yl)-6-methyl-1,4-dihydropyridine-3,5-dicarboxylate 3-(Cyclopropylmethyl) 5-methyl 2-amino-4-(7-cyanobenzo[b]thiophen-3-yl)-6-(trifluoromethyl)-1,4-dihydropyridine-3,5-dicarboxylate 4-(Benzo[b]thiophen-3-yl)-2,6-dimethyl-1,4-dihydropyridine-3,5-dicarbonitrile 4-(6-hydroxybenzo[b]thiophen-3-yl)-2,6-dimethyl-1,4-dihydropyridine-3,5-dicarbonitrile 4-(6-methoxybenzo[b]thiophen-3-yl)-2,6-dimethyl-1,4-dihydropyridine-3,5-dicarbonitrile 2,6-dimethyl-4-(thieno[2,3-b]pyridin-3-yl)-1,4-dihydropyridine-3,5-dicarbonitrile 4-(benzo[b]thiophen-3-yl)-2-methyl-6-phenyl-1,4-dihydropyridine-3,5-dicarbonitrile 4-(benzo[b]thiophen-3-yl)-2-cyclopropyl-6-methyl-1,4-dihydropyridine-3,5-dicarbonitrile 5-acetyl-4-(benzo[b]thiophen-3-yl)-2,6-dimethyl-1,4-dihydropyridine-3-carbonitrile Ethyl 4-(benzo[b]thiophen-3-yl)-5-cyano-2,6-dimethyl-1,4-dihydropyridine-3-carboxylate Ethyl 4-(benzo[b]thiophen-3-yl)-5-cyano-2-methyl-6-phenyl-1,4-dihydropyridine-3-carboxylate Ethyl 4-(benzo[b]thiophen-3-yl)-5-cyano-2-cyclopropyl-6-methyl-1,4-dihydropyridine-3-carboxylate Methyl 4-(benzo[b]thiophen-3-yl)-5-cyano-2-cyclopropyl-6-methyl-1,4-dihydropyridine-3-carboxylate 1,1'-(4-(benzo[b]thiophen-3-yl)-2,6-dimethyl-1,4-dihydropyridine-3,5-diyl)diethanone 1,1'-(4-(6-hydroxybenzo[b]thiophen-3-yl)-2,6-dimethyl-1,4-dihydropyridine-3,5-diyl)bis(ethan-1-one)

1,1'-(4-(6-Methoxybenzo[b]thiophen-3-yl)-2,6-dimethyl-1,4-dihydropyridine-3,5-diyl)diethanone 1,1'-(4-(Benzo[b]thiophen-3-yl)-2,6-dicyclopropyl-1,4-dihydropyridine-3,5-diyl)diethanone 1,1'-(4-(5-chlorobenzo[b]thiophen-3-yl)-2,6-dimethyl-1,4-dihydropyridine-3,5-diyl)diethanone 1,1'-(4-(5-bromobenzo[b]thiophen-3-yl)-2,6-dimethyl-1,4-dihydropyridine-3,5-diyl)diethanone 1,1'-(4-(5-fluorobenzo[b]thiophen-3-yl)-2,6-dimethyl-1,4-dihydropyridine-3,5-diyl)bis(ethan-1-one)

1,1'-(2,6-dimethyl-4-(5-morpholinobenzo[b]thiophen-3-yl)-1,4-dihydropyridine-3,5-diyl)bis(ethan-1-one)

1,1'-(2,6-dimethyl-4-(5-(4-methylpiperazin-1-yl)benzo[b]thiophen-3-yl)-1,4-dihydropyridine-3,5-diyl)bis(ethan-1-one)

1,1'-(4-(5-(benzylamino)benzo[b]thiophen-3-yl)-2,6-dimethyl-1,4-dihydropyridine-3,5-diyl)bis(ethan-1-one)

3-(3,5-diacetyl-2,6-dimethyl-1,4-dihydropyridin-4-yl)benzo[b]thiophene-5-carbonitrile 3-(3,5-diacetyl-2,6-dimethyl-1,4-dihydropyridin-4-yl)benzo[b]thiophene-5-carboxylic acid N-cyclopropyl-3-(3,5-diacetyl-2,6-dimethyl-1,4-dihydropyridin-4-yl)benzo[b]thiophene-5-carboxamide N-(cyclopropylmethyl)-3-(3,5-diacetyl-2,6-dimethyl-1,4-dihydropyridin-4-yl)benzo[b]thiophene-5-carboxamide 1,1'-(2,6-Dimethyl-4-(5-(4-methylpiperazine-1-carbonyl)benzo[b]thiophen-3-yl)-1,4-dihydropyridine-3,5-diyl)bis(ethan-1-one)

1,1'-(2,6-Dimethyl-4-(5-(morpholine-4-carbonyl)benzo[b]thiophen-3-yl)-1,4-dihydropyridine-3,5-diyl)bis(ethan-1-one)

1,1'-(2,6-Dimethyl-4-(thieno[3,2-c]pyridin-3-yl)-1,4-dihydropyridine-3,5-diyl)bis(ethan-1-one)

1,1'-(2,6-Dimethyl-4-(thieno[2,3-c]pyridin-3-yl)-1,4-dihydropyridine-3,5-diyl)bis(ethan-1-one)

1,1'-(2,6-Dimethyl-4-(thieno[2,3-b]pyridin-3-yl)-1,4-dihydropyridine-3,5-diyl)bis(ethan-1-one)

Dimethyl 5-acetyl-4-(benzo[b]thiophen-3-yl)-6-methyl-1,4-dihydropyridine-2,3-dicarboxylate
Dimethyl 5-acetyl-4-(7-cyanobenzo[b]thiophen-3-yl)-6-methyl-1,4-dihydropyridine-2,3-dicarboxylate
Methyl 5-acetyl-4-(benzo[b]thiophen-3-yl)-2-cyclopropyl-6-methyl-1,4-dihydropyridine-3-carboxylate
Dimethyl 4-(benzo[b]thiophen-3-yl)-2,6-dicyclopropyl-1,4-dihydropyridine-3,5-dicarboxylate
Ethyl 5-acetyl-4-(benzo[b]thiophen-3-yl)-2,6-dimethyl-1,4-dihydropyridine-3-carboxylate
Methyl 5-acetyl-4-(5-chlorobenzo[b]thiophen-3-yl)-2,6-dimethyl-1,4-dihydropyridine-3-carboxylate
1,1'-(4-(benzo[b]thiophen-3-yl)-2-cyclopropyl-6-methyl-1,4-dihydro-pyridine-3,5-diyl)diethanone
1-(4-(benzo[b]thiophen-3-yl)-2,6-dimethyl-5-(methylsulfonyl)-1,4-dihydro-pyridin-3-yl)ethanone
Methyl 5-acetyl-4-(5-fluorobenzo[b]thiophen-3-yl)-2,6-dimethyl-1,4-dihydropyridine-3-carboxylate
Methyl 5-acetyl-4-(5-bromobenzo[b]thiophen-3-yl)-2,6-dimethyl-1,4-dihydropyridine-3-carboxylate
methyl 5-acetyl-4-(5-cyanobenzo[b]thiophen-3-yl)-2,6-dimethyl-1,4-dihydropyridine-3-carboxylate
3-(3-acetyl-5-(methoxycarbonyl)-2,6-dimethyl-1,4-dihydropyridin-4-yl)benzo[b]thiophene-5-carboxylicacid
methyl 5-acetyl-4-(5-(cyclopropylcarbamoyl)benzo[b]thiophen-3-yl)-2,6-dimethyl-1,4-dihydropyridine-3-carboxylate
Methyl 5-acetyl-4-(5-((cyclopropylmethyl)carbamoyl)benzo[b]thiophen-3-yl)-2,6-dimethyl-1,4-dihydropyridine-3-carboxylate
Methyl 5-acetyl-2,6-dimethyl-4-(5-(4-methylpiperazine-1-carbonyl)benzo[b]thiophen-3-yl)-1,4-dihydropyridine-3-carboxylate
Methyl 5-acetyl-2,6-dimethyl-4-(5-(morpholine-4-carbonyl)benzo[b]thiophen-3-yl)-1,4-dihydropyridine-3-carboxylate
Methyl 5-acetyl-2,6-dimethyl-4-(thieno[3,2-c]pyridin-3-yl)-1,4-dihydropyridine-3-carboxylate
Methyl 5-acetyl-2,6-dimethyl-4-(thieno[2,3-c]pyridin-3-yl)-1,4-dihydropyridine-3-carboxylate
Methyl 5-acetyl-2,6-dimethyl-4-(thieno[2,3-b]pyridin-3-yl)-1,4-dihydropyridine-3-carboxylate
Methyl 5-acetyl-2-cyclopropyl-4-(5-fluorobenzo[b]thiophen-3-yl)-6-methyl-1,4-dihydropyridine-3-carboxylate
Dimethyl 2,6-dicyclopropyl-4-(5-fluorobenzo[b]thiophen-3-yl)-1,4-dihydropyridine-3,5-dicarboxylate
Methyl 5-acetyl-2-cyclopropyl-6-methyl-4-(thieno[2,3-b]pyridin-3-yl)-1,4-dihydropyridine-3-carboxylate
Dimethyl 2,6-dicyclopropyl-4-(thieno[2,3-b]pyridin-3-yl)-1,4-dihydropyridine-3,5-dicarboxylate
Methyl 5-acetyl-4-(benzo[b]thiophen-3-yl)-2,6-dicyclopropyl-1,4-dihydropyridine-3-carboxylate
Methyl 5-acetyl-4-(5-chlorobenzo[b]thiophen-3-yl)-2-cyclopropyl-6-methyl-1,4-dihydropyridine-3-carboxylate
Dimethyl 4-(5-chlorobenzo[b]thiophen-3-yl)-2,6-dicyclopropyl-1,4-dihydropyridine-3,5-dicarboxylate
Methyl 5-acetyl-4-(7-bromobenzo[b]thiophen-3-yl)-2-cyclopropyl-6-methyl-1,4-dihydropyridine-3-carboxylate
Methyl 5-acetyl-2-cyclopropyl-4-(7-(cyclopropylcarbamoyl)benzo[b]thiophen-3-yl)-6-methyl-1,4-dihydropyridine-3-carboxylate
Methyl 5-acetyl-4-(7-cyanobenzo[b]thiophen-3-yl)-2-cyclopropyl-6-methyl-1,4-dihydropyridine-3-carboxylate
Dimethyl 4-(7-cyanobenzo[b]thiophen-3-yl)-2,6-dicyclopropyl-1,4-dihydropyridine-3,5-dicarboxylate
Methyl 5-acetyl-2-cyclopropyl-4-(7-(methoxycarbonyl)benzo[b]thiophen-3-yl)-6-methyl-1,4-dihydropyridine-3-carboxylate
Dimethyl 2,6-dicyclopropyl-4-(7-(methoxycarbonyl)benzo[b]thiophen-3-yl)-1,4-dihydropyridine-3,5-dicarboxylate
3-(3-Acetyl-6-cyclopropyl-5-(methoxycarbonyl)-2-methyl-1,4-dihydropyridin-4-yl)benzo[b]thiophene-7-carboxylic acid
Benzyl 5-acetyl-2-cyclopropyl-6-methyl-4-(thieno[2,3-b]pyridin-3-yl)-1,4-dihydropyridine-3-carboxylate
Pyridin-4-ylmethyl 5-acetyl-4-(benzo[b]thiophen-3-yl)-2-cyclopropyl-6-methyl-1,4-dihydropyridine-3-carboxylate
bis(pyridin-4-ylmethyl) 2,6-dicyclopropyl-4-(thieno[2,3-b]pyridin-3-yl)-1,4-dihydropyridine-3,5-dicarboxylate
Pyridin-4-ylmethyl 5-acetyl-4-(7-bromobenzo[b]thiophen-3-yl)-2,6-dimethyl-1,4-dihydropyridine-3-carboxylate
Pyridin-4-ylmethyl 5-acetyl-4-(5-chlorobenzo[b]thiophen-3-yl)-2-cyclopropyl-6-methyl-1,4-dihydropyridine-3-carboxylate
Pyridin-4-ylmethyl 5-acetyl-4-(7-cyanobenzo[b]thiophen-3-yl)-2-cyclopropyl-6-methyl-1,4-dihydropyridine-3-carboxylate
Pyridin-4-ylmethyl 5-acetyl-2-cyclopropyl-6-methyl-4-(thieno[2,3-b]pyridin-3-yl)-1,4-dihydropyridine-3-carboxylate
Benzyl 5-acetyl-2-cyclopropyl-4-(7-(methoxycarbonyl)benzo[b]thiophen-3-yl)-6-methyl-1,4-dihydropyridine-3-carboxylate
Dibenzyl 2,6-dicyclopropyl-4-(7-(methoxycarbonyl)benzo[b]thiophen-3-yl)-1,4-dihydropyridine-3,5-dicarboxylate
Benzyl 5-acetyl-4-(7-(methoxycarbonyl)benzo[b]thiophen-3-yl)-2,6-dimethyl-1,4-dihydropyridine-3-carboxylate
Methyl 3-(3,5-diacetyl-2,6-dimethyl-1,4-dihydropyridin-4-yl)benzo[b]thiophene-7-carboxylate
3-(3,5-Diacetyl-2,6-dimethyl-1,4-dihydropyridin-4-yl)benzo[b]thiophene-7-carbonitrile
Pyridin-4-ylmethyl 5-acetyl-4-(7-bromobenzo[b]thiophen-3-yl)-2-cyclopropyl-6-methyl-1,4-dihydropyridine-3-carboxylate
4-Fluorobenzyl 5-acetyl-2-cyclopropyl-6-methyl-4-(thieno[2,3-b]pyridin-3-yl)-1,4-dihydropyridine-3-carboxylate
bis(4-fluorobenzyl) 2,6-dicyclopropyl-4-(thieno[2,3-b]pyridin-3-yl)-1,4-dihydropyridine-3,5-dicarboxylate
4-cyanobenzyl 5-acetyl-2-cyclopropyl-6-methyl-4-(thieno[2,3-b]pyridin-3-yl)-1,4-dihydropyridine-3-carboxylate
Methyl 5-acetyl-4-(7-chlorobenzo[b]thiophen-3-yl)-2-cyclopropyl-6-methyl-1,4-dihydropyridine-3-carboxylate
methyl 5-acetyl-2-cyclopropyl-6-methyl-4-(7-(trifluoromethyl)benzo[b]thiophen-3-yl)-1,4-dihydropyridine-3-carboxylate
3-chlorobenzyl 5-acetyl-2,6-dimethyl-4-(thieno[2,3-b]pyridin-3-yl)-1,4-dihydropyridine-3-carboxylate
2-phenylpropan-2-yl 5-acetyl-4-(7-bromobenzo[b]thiophen-3-yl)-2-cyclopropyl-6-methyl-1,4-dihydropyridine-3-carboxylate
Cyclohexyl 5-acetyl-2-cyclopropyl-6-methyl-4-(thieno[2,3-b]pyridin-3-yl)-1,4-dihydropyridine-3-carboxylate
2-Phenylpropan-2-yl 5-acetyl-2-cyclopropyl-6-methyl-4-(thieno[2,3-b]pyridin-3-yl)-1,4-dihydropyridine-3-carboxylate
1-(4-(7-Bromobenzo[b]thiophen-3-yl)-5-(cyclopropanecarbonyl)-6-cyclopropyl-2-methyl-1,4-dihydropyridin-3-yl)ethan-1-one
3-chlorobenzyl 5-acetyl-2-cyclopropyl-6-methyl-4-(thieno[2,3-b]pyridin-3-yl)-1,4-dihydropyridine-3-carboxylate 2-(4-Fluorophenyl)propan-2-yl 5-acetyl-2,6-dimethyl-4-(thieno[2,3-b]pyridin-3-yl)-1,4-dihydropyridine-3-carboxylate 2-(4-fluorophenyl)propan-2-yl 5-acetyl-4-(7-bromobenzo[b]thiophen-3-yl)-2-cyclopropyl-6-methyl-1,4-dihydropyridine-3-carboxylate 2-(4-fluorophenyl)propan-2-yl 5-acetyl-2-cyclopropyl-6-methyl-4-(thieno[2,3-b]pyridin-3-yl)-1,4-dihydropyridine-3-carboxylate Methyl 5-acetyl-2-cyclopropyl-4-(7-fluorobenzo[b]thiophen-3-yl)-6-methyl-1,4-dihydropyridine-3-carboxylate Cyclopropylmethyl 5-acetyl-2-cyclopropyl-6-methyl-4-(thieno[2,3-b]pyridin-3-yl)-1,4-dihydropyridine-3-carboxylate Cyclopentyl 5-acetyl-2-cyclopropyl-6-methyl-4-(thieno[2,3-b]pyridin-3-yl)-1,4-dihydropyridine-3-carboxylate Cyclopropylmethyl 5-acetyl-4-(7-cyanobenzo[b]thiophen-3-yl)-2-cyclopropyl-6-methyl-1,4-dihydropyridine-3-carboxylate Methyl 5-acetyl-4-(7-bromobenzo[b]thiophen-3-yl)-2-cyclobutyl-6-methyl-1,4-dihydropyridine-3-carboxylate Dimethyl 4-(7-cyanobenzo[b]thiophen-3-yl)-2-cyclopropyl-6-methyl-1,4-dihydropyridine-3,5-dicarboxylate Methyl 5-cyano-4-(7-cyanobenzo[b]thiophen-3-yl)-2-cyclopropyl-6-methyl-1,4-dihydropyridine-3-carboxylate Methyl 5-acetyl-4-(7-bromobenzo[b]thiophen-3-yl)-2-cyclopentyl-6-methyl-1,4-dihydropyridine-3-carboxylate Methyl 5-acetyl-4-(7-bromobenzo[b]thiophen-3-yl)-2-cyclohexyl-6-methyl-1,4-dihydropyridine-3-carboxylate Methyl 5-cyano-4-(7-cyanobenzo[b]thiophen-3-yl)-2,6-dicyclopropyl-1,4-dihydropyridine-3-carboxylate 3-((4-Methylpiperazin-1-yl)methyl)benzyl 5-acetyl-4-(7-bromobenzo[b]thiophen-3-yl)-2,6-dimethyl-1,4-dihydropyridine-3-carboxylate 3-(cyclopropylmethyl) 5-methyl 4-(7-cyanobenzo[b]thiophen-3-yl)-2-cyclopropyl-6-methyl-1,4-dihydropyridine-3,5-dicarboxylate 3-(cyclopropylmethyl) 5-methyl 4-(7-cyanobenzo[b]thiophen-3-yl)-2,6-dicyclopropyl-1,4-dihydropyridine-3,5-dicarboxylate cyclopropylmethyl 5-cyano-4-(7-cyanobenzo[b]thiophen-3-yl)-2-cyclopropyl-6-methyl-1,4-dihydropyridine-3-carboxylate dimethyl 2-cyano-4-(7-cyanobenzo[b]thiophen-3-yl)-6-cyclopropyl-1,4-dihydropyridine-3,5-dicarboxylate dimethyl 2-cyano-4-(7-cyanobenzo[b]thiophen-3-yl)-6-methyl-1,4-dihydropyridine-3,5-dicarboxylate methyl 5-acetyl-2-((2-aminoethoxy)methyl)-4-(benzo[b]thiophen-3-yl)-6-methyl-1,4-dihydropyridine-3-carboxylate methyl 5-acetyl-2-((2-aminoethoxy)methyl)-4-(7-bromobenzo[b]thiophen-3-yl)-6-methyl-1,4-dihydropyridine-3-carboxylate methyl 5-acetyl-2-((2-aminoethoxy)methyl)-4-(7-cyanobenzo[b]thiophen-3-yl)-6-methyl-1,4-dihydropyridine-3-carboxylate Dimethyl 4-(7-cyanobenzo[b]thiophen-3-yl)-2-cyclopropyl-6-formyl-1,4-dihydropyridine-3,5-dicarboxylate Dimethyl 4-(7-cyanobenzo[b]thiophen-3-yl)-2-cyclopropyl-6-(hydroxymethyl)-1,4-dihydropyridine-3,5-dicarboxylate Dimethyl 4-(7-cyanobenzo[b]thiophen-3-yl)-2-formyl-6-methyl-1,4-dihydropyridine-3,5-dicarboxylate Dimethyl 4-(7-cyanobenzo[b]thiophen-3-yl)-2-(hydroxymethyl)-6-methyl-1,4-dihydropyridine-3,5-dicarboxylate Dimethyl 2-cyano-6-methyl-4-(thieno[2,3-b]pyridin-3-yl)-1,4-dihydropyridine-3,5-dicarboxylate Cyclopropylmethyl 5-acetyl-4-(6-cyanobenzo[b]thiophen-3-yl)-2-cyclopropyl-6-methyl-1,4-dihydropyridine-3-carboxylate Cyclopropylmethyl 2,5-diacetyl-4-(7-cyanobenzo[b]thiophen-3-yl)-6-methyl-1,4-dihydropyridine-3-carboxylate Methyl 5-acetyl-2-amino-4-(benzo[b]thiophen-3-yl)-6-methyl-1,4-dihydropyridine-3-carboxylate hydrochloride Methyl 5-acetyl-2-amino-4-(benzo[b]thiophen-3-yl)-6-methyl-1,4-dihydropyridine-3-carboxylate trifluoromethanesulfonate 4-(Pyridin-4-yl)benzyl 5-acetyl-2,6-dimethyl-4-(thieno[2,3-b]pyridin-3-yl)-1,4 dihydropyridine-3-carboxylate 4-(Pyridin-3-yl)benzyl 5-acetyl-2,6-dimethyl-4-(thieno[2,3-b]pyridin-3-yl)-1,4-dihydropyridine-3-carboxylate 3-(Pyridin-4-yl)benzyl 5-acetyl-2,6-dimethyl-4-(thieno[2,3-b]pyridin-3-yl)-1,4-dihydropyridine-3-carboxylate 3-(Pyridin-3-yl)benzyl 5-acetyl-2,6-dimethyl-4-(thieno[2,3-b]pyridin-3-yl)-1,4-dihydropyridine-3-carboxylate 2-(Pyridin-4-yl)benzyl 5-acetyl-2,6-dimethyl-4-(thieno[2,3-b]pyridin-3-yl)-1,4-dihydropyridine-3-carboxylate 2-(pyridin-3-yl)benzyl 5-acetyl-2,6-dimethyl-4-(thieno[2,3-b]pyridin-3-yl)-1,4-dihydropyridine-3-carboxylate

[3,4'-Bipyridin]-5-ylmethyl 5-acetyl-2,6-dimethyl-4-(thieno[2,3-b]pyridin-3-yl)-1,4-dihydropyridine-3-carboxylate

[3,3'-Bipyridin]-5-ylmethyl 5-acetyl-2,6-dimethyl-4-(thieno[2,3-b]pyridin-3-yl)-1,4-dihydropyridine-3-carboxylate

[2,4'-Bipyridin]-5-ylmethyl 5-acetyl-2,6-dimethyl-4-(thieno[2,3-b]pyridin-3-yl)-1,4-dihydropyridine-3-carboxylate

[2,3'-Bipyridin]-5-ylmethyl 5-acetyl-2,6-dimethyl-4-(thieno[2,3-b]pyridin-3-yl)-1,4-dihydropyridine-3-carboxylate

[2,3'-Bipyridin]-4-ylmethyl 5-acetyl-2,6-dimethyl-4-(thieno[2,3-b]pyridin-3-yl)-1,4-dihydropyridine-3-carboxylate

[2,4'-Bipyridin]-4-ylmethyl 5-acetyl-2,6-dimethyl-4-(thieno[2,3-b]pyridin-3-yl)-1,4-dihydropyridine-3-carboxylate Methyl 5-acetyl-2-cyclopropyl-6-methyl-4-(7-(pyridin-4-yl)benzo[b]thiophen-3-yl)-1,4-dihydropyridine-3-carboxylate Methyl 5-acetyl-2-cyclopropyl-4-(7-cyclopropylbenzo[b]thiophen-3-yl)-6-methyl-1,4-dihydropyridine-3-carboxylate 3-(Pyridin-4-yl)benzyl 5-acetyl-2-cyclopropyl-6-methyl-4-(thieno[2,3-b]pyridin-3-yl)-1,4-dihydropyridine-3-carboxylate 1,1'-(2,6-Dimethyl-4-(5-(pyridin-3-yl)benzo[b]thiophen-3-yl)-1,4-dihydro-pyridine-3,5-diyl)diethanone Methyl 5-acetyl-2-cyclopropyl-6-methyl-4-(7-phenylbenzo[b]thiophen-3-yl)-1,4-dihydropyridine-3-carboxylate When the compounds of the present invention are combined with other therapeutic agents, said other therapeutic agents are selected from the group consisting of:

A—hormone therapy agents such as:
    1—gonadotropin-releasing hormone (GnRH) receptor agonists or antagonists;
    2—androgen receptor antagonists and CYP17 inhibitors;

B—blockers of oncogenic kinases signaling pathways such as:
    1—inhibitors of Vascular Endothelial Growth Factor (VEGF),
    2—inhibitors of Epidermal Growth Factor Receptor (EGFR),
    3—inhibitors of phosphoinositide 3-kinase (PI3K),
    4—Protein kinase B, also known as AKT,
    5—mechanistic target of rapamycin (mTOR),
    6—c-Met, also called MET or hepatocyte growth factor receptor (HGFR)
    7—Src, (nonreceptor tyrosine kinases)
    8—poly(ADP-ribose) polymerase (PARP), 9—angiopoietin,
10—Anaplastic lymphoma kinase also known as ALK tyrosine kinase receptor, and
11—anti-Insulin-like growth factors (IGF) antibodies;
C—cancer chemotherapy agents such as:
1—taxane anti-neoplastic agents,
2—topoisomerase II inhibitors,
3—anti-tumor antibiotics;
4—HSP90 (heat shock protein 90) inhibitors;
D—agents targeting neuroendocrine differentiation such as:
1—Aurora kinase inhibitors;
E—agents targeting immune evasion such as Prostate Specific Antigen (PSA)-directed vaccines
F—agents or natural extracts known to promote hair growth;
G—agents or natural extracts known to treat acne;
H—agents or natural extracts known to treat hirsutism; and
I—agents known to treat conditions caused by elevated levels of cortisol such as:
1—GR antagonists,
2—11-beta HSD inhibitors.

In an embodiment of the present invention the other therapeutic agent is one or more immunotherapeutic agent selected from the group consisting of antibodies anti-CTLA4, antibodies anti-PD1 and antibodies anti-PDL1. More preferably, the immunotherapeutic agent is selected from the group consisting of ipilimumab, tremelimumab, nivolumab, pembrolizumab, CT-011, AMP-224, MPDL3280A, MEDI4736 and MDX-1105.

Examples of gonadotropin-releasing hormone (GnRH) receptor agonists include, but are not limited to leuprolide, goserelin, and buserelin. Examples of gonadotropin-releasing hormone (GnRH) receptor antagonist include, but are not limited to degarelix and abarelix, among others.

Examples of androgen receptor antagonists include but are not limited to nilutamide, bicalutamide, flutamide and enzalutamide.

Examples of CYP17 inhibitors include but are not limited to abiraterone and gleterone.

Examples of VEGF receptor inhibitors include, but are not limited to bevacizumab, axitinib and brivanib alaninate.

Examples of EGFR inhibitors include, but are not limited to gefitinib, afatinib, cetuximab and panitumumab.

Examples of PI3K inhibitors include, but are not limited to pictilisib (also known as GDC 0941) and BKM120.

Examples of mTOR inhibitors include, but are not limited to temsirolimus, ridaforolimus and everolimus.

Examples of dual PI3K and mTOR inhibitors include, but are not limited to Apitolisib (GDC-0980), dactolisib (BEZ 235) and LY3023414.

Examples of AKT inhibitors include, but are not limited to A-443654, perifosine and ipatasertib.

Examples of c-Met inhibitors include, but are not limited to tivantinib, JNJ-38877605, cabozantinib and capmatinib.

Examples of Src blockers include, but are not limited to dasatinib, saracatinib, bosutinib, and KX01, which are in clinical development.

Examples of PARP inhibitors include, but are not limited to olaparib and veliparib.

Examples of ALK inhibitors include, but are not limited to X-396, alectinib, ceritinib, lorlatinib and crizotinib (dual ALK and ROS-1 inhibitor).

Examples of anti-IGF antibodies include, but are not limited to figitumumab, ganitumab and B1836845.

Examples of taxane anti-neoplastic agents include, but are not limited to cabazitaxel and larotaxel.

Examples of topoisomerase II inhibitors include, but are not limited to etoposide and teniposide.

Examples of anti-tumor antibiotics include, but are not limited to doxorubicin, bleomycin, daunorubicin, daunorubicin liposomal, mitoxantrone, epirubicin, idarubicin, and mitomycin C.

Examples of HSP90 (heat shock protein 90) inhibitors include, but are not limited to Debio 0932, MPC-3100, IPI-504, NVP-AUY922.

Examples of Aurora kinase inhibitors include, but are not limited to alisertib, tozasertib, danusertib and barasertib.

Examples of PSA-directed vaccine include, but are not limited to ProstVac-VF.

The compounds of this invention can be prepared by using the procedures described below. To facilitate the description of the procedures, concrete examples have been used in some cases, however they do not restrict in any way the scope of the present invention.

When one of $X^1$, $X^2$, $X^3$, $X^4$ and $X^5$ represents C—$B^1$ and the rest of $X^1$, $X^2$, $X^3$, $X^4$ and $X^5$ represent C—H the compounds of formula (I) are benzothiophenes of formula (1-a3), as depicted in Scheme 1-a and can be obtained be reacting thiophenol precursor (1-a1), where $B^1$ is selected from halogen, alkyl, haloalkyl, cycloalkyl, heterocycloalkyl and aryl, with 2-bromo-1,1-diethoxyethane and potassium carbonate in acetone affording intermediates (1-a2) which are cyclized to benzothiophenes (1-a3) by heating with polyphosphoric acid in toluene.

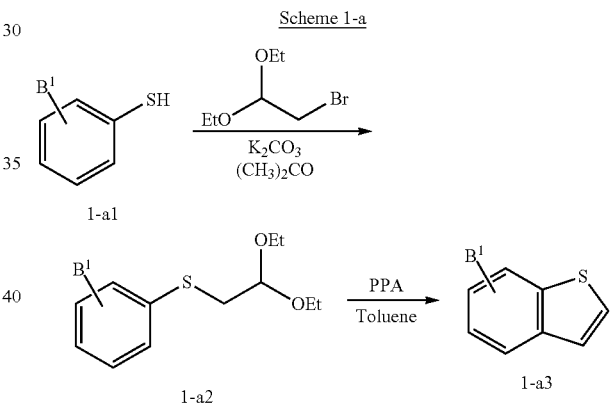

Scheme 1-a

When one of $X^1$, $X^2$, $X^3$, $X^4$ and $X^5$ represents C—$B^1$ and the rest of $X^1$, $X^2$, $X^3$, $X^4$ and $X^5$ represent C—H the compounds of formula (I) are benzothiophene intermediates of formula (III), as depicted in Scheme 1-b, can be obtained from halogen precursor (II), where halogen (Hal) is selected from chloro, iodo or preferentially bromo.

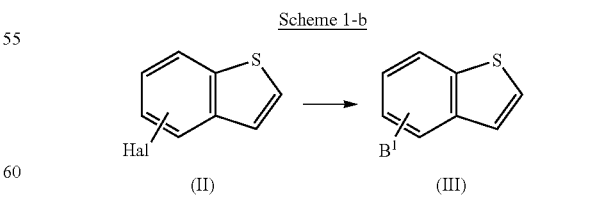

Scheme 1-b

More specifically, when $B^1$ represents —C(O)CF$_3$, one way to synthesize benzothiophene derivatives of formula (III) is by reacting the halogen precursor (II), specifically bromo precursor, with n-butyllithium and 2,2,2-trifluoro-1-morpholinoethan-1-one in diethyl ether at −60° C.

When $B^1$ represents —CN, the cyano group can be introduced by heating the halogen precursor (II), specifically bromo precursor, with zinc cyanide and tetrakis(triphenylphosphine)palladium(0) in a sealed tube at 90° C. The cyano derivative (III) can be converted into the carboxylic acid by heating with potassium hydroxide in methanol and water at 80° C., which can be further transformed into the methyl ester by refluxing in saturated HCl in methanol.

When $B^1$ represents mono- or dialkylamino, one way to synthesize benzothiophene derivatives of formula (III) is by refluxing the halogen precursor (II), specifically bromo precursor, with the corresponding amine, $Pd_2(dba)_3$, tricyclohexylphosphine and NaOtBu in dry toluene.

When $B^1$ represents mono- or dialkylaminocarbonyl, benzothiophene intermediates of formula (V) can be obtained by reacting carboxylic acid precursor (IV) with the corresponding amine, HOBT and DIPEA in DMF at room temperature, as depicted in Scheme 2.

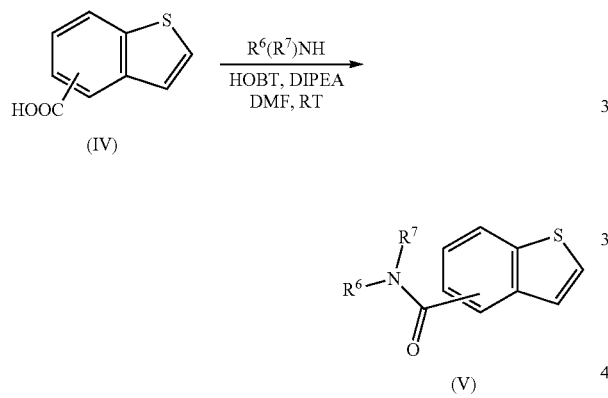

3-formylbenzo[b]thiophenes of formula (VII) can be obtained by reacting precursor (VI) with dichloro(methoxy)methane and titanium tetrachloride in dichloroethane at room temperature as represented in reaction Scheme 3.

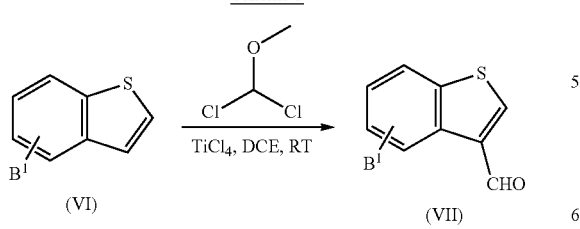

Another way of introducing a formyl group in position 3 of the bicyclic heterocycle (X), as depicted in reaction Scheme 4, is by heating the 3-bromo derivative (VIII) with copper(I) cyanide in NMP at 200° C. and subsequent reduction with DIBAL in toluene.

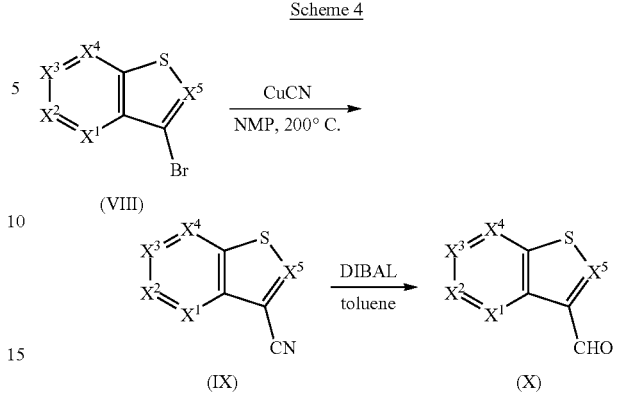

One way to synthesize dicarbonyl intermediates of formula (XI) and (XII) (used in the synthesis of compounds of formula (I) wherein $R^2$ represents —$COOR^8$ or —C(O)N($R^8$)$R^9$) is by heating commercially available 2,2,6-trimethyl-4H-1,3-dioxin-4-one and the corresponding alcohol or amine in toluene at 150° C., as represented by the acetoacetylation reaction depicted in reaction Scheme 5.

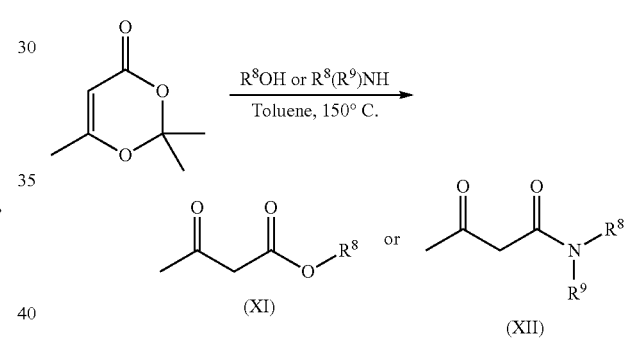

One way to synthetize dicarbonyl intermediates (XIV) (used in the synthesis of compounds of formula (I) wherein $R^4$ represents alkyl, cycloalkyl, phenyl or heteroaryl) is by reesterification in which methyl ester (XIII) and an alcohol are refluxed in dry toluene using a Dean-Stark trap, as shown in Scheme 6.

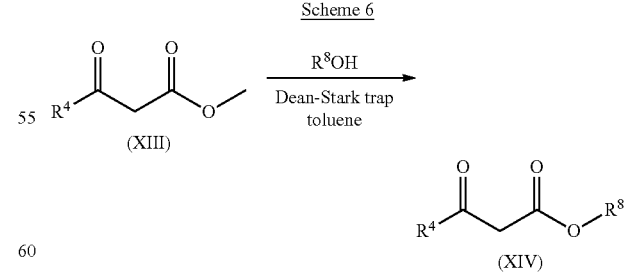

Another reesterification method affords dicarbonyl intermediates (XIV) by refluxing methyl ester (XIII) and an alcohol in dry toluene in a sealed tube using 10 mol-% trichlorobismuthane and molecular sieves, as represented in Scheme 7.

Scheme 7

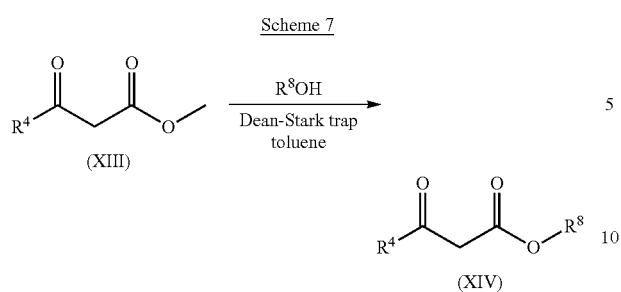

Dicarbonyl intermediates of formula (XIII) and (XVII) (used in the synthesis of compounds of formula (I) wherein $R^2$ represents —$COR^8$ or —$COOR^8$) can be synthesized via Claysen condensation by treating a methylketone derivative (XV) or acetone with potassium tert-butoxide in THF and reacting the mixture with either dimethyl carbonate or a methyl or ethyl ester (XVI), as represented in reaction Scheme 8.

Scheme 8

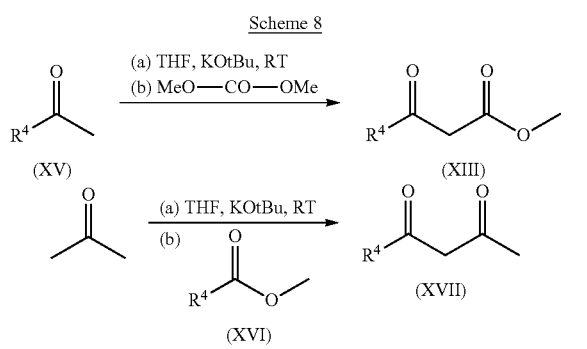

Ketoester intermediates of formula (XVIII) (used in the synthesis of compounds of formula (I) wherein $R^2$ represents —$COOR^8$ and $R^4$ represent —$CH_2OR^6$ or —$CH_2N(R^6)R^7$) can be synthesized by deprotonating an alcohol with sodium hydride in THF and treating the mixture with methyl 4-chloro-3-oxobutanoate, as represented in reaction Scheme 9. Ketoester intermediates of formula (XIX) can be synthesized accordingly by heating methyl 4-chloro-3-oxobutanoate with an amine in acetone and trimethylamine.

Scheme 9

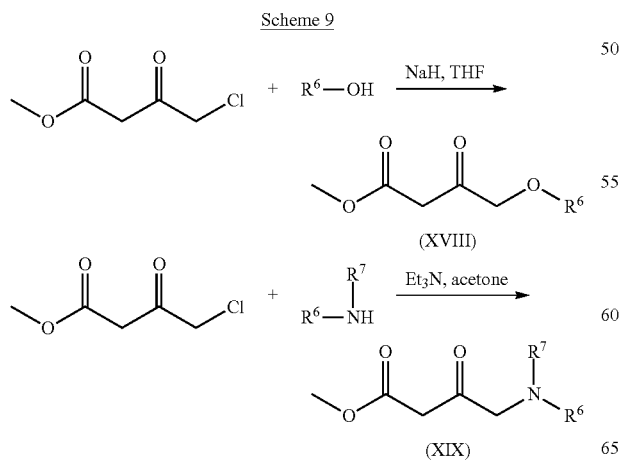

1,3-ketoester intermediates of formula (XIV) can be transformed into enamines (XX) either by heating with ammonium acetate, acetic acid and molecular sieves in THF or by reacting with ammonium bicarbonate in methanol, as represented in reaction Scheme 10. Accordingly, 1,3-diketones (XXI) can be converted into a mixture of enamines (XXII) and (XXIII) using the procedure described above or, alternatively, by reaction in aqueous ammonia.

Scheme 10

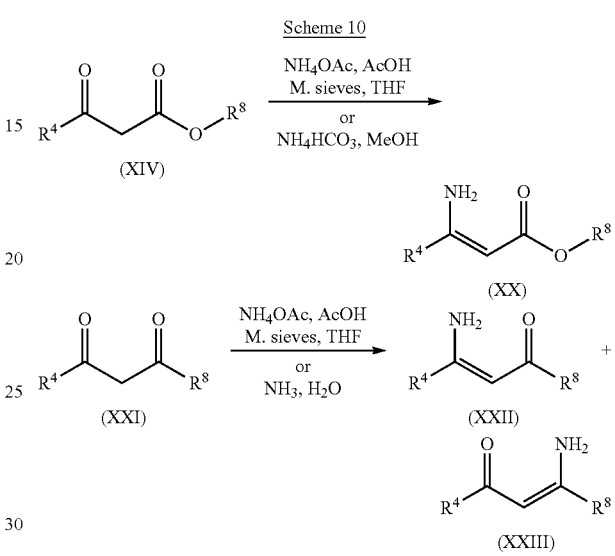

Knoevenagel products of formula (XXIV) and (XXVI) can be prepared by reacting aldehydes (X) (e.g. benzo[b]thiophene-3-carbaldehyde) and 1,3-dicarbonyl intermediates (XIV) or (XXV), respectively, with acetic acid, piperidine and molecular sieves in toluene in the microwave oven, as adapted from Liu & Zhang, Angew. Chem. Int. Ed. 2009, 48, 6093-6 and represented in reaction Scheme 11.

Scheme 11

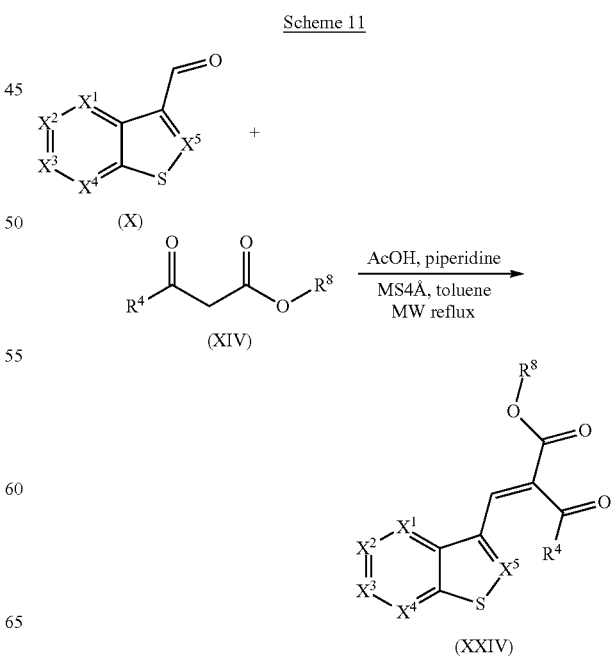

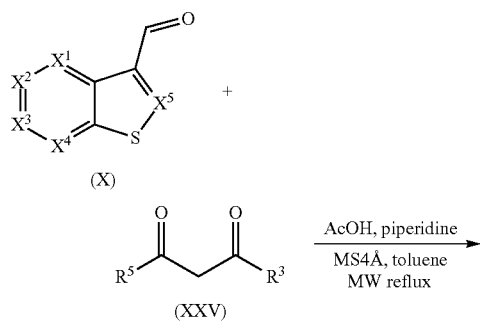

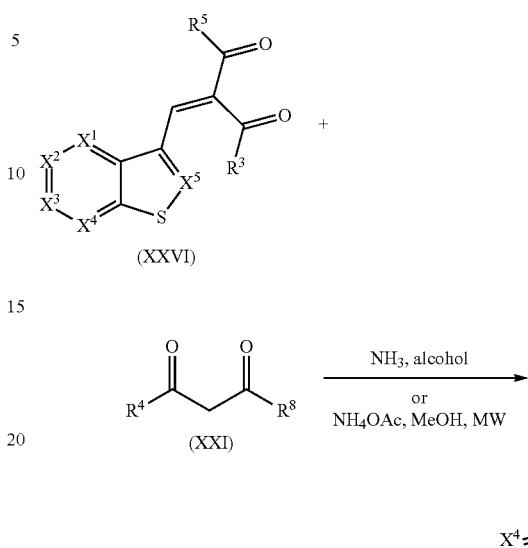

Dihydropyridines of formula (XXVII) and (XXVIII) can be prepared in a 3-component Hantzsch synthesis by heating Knoevenagel products (XXVI) with 1,3-dicarbonyl compounds (XIV), (XXI) or (XXIX) and ammonia in alcohols such as e.g. isopropanol, ethanol or 2,2,2-trifluoroethanol, as represented in reaction Scheme 12. Instead of ammonia, NH₄OAc in MeOH under microwave conditions can be used to synthesize dihydropyridines of formula (XXVII), (XXVIII) and (XXX).

Scheme 12

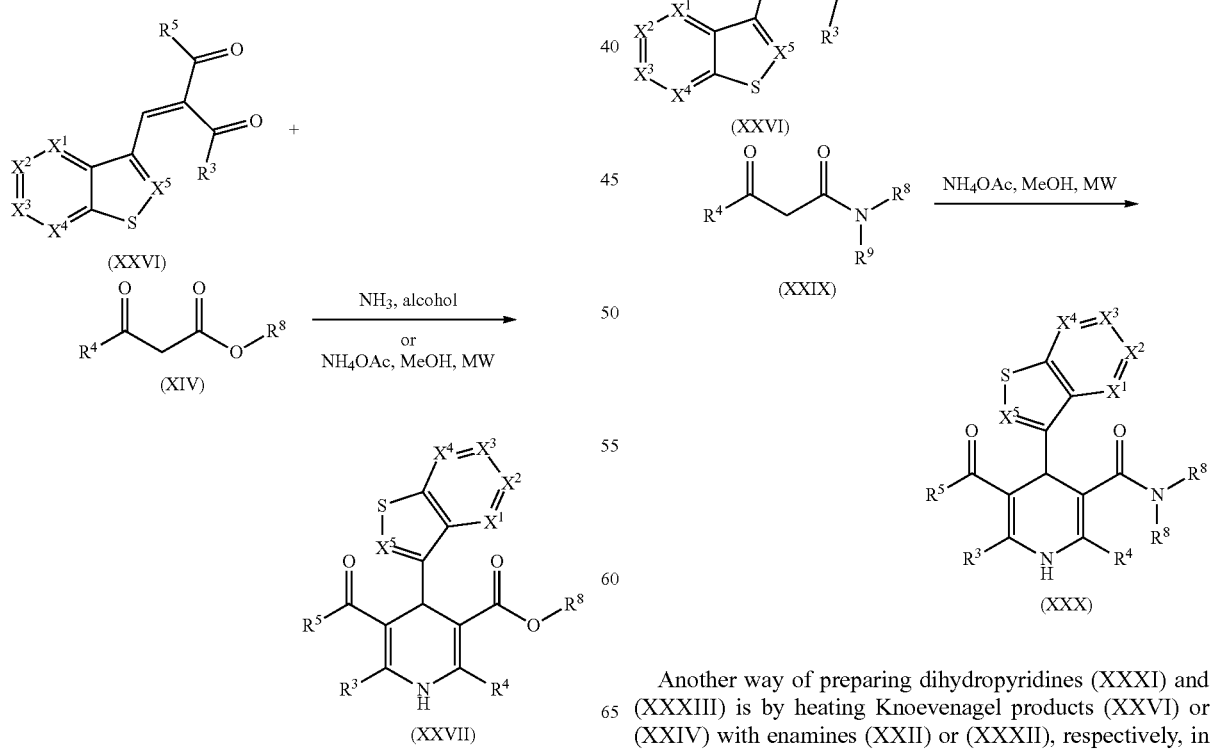

Another way of preparing dihydropyridines (XXXI) and (XXXIII) is by heating Knoevenagel products (XXVI) or (XXIV) with enamines (XXII) or (XXXII), respectively, in methanol under microwave conditions (Scheme 13).

Scheme 13

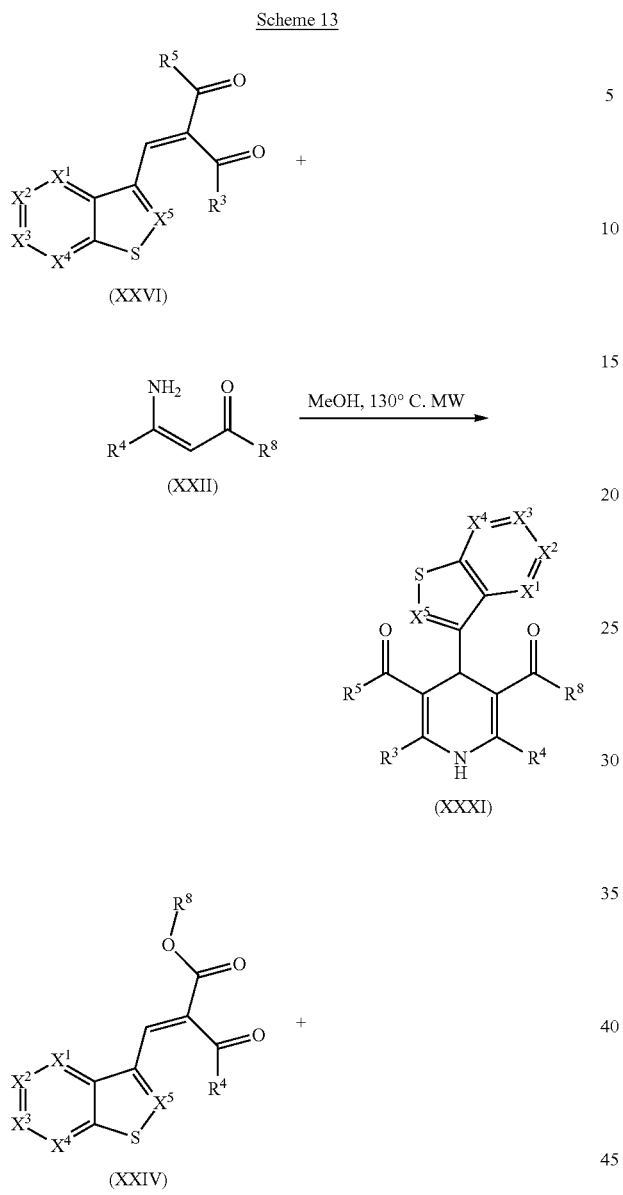

Dihydropyridines of formula (XXXIII) can also be prepared by heating Knoevenagel products (XXVI) and enamines (XX) in AcOH, as represented in reaction Scheme 14.

Scheme 14

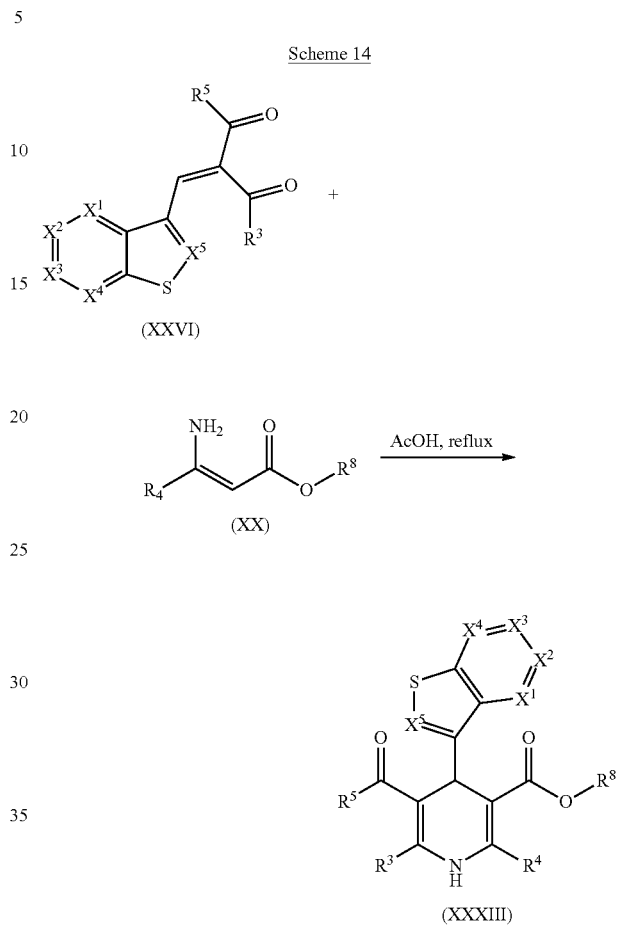

Dihydropyridines of formula (XXXV) (which are used as intermediates in the synthesis of compounds of formula (I) wherein $R^4$ represents —$NH_2$) can be synthesized by heating Knoevenagel product (XXVI) and amidine (XXXIV) with piperidine in isopropanol, as represented in reaction Scheme 15.

Scheme 15

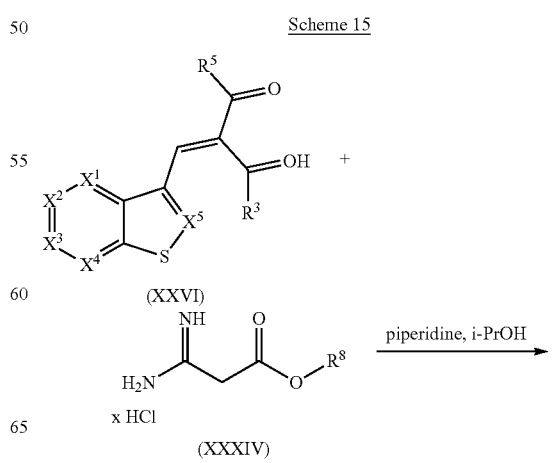

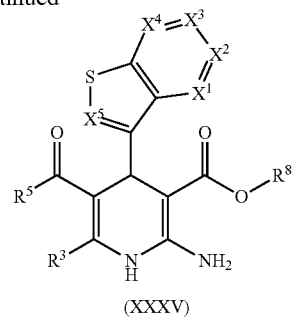

(XXXV)

The dihydropyridine scaffold can be assembled without prior formation of a Knoevenagel product. For example, compounds of formula (I) in which $R^1$ and $R^2$ both represent —CN, can be synthesized by heating aldehyde (X) and enamines (XXXVIa) and (XXXVIb) with acetic acid in isopropanol, as represented in reaction Scheme 16. When $R^3$ is not equal to $R^4$, mixtures of dihydropyridines (XXXVIIa), (XXXVIIb) and (XXXVIIc) are obtained that need to be separated, e.g. by column chromatography.

Scheme 16

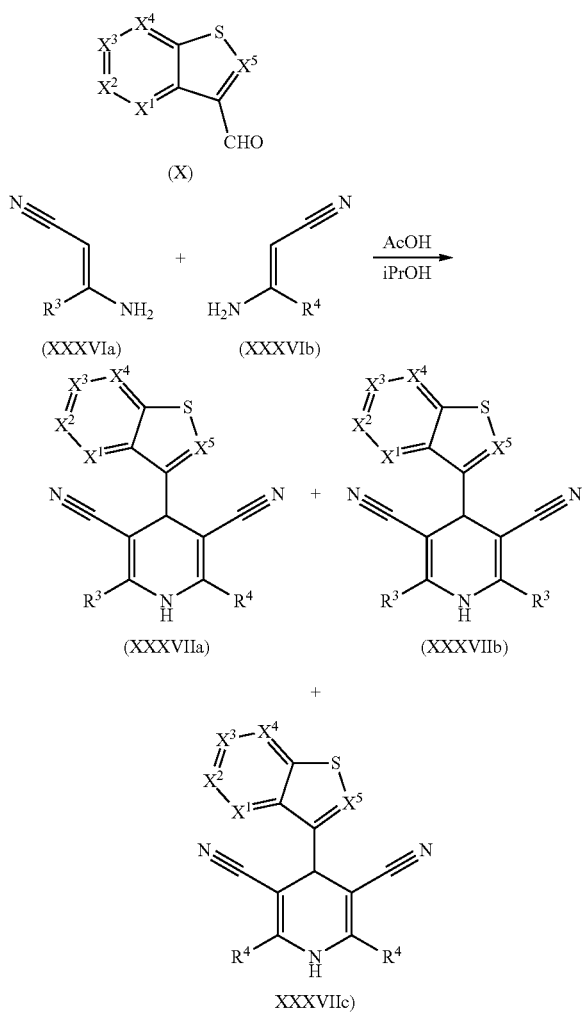

In a variation of the method described above, one of the enamines, e.g. (XXXVIb), can be replaced by a ketone, e.g. (XXXVIc), to prepare the same mixture of dihydropyridines (XXXVIIa), (XXXVIIb) and (XXXVIIc).

(XXXVIc)

The reaction conditions described above in Scheme 16 (heating with acetic acid in alcohols such as e.g. isopropanol, optionally in the presence of substoichiometric amounts of piperidine) can be utilized in a wider scope to synthesize dihydropyridines of formula (I), in which $R^1$ represents either —CHO, —COR$^5$ or —CN and $R^2$ is selected from —COR$^8$, —S(O)$_n$R$^8$ (wherein n is 1 or 2), —COOR$^8$ and —C(O)N(R$^8$)R$^9$, provided that an aldehyde (X) (e.g. benzo[b]thiophene-3-carbaldehyde) is reacted with:

(a) two enamines as exemplified by, but not limited to, the compounds of formulae (XX), (XXII), (XXIII), (XXXII) or (XXXVIa/b), or (b) one enamine as exemplified by, but not limited to, the compounds of formulae (XX), (XXII), (XXIII), (XXXII) or (XXXVIa/b) and a 1,3-dicarbonyl compound as exemplified by, but not limited to, the compounds of formulae (XIV), (XXV) or (XXIX).

The enamines described above can also be formed in situ giving rise to yet another variation of the Hantzsch synthesis of the dihydropyridine scaffold in which compounds of formula (I) are prepared in a 4-component reaction by heating an aldehyde (e.g. benzo[b]thiophene-3-carbaldehyde), two 1,3-dicarbonyl compounds (e.g. compounds of formula (XIV), (XXV) or (XXIX)) and aqueous ammonia in alcohols (e.g. ethanol).

The methods for synthesizing the 1,4-dihydropyridine scaffold, as described above, are variations of the well documented Hantzsch Reaction that has been reviewed, for example, in "Hantzsch reaction: Recent advances in Hantzsch 1,4-dihydropyridines", A. Saini et al., J Scient Indust Res 2008, 67, 95-111.

Dihydropyridines of formula (I) bearing halogen atoms, such as —Br, on an aromatic ring, can be further derivatized by metal-catalyzed coupling reactions in which the halogen atom is replaced by e.g. aryl, heteroaryl or small alkyl groups (Suzuki coupling), by amines (Buchwald coupling) or by a cyano group (Zn coupling).

For example, halogen-substituted benzyl esters of formula (XXXVIII) can be coupled with pyridinylboronic acid (or other heteroaryl, phenyl or alkyl boronic acids) by heating both components with a palladium catalyst, e.g. palladium-tetrakis(triphenylphosphine), and a base, e.g. potassium carbonate, in a 3:1 mixture of DME and water to afford dihydropyridine (XXXIX) as represented in Scheme 17.

Scheme 17

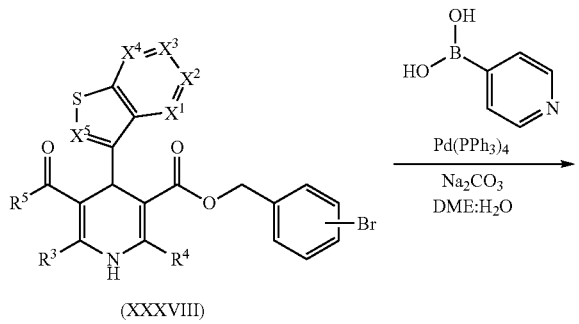

(XXXVIII)

18, can be converted into compounds of formula (XLI) by Suzuki coupling with pyridylboronic acid utilizing a catalyst (e.g. Pd(dppf)Cl$_2$*DCM) and aqueous Cs$_2$CO$_3$ in dichloromethane at reflux temperature. In yet another example, coupling of halogen-substituted benzothiophenes (XL) with stannanes, like e.g. tributyl(phenyl) stannane, using catalysts such as palladium(II)bis(triphenyl-phosphine)dichloride in hot toluene (2 mL) afford compounds of formula (XLII).

The bromine atom of benzothiophenes (XL) shown in Scheme 18 can be displaced by a cyano group by heating with Zn(CN)$_2$ and Pd(PPh$_3$)$_4$ in DMF to afford dihydropyridines of formula (XLIII).

Scheme 18

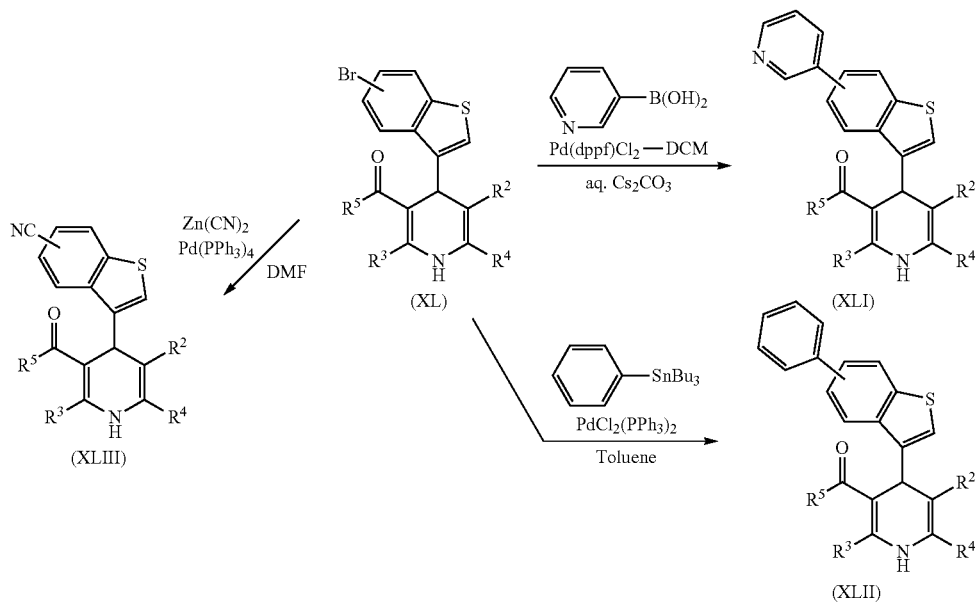

-continued

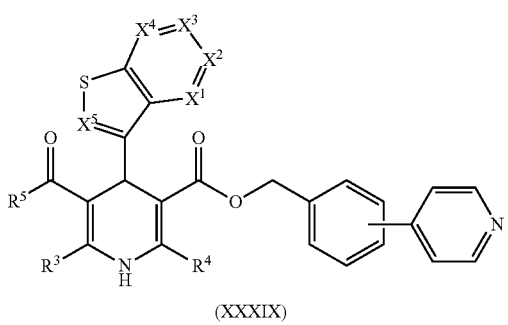

(XXXIX)

In another example, benzothiophenes of formula (XL) that are substituted with halogen atoms as depicted in Scheme

Pharmacological Activity

Rat Androgen Receptor Binding

The assay was carried out following the instructions of polarscreen AR competitor assay green kit (Life Technologies, Cat #.: A15880). Briefly, the test is based on measuring the changes of fluorescence polarization shown by the Fluormone AL Green. Thus, when the Fluormone is bound to the receptor, a fluorescence polarization is observed that diminishes when a ligand competes for the receptor binding site and the Fluormone gets displaced.

The inhibition values for each of the compounds are measured in duplicate at 1 and 10 μM and the plate is incubated for 4 hours at RT. Fluorescence polarization is the measured in a Tecan Infinite M1000 Pro reader (λexc=485 nm, λem=535 nm). In order to obtain a dose-response curve and calculate the potency of inhibition (expressed as IC$_{50}$) for AR, a series of 1:10 dilutions in test in 1× buffer from 10 μM to 0.1 nM for each compound was carried out.

Human Androgen Receptor Binding

Radioligand binding studies were carried out on endogenously expressed human androgen receptor using the LnCap prostate cancer cell line. The test is based on measuring radioactively labelled AR ligand [$^3$H]-methyltrienolone that gets displaced by increasing concentrations of test compound. The test is performed in 96-well plates (Falcon, #353072). Positive and negative controls are also required in each analyzed plate to evaluate the total and non-specific binding binding of the radioligand to the receptor. Cells (60000 per well) were incubated for 24 hours before executing the experiment at 37° C. and in a 5% $CO_2$ atmosphere. Medium was replaced by assay buffer (RPMI-640 (ATCC #30-2001) supplemented with 0.1% bovine serum albumin (Sigma #8806-56) and Triamcinolone acetonide (Sigma #T6501)). The compounds at the desired concentrations and [$^3$H]methyltrienolone (Perkin Elmer #NET590) were added to the wells.

TABLE 1

Test conditions

| | Sample | Non-specific binding | Total binding |
|---|---|---|---|
| Assay buffer | 80 μL | 80 μL | 90 μL |
| Compound (10x) | 10 μL | | |
| [$^3$H]methyltrienolone (20 nM) | 10 μL | 10 μL | 10 μL |
| Testosterone (200 μM) | | 10 μL | |

In order to obtain a dose-response curve and calculate the potency of inhibition (expressed as $IC_{50}$) for AR, a series of 1:10 dilutions in test in 1× buffer from 10 μM to 0.1 nM for each compound was carried out.

Cells were incubated for 2 hours at 37° C. in a 5% $CO_2$ atmosphere and then washed twice with ice-cold HBSS. Then cells were lysed with solubilization buffer (Hank's Balanced Salt Solution (HBSS, Sigma #H6648), 0.5% Sodium dodecyl sulfate 0.5% (SDS, Sigma #L7390-500G, Lote: 078K0102) and 20% Glycerol (Sigma Aldrich, #G2025) for 30 minutes at RT. 75 μL aliquots were taken from each well and transferred to a 96-well flexiplate (Perkin Elmer #1450-401) and mixed with 100 μL of scintillation cocktail (Optiphase supermix, PerkinElmer, #1200-439). Plates are shaken for 60 minutes and radioactivity was measured in a beta scintillation counter (Microbeta Trilux, Perkin Elmer).

Competition Binding in IM-9 Human Glucocorticoid Receptor (GR IM-9)

Glucocorticoid receptor competition binding assays were carried out in a polypropylene 96-well plate. In each well was incubated 100 μg of cytosol from IM-9 cell line, 1.5 nM [3H]-Dexamethasone (71 Ci/mmol, 1 mCi/ml, Perkin Elmer NET1192001MC) and compounds studied and standard. Non-specific binding was determined in the presence of Triamcinolone 10 μM (Sigma Aldrich T6376).

The reaction mixture (Vt: 200 μl/well) was incubated at 4° C. for 6 hours, 180 μL was transferred to GF/B 96-well plate (Millipore, Madrid, Spain) pretreated with 0.5% of PEI and treated with binding buffer (TES 10 mM, sodium molybdate 10 mM, EDTA 1 mM, pH 7.4, 2-mercaptoethanol 20 mM, Glycerol 10%) after was filtered and washed six times with 250 μl wash buffer (TES 10 mM, sodium molybdate 10 mM, EDTA 1 mM, pH 7.4, 2-mercaptoethanol 20 mM Glycerol 10%), before measuring in a microplate beta scintillation counter (Microbeta Trilux, PerkinElmer, Madrid, Spain).

Functional Assay AR-Receptor

MDA-MB-453 cells were cultured in DMEM (ATCC, ref 30-2002), 10% FBS, 1% penicillin, 1% streptomycin, 75 μg/ml gentamycin.

The day before performing assay, the cells were trypsinized and seeded in a 384-well plate (Greiner, ref 781098) (8000 cells/well) in 50 μl of complete culture medium. Cells were stores at 37° C. in a 5% $CO_2$ atmosphere overnight.

The medium was replaced by 50 μl complete growth medium with 0.1% FBS. Compounds were dispensed with Echo 550 (Labcyte) and incubated for 24 h at 37° C. in a 5% $CO_2$ atmosphere. Antagonist effect was measured in the presence of DHT 1 nM.

After incubation, assay medium removed and 20 μl of 1× Promega lysis buffer were added to each well. The plate was incubated 15 minutes at RT and quick-frozen to −80° C. and the thaw to room temperature. 50 μl of luciferase substrate (E4550, Promega) were added to each well and luminescence (integration time 1000 msec) was read in an EnSpire multilabel reader (Perkin Elmer).

Results

Table shows the binding of some compounds of the present invention in the differents assays.

| Example | AR rat-fluorimetric | AR LNCaP | GR IM-9 | AR antag KB |
|---|---|---|---|---|
| A1 | A | | | |
| A2 | B | | | |
| A3 | A | | | |
| A10 | A | | | |
| B6 | B | C | B | B |
| B12 | C | C | | A |
| B18 | A | | | |
| B21 | B | C | | B |
| C1 | B | | | |
| C2 | B | C | B | B |
| C3 | A | | | |
| C6 | B | B | A | |
| C7 | B | | | |
| C10 | C | | | B |
| C14 | B | A | B | |
| C19 | C | | | |
| C20 | B | B | | |
| C21 | A | | | |
| C23 | A | | | |
| C24 | A | A | A | C |
| C26 | A | | | |
| C27 | C | | | |
| C28 | B | | | |
| C29 | A | | | |
| C32 | | C | | |
| C34 | | C | A | |
| C35 | B | | A | |
| C36 | | B | A | C |
| C37 | | A | A | |
| C38 | | A | | |
| C39 | | B | A | C |
| C41 | | C | B | B |
| C42 | | C | A | A |
| C43 | | C | B | A |
| C44 | | C | B | B |
| C45 | | C | | |
| C46 | | B | A | B |
| C47 | | B | A | |
| C48 | | C | B | B |
| C52 | B | | | B |
| C53 | | A | | |
| C56 | | B | A | |
| C57 | | | | B |
| C58 | | A | A | B |
| C60 | | | | B |
| C61 | | | C | B |
| C62 | | | | B |
| C64 | | | C | B |
| C65 | | C | A | B |
| C66 | | B | A | A |
| C67 | A | A | A | A |
| C68 | | C | | |

-continued

| Example | AR rat-fluorimetric | AR LNCaP | GR IM-9 | AR antag KB |
|---|---|---|---|---|
| C71 | | C | A | C |
| C72 | | C | A | C |
| C73 | | C | A | C |
| C74 | | | B | C |
| C75 | | | B | C |
| C76 | | C | A | |
| C77 | | | B | |
| C78 | | C | B | |
| C79 | | | A | C |
| C80 | | | C | C |
| C81 | | | A | |
| C82 | | | A | |
| C83 | | | B | |
| C84 | | | A | |
| C85 | | | C | |
| C86 | | | B | |
| C91 | | | A | |
| C92 | | | A | |
| C93 | | | B | |
| C94 | | | A | |
| C95 | | | A | |
| C96 | | | B | |
| C97 | | | A | |
| C98 | | | B | |
| C99 | | | B | |
| C100 | | | A | |
| C101 | | | A | |
| C102 | | | B | |
| C103 | | | A | |
| C104 | | | A | |
| C105 | | | B | |
| C106 | | | B | |
| C107 | | | A | C |
| C108 | | | A | C |
| C109 | | | A | |
| C110 | | | A | |
| C111 | | | A | |
| C112 | | B | A | |
| C113 | | B | A | |
| C114 | | | C | |
| C115 | | | C | |
| C116 | | | B | |
| C117 | | B | A | B |
| C118 | | A | A | B |
| C119 | | C | A | B |
| C120 | | B | A | |
| C121 | | C | B | |
| C122 | | B | A | A |
| C123 | | A | A | |
| D1 | A | B | C | |
| D2 | C | | | |
| D3 | A | | | |
| D5 | | | A | |
| D6 | | | B | C |
| D7 | | | A | C |
| D8 | | | A | |
| D10 | | | A | |
| D11 | | | A | |
| D12 | | | A | |
| D13 | | | A | |
| D14 | | | C | |
| D15 | | | B | |
| D16 | | | A | |
| D17 | | | A | |
| D18 | | | A | |
| D19 | | | A | |
| D20 | | | B | |
| D21 | | | A | |
| D22 | | C | A | |
| D23 | | B | A | |
| D24 | | | A | B |
| D25 | | C | A | |
| D26 | | B | B | |
| D27 | | B | A | B |
| D28 | | | B | |
| D29 | | B | A | |

| Example | AR rat-fluorimetric | AR LNCaP | GR IM-9 | AR antag KB |
|---|---|---|---|---|
| D30 | | B | A | B |
| D31 | | B | A | B |
| D32 | | B | A | B |
| D33 | | B | A | |
| D34 | | B | A | |
| D35 | | B | B | |
| D36 | | B | A | |
| D37 | | B | A | B |
| D38 | | B | A | |
| D39 | | B | A | B |
| D40 | | B | A | |
| D41 | | B | A | A |
| D42 | | B | A | |
| D43 | | B | A | C |
| D44 | | | A | |
| D45 | | B | A | |
| D46 | | C | A | C |
| D47 | | B | A | C |
| D48 | | | A | |
| D49 | | A | A | |
| D50 | | | A | |
| D51 | | | A | |
| D52 | | | A | |
| D53 | | | A | |
| D54 | | | A | |
| D55 | | | A | |
| D56 | | | A | |
| E1 | | A | A | |
| G1 | | A | A | |
| G2 | | C | | |
| G3 | | C | | |
| G4 | | C | | |
| H1 | | A | | |
| H2 | | A | | |
| H3 | | C | | |
| H4 | | C | | |
| H5 | | C | | |
| H6 | | C | | |
| H7 | | C | | |
| H8 | | C | | |
| H9 | | C | | |
| H10 | | C | | |
| H11 | | C | | |
| H12 | | C | | |
| H13 | | C | | |
| H14 | | C | | |
| H15 | | A | B | |
| I2 | | B | B | |
| J1 | | A | | |
| J2 | | A | | |
| J3 | | B | | |
| J6 | | C | | |
| J10 | | B | | |
| J11 | | A | | |
| J12 | | A | | |
| J13 | | C | | |
| J14 | | C | | |
| J15 | | C | | |
| J16 | | C | | |
| J17 | | C | | |
| J18 | | C | | |
| J19 | | C | | |
| J20 | | B | | |
| J21 | | A | A | |
| J22 | | A | A | A |
| J23 | | A | A | B | C |
| J24 | | C | | |
| J25 | | B | | |
| J25-a | | | | B |
| J26 | | A | A | B |
| J27 | | C | C | |
| J28 | | A | A | |
| J28-a | | B | A | |
| J29 | | B | | |
| J30 | | C | | |
| J31 | | C | A | |

-continued

| Example | AR rat-fluorimetric | AR LNCaP | GR IM-9 | AR antag KB |
|---|---|---|---|---|
| J32 | | C | | B |
| J33 | | B | | B |
| J34 | | | | B |
| J36 | | | C | |
| J38 | | | | B |
| J40 | | C | | |
| J41 | | A | A | B |
| J42 | | B | A | A |
| J42-a | | | B | |
| J43 | | | A | B |
| K1 | B | | | |
| K2 | C | | | |
| L1 | | C | A | B |
| L2 | | C | A | B |
| L3 | | A | A | B |
| L4 | | A | A | B |
| L5 | | | A | C |
| L7 | | | B | C |
| L8 | C | | | |
| L9 | | | | B |
| L12 | | | B | |
| L13 | | | B | |
| L14 | | | C | |
| M1 | C | | | |
| N1 | | | C | |

Range:
A: $IC_{50} < 100$ nM
B: $100$ nM $=< IC_{50} < 1$ μM
C: $IC_{50} >= 1$ μM As can be seen from the results described in Table 1, the compounds of the present invention are modulators of nuclear receptor selected from androgen receptor and glucocorticoid receptor.

The derivatives of the present invention are useful in the treatment or prevention of diseases known to be susceptible to improvement by treatment with a modulator of androgen receptor and glucocorticoid receptor, such as prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism. Accordingly, the derivatives of the invention and pharmaceutically acceptable salts thereof, and pharmaceutical compositions comprising such compounds and/or salts thereof, may be used in a method of treatment of disorders of the human body which comprises administering to a subject requiring such treatment an effective amount of the dihydropyridine derivative of the invention or a pharmaceutically acceptable salt thereof.

The present invention also provides pharmaceutical compositions which comprise, as an active ingredient, at least a dihydropyridine derivative of formula (I) or a pharmaceutically acceptable salt thereof in association with other therapeutics agents, as have been mentioned above, and with a pharmaceutically acceptable excipient such as a carrier or diluent. The active ingredient may comprise 0.001% to 99% by weight, preferably 0.01% to 90% by weight of the composition depending upon the nature of the formulation and whether further dilution is to be made prior to application. Preferably, the compositions are made up in a form suitable for oral, topical, nasal, rectal, percutaneous or injectable administration.

The pharmaceutically acceptable excipients, which are admixed with the active compound or salts of such compound, to form the compositions of this invention, are well known per se and the actual excipients used depend inter alia on the intended method of administering the compositions.

Compositions of this invention are preferably adapted for injectable and oral (per os) administration. In this case, the compositions for oral administration may take the form of tablets, sustained release tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents, which may be used in the preparation of the compositions, include those liquid and solid diluents, which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Effective doses are normally in the range of 2-2000 mg of active ingredient per day. Daily dosage may be administered in one or more treatments, preferably from 1 to 4 treatments, per day.

The present invention will be further illustrated by the following examples. The following are given by way of illustration and do not limit the scope of the invention in any way. The synthesis of the compounds of the invention is illustrated by the following examples including the preparation of the intermediates, which do not limit the scope of the invention in any way.

EXAMPLES

General

Reagents, solvents and starting products were acquired from commercial sources and used without further purification. All reactions were performed under an atmosphere of air and with anhydrous solvents unless otherwise stated. The term "concentration" refers to the vacuum evaporation using a Buchi rotavapor. When indicated, the reaction products were purified by "flash" chromatography on silica gel (40-63 μm) with the indicated solvent system. Yields refer to isolated compounds estimated to be >95% pure as determined by $^1$H NMR. All the dihydropyridines were obtained as racemic mixtures.

Mass spectrometry was carried out on a Varian MAT-711 spectrometer employing EI and ESI methods. HPLC experiments were carried out on a LaChrom Elite L-2350 instrument (Sunfire silica gel column 5 μm, 4.6 mm×150 mm) equipped with an L-2455 diode array detector. HPLC-MS analysis was performed on a Gilson instrument equipped with a Gilson 321 piston pump, a Gilson 864 vacuum degasser, a Gilson 189 injection module, a 1/1000 Gilson splitter, a Gilson 307 pump, a Gilson 170 detector, and a Thermoquest Fennigan aQa detector.

$^1$H and $^{13}$C nuclear magnetic resonance experiments were carried out using either a Varian Inova 500 MHz or Varian Mercury 300 or 400 MHz NMR spectrometers. Chemical shifts are reported relative to the deuterated solvent signal or tetramethylsilane as an internal reference. Coupling constants J are given in Hertz (Hz) and multiplicities as follows: s=singlet, d=doublet, t=triplet, q=quartet, m=multiplet or as a combination of them.

Preparation of Intermediates

General Procedure aa

Intermediate 1: 7-chlorobenzo[b]thiophene

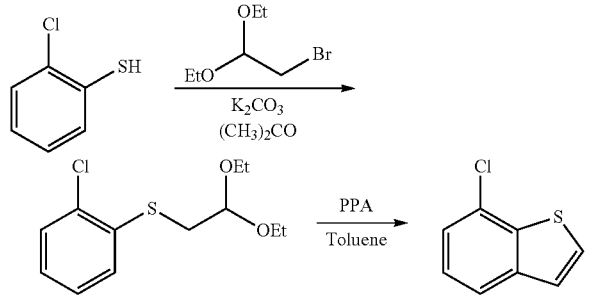

To a solution of 2-chlorobenzenethiol (1.53 g, 10.58 mmol, 1.0 eq.) and 2-bromo-1,1-diethoxyethane (2.4 mL, 15.87 mmol, 1.5 eq.) in acetone (10 ml) was added potassium carbonate (3.65 g, 26.45 mmol, 2.5 eq). The mixture was refluxed for 90 minutes and then 0.5 eq of 2-bromo-1, 1-diethoxyethane was added. The mixture was refluxed for another 2 hours, cooled to room temperature and concentrated. The resulting residue was purified by flash column chromatography on silica gel using hexane/diethyl ether (2%) as eluent to afford (2-chlorophenyl)(2,2-diethoxyethyl) sulfane as a light yellow oil (2.71 g, 97%).

To a solution of polyphosphoric acid (6.0 g, 51.97 mmol, 9 eq.) in toluene (15 ml) was added under vigorous stirring a solution of (2-chlorophenyl)(2,2-diethoxyethyl)sulfane (1.5 g, 5.77 mmol, 1 eq) in toluene (5 mL). The mixture was stirred at reflux temperature for 5 hours and was then poured into ice cold water (30 mL) and stirred for 10 minutes. The mixture was washed with toluene, sat. aq. bicarbonate solution and brine, dried (Na$_2$SO$_4$) and concentrated. The resulting residue was purified by flash column chromatography on silica gel using hexane as eluent (as described in WO 2009/008992 A2) to afford 7-chlorobenzo[b]thiophene as a light-yellow oil (0.68 g, 70%).

$^1$H-NMR (300 MHz, CDCl$_3$-d) δ (ppm): 7.77-7.71 (m, 1H), 7.50 (d, J=5.4 Hz, 1H), 7.41-7.30 (m, 3H).

Intermediate 2: 7-(trifluoromethyl)benzo[b]thiophene

General procedure aa yielded the title compound as a light-yellow oil (0.44 g, 41%).

$^1$H-NMR (300 MHz, CDCl$_3$-d) δ (ppm): 8.00 (d, J=7.9 Hz, 1H), 7.66 (d, J=7.3 Hz, 1H), 7.57 (d, J=5.5 Hz, 1H), 7.51-7.37 (m, 2H).

$^{19}$F NMR (282 MHz, CDCl$_3$-d) δ (ppm): −63.13 (CF$_3$).

Intermediate 3: 7-fluorobenzo[b]thiophene

General procedure aa yielded the title compound as a yellow oil (1.78 g, 52%).

$^1$H-NMR (300 MHz, CDCl$_3$-d) δ (ppm) δ 7.63 (d, J=8.0 Hz, 1H), 7.49 (d, J=5.3 Hz, 1H), 7.41-7.30 (m, 2H), 7.07 (dd, J=9.8, 8.0 Hz, 1H).

$^{19}$F NMR (282 MHz, CDCl$_3$-d) δ (ppm): −115.37 (CF).

Intermediate 4: 1-(Benzo[b]thiophen-7-yl)-2,2,2-trifluoroethan-1-one

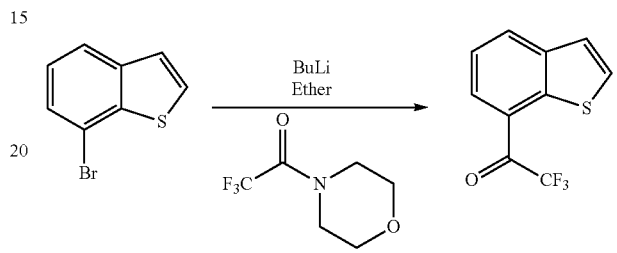

This compound was synthetized using a modified procedure of J. Med. Chem. 2002, 45, 4038-4046. 7-bromobenzo[b]thiophene (1.0 g, 4.69 mmol, 1.0 eq.) was dissolved in diethyl ether (25 ml) and cooled at −40° C. Then n-butyllithium 1.6 M (3.23 ml, 5.16 mmol, 1.1 eq) was added dropwise and the solution was warmed to 0° C. over a 1 h period. The solution was cooled to −60° C. and a solution of 2,2,2-trifluoro-1-morpholinoethan-1-one (0.86 g, 4.69 mmol, 1.0 eq) in diethyl ether (5 ml) was added in portions. The resultant mixture was stirred at −60° C. for 7 h and then warmed up to room temperature. The solution was hydrolyzed with saturated NH$_4$Cl (5 ml), washed with NH$_4$Cl (3×5 ml) and water (3×5 ml), dried (Na$_2$SO$_4$) and concentrated. The resulting residue was purified by flash column chromatography on silica gel using ethyl hexane:ethyl acetate (10:1) as eluent to afford a light-yellow solid (0.98 g, 91%).

$^1$H-NMR (300 MHz, CDCl$_3$) δ=8.20 (ddd, J=7.9, 4.5, 1.4 Hz, 2H), 7.70 (d, J=5.5 Hz, 1H), 7.58 (t, J=7.9 Hz, 1H), 7.49 (d, J=5.5 Hz, 1H). $^{19}$F NMR (282 MHz, CDCl$_3$) δ=−69.54 (s, CF$_3$).

Intermediate 5: Benzo[b]thiophene-5-carbonitrile

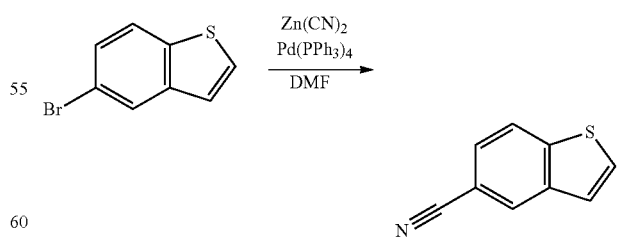

Nitrogen gas was bubbled through a mixture of 5-bromobenzo[b]thiophene (510 mg, 2.34 mmol) and zinc cyanide (299 mg, 2.49 mmol) in dry DMF (3 mL) for 5 minutes. Tetrakis(triphenylphosphine)palladium(0) (153 mg, 0.13 mmol) was added, the tube sealed and the mixture stirred at 90° C. for 7 h. The reaction mixture was filtered over Celite, and the filtrate was extracted using AcOEt and NaHCO₃. The organic phase was concentrated and the residue purified by column chromatography (Yield: 82%).

¹H-NMR (400 MHz, DMSO-d₆) δ=7.58 (dd, 1H), 7.72 (m, 1H), 7.99 (d, 1H), 8.26 (m, 1H), 8.43 (d, 1H).

Intermediate 6: Benzo[b]thiophene-7-carbonitrile

The title compound was synthesized according to the method described above for benzo[b]thiophene-5-carbonitrile.

¹H-NMR (400 MHz, DMSO) δ=7.59 (dd, 1H), 7.65 (d, 1H), 7.96 (dd, 1H), 8.01 (d, 1H), 8.26 (dd, 1H).

Intermediate 7: Benzo[b]thiophene-5-carboxylic acid

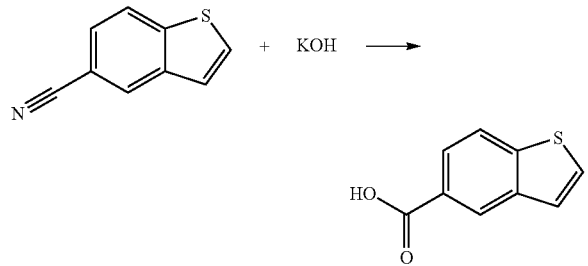

To a solution of benzo[b]thiophene-5-carbonitrile (400 mg, 2.51 mmol) in MeOH (40 mL), KOH (2.0 g, 35 mmol) and water 10 mL were added in portions, and the mixture was stirred at 80° C. for 36 hours. After acidification with 2N HCl (pH 4-5), the solid was filtered off and washed with pentane to yield the title compound as an off-white solid (390 mg, 87%).

¹H-NMR (400 MHz, DMSO-d₆) δ=7.58 (dd, 1H), 7.72 (m, 1H), 8.01 (d, 1H), 8.29 (m, 1H), 8.46 (d, 1H), 12.11 (s, 1H).

Intermediate 8: Methyl benzo[b]thiophene-5-carboxylate

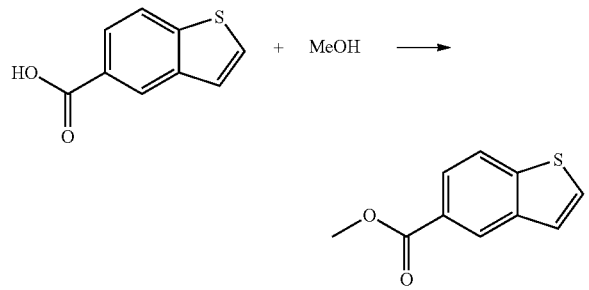

Benzo[b]thiophene-5-carboxylic acid (390 mg, 2.19 mmol) was refluxed in sat. HCl in MeOH (30 mL) for 24 hours. The methyl ester was obtained after evaporation of the solvent (340 mg, 76%).

¹H-NMR (400 MHz, DMSO-d₆) δ=3.85 (s, 3H), 7.59 (dd, 1H), 7.73 (m, 1H), 7.98 (d, 1H), 8.27 (m, 1H), 8.44 (d, 1H).

Intermediate 9: 5-Fluorobenzo[b]thiophene-7-carbonitrile

Synthesis of 7-Bromo-5-fluorobenzo[b]thiophene

General procedure aa afforded the title compound as a light-yellow oil (1.02 g) that was used as such in the next step.

Synthesis of 5-Fluorobenzo[b]thiophene-7-carbonitrile

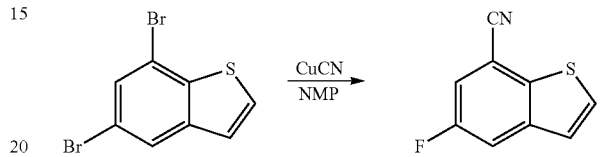

A solution of 7-bromo-5-fluorobenzo[b]thiophene (1.02 g, 4.41 mmol, 1.0 eq.) and copper cyanide (0.590 g, 6.62 mmol, 1.5 eq.) in N-methyl-2-pirrolydone (12 ml) was stirred for 2 days in a sealed tube at 200° C. The mixture was cooled to room temperature, poured into sat. aq. NaHCO₃ (30 mL) and kept at 4° C. for 60 min. The solid was filtered off and dissolved in a mixture of 40 mL NH₄OH (28%)/NH₄Cl(sat) (1:1) and ethyl acetate (60 mL) and stirred for 1 h. Then, it was washed with ethyl acetate (×3), dried (Na₂SO₄), concentrated and purified by flash column chromatography on silica gel using hexane/diethyl ether (2%) as eluent to afford 5-fluoro-3-formylbenzo[b]thiophene-7-carbonitrile as a white solid (0.23 g, 29%).

¹H-NMR (300 MHz, CDCl₃) δ (ppm): 7.73 (dd, J=8.8, 2.3 Hz, 1H), 7.69 (d, J=5.5 Hz, 1H), 7.47 (dd, J=8.1, 2.2 Hz, 1H), 7.39 (d, J=5.5 Hz, 1H).

Intermediate 10: 4-Fluorobenzo[b]thiophene-7-carbonitrile

The title compound was prepared in a 2-step synthesis as described above for Intermediate 9 and was afforded as a white solid (0.33 g).

¹H-NMR (300 MHz, CDCl₃) δ (ppm): 7.70 (dd, J=8.2, 4.5 Hz, 1H), 7.61 (d, J=5.5 Hz, 1H), 7.53 (d, J=5.5 Hz, 1H), 7.13 (t, J=8.8 Hz, 1H).

Intermediate 11: 5,7-Dichlorobenzo[b]thiophene

General procedure aa afforded the title compound as a light-yellow oil (1.57 g).

¹H-NMR (300 MHz, CDCl₃) δ (ppm): 7.78 (dd, J=8.0, 0.8 Hz, 1H), 7.52 (s, 1H), 7.50 (s, 1H), 7.46-7.42 (m, 1H).

Intermediate 12: 3-Bromo-6-chlorobenzo[b]thiophene-7-carbonitrile

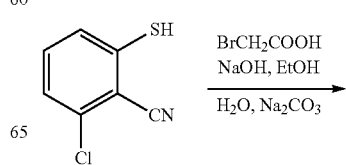

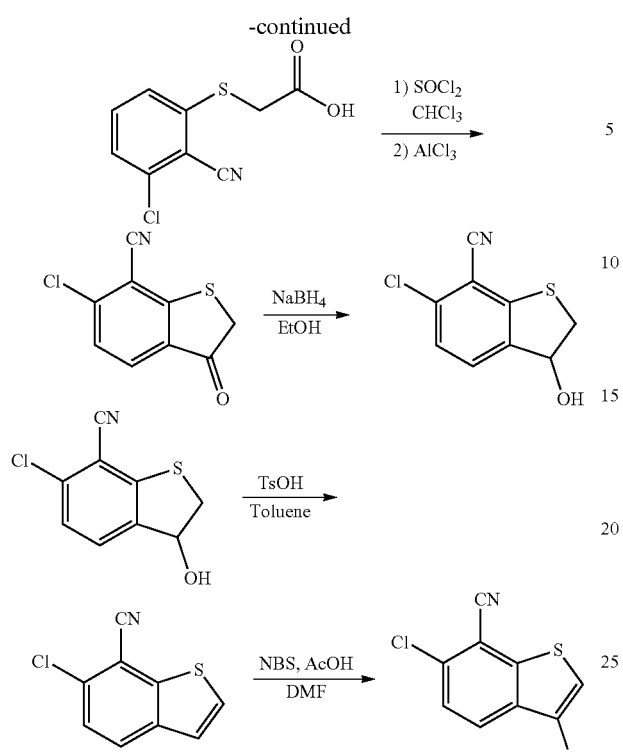

A solution of 6-chloro-3-hydroxy-2,3-dihydrobenzo[b]thiophene-7-carbonitrile (7.79 mmol, 1.0 eq.) and p-toluenesulfonic acid (0.15 g, 78 mmol, 0.1 eq.) in toluene (20 ml) was refluxed for 1 hour, concentrated and purified by flash column chromatography on silica gel using hexane/ethyl acetate (6:1) as eluent to afford 6-chlorobenzo[b]thiophene-7-carbonitrile (1.26 g, 83%).

$^1$H-NMR (300 MHz, CDCl$_3$) δ (ppm): 7.93 (d, J=8.6 Hz, 1H), 7.60 (d, J=5.4 Hz, 1H), 7.47 (d, J=8.6 Hz, 1H), 7.39 (d, J=5.5 Hz, 1H).

A solution of 6-chlorobenzo[b]thiophene-7-carbonitrile (1.26 g, 6.50 mmol, 1.0 eq.), N-Bromo succinimide (1.74 g, 9.76 mmol, 1.5 eq.), acetic acid (0.04 mL, 0.64 mmol, 0.1 eq.), in N, N-dimethylformamide (10 ml) was heated at 130° C. for 1 h in a microwave reactor. Then water was added, and the mixture was extracted with ethyl acetate (×3). The organic phase was dried (Na$_2$SO$_4$), concentrated and purified by flash column chromatography on silica gel using hexane/ethyl acetate (8:1) as eluent to afford 3-bromo-6-chlorobenzo[b]thiophene-7-carbonitrile (1.33 g, 75%).

Intermediate 13:
3-Bromo-5-fluorothieno[2,3-b]pyridine

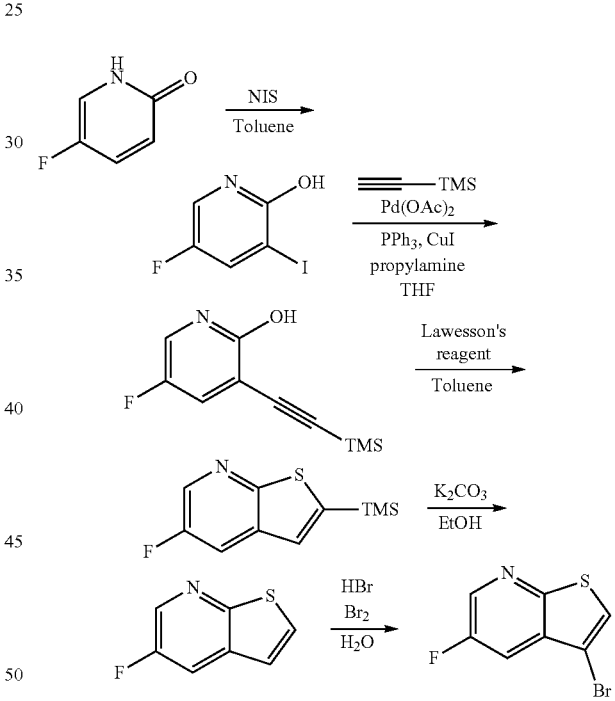

To a solution of 2-chloro-6-mercaptobenzonitrile (1.5 g, 8.84 mmol, 1.0 eq.) in ethanol (20 ml) was added a solution of sodium hydroxide (0.35 g, 8.84 mmol, 1.0 eq.) in water (7 ml). Then, a solution of 2-bromoacetic acid (1.35 g, 9.73 mmol, 1.1 eq.), sodium carbonate (0.51 g, 4.86 mmol, 0.5 eq.) in water (8 mL) was added, and the mixture was stirred for 2 hours. The pH of the mixture was adjusted (~2) with HCl (2N) and extracted with ethyl acetate (×2) and DCM (×2). The organic phase was dried (Na$_2$SO$_4$) and concentrated affording 2-((3-chloro-2-cyanophenyl) thio) acetic acid as a yellow oil. This product was used in the next step without further purification.

$^1$H-NMR (300 MHz, CDCl$_3$) δ (ppm): 7.51-7.44 (m, 2H), 7.42-7.35 (m, 1H), 3.79 (s, 2H), 2.83 (bs, 1H).

To a solution of 2-((3-chloro-2-cyanophenyl) thio) acetic acid (2.0 g, 8.78 mmol, 1.0 eq.) in chloroform (60 ml), thionyl chloride (0.96 mL, 13.18 mmol, 1.5 eq.) was dropwise added. The mixture was refluxed for 1 hour and then cooled to 0° C., when aluminum chloride (10.54 g, 79.06 mmol, 9 eq.) was added in portions. The mixture was stirred at RT overnight, cooled to 0° C. before adding water, and then extracted with ethyl acetate (×3). The organic phase was dried (Na$_2$SO$_4$), concentrated and purified by flash column chromatography on silica gel using hexane/ethyl acetate (4:1) as eluent to afford 6-chloro-3-oxo-2,3-dihydrobenzo[b]thiophene-7-carbonitrile (1.53 g, 83%).

$^1$H-NMR (300 MHz, CDCl$_3$) δ (ppm): 7.48 (d, J=8.5 Hz, 1H), 7.35 (d, J=8.5 Hz, 1H), 3.95 (s, 2H).

A solution of 6-chloro-3-oxo-2,3-dihydrobenzo[b]thiophene-7-carbonitrile (1.53 g, 7.79 mmol, 1.0 eq.) and sodium borohydride (0.32 g, 8.57 mmol, 1.1 eq.) in ethanol (60 ml) was stirred for 1 hour at RT, concentrated, redissolved in ethyl acetate and washed with water. The organic phase was dried over Na$_2$SO$_4$ and concentrated to afford 6-chloro-3-hydroxy-2,3-dihydrobenzo[b]thiophene-7-carbonitrile which was used in the next step without further purification.

To a solution of 5-fluoropyridin-2(1H)-one (1.0 g, 8.84 mmol, 1.0 eq.) in dry toluene (20 ml) was added N-iodosuccinimide (1.99 g, 8.84 mmol, 1.0 eq). The resultant mixture was stirred for 30 minutes at 90° C., then cooled to RT and concentrated. The residue was purified by flash column chromatography on silica gel using hexane/ethyl acetate (2:1) as eluent to afford 5-fluoro-3-iodopyridin-2-ol as a yellow solid (1.4 g, 65%).

$^1$H-NMR (300 MHz, DMSO-d$_6$) δ (ppm): 11.81 (s, 1H), 10.99 (bs, 1H), 8.18 (dd, J=7.2, 3.1 Hz, 1H), 7.65 (t, J=3.1 Hz, 1H).

A solution of 5-fluoro-3-iodopyridin-2-ol (0.5 g, 2.06 mmol, 1 eq.), palladium acetate (0.005 g, 0.02 mmol, 0.01 eq.), triphenylphosphine (0.011 g, 0.041 mmol, 0.02 eq.), copper iodide (0.008 g, 0.041 mmol, 0.02 eq.) in dry tetrahydrofuran (15 ml) was purged with argon gas for 5 minutes. Then, trimethylsilylacetylene (0.43 mL, 3.10 mmol, 1.5 eq) and propylamine (0.34 mL, 4.13 mmol, 2 eq) was added, and the mixture was stirred at 38° C. for 60 minutes, concentrated, taken up in ethyl acetate and washed with Rochelle salt (×2), hydrochloride acid 0.1 N (×2) and saturated sodium bicarbonate (×2). The organic phase was dried (Na$_2$SO$_4$), filtered, concentrated and purified by flash column chromatography on silica gel using hexane/ethyl acetate (2:1) as eluent to afford 5-fluoro-3-((trimethylsilyl)ethynyl)pyridin-2-ol as a light yellow oil (0.263 g, 61%).

$^1$H-NMR (300 MHz, DMSO-d$_6$) δ (ppm): 13.57 (bs, 1H), 7.60 (dd, J=7.6, 3.1 Hz, 1H), 7.39 (t, J=3.1 Hz, 1H), 0.26 (s, 9H).

To a solution of 5-fluoro-3-((trimethylsilyl)ethynyl)pyridin-2-ol (0.26 g, 1.25 mmol, 1 eq.) in dry toluene (10 ml) was added Lawesson's reagent (0.0.25 mL, 0.63 mmol, 0.5 eq). The mixture was stirred at 120° C. for 60 minutes, concentrated and purified by flash column chromatography on silica gel using ethyl hexane:ethyl acetate (7:1) as eluent to afford 5-fluoro-2-(trimethylsilyl)thieno[2,3-b]pyridine as a yellow solid (0.22 g, 76%).

$^1$H-NMR (300 MHz, DMSO-d$_6$) δ (ppm): 3.68 (d, J=2.4 Hz, 1H), 2.95 (dd, J=9.0, 2.4 Hz, 1H), 2.58 (s, 1H), −4.37 (s, 9H).

To a solution of 5-fluoro-2-(trimethylsilyl)thieno[2,3-b]pyridine (0.22 g, 0.96 mmol, 1 eq.) in ethanol (4 ml) was added potassium carbonate (0.332 g, 2.40 mmol, 2.5 eq.). The mixture was stirred at 65° C. for 60 minutes. Then, the solid was filtered off and washed with dichloromethane. The filtrate was concentrated, taken up in ethyl acetate, washed with water (×2) and brine (×2), dried (Na$_2$SO$_4$) and concentrated, and the residue was purified by flash column chromatography on silica gel using hexane/ethyl acetate (20:1) as eluent to afford 5-fluorothieno[2,3-b]pyridine as a light yellow oil (0.111 g, 75%).

$^1$H-NMR (300 MHz, CDCl$_3$) δ (ppm): 8.47 (d, J=2.4 Hz, 1H), 7.75 (dd, J=8.9, 2.7 Hz, 1H), 7.63 (d, J=6.0 Hz, 1H), 7.24 (d, J=6.0 Hz, 1H).

To a solution of 5-fluorothieno[2,3-b]pyridine (0.78 g, 5.12 mmol, 1 eq.) in water (8 mL) was added hydrobromic acid (5.22 mL, 46.09 mmol, 9 eq.) and bromine (0.39 g, 7.68 mmol, 1.5 eq.) and this mixture was stirred at 55° C. for 20 hours. The solid was filtered off and washed with saturated sodium bicarbonate, then taken up in ethyl acetate, washed with saturated sodium bicarbonate (×2), dried (Na$_2$SO$_4$), concentrated and purified by flash column chromatography on silica gel using hexane/ethyl acetate (20:1) as eluent to afford 3-bromo-5-fluorothieno[2,3-b]pyridine as a light yellow oil (0.73 g, 62%).

$^1$H-NMR (300 MHz, CDCl$_3$) δ (ppm): 8.51 (s, 1H), 7.76 (dd, J=8.5, 2.5 Hz, 1H), 7.64 (s, 1H).

General Procedure a

Intermediate a1: N-Cyclopropylbenzo[b]thiophene-5-carboxamide

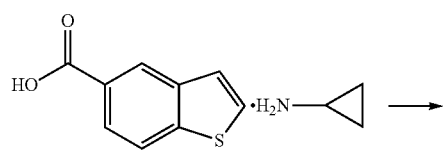

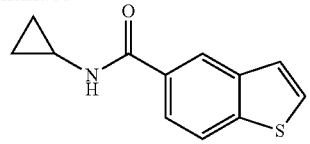

To a solution of benzo[b]thiophene-5-carboxylic acid (700 mg, 3.93 mmol), EDC*HCl (1130 mg, 5.89 mmol), HOBT (601 mg, 3.93 mmol) in 15 mL of DMF at 5° C., were added cyclopropyl amine (336 mg, 5.89 mmol) and DIPEA (1270 g, 9.89 mmol). The reaction mixture was stirred for 18 hours at room temperature. The solution was poured into NaHCO$_3$ saturated and the precipitate was washed with three times of cold water and one time of pentane to obtain the desired amide derivative (700 mg, 82%).

$^1$H-NMR (400 MHz, DMSO-d$_6$) δ=0.60 (m, 2H), 0.71 (m, 2H), 2.93 (m, 1H), 7.56 (dd, 1H), 7.67 (d, 1H), 7.93 (d, 1H), 8.22 (dd, 1H), 8.46 (d, 1H).

The following derivatives were synthesized according to General procedure a as described above and were used in the next step without further purification.

Intermediate a2: N-(Cyclopropylmethyl)benzo[b]thiophene-5-carboxamide $^1$H-NMR (400 MHz, DMSO-d$_6$) δ=0.20 (m, 2H), 0.47 (m, 2H), 1.05 (m, 1H), 3.14 (m, 2H), 7.49 (dd, 1H), 7.63 (d, 1H), 7.89 (d, 1H), 8.18 (dd, 1H), 8.30 (t, 1H), 8.42 (d, 1H).

Intermediate a3: Benzo[b]thiophen-5-yl(4-methylpiperazin-1-yl)methanone $^1$H-NMR (400 MHz, DMSO-d$_6$) δ=2.15 (s, 3H), 2.29 (m, 4H), 3.41 (m, 4H), 7.47 (dd, 1H), 7.61 (d, 1H), 7.97 (d, 1H), 8.15 (dd, 1H), 8.50 (d, 1H).

Intermediate a4: Benzo[b]thiophen-5-yl(morpholino)methanone $^1$H-NMR (400 MHz, DMSO-d$_6$) δ=3.49 (m, 4H), 3.65 (m, 4H), 7.47 (dd, 1H), 7.61 (d, 1H), 7.97 (d, 1H), 8.15 (dd, 1H), 8.50 (d, 1H).

Intermediate a5: N-Cyclopropylbenzo[b]thiophene-7-carboxamide $^1$H-NMR (400 MHz, DMSO) δ=0.62 (m, 2H), 0.74 (m, 2H), 2.91 (m, 1H), 7.47 (dd, 2H), 7.81 (d, 1H), 7.92 (d, 1H), 8.04 (dd, 1H), 8.69 (d, 1H).

Intermediate a6: Benzo[b]thiophen-7-yl(4-methylpiperazin-1-yl)methanone $^1$H-NMR (400 MHz, DMSO) δ=2.19 (s, 3H), 2.28 (d, 4H), 3.42 (t, 4H), 7.37 (d, 1H), 7.46 (dd, 1H), 7.51 (d, 1H), 7.83 (d, 1H), 7.96 (dd, 1H).

General Procedure b

Intermediate b1: 4-(Benzo[b]thiophen-5-yl)morpholine

-continued

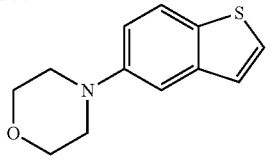

A solution of 5-bromobenzo[b]thiophene (600 mg, 2.82 mmol), morpholine (368 mg, 4.23 mmol), Pd$_2$(dba)$_3$ (129 mg, 0.14 mmol), tricyclohexylphosphine (119 mg, 0.42 mmol) and NatButO (541 mg, 8.46 mmol) in dry toluene (20 mL) under N$_2$ atmosphere was refluxed for 24 hours. After cooling, the mixture was poured into sat. aq. NaHCO$_3$, extracted with AcOEt (3×), dried over Na$_2$SO$_4$, filtered over and concentrated. The product was isolated as grey solid after flash column chromatography (230 mg, 37%).

$^1$H-NMR (400 MHz, DMSO-d$_6$) δ=3.45 (m, 4H), 3.23 (m, 4H), 6.94 (d, 1H), 7.42 (d, 1H), 7.54 (dd, 1H), 7.66 (d, 1H), 7.71 (d, 1H).

The following derivatives were synthesized according to General procedure b as described above and were used in the next step without further purification:

Intermediate b2: 1-(Benzo[b]thiophen-5-yl)-4-methylpiperazine $^1$H-NMR (400 MHz, DMSO-d$_6$) δ=2.25 (s, 3H), 2.53 (m, 4H), 3.16 (m, 4H), 6.93 (d, 1H), 7.39 (d, 1H), 7.61 (d, 1H), 7.51 (dd, 1H), 7.68 (d, 1H).

Intermediate b3: N-Benzylbenzo[b]thiophen-5-amine $^1$H-NMR (400 MHz, DMSO-d$_6$) δ=5.06 (d, 2H), 6.91 (d, 1H), 7.17 (m, 1H), 7.24 (m, 2H), 7.27 (m, 2H) 7.32 (d, 1H), 7.49 (d, 1H), 7.51 (dd, 1H), 7.74 (t, 1H), 7.81 (d, 1H).

Intermediate b4: 1-(Benzo[b]thiophen-7-yl)-4-methylpiperazine $^1$H-NMR (400 MHz, DMSO-d$_6$) δ=2.27 (s, 3H), 2.54 (m, 4H), 3.14 (m, 4H), 6.97 (d, 1H), 7.33 (t, 1H), 7.43 (d, 1H), 7.55 (d, 1H), 7.71 (d, 1H).

Preparation of 3-Formylbenzo[b]Thiophene Intermediates

General Procedure c

Intermediate c1: 3-Formylbenzo[b]thiophene-5-carbonitrile

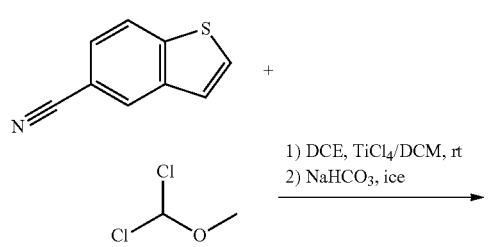

1) DCE, TiCl$_4$/DCM, rt
2) NaHCO$_3$, ice

-continued

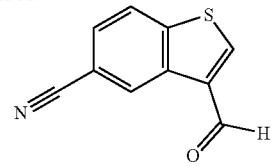

5-cyanebenzo[b]thiophene (320 mg, 2 mmol) was dissolved in dry dichloroethane (4 mL) under a nitrogen atmosphere. Dichloro(methoxy)methane (0.277 mL, 3 mmol) and titanium tetrachloride (0.33 mL) were added dropwise. The mixture was stirred at RT for 20 h, then poured onto a mixture of NaHCO$_3$ solution and ice and extracted with DCM. The organic phases were combined and concentrated, and the residue was filtered off and rinsed with diethyl ether. (Yield: 32%).

$^1$H-NMR (400 MHz, DMSO-d$_6$) δ=7.89 (dd, 1H), 8.39 (m, 1H), 8.86 (m, 1H), 9.16 (s, 1H), 10.16 (d, 1H).

The following derivatives were synthesized according to General procedure c as described above and were used in the next step without further purification:

Intermediate c2: 5-Fluorobenzo[b]thiophene-3-carbaldehyde 535 mg, 90%.

$^1$H-NMR (400 MHz, DMSO-d$_6$) δ=7.42 (m, 1H) 8.21 (m, 2H), 9.09 (s, 1H), 10.11 (s, 1H).

Intermediate c3: 5-Morpholinobenzo[b]thiophene-3-carbaldehyde $^1$H-NMR (400 MHz, DMSO-d$_6$) δ=3.46 (m, 4H), 3.23 (m, 4H), 6.95 (d, 1H), 7.55 (dd, 1H), 7.73 (d, 1H), 9.05 (s, 1H), 10.16 (s, 1H).

Intermediate c4: 5-(4-Methylpiperazin-1-yl)benzo[b]thiophene-3-carbaldehyde $^1$H-NMR (400 MHz, DMSO-d$_6$) δ=2.19 (s, 3H), 2.49 (m, 4H), 3.25 (m, 4H), 7.23 (d, 1H), 7.89 (d, 1H), 8.05 (d, 1H), 8.31 (s, 1H), 10.11 (s, 1H).

Intermediate c5: 5-(Benzylamino)benzo[b]thiophene-3-carbaldehyde $^1$H-NMR (400 MHz, DMSO-d$_6$) δ=4.98 (d, 2H), 6.98 (d, 1H), 7.23 (dd, 1H), 7.17 (m, 1H), 7.24 (m, 2H), 7.27 (m, 2H), 7.99 (d, 1H), 8.24 (t, 1H) 8.51 (s, 1H), 10.12 (s, 1H).

Intermediate c6: N-Cyclopropyl-3-formylbenzo[b]thiophene-5-carboxamide $^1$H-NMR (400 MHz, DMSO-d$_6$) δ=0.60 (m, 2H), 0.71 (m, 2H), 2.93 (m, 1H), 7.68 (t, 1H), 7.97 (d, 1H), 8.16 (d, 1H), 8.56 (dd, 1H), 9.09 (s, 1H), 10.15 (s, 1H).

Intermediate c7: N-(Cyclopropylmethyl)-3-formylbenzo[b]thiophene-5-carboxamide $^1$H-NMR (400 MHz, DMSO-d$_6$) δ=0.27 (m, 2H), 0.52 (m, 2H), 2.26 (m, 1H), 3.27 (m, 2H), 7.95 (d, 1H), 8.18 (dd, 1H), 8.48 (t, 1H), 8.53 (d, 1H) 9.04 (s, 1H), 10.12 (s, 1H).

Intermediate c8: 5-(4-Methylpiperazine-1-carbonyl)benzo[b]thiophene-3-carbaldehyde $^1$H-NMR (400 MHz, DMSO-d$_6$) δ=2.16 (s, 3H), 2.29 (m, 4H), 3.41 (m, 4H), 7.97 (d, 1H), 8.17 (d, 1H), 8.50 (d, 1H), 9.06 (s, 1H), 10.11 (s, 1H).

Intermediate c9: 5-(morpholine-4-carbonyl)benzo[b]thiophene-3-carbaldehyde $^1$H-NMR (400 MHz, DMSO-d$_6$) δ=3.51 (m, 4H), 3.66 (m, 4H), 7.96 (d, 1H), 8.18 (d, 1H), 8.51 (d, 1H), 9.08 (s, 1H), 10.13 (s, 1H).

Intermediate c10: 3-Formylbenzo[b]thiophene-7-carbonitrile $^1$H-NMR (400 MHz, DMSO-d$_6$) δ=7.70 (t, 1H), 8.16 (d, 1H), 8.81 (d, 1H), 9.08 (s, 1H), 10.16 (s, 1H).

Intermediate c11: 7-(4-Methylpiperazin-1-yl)benzo[b]thiophene-3-carbaldehyde $^1$H-NMR (400 MHz, DMSO-d$_6$) δ=2.91 (s, 4H), 3.30 (s, 6H), 3.49 (s, 9H), 7.16 (d, 1H), 7.35 (t, 1H), 7.97 (d, 1H), 8.04 (d, 1H), 8.30 (d, 1H), 10.10 (s, 1H).

Intermediate c12: 7-(4-methylpiperazine-1-carbonyl)benzo[b]thiophene-3-carbaldehyde $^1$H-NMR (400 MHz, DMSO-d$_6$) δ=3.41 (dd, 4H), 3.49 (dd, 4H), 3.90 (s, 3H), 7.66 (m, 1H), 8.23 (s, 2H), 9.08 (s, 1H), 10.15 (s, 1H).

Intermediate c13: N-Cyclopropyl-3-formylbenzo[b]thiophene-7-carboxamide $^1$H-NMR (400 MHz, DMSO-d$_6$) δ=0.64 (dt, 2H), 0.75 (td, 2H), 2.93 (m, 1H), 7.64 (t, 1H), 8.08 (dd, 1H), 8.72 (dd, 1H), 8.84 (d, 1H), 9.04 (s, 1H), 10.14 (s, 1H).

Intermediate c14: Methyl 3-formylbenzo[b]thiophene-5-carboxylate

The title compound was synthesized according to General procedure c and purified by trituration with n-pentane to yield a pale brown solid (320 mg, 83%).

$^1$H-NMR (400 MHz, DMSO-d$_6$) δ=3.97 (s, 3H), 7.73 (m, 1H), 8.20 (m, 1H), 8.85 (dd, 1H), 9.08 (s, 1H), 10.15 (s, 1H).
The ester was hydrolysed as follows:

Intermediate c15: 3-Formylbenzo[b]thiophene-5-carboxylic acid

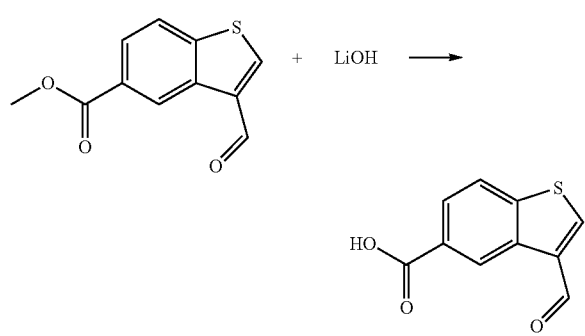

To a solution of methyl 3-formylbenzo[b]thiophene-5-carboxylate (320 mg, 1.45 mmol) in EtOH (15 mL) and water (5 mL), lithium hydroxide (230 mg, 9.6 mmol) was added at 0° C. The mixture was stirred for 24 hours at room temperature. The product was isolated as a pale yellow solid after acidification (pH 4-5) with 2N HCl, followed by filtration and pentane washing (260 mg, 92% yield).

$^1$H-NMR (400 MHz, DMSO-d$_6$) δ=7.81 (m, 1H), 8.23 (m, 1H), 8.88 (dd, 1H), 9.08 (s, 1H), 10.15 (s, 1H), 12.45 (s, 1H).

Intermediate c16: 7-(2,2,2-Trifluoroacetyl)benzo[b]thiophene-3-carbaldehyde

The title compound was synthesized according to General procedure c and purified by flash column chromatography yielding a yellow solid (0.31 g, 91%).

$^1$H-NMR (300 MHz, CDCl$_3$) δ=10.22 (s, 1H), 9.20 (s, 1H), 9.03 (d, J=8.0 Hz, 1H), 8.34 (d, J=7.0 Hz, 1H), 7.88 (t, J=7.9 Hz, 1H). $^{19}$F NMR (282 MHz, CDCl$_3$) δ=−68.92 (s, CF$_3$).

Intermediate c17: 7-Chlorobenzo[b]thiophene-3-carbaldehyde

The title compound was synthesized according to General procedure c and purified by flash column chromatography yielding a yellow solid (0.38 g, 48%).

$^1$H-NMR (300 MHz, CDCl$_3$-d) δ (ppm) δ 10.13 (s, 1H), 8.66-8.51 (m, 1H), 8.35 (s, 1H), 7.53-7.41 (m, 2H).

Intermediate c18: 7-(Trifluoromethyl)benzo[b]thiophene-3-carbaldehyde

The title compound was synthesized according to General procedure c and purified by flash column chromatography yielding a yellow solid (0.081 g, 16%).

$^1$H-NMR (300 MHz, CDCl$_3$-d) δ (ppm): 10.18 (s, 1H), 8.92 (d, J=8.0 Hz, 1H), 8.43 (s, 1H), 7.78 (d, J=7.5 Hz, 1H), 7.63 (t, J=8.0 Hz, 1H).
$^{19}$F NMR (282 MHz, CDCl$_3$-d) δ (ppm): −62.56 (CF$_3$).

Intermediate c19: 7-Fluorobenzo[b]thiophene-3-carbaldehyde

The title compound was synthesized according to General procedure c and purified by flash column chromatography yielding a yellow solid (0.27 g, 19%).

$^1$H-NMR (300 MHz, CDCl$_3$-d) δ (ppm): 10.15 (s, 1H), 8.45 (d, J=8.1 Hz, 1H), 8.34 (s, 1H), 7.48 (td, J=8.1, 5.1 Hz, 1H), 7.22-7.09 (m, 1H).
$^{19}$F NMR (282 MHz, CDCl$_3$-d) δ (ppm): −115.33 (CF).

Intermediate c20: Thieno[2,3-b]pyridine-3-carbaldehyde

Step 1: 3-Bromo-thieno[2,3-b]pyridine (500 mg, 2.35 mmol) and copper (I) cyanide (315 mg, 3.53 mmol) were suspended in NMP (10 mL) and stirred at 200° C. for 20 hours under N$_2$ atmosphere. The solution was poured into sat. aq. NaHCO$_3$, filtered and washed with water to afford thieno[2,3-b]pyridine-3-carbonitrile as a grey solid (376 mg, 95% yield).

$^1$H-NMR (400 MHz, DMSO-d$_6$) δ=7.65 (m, 1H), 8.39 (dd, 1H), 8.75 (m, 1H), 9.04 (d, 1H).

Step 2: To a solution of diisobutylaluminum hydride (DIBAL) (25% w in toluene, 2.7 mL, 4.1 mmol) in toluene (45 mL) at −78° C. under N$_2$ atmosphere, a solution of thieno[2,3-b]pyridine-3-carbonitrile (660 mg, 4.1 mmol) in toluene (4 mL) was added dropwise. The temperature was allowed to rise to 0° C. and the mixture was stirred until completion. Then, water (30 mL) was added slowly and the product was extracted with AcOEt (3×), dried over Na$_2$SO$_4$, filtered over silica gel and concentrated. The title compound was obtained as a brown solid and used in the next step without further purification (569 mg, 85% yield).

$^1$H-NMR (400 MHz, DMSO-d$_6$) δ=7.60 (m, 1H), 8.68 (t, 1H), 8.80 (d, 1H), 9.08 (d, 1H), 10.06 (s, 1H).

Intermediate c21: 5-Fluoro-3-formylbenzo[b]thiophene-7-carbonitrile

General procedure c gave the title compound as a yellow solid (0.153 g, 58%).

$^1$H-NMR (300 MHz, CDCl$_3$-d) δ (ppm): 10.14 (s, 1H), 8.68 (d, J=9.1 Hz, 1H), 8.53 (s, 1H), 7.59 (d, J=9.1 Hz, 1H).

Intermediate c22: 4-Fluoro-3-formylbenzo[b]thiophene-7-carbonitrile

General procedure c gave the title compound as a yellow solid (0.125 g, 33%).

$^1$H-NMR (300 MHz, CDCl$_3$-d) δ (ppm): 10.40 (s, 1H), 8.57 (s, 1H), 7.82 (dd, J=8.1, 4.4 Hz, 1H), 7.40-7.28 (m, 1H).

Intermediate c23: 3-Formylthieno[3,2-b]pyridine-7-carbonitrile

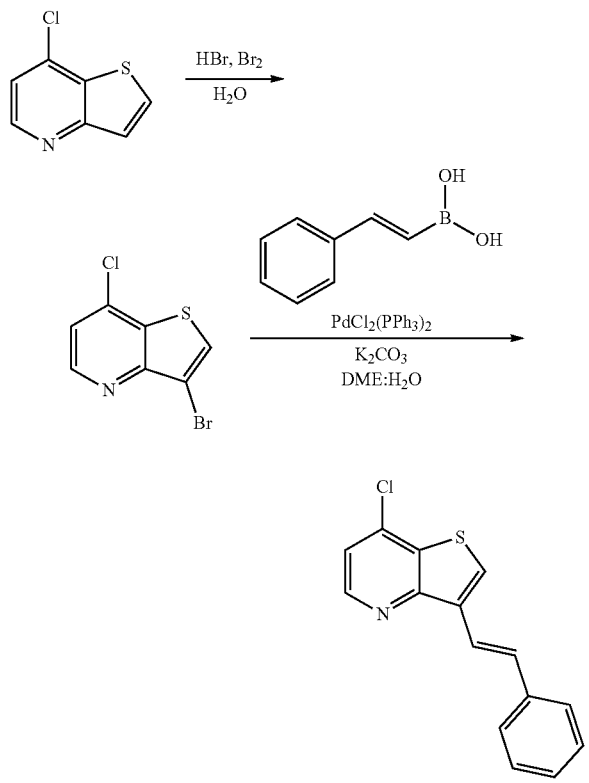

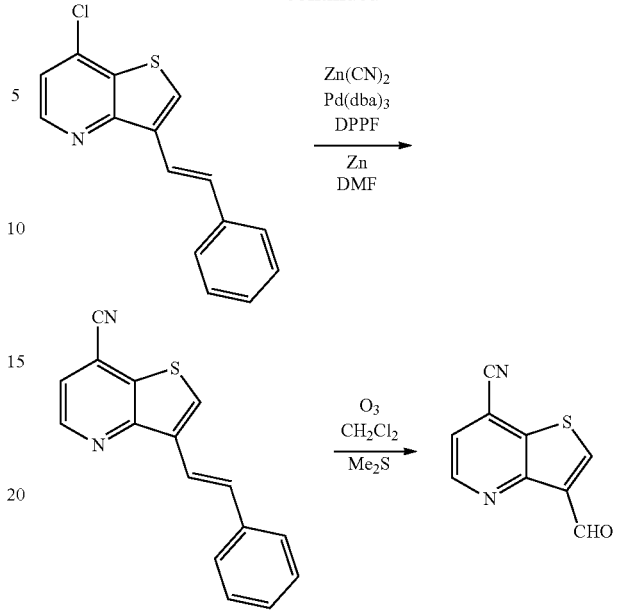

This aldehyde was prepared in 4 steps using a different method.

First step: A solution of 7-chlorothieno[3,2-b]pyridine (3.0 g, 17.68 mmol, 1.0 eq.), hydrobromic acid (30 mL, 265.28 mmol, 15 eq.) and bromine (2.28 mL, 44.20 mmol, 2.5 eq.) in water (40 ml) was stirred at 80° C. for 2 days. The mixture was cooled to room temperature and NaHCO$_3$ was added until pH 8. The mixture was washed with ethyl acetate (×3) and dichloromethane (×2), dried over Na$_2$SO$_4$, concentrated and purified by flash column chromatography on silica gel using hexane/ethyl acetate (15:1) as eluent to afford 3-bromo-7-chlorothieno[3,2-b]pyridine as a yellow solid (3.45 g, 79%).

$^1$H-NMR (300 MHz, CDCl$_3$-d) δ (ppm): 8.74 (dd, J=5.0, 0.4 Hz, 1H), 7.84 (s, 1H), 7.44-7.30 (m, 1H).

Second step: To a solution of 3-bromo-7-chlorothieno[3,2-b]pyridine (1.2 g, 4.82 mmol, 1.0 eq.), bis(triphenylphosphine)palladium (II) dichloride (0.338 g, 0.48 mmol, 0.1 eq.) and potassium carbonate (2.0 g, 14.48 mmol, 3 eq.) in a mixture of dimethylether and water (3:1) (32 mL) was added (E)-styrylboronic acid (0.92 g, 6.28 mmol, 1.3 eq). The resultant mixture was stirred at 110° C. for 1 hour. The mixture was cooled to RT, filtered over celite, washed with DCM, concentrated and purified by flash column chromatography on silica gel using hexane/ethyl acetate (10:1) as eluent to afford (E)-7-chloro-3-styrylthieno[3,2-b]pyridine as a yellow oil (0.870 g, 66%).

$^1$H-NMR (300 MHz, CDCl$_3$-d) δ (ppm): 8.69 (d, J=5.6 Hz, 1H), 7.83 (s, 1H), 7.76 (d, J=16.4 Hz, 1H), 7.61 (d, J=8.2 Hz, 2H), 7.53 (d, J=16.4 Hz, 1H), 7.42-7.33 (m, 3H), 7.29 (d, J=7.1 Hz, 1H).

Third step: A solution of (E)-7-chloro-3-styrylthieno[3,2-b]pyridine (0.870 g, 3.20 mmol, 1.0 eq.), zinc cyanide (0.75 g, 6.40 mmol, 2 eq.), tris(benzylideneacetone)dipalladium (0) (0.092 g, 0.16 mmol, 0.05 eq.), 1,1'-ferrocenediyl-bis-(diphenylphosphine) (0.234 g, 0.32 mmol, 0.1 eq.) and zinc (0.063 mL, 0.96 mmol, 0.3 eq.) in N,N-dimethylformamide (7 ml) was stirred at 160° C. for 90 min. The mixture was cooled to RT, filtered over celite, washed with DCM, concentrated and purified by flash column chromatography on silica gel using hexane/ethyl acetate (7:1) as eluent to afford (E)-3-styrylthieno[3,2-b]pyridine-7-carbonitrile as a light yellow solid (0.38 g, 47%).

Fourth step: A mixture of (E)-3-styrylthieno[3,2-b]pyridine-7-carbonitrile (0.370 g, 1.47 mmol, 1 eq.) and DCM (10 mL) at −78° C. was purged with $N_2$ for 5 min. Then, ozone was bubbled into the mixture for 15 min and dimethyl sulphide (1.1 mL, 14.78 mmol, 10 eq.) was added. The mixture was stirred at −78° C. with a nitrogen current for 30 min, concentrated and purified by flash column chromatography on silica gel using hexane/ethyl acetate (7:1) as eluent to afford 3-formylthieno[3,2-b]pyridine-7-carbonitrile as a light yellow solid (0.125 g, 45%).

$^1$H-NMR (300 MHz, $CDCl_3$-d) δ (ppm): 10.53 (s, 1H), 9.01 (d, J=4.7 Hz, 1H), 8.78 (s, 1H), 7.67 (d, J=4.7 Hz, 1H).

Intermediate c24: 3-Formylbenzo[b]thiophene-5,7-dicarbonitrile

This aldehyde was prepared starting from 5,7-dichlorobenzo[b]thiophene following the 4-step synthesis described for Intermediate c23, except that the cyanation reaction was done before the bromination step.

Yellow solid (0.22 g).

$^1$H-NMR (300 MHz, $CDCl_3$-d) δ (ppm): 10.18 (s, 1H), 9.28 (d, J=1.2 Hz, 1H), 8.60 (s, 1H), 8.04 (d, J=1.2 Hz, 1H).

Intermediate c25: 6-Chloro-3-formylbenzo[b]thiophene-7-carbonitrile

This aldehyde was prepared starting from 3-bromo-6-chlorobenzo[b]thiophene-7-carbonitrile following Steps 2 and 4 of the synthesis described for Intermediate c23.

Yellow solid (0.29 g).

$^1$H-NMR (300 MHz, $CDCl_3$-d) δ (ppm): 10.13 (s, 1H), 8.84 (d, J=8.8 Hz, 1H), 8.44 (s, 1H), 7.63 (d, J=8.8 Hz, 1H).

Intermediate 26: 5-Fluorothieno[2,3-b]pyridine-3-carbaldehyde

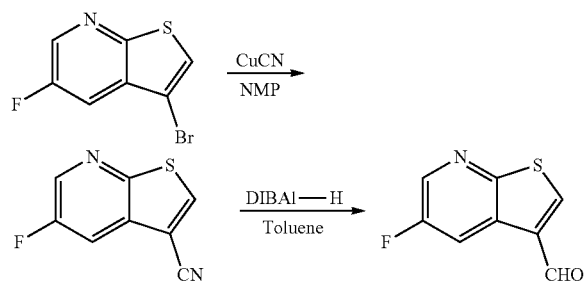

A solution of 3-bromo-5-fluorothieno[2,3-b]pyridine (0.73 g, 3.14 mmol, 1.0 eq.) and copper cyanide (0.42 g, 4.72 mmol, 1.5 eq.) in N-methyl-2-pirrolydone (18 ml) was stirred for 2 days in a sealed tube at 200° C., then cooled to RT and poured into saturated aqueous $NaHCO_3$ (30 mL). This mixture was stirred at 4° C. for 60 min. The solid was filtered off and dissolved in a mixture of 40 mL of $NH_4OH_{(28\%)}/NH_4Cl_{(sat)}$ (1:1) and ethyl acetate (60 mL) which was stirred for 1 h and then extracted with ethyl acetate (×3). The organic phase was dried over $Na_2SO_4$, filtered, concentrated and purified by flash column chromatography on silica gel using hexane/ethyl acetate (20:1) as eluent to afford 5-fluorothieno[2,3-b]pyridine-3-carbonitrile as a white solid (0.32 g, 56%).

$^1$H-NMR (300 MHz, $CDCl_3$-d) δ (ppm): 8.61 (d, J=2.4 Hz, 1H), 8.32 (s, 1H), 7.96 (dd, J=8.1, 2.7 Hz, 1H).

To a solution of 5-fluorothieno[2,3-b]pyridine-3-carbonitrile (0.32 g, 1.77 mmol, 1 eq.) in toluene (30 ml) at −78° C. was dropwise added a solution of DIBAl-H (1.98 mL, 1.94 mmol, 1.1 eq) in toluene. This mixture was stirred at −78° C. for 5 minutes, then at −40° C. for 6 hours, and finally it was allowed to warm up to RT. After the addition of water the mixture was extracted with ethyl acetate (×2) which was dried ($Na_2SO_4$), concentrated and the residue purified by flash column chromatography on silica gel using hexane/ethyl acetate (10:1) as eluent to afford 5-fluorothieno[2,3-b]pyridine-3-carbaldehyde as a light yellow oil (0.149 g, 47%).

$^1$H-NMR (300 MHz, $CDCl_3$-d) δ (ppm): 10.05 (s, 1H), 8.63 (dd, J=8.8, 2.6 Hz, 1H), 8.56 (d, J=2.6 Hz, 1H), 8.50 (s, 1H).

Preparation of Dicarbonyl Intermediates

Dicarbonyl compounds were synthesized according to the literature as described in the general procedures below.

General Procedure d (Adapted from Haibin Mao et al., Chem. Int. Ed. 2013, 52, 6288-6291)

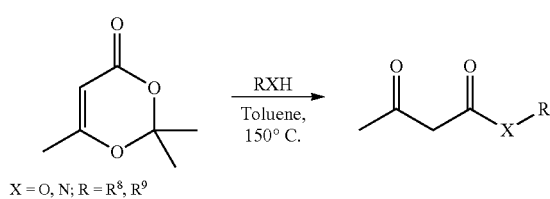

X = O, N; R = $R^8$, $R^9$

To a solution of 2,2,6-trimethyl-4H-1,3-dioxin-4-one (1 eq) in toluene (5 M) at room temperature, the corresponding alcohol or amine (1 eq) was added. The mixture was heated at 150° C. for 6 hours, then allowed to cool to room temperature and concentrated in vacuum. The remaining residue was purified by flash column chromatography on silica gel using ethyl acetate/hexane as eluent to afford the dicarbonyl compound.

The following dicarbonyl compounds were synthesized following General procedure d.

Intermediate d1: 2,2,2-Trifluoroethyl 3-oxobutanoate

Light brown oil (8.93 g, 70%).

$^1$H-NMR (300 MHz, $CDCl_3$) δ=4.53 (q, J=8.4 Hz, 1H), 3.57 (s, 1H), 2.28 (s, 1H). $^{19}$F NMR (282 MHz, $CDCl_3$) δ=−73.92.

Intermediate d2: N,N-Diethyl-3-oxobutanamide

Yellow oil (1.5 g, 91%).

$^1$H-NMR (300 MHz, $CDCl_3$) δ=3.49 (s, 2H), 3.39 (q, J=7.1 Hz, 2H), 3.28 (q, J=7.2 Hz, 2H), 2.28 (s, 3H), 1.15 (dt, J=10.6, 7.1 Hz, 6H).

Intermediate d3: 1-(4-Methylpiperazin-1-yl)butane-1,3-dione

Yellow oil (1.8 g, 91%).
¹H-NMR (300 MHz, CDCl₃) δ=3.69-3.61 (m, 2H), 3.55 (s, 2H), 3.47-3.38 (m, 2H), 2.44-2.33 (m, 4H), 2.30 (s, 3H), 2.27 (s, 3H).

Intermediate d4: 1-Morpholinobutane-1,3-dione

Dark yellow oil (1.6 g, 88%).
¹H-NMR (300 MHz, CDCl₃) δ=3.72-3.58 (m, 6H), 3.56 (s, 2H), 3.50-3.35 (m, 2H), 2.28 (s, 3H).

Intermediate d5: 2-Methoxyethyl 3-oxobutanoate

Yellow oil (1.5 g, 91%).
¹H-NMR (300 MHz, CDCl₃) δ=4.34-4.24 (m, 2H), 3.65-3.55 (m, 2H), 3.49 (s, 2H), 3.38 (s, 3H), 2.27 (s, 3H).

Intermediate d6: 3-Acetamidopropyl 3-oxobutanoate

General procedure d using N-(3-hydroxypropyl)acetamide (prepared according to K. Veejendra et al., J. Org. Chem. 2004, 69, 577-580) yielded light yellow oil (2.1 g, 92%).
¹H-NMR (300 MHz, CDCl₃) δ=5.96 (bs, 1H), 4.22 (t, J=6.0 Hz, 2H), 3.50 (s, 2H), 3.33 (q, J=6.3 Hz, 2H), 2.28 (s, 3H), 1.98 (s, 3H), 1.93-1.80 (m, 2H).

Intermediate d7: Benzyl 3-oxobutanoate

Light yellow oil (2 g, 98%).
¹H-NMR (300 MHz, CDCl₃) δ=7.36 (s, 5H), 5.18 (s, 2H), 3.50 (s, 2H), 2.25 (s, 3H).

Intermediate d8: 2-Morpholinoethyl 3-oxobutanoate

Light yellow oil (2 g, 98%).
¹H-NMR (300 MHz, CDCl₃) δ=4.27 (t, J=5.8 Hz, 2H), 3.73-3.64 (m, 4H), 3.47 (s, 2H), 2.63 (t, J=5.8 Hz, 2H), 2.51-2.44 (m, 4H), 2.28 (s, 3H).

Intermediate d9: 2-(Dimethylamino)ethyl 3-oxobutanoate

Light yellow oil (2.1 g, 92%).
¹H-NMR (300 MHz, CDCl₃) δ=4.24 (t, J=5.7 Hz, 2H), 3.48 (s, 2H), 2.57 (t, J=5.7 Hz, 2H), 2.27 (s, 9H).

Intermediate d10: 2-Acetamidoethyl 3-oxobutanoate

Yellow oil (1.1 g, 91%).
¹H-NMR (300 MHz, CDCl₃) δ=4.26 (t, J=4.6 Hz, 2H), 3.56-3.51 (m, 4H), 2.28 (s, 3H), 2.00 (s, 3H).

Intermediate d11: Cyclohexylmethyl 3-oxobutanoate

Light yellow oil (1.4 g, 67%).
¹H-NMR (300 MHz, CDCl₃) δ=3.95 (d, J=6.4 Hz, 2H), 3.44 (s, 2H), 2.27 (s, 3H), 1.78-1.56 (m, 6H), 1.33-1.09 (m, 3H), 1.06-0.83 (m, 2H).

Intermediate d12: Pyridin-4-ylmethyl 3-oxobutanoate

Yellow oil (1.2 g, 89%).
¹H-NMR (300 MHz, CDCl₃) δ=8.61 (d, J=5.6 Hz, 2H), 7.25 (d, J=4.1 Hz, 2H), 5.19 (s, 2H), 3.57 (s, 2H), 2.28 (s, 3H).

Intermediate d13: Pyridin-2-ylmethyl 3-oxobutanoate

Yellow oil (1.0 g, 74%).
¹H-NMR (300 MHz, CDCl₃) δ=8.58 (ddd, J=4.9, 1.8, 1.0 Hz, 1H), 7.71 (td, J=7.7, 1.8 Hz, 1H), 7.38 (ddt, J=7.8, 1.1, 0.6 Hz, 1H), 7.26-7.20 (m, 1H), 5.29 (s, 2H), 3.57 (s, 2H), 2.28 (s, 3H).

Intermediate d14: 4-Methoxybenzyl 3-oxobutanoate

Light yellow oil (1.0 g, 43%).
¹H-NMR (300 MHz, CDCl₃) δ=7.29 (d, J=8.5 Hz, 2H), 6.88 (d, J=8.5 Hz, 2H), 5.10 (s, 2H), 3.80 (s, 3H), 3.46 (s, 2H), 2.22 (s, 3H).

Intermediate d15: 2-((tert-Butoxycarbonyl)oxy)ethyl 3-oxobutanoate

Colorless oil (1.2 g, 46%).
¹H-NMR (300 MHz, CDCl₃) δ=4.32 (dd, J=19.8, 5.3 Hz, 4H), 3.47 (s, 2H), 2.27 (s, 2H), 1.49 (s, 9H).

Intermediate d16: tert-butyl 4-(((3-oxobutanoyl)oxy)methyl)piperidine-1-carboxylate Yellow oil (0.46 g, 67%).
¹H-NMR (300 MHz, CDCl₃) δ=4.12 (d, J=14.5 Hz, 2H), 4.00 (d, J=6.5 Hz, 2H), 3.46 (s, 2H), 2.69 (t, J=12.5 Hz, 2H), 2.27 (s, 3H), 1.82 (s, 1H), 1.68 (d, J=13.6 Hz, 2H), 1.45 (s, 9H), 1.31-1.05 (m, 2H).

Intermediate d17: Tetrahydro-2H-(pyran-4-yl)methyl-3-oxobutanoate

Colorless oil (0.58 g, 83%).
¹H-NMR (300 MHz, CDCl₃) δ=4.05-3.92 (m, 4H), 3.47 (d, J=0.4 Hz, 2H), 3.39 (td, J=11.9, 2.3 Hz, 2H), 2.27 (s, 3H), 2.03-1.83 (m, 1H), 1.63 (ddd, J=12.8, 3.9, 1.9 Hz, 2H), 1.37 (dtd, J=13.3, 11.8, 4.5 Hz, 2H).

Intermediate d18: Cyclohexyl 3-oxobutanoate

Colorless oil (1.08 g, 84%).
¹H-NMR (300 MHz, CDCl₃) δ=4.81 (td, J=8.8, 3.8 Hz, 1H), 3.42 (s, 2H), 2.26 (s, 3H), 1.91-1.80 (m, 2H), 1.77-1.66 (m, 2H), 1.61-1.49 (m, 2H), 1.47-1.29 (m, 4H).

Intermediate d19: Tetrahydro-2H-(pyran-4-yl)-3-oxobutanoate

Colorless oil (0.6 g, 92%).
¹H-NMR (300 MHz, CDCl₃) δ=5.07-4.96 (m, 1H), 3.90 (dt, J=11.9, 4.6 Hz, 2H), 3.54 (ddd, J=11.9, 8.9, 3.0 Hz, 2H), 3.46 (s, 2H), 2.27 (s, 3H), 1.97-1.91 (m, 2H), 1.70 (dtd, J=13.0, 8.9, 4.0 Hz, 2H).

Intermediate d20: Cyclopropylmethyl 3-oxobutanoate

Colorless oil (0.9 g, 82%).
$^1$H-NMR (300 MHz, CDCl$_3$) δ=3.97 (d, J=7.3 Hz, 2H), 3.46 (s, 2H), 2.28 (s, 3H), 1.23-1.06 (m, 1H), 0.63-0.52 (m, 2H), 0.33-0.25 (m, 2H).

Intermediate d21: tert-Butyl 4-(((3-oxobutanoyl)oxy)methyl)piperidine-1-carboxylate Colorless oil (0.45 g, 71%).
$^1$H-NMR (300 MHz, CDCl$_3$) δ=4.13 (bs, 2H), 4.00 (d, J=6.5 Hz, 2H), 3.46 (s, 2H), 2.69 (t, J=12.7 Hz, 2H), 2.27 (s, 3H), 1.82 (tdd, J=15.2, 6.5, 3.5 Hz, 1H), 1.68 (d, J=12.7 Hz, 2H), 1.45 (s, 9H), 1.19 (dtd, J=12.7, 12.3, 5.7 Hz, 2H).

Intermediate d22: phenethyl 3-oxobutanoate

Yellow oil (0.97 g, 58%).
$^1$H-NMR (300 MHz, CDCl$_3$) δ=7.34-7.27 (m, 2H), 7.25-7.17 (m, 3H), 4.37 (t, J=7.0 Hz, 2H), 3.43 (s, 2H), 2.97 (t, J=7.0 Hz, 2H), 2.20 (s, 3H).

Intermediate d23: 1,3-dicyclopropylpropane-1,3-dione

Colorless oil (1.3 g, 87%).
$^1$H-NMR (300 MHz, CDCl$_3$) δ=3.78 (s, 2H), 1.56 (td, J=8.0, 4.1 Hz, 2H), 1.15-1.03 (m, 4H), 0.98-0.85 (m, 4H).

Intermediate d24: methyl 3-cyclopropyl-3-oxopropanoate

Light-yellow oil (2.01 g, 79%).
$^1$H-NMR (300 MHz, CDCl$_3$) δ=3.74 (d, J=1.5 Hz, 3H), 3.58 (d, J=1.2 Hz, 2H), 2.17-1.95 (m, 1H), 1.28-1.07 (m, 2H), 1.07-0.82 (m, 2H).

Intermediate d25: methyl 4-fluoro-3-oxobutanoate

Light-yellow oil (2.8 g, 78%).
$^1$H-NMR (300 MHz, CDCl$_3$) δ=4.91 (d, J=47.5 Hz, 2H), 3.76 (s, 3H), 3.61 (d, J=3.7 Hz, 2H). $^{19}$F NMR (282 MHz, CDCl$_3$) δ=123.96 (t, J=47.5 Hz).

Intermediate d26: Methyl 4-(benzyloxy)-3-oxobutanoate

Yellow oil (0.75 g, 51%).
$^1$H-NMR (300 MHz, CDCl$_3$) δ=7.41-7.29 (m, 5H), 4.59 (s, 2H), 4.14 (s, 2H), 3.71 (s, 3H), 3.56 (s, 2H).

Intermediate d27: Methyl 3-oxo-4-phenoxybutanoate

Yellow oil (47%).
$^1$H-NMR (300 MHz, CDCl$_3$) δ=7.53-7.31 (m, 5H), 4.32 (s, 2H), 3.69 (s, 3H), 3.55 (s, 2H).

Intermediate d28: 3-oxo-N-phenylbutanamide

Yellow oil (0.98 g, 79%).
$^1$H-NMR (300 MHz, CDCl$_3$) δ=9.08 (bs, 1H), 7.54 (dt, J=8.8, 1.7 Hz, 2H), 7.38-7.28 (m, 2H), 7.12 (tt, J=7.1, 1.1 Hz, 1H), 3.59 (s, 2H), 2.33 (s, 3H).

Intermediate d29: tert-butyl 4-((3-oxobutanoyl)oxy)piperidine-1-carboxylate

Light yellow oil (1.3 g, 89%).
$^1$H-NMR (300 MHz, CDCl$_3$) δ=4.99 (tt, J=8.5, 3.6 Hz, 1H), 3.77-3.61 (m, 2H), 3.46 (s, 2H), 3.24 (ddd, J=13.3, 8.5, 3.6 Hz, 2H), 2.27 (s, 3H), 1.87 (ddt, J=12.9, 6.5, 3.4 Hz, 2H), 1.63 (dp, J=12.9, 4.3 Hz, 2H), 1.46 (s, 9H).

Intermediate d30: Cyclopentylmethyl 3-oxobutanoate

Colorless oil (1.63 g, 84%).
$^1$H-NMR (300 MHz, CDCl$_3$) δ=4.03 (d, J=7.1 Hz, 2H), 3.45 (s, 2H), 2.27 (s, 3H), 2.24-2.15 (m, 1H), 1.81-1.69 (m, 2H), 1.64-1.51 (m, 4H), 1.34-1.17 (m, 2H).

Intermediate d31: 1-Methylpiperidin-4-yl 3-oxobutanoate

Yellow oil (1.2 g, 57%).
$^1$H-NMR (300 MHz, CDCl$_3$) δ=4.84 (tt, J=7.9, 3.8 Hz, 1H), 3.44 (s, 2H), 2.70-2.55 (m, 2H), 2.34-2.18 (m, 8H), 2.02-1.86 (m, 2H), 1.73 (dtd, J=12.7, 8.6, 3.8 Hz, 2H).

Intermediate d32: Cyclopentyl 3-oxobutanoate

Colorless oil (1.25 g, 70%).
$^1$H-NMR (300 MHz, CDCl$_3$) δ=5.28-5.16 (m, 1H), 3.40 (s, 2H), 2.26 (s, 3H), 1.92-1.81 (m, 2H), 1.76-1.66 (m, 4H), 1.63-1.54 (m, 2H).

Intermediate d33: 4,4-Dimethylcyclohexyl 3-oxobutanoate

Light yellow oil (0.42 g, 57%).
$^1$H-NMR (300 MHz, CDCl$_3$) δ=4.80 (tt, J=8.8, 4.1 Hz, 1H), 3.42 (s, 2H), 2.27 (s, 3H), 1.82-1.70 (m, 2H), 1.65-1.52 (m, 2H), 1.48-1.38 (m, 2H), 1.25 (ddd, J=14.0, 10.4, 4.1 Hz, 2H), 0.93 (s, 3H), 0.91 (s, 3H).

Intermediate d34: Cyclobutyl 3-oxobutanoate

Colorless oil (1.06 g, 51%).
$^1$H-NMR (300 MHz, CDCl$_3$) δ=5.09-4.96 (m, 1H), 3.41 (s, 2H), 2.42-2.29 (m, 2H), 2.26 (s, 3H), 2.14-2.00 (m, 2H), 1.86-1.54 (m, 2H).

Intermediate d35: 4-Fluorobenzyl 3-oxobutanoate

Colorless oil (1.32 g, 89%).
$^1$H-NMR (300 MHz, CDCl$_3$) δ=7.41-7.28 (m, 2H), 7.13-6.96 (m, 2H), 5.14 (s, 2H), 3.49 (s, 2H), 2.24 (s, 3H). $^{19}$F NMR (282 MHz, CDCl$_3$) δ=−113.31.

Intermediate d36: Pyridin-3-ylmethyl 3-oxobutanoate

Light-yellow oil (0.95 g, 70%).
$^1$H-NMR (300 MHz, CDCl$_3$) δ=8.62 (d, J=2.2 Hz, 1H), 8.59 (dd, J=4.8, 1.6 Hz, 1H), 7.76-7.65 (m, 1H), 7.31 (ddd, J=7.9, 4.8, 0.9 Hz, 1H), 5.19 (s, 2H), 3.51 (s, 2H), 2.25 (s, 3H).

Intermediate d37: tert-butyl 4-(((3-oxobutanoyl)oxy)methyl)benzoate

Light-yellow solid (0.59 g, 79%).
$^1$H-NMR (300 MHz, CDCl$_3$) δ=7.96 (d, J=8.0 Hz, 2H), 7.39 (d, J=8.0 Hz, 2H), 5.15 (s, 2H), 1.93 (s, 2H), 1.93 (s, 3H), 1.59 (s, 9H).

Intermediate d38: 4-(Cyclopropylcarbamoyl)benzyl 3-oxobutanoate

General procedure d using N-cyclopropyl-4-(hydroxymethyl)benzamide (J. Med. Chem., 2001, 44, 1491-1508) yielded yellow oil (0.14 g, 76%).
$^1$H-NMR (300 MHz, CDCl$_3$) δ=7.73 (d, J=8.2 Hz, 2H), 7.40 (d, J=8.2 Hz, 2H), 6.23 (bs, 1H), 5.20 (s, 2H), 3.52 (s, 2H), 2.90 (dq, J=7.2, 3.5 Hz, 1H), 2.25 (s, 3H), 0.88 (q, J=6.5 Hz, 2H), 0.67-0.52 (m, 2H).

Intermediate d39: 4-bromobenzyl 3-oxobutanoate

Yellow oil (0.5 g, 34%).
$^1$H-NMR (300 MHz, CDCl$_3$) δ=7.49 (d, J=8.0 Hz, 2H), 7.23 (d, J=8.0 Hz, 2H), 5.12 (s, 2H), 3.50 (s, 2H), 2.24 (s, 3H).

Intermediate d40: 3-bromobenzyl 3-oxobutanoate

Yellow oil (1.5 g, 69%).
$^1$H-NMR (300 MHz, CDCl$_3$) δ=7.50 (d, J=1.8 Hz, 1H), 7.46 (dt, J=7.5, 1.8 Hz, 1H), 7.29-7.21 (m, 2H), 5.13 (s, 2H), 3.51 (s, 2H), 2.25 (s, 3H).

Intermediate d41: 2-bromobenzyl 3-oxobutanoate

Yellow oil (1.2 g, 83%).
$^1$H-NMR (300 MHz, CDCl$_3$) δ=7.56 (dd, J=7.8, 1.1 Hz, 1H), 7.41 (dd, J=7.5, 1.6 Hz, 1H), 7.31 (td, J=7.5, 1.1 Hz, 1H), 7.18 (td, J=7.8, 1.6 Hz, 1H), 5.25 (s, 2H), 3.52 (s, 2H), 2.26 (s, 3H).

Intermediate d42: (3-Fluoropyridin-4-yl)methyl 3-oxobutanoate

Yellow oil (0.305 g, 41%).
$^1$H-NMR (300 MHz, CDCl$_3$) δ=8.54-8.38 (m, 2H), 7.46-7.31 (m, 1H), 5.29 (s, 2H), 3.57 (s, 2H), 2.29 (s, 3H). $^{19}$F NMR (282 MHz, CDCl$_3$) δ=−132.13 (s, CF).

Intermediate d43: Pyrimidin-5-ylmethyl 3-oxobutanoate

Yellow oil (0.65 g, 96%).
$^1$H-NMR (300 MHz, CDCl$_3$) δ=9.20 (s, 1H), 8.77 (s, 2H), 5.20 (s, 2H), 3.53 (s, 2H), 2.26 (s, 3H).

Intermediate d44: (5-Bromopyridin-3-yl)methyl 3-oxobutanoate

Yellow oil (0.5 g, 63%).
$^1$H-NMR (300 MHz, CDCl$_3$) δ=8.65 (d, J=2.0 Hz, 1H), 8.53 (s, 1H), 7.87 (s, 1H), 5.17 (s, 2H), 3.53 (s, 2H), 2.26 (s, 3H).

Intermediate d45: 3-cyanobenzyl 3-oxobutanoate

Yellow oil (0.57 g, 75%).
$^1$H-NMR (300 MHz, CDCl$_3$) δ=7.68-7.57 (m, 3H), 7.53-7.45 (m, 1H), 5.20 (s, 2H), 3.54 (s, 2H), 2.27 (s, 3H).

Intermediate d46: 4-cyanobenzyl 3-oxobutanoate

Yellow oil (0.62 g, 82%).
$^1$H-NMR (300 MHz, CDCl$_3$) δ=7.66 (d, J=8.1 Hz, 2H), 7.46 (d, J=8.1 Hz, 2H), 5.22 (s, 2H), 3.54 (s, 2H), 2.26 (s, 3H).

Intermediate d47: (6-chloropyridin-3-yl)methyl 3-oxobutanoate

Yellow oil (0.69 g, 87%).
$^1$H-NMR (300 MHz, CDCl$_3$) δ=8.31 (s, 1H), 7.79-7.52 (m, 1H), 7.26 (d, J=8.2 Hz, 1H), 5.09 (s, 2H), 3.45 (s, 2H), 2.17 (s, 3H).

Intermediate d48: 3-morpholinobenzyl 3-oxobutanoate

Yellow oil (0.71 g, 92%).
$^1$H-NMR (300 MHz, CDCl$_3$) δ=7.30 (d, J=7.9 Hz, 1H), 6.94-6.86 (m, 3H), 5.16 (s, 2H), 3.90-3.86 (m, 4H), 3.51 (s, 2H), 3.21-3.17 (m, 4H), 2.27 (s, 3H).

Intermediate d49: (2-Chloropyridin-4-yl)methyl 3-oxobutanoate

Yellow oil (0.50 g, 63%).
$^1$H-NMR (300 MHz, CDCl$_3$) δ=8.41-8.33 (m, 1H), 7.32 (s, 1H), 7.19 (d, J=5.1 Hz, 1H), 5.17 (s, 2H), 3.58 (s, 2H), 2.28 (s, 3H).

Intermediate d50: 4,4-Difluorocyclohexyl 3-oxobutanoate

Yellow oil (0.35 g, 91%).
$^1$H-NMR (300 MHz, CDCl$_3$) δ=4.93 (s, 1H), 4.53 (s, 2H), 2.04 (d, J=1.1 Hz, 3H), 1.89-1.78 (m, 8H). $^{19}$F NMR (282 MHz, CDCl$_3$) δ=−94.48 (d, J=252.2 Hz, CF), −100.51 (d, J=235.8 Hz, CF).

Intermediate d51: N-benzyl-N-methyl-3-oxobutanamide

Yellow oil (2.50 g, 86%).
$^1$H-NMR (300 MHz, CDCl$_3$) δ=7.38-7.23 (m, 5H), 4.56 (d, J=32.5 Hz, 3H), 3.60 (d, J=12.5 Hz, 2H), 2.89 (s, 2H), 2.29 (s, 3H).

Intermediate d52: 4-chlorobenzyl 3-oxobutanoate

Yellow oil (0.5 g, 34%).
$^1$H-NMR (300 MHz, CDCl$_3$) δ=7.49 (d, J=8.0 Hz, 2H), 7.23 (d, J=8.0 Hz, 2H), 5.12 (s, 2H), 3.50 (s, 2H), 2.24 (s, 3H).

Intermediate d53: 3-chlorobenzyl 3-oxobutanoate

Yellow oil (0.119 g, 75%).
$^1$H-NMR (300 MHz, CDCl$_3$-d) δ (ppm): 7.35 (s, 1H), 7.33-7.27 (m, 2H), 7.25-7.19 (m, 1H), 5.14 (s, 2H), 3.52 (s, 2H), 2.26 (s, 3H).

Intermediate d54: 2-phenylpropan-2-yl 3-oxobutanoate

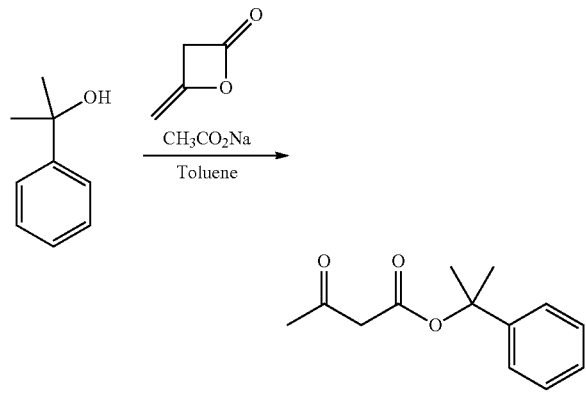

Modified procedure d using 4-methyleneoxetan-2-one (1 eq) and sodium acetate (0.1 eq) yielded the title compound as yellow oil (2.46 g, 76%).
$^1$H-NMR (300 MHz, CDCl$_3$) δ=7.41-7.27 (m, 5H), 3.42 (s, 2H), 2.25 (s, 3H), 1.80 (s, 6H).

Intermediate d55: 2-(4-Fluorophenyl)propan-2-yl 3-oxobutanoate

Modified procedure d using 4-methyleneoxetan-2-one (1 eq) yielded the title compound as yellow oil (0.52 g, 34%).
$^1$H-NMR (300 MHz, CDCl$_3$-d) δ (ppm): 7.40-7.31 (m, 2H), 7.05-6.95 (m, 2H), 3.41 (s, 2H), 2.23 (s, 3H), 1.78 (s, 6H).
$^{19}$F NMR (282 MHz, CDCl$_3$-d) δ (ppm): −115.79 (CF).

Intermediate d56: 2H-thiopyran-3,5(4H,6H)-dione

Synthesis according to literature procedure J. Org. Chem. 1977, 42, 1163-1169 yielded yellow oil (2.1 g, 52%).
$^1$H-NMR (300 MHz, CDCl$_3$) δ=3.57 (s, 2H), 3.39 (s, 4H).

Intermediate d57: 3-((4-Methylpiperazin-1-yl)methyl)benzyl 3-oxobutanoate

Step 1: Synthesis of 3-((4-methylpiperazin-1-yl)methyl)benzoate

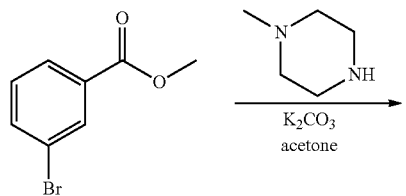

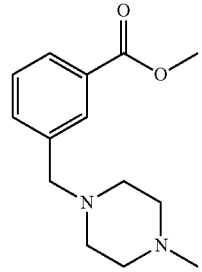

To a solution of 1-methylpiperazine (3.0 mL, 26.89 mmol, 3.08 eq.) in acetone (35 ml) was added potassium carbonate (2.41 g, 17.46 mmol, 2 eq). The mixture was stirred for 10 minutes. Then methyl 3-bromobenzoate (2.0 g, 8.73 mmol, 1.0 eq.) was added, and the mixture was stirred at room temperature overnight. The solid was removed by filtration, and the filtrate was concentrated and purified by flash column chromatography on silica gel using dichloromethane/3% methanol as eluent to afford methyl 3-((4-methylpiperazin-1-yl)methyl)benzoate as a yellow oil (2.1 g, 97%).
$^1$H-NMR (300 MHz, CDCl$_3$-d) δ (ppm): 7.97 (s, 1H), 7.92 (dt, J=7.7, 1.4 Hz, 1H), 7.53 (d, J=7.7 Hz, 1H), 7.38 (t, J=7.7 Hz, 1H), 3.91 (s, 3H), 3.55 (s, 2H), 2.48 (bs, 8H), 2.29 (s, 3H).

Step 2: Synthesis of (3-((4-methylpiperazin-1-yl)methyl)phenyl)methanol

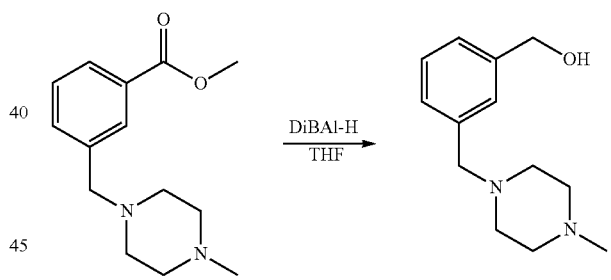

To a solution of methyl 3-((4-methylpiperazin-1-yl)methyl)benzoate (2.02 g, 8.13 mmol, 1 eq.) in tetrahydrofurane (60 ml) was added under vigorous stirring diisobutylaluminum hydride (18.73 mL, 18.73 mmol, 2.26 eq). The mixture was stirred at room temperature for 5 hours. Then Rochele's salt solution (105 mL) and dichloromethane (105 mL) were added. The mixture was stirred at room temperature for 60 minutes and then extracted with dichloromethane (×3) and dried (Na$_2$SO$_4$). The solvent was removed under reduced pressure, and the resulting residue was purified by flash column chromatography on silica gel using dichloromethane/7% methanol as eluent to afford (3-((4-methylpiperazin-1-yl)methyl)phenyl)methanol as a yellow oil (1.75 g, 98%).
$^1$H-NMR (300 MHz, CDCl$_3$-d) δ (ppm): 7.32-7.15 (m, 4H), 4.62 (s, 2H), 3.71 (t, J=6.2 Hz, 1H), 3.45 (s, 2H), 2.37 (bs, 8H), 2.20 (s, 3H).

Step 3: Synthesis of 3-((4-Methylpiperazin-1-yl)methyl)benzyl 3-oxobutanoate Transformation of (3-((4-methylpiperazin-1-yl)methyl) phenyl)methanol using General procedure d yielded the title compound as a yellow oil (0.55 g, 81%).
$^1$H-NMR (300 MHz, CDCl$_3$-d) δ (ppm): 7.36-7.28 (m, 3H), 7.24-7.20 (m, 1H), 5.17 (s, 2H), 3.52 (s, 2H), 3.50 (s, 2H), 2.53 (bs, 8H), 2.34 (s, 3H), 2.25 (s, 3H).

Intermediate d58: Cyclopropyl 3-oxobutanoate

Modified procedure d using 4-methyleneoxetan-2-one (1 eq) and sodium acetate (0.1 eq) yielded the title compound as a yellow oil (1.99 g, 81%).
$^1$H-NMR (300 MHz, CDCl$_3$) δ=4.19-4.04 (m, 1H), 3.39 (s, 2H), 2.22 (s, 3H), 0.79-0.58 (m, 4H).

Intermediate d59: Prop-2-yn-1-yl 3-oxobutanoate

General procedure d yielded the title compound as a yellow oil (2.5 g, 91%).
$^1$H-NMR (300 MHz, CDCl$_3$) δ=4.74 (d, J=2.5 Hz, 2H), 3.50 (s, 2H), 2.50 (t, J=2.5 Hz, 1H), 2.28 (s, 3H).

Intermediate d60: But-2-yn-1-yl 3-oxobutanoate

General procedure d yielded the title compound as a yellow oil (3.0 g, 92%).
$^1$H-NMR (300 MHz, CDCl$_3$) δ=4.65 (q, J=2.2 Hz, 2H), 3.44 (s, 2H), 2.22 (s, 3H), 1.80 (t, J=2.2 Hz, 3H).

Intermediate d61: 2,2,2-Trifluoroethyl 3-oxobutanoate

General procedure d yielded the title compound as a yellow oil (2.1 g, 81%).
$^1$H-NMR (300 MHz, CDCl$_3$) δ=4.53 (q, J=7.6, 6.9 Hz, 2H), 3.57 (s, 2H), 2.29 (s, 3H).

General Procedure e

Intermediate e1: Oxetan-3-yl 3-cyclopropyl-3-oxopropanoate

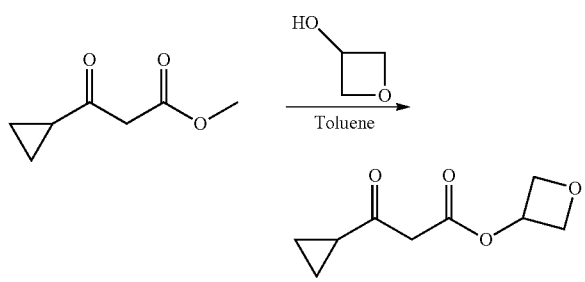

To a solution of methyl 3-cyclopropyl-3-oxopropanoate (1 g, 7.03 mmol, 1.2 eq.) in toluene (5 ml) was added oxetan-3-ol (0.37 ml, 5.87 mmol, 1 eq). The resultant mixture was refluxed using a Dean-Stark trap for 12 hours, cooled to RT and concentrated. The resulting residue was purified by flash column chromatography on silica gel using ethyl acetate/hexane (1:3) as eluent to afford the title compound as a light-yellow oil (0.52 g, 44%).

$^1$H-NMR (300 MHz, CDCl$_3$) δ=5.50 (p, J=5.8 Hz, 1H), 4.99-4.81 (m, 2H), 4.66 (dd, J=7.8, 5.8 Hz, 2H), 3.63 (s, 2H), 2.02 (tt, J=7.8, 4.5 Hz, 1H), 1.17-1.08 (m, 2H), 1.05-0.93 (m, 2H).

Intermediate e2: Isopropyl 3-cyclopropyl-3-oxopropanoate

General procedure e yielded the title compound as a light-yellow oil (0.9 g, 75%).
$^1$H-NMR (300 MHz, CDCl$_3$) δ=5.06 (hept, J=6.4 Hz, 1H), 3.52 (s, 2H), 2.14-1.93 (m, 1H), 1.26 (s, 3H), 1.24 (s, 3H), 1.15-1.06 (m, 2H), 1.00-0.90 (m, 2H).

Intermediate e3: Benzyl 4,4,4-trifluoro-3-oxobutanoate

General procedure e yielded the title compound as a red oil (1.8 g, 62%).
$^1$H-NMR (300 MHz, CDCl$_3$) δ=7.37 (s, 5H), 5.24 (s, 2H), 2.86 (s, 2H). $^{19}$F NMR (282 MHz, CDCl$_3$) δ=−87.15.

Intermediate e4: 2-Phenylpropan-2-yl 3-cyclopropyl-3-oxopropanoate

General procedure e using 1 eq of DMAP yielded the title compound as a yellow oil (0.41 g, 29%).
$^1$H-NMR (300 MHz, CDCl$_3$-d) δ (ppm): 7.40-7.31 (m, 4H), 7.23 (d, J=6.9 Hz, 1H), 3.53 (s, 2H), 2.03-1.99 (m, 1H), 1.80 (s, 6H), 1.15-1.09 (m, 2H), 1.00-0.89 (m, 2H).

Intermediate e5: Cyclohexyl 3-cyclopropyl-3-oxopropanoate

General procedure e yielded the title compound as a light-yellow solid (1.2 g, 85%).
$^1$H-NMR (300 MHz, CDCl$_3$-d) δ (ppm): 4.91-4.75 (m, 1H), 3.52 (s, 2H), 2.12-1.95 (m, 1H), 1.93-1.79 (m, 2H), 1.78-1.60 (m, 2H), 1.53-1.23 (m, 6H), 1.18-1.04 (m, 2H), 1.03-0.88 (m, 2H).

Intermediate e6: 3-Chlorobenzyl 3-cyclopropyl-3-oxopropanoate

General procedure e yielded the title compound as a yellow oil (0.69 g, 78%).
$^1$H-NMR (300 MHz, CDCl$_3$-d) δ (ppm): 7.35 (s, 1H), 7.32-7.27 (m, 2H), 7.25-7.20 (m, 1H), 5.15 (s, 2H), 3.63 (s, 2H), 2.09-1.92 (m, 1H), 1.20-1.05 (m, 2H), 1.03-0.87 (m, 2H).

Intermediate e7: 2-(4-Fluorophenyl)propan-2-yl 3-cyclopropyl-3-oxopropanoate General procedure e yielded the title compound as a yellow oil (0.52 g, 35%).
$^1$H-NMR (300 MHz, CDCl$_3$-d) δ (ppm): 7.40-7.31 (m, 2H), 7.05-6.96 (m, 2H), 3.53 (s, 2H), 2.01 (tt, J=7.7, 4.4 Hz, 1H), 1.78 (s, 6H), 1.12 (pd, J=3.5, 1.4 Hz, 2H), 0.96 (dt, J=7.7, 3.5 Hz, 2H).
$^{19}$F NMR (282 MHz, CDCl$_3$-d) δ (ppm): −115.92 (CF).

Intermediate e8: Cyclopropylmethyl 3-cyclopropyl-3-oxopropanoate

General procedure e using 1 eq DMAP yielded the title compound as a light-yellow oil (2.2 g, 84%).
$^1$H-NMR (300 MHz, CDCl$_3$-d) δ (ppm): 3.98 (d, J=7.3 Hz, 2H), 3.58 (s, 2H), 2.05 (tt, J=7.9, 4.6 Hz, 1H), 1.24-1.04

(m, 3H), 1.02-0.91 (m, 2H), 0.61-0.51 (m, 2H), 0.29 (dt, J=6.4, 4.6 Hz, 2H).

Intermediate e9: 3-Bromobenzyl 3-cyclopropyl-3-oxopropanoate

General procedure e yielded the title compound as a yellow oil (0.28 g, 27%).

$^1$H-NMR (300 MHz, CDCl$_3$-d) δ (ppm): 7.51 (s, 1H), 7.45 (dt, J=7.5, 1.7 Hz, 1H), 7.31-7.21 (m, 2H), 5.14 (s, 2H), 3.63 (s, 2H), 2.01 (tt, J=7.7, 4.5 Hz, 1H), 1.21-1.06 (m, 2H), 1.01-0.87 (m, 2H).

Intermediate e10: Cyclopentyl 3-cyclopropyl-3-oxopropanoate

General procedure e yielded the title compound as a light-yellow oil (0.54 g, 79%).

$^1$H-NMR (300 MHz, CDCl$_3$-d) δ (ppm): 5.22 (tt, J=6.0, 2.7 Hz, 1H), 3.51 (s, 2H), 2.02 (tt, J=7.8, 4.5 Hz, 1H), 1.92-1.78 (m, 2H), 1.77-1.65 (m, 4H), 1.64-1.53 (m, 2H), 1.16-1.04 (m, 2H), 0.95 (dt, J=7.8, 3.2 Hz, 2H).

Intermediate e11: Cyclopentyl 2-cyanoacetate

General procedure e yielded the title compound as a light-yellow oil (2.34 g, 50%).

$^1$H-NMR (300 MHz, CDCl$_3$-d) δ (ppm): 5.25 (td, J=5.8, 2.9 Hz, 1H), 3.41 (s, 2H), 1.96-1.82 (m, 2H), 1.81-1.68 (m, 4H), 1.67-1.55 (m, 2H).

General Procedure f

The synthetic method was adapted from Sabitha-G et al., Bismuth(III)Chloride-Catalyzed Highly Efficient Transeterification of β-Keto Esters, Helvetica Chimica Acta, Vol. 94; 2011.

Intermediate f1: Pyridin-4-ylmethyl 3-cyclopropyl-3-oxopropanoate

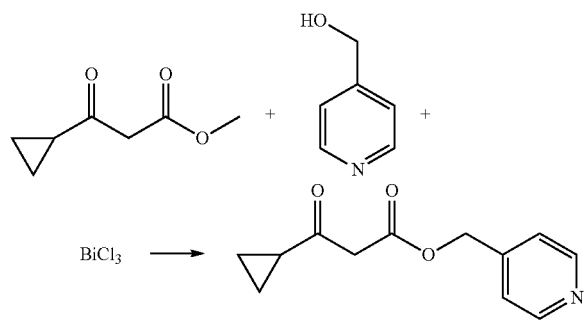

In a sealed flask, a mixture of 2.0 g of molecular sieves, 500 mg (4.58 mmol) of pyridin-4-ylmethanol, 0.83 mL (6.87 mmol) of methyl 3-cyclopropyl-3-oxopropanoate and 10% (0.45 mmol) of trichlorobismuthane in 10 mL of dry toluene was stirred at reflux for 36 hours. The reaction mixture was filtered and the filtrate concentrated, the remaining solid was purified by silica gel chromatography column (cyclohexane/ethyl acetate) to yield the desired p-keto ester (455 mg, 45%).

$^1$H-NMR (400 MHz, DMSO-d$_6$) δ=0.94 (m, 4H), 2.12 (ddd, 1H), 3.86 (s, 2H), 5.20 (s, 2H), 7.36 (d, 2H), 8.56 (d, 2H).

HPLC-MS: Rt 3.040; m/z 220.1 (MH$^+$).

The following intermediates were synthesized according to General procedure f.

Intermediate f2: 4-Fluorobenzyl 3-cyclopropyl-3-oxopropanoate $^1$H-NMR (400 MHz, DMSO-d$_6$) δ=0.91 (m, 4H), 2.08 (m, 1H), 3.77 (s, 2H), 5.12 (s, 2H), 7.21 (t, 2H), 7.43 (dd, 2H).

Intermediate f3: 4-Cyanobenzyl 3-cyclopropyl-3-oxopropanoate

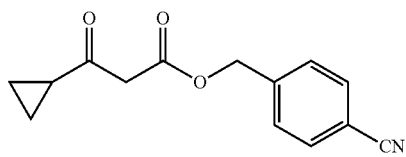 [SMILES: N#Cc1ccc(COC(=O)CC(=O)C2CC2)cc1]

$^1$H-NMR (400 MHz, DMSO-d$_6$) δ=0.93 (m, 4H), 2.10 (ddd, 1H), 3.83 (s, 2H), 5.24 (s, 2H), 7.56 (d, 2H), 7.86 (d, 2H).

HPLC-MS: Rt 4.133; m/z 244.0 (MH$^+$).

General Procedure q (Adapted from M. A. Walker et al, Bioorg. Med. Chem. Lett. 2006, 16, 2920-2924)

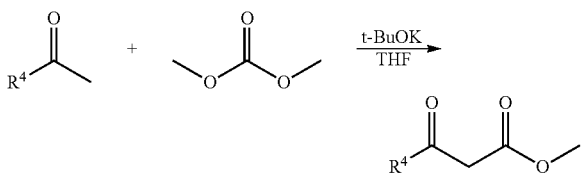

An aromatic ketone (1 eq) was dissolved in THF (0.5 M) at room temperature, and potassium tert-butoxide (3 eq) was added. The mixture was stirred for 5 minutes before dimethyl carbonate (10 eq) was added. The reaction mixture was stirred at RT for 5 hours, concentrated and quenched by the addition of water. The mixture was extracted with dichloromethane (×3), and the combined organic layers were washed with brine, dried (Na$_2$SO$_4$), filtered and concentrated. The crude product was purified by flash column chromatography on silica gel using ethyl acetate/hexane as eluent to afford the corresponding dicarbonyl compound.

The following intermediates were synthesized according to General procedure g.

Intermediate g1: Methyl 3-oxo-3-phenylpropanoate

Yellow oil (1.11 g, 66%).

$^1$H-NMR (300 MHz, CDCl$_3$) δ=7.95 (d, J=7.8 Hz, 2H), 7.65-7.41 (m, 3H), 4.01 (s, 2H), 3.76 (s, 3H).

Intermediate g2: Methyl 3-oxo-3-(pyridin-3-yl)propanoate

Yellow oil (1.22 g, 83%).

$^1$H-NMR (300 MHz, CDCl$_3$) δ=9.15 (dd, J=2.3, 1 Hz, 1H), 8.81 (dd, J=4.8, 1.7 Hz, 1H), 8.23 (ddd, J=8.0, 2.3, 1.7

Hz, 1H), 7.45 (ddd, J=8.0, 4.8, 0.9 Hz, 1H), 4.02 (s, 2H), 3.76 (s, 3H).

Intermediate g3: 1-Phenylpentane-2,4-dione

Yellow oil (1.11 g, 66%).
$^1$H-NMR (300 MHz, CDCl$_3$) δ=7.37-7.26 (m, 5H), 3.59 (s, 4H), 2.02 (s, 3H).

Intermediate g4: 1,3-Dicyclopropylpropane-1,3-dione

Light-yellow oil (1.3 g, 87%).
$^1$H-NMR (300 MHz, CDCl$_3$) δ=3.78 (s, 2H), 2.03 (td, J=7.9, 3.9 Hz, 2H), 1.14-1.04 (m, 8H).

Intermediate g5: tert-Butyl 3-(3-methoxy-3-oxopropanoyl)azetidine-1-carboxylate Yellow oil (0.4 g, 63%).
$^1$H-NMR (300 MHz, CDCl$_3$) δ=4.11-3.98 (m, 4H), 3.73 (s, 3H), 3.66-3.53 (m, 1H), 3.47 (s, 2H), 1.42 (s, 9H).

Intermediate g6: 1-(Pyridin-3-yl)butane-1,3-dione

Yellow oil (0.20 g, 30%).
$^1$H-NMR (300 MHz, CDCl$_3$) δ=15.95 (s, 1H), 9.05 (d, J=2.1 Hz, 1H), 8.71 (dd, J=4.8, 1.6 Hz, 1H), 8.14 (dt, J=8.0, 2.0 Hz, 1H), 7.38 (ddd, J=8.0, 4.9, 0.9 Hz, 1H), 6.17 (s, 1H), 2.21 (s, 3H).

Intermediate g7: Methyl 3-cyclobutyl-3-oxopropanoate

Colorless oil (1.97 g, 62%).
$^1$H-NMR (300 MHz, CDCl$_3$-d) δ (ppm): 3.71 (s, 3H), 3.45-3.31 (m, 3H), 2.32-2.06 (m, 4H), 2.05-1.74 (m, 2H).

Intermediate g8: Methyl 3-cyclopentyl-3-oxopropanoate

Colorless oil (0.51 g, 67%).
$^1$H-NMR (300 MHz, CDCl$_3$-d) δ (ppm): 3.73 (s, 3H), 3.50 (s, 2H), 2.98 (p, J=7.9 Hz, 1H), 1.89-1.73 (m, 4H), 1.68-1.57 (m, 4H).

Intermediate g9: Methyl 3-cyclohexyl-3-oxopropanoate

Colorless oil (1.14 g, 78%).
$^1$H-NMR (300 MHz, CDCl$_3$-d) δ (ppm): 3.71 (s, 3H), 3.48 (s, 2H), 2.44 (tt, J=11.1, 3.4 Hz, 1H), 1.91-1.83 (m, 2H), 1.84-1.71 (m, 2H), 1.44-1.13 (m, 6H).

Intermediate g10: (Z)-3-Amino-3-cyclopropylacrylonitrile

Colorless oil (1.3 g, 81%).
$^1$H-NMR (300 MHz, CDCl$_3$-d) δ (ppm): 4.63 (bs, 2H), 3.78 (s, 1H), 1.54-1.35 (m, 1H), 1.00-0.81 (m, 2H), 0.81-0.60 (m, 2H).

General Procedure h (Adapted from S. Mitsuhashi et al, J. Am. Chem. Soc. 2008, 130, 4140)

Preparation of Keto Ethers:

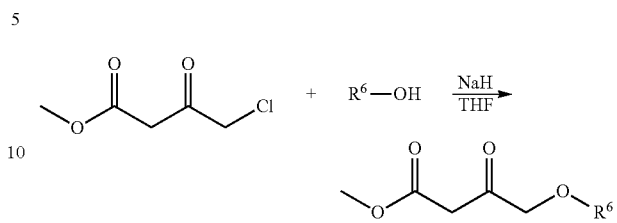

To a suspension of sodium hydride (2.2 eq) in THF (0.5 M) at RT, an alcohol (1.1 eq) was added dropwise. The mixture was stirred for 5 min before methyl 4-chloro-3-oxobutanoate (1 eq) was dropwise added. This mixture was stirred for 30 min and then concentrated in vacuum. Water was added, and the pH was adjusted to 6-7 by the addition of 2N aq. HCl. The resulting mixture was extracted with dichloromethane (×2) and ethyl acetate (×2), and the combined organic layers were washed with brine, dried (Na$_2$SO$_4$), filtered and concentrated. The resulting residue was purified by flash column chromatography on silica gel using ethyl acetate/hexane as eluent to afford the corresponding dicarbonyl compound.

Preparation of Keto Amines:

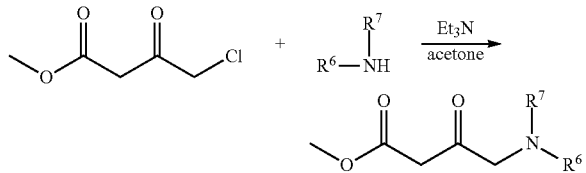

Methyl 4-chloro-3-oxobutanoate (1 eq) was dissolved in acetone (0.5 M) at RT, and an amine (1.1 eq) was added. The mixture was stirred for 5 min before trimethylamine (2 eq) was added. This mixture was stirred at 100° C. for 3 h and then concentrated under vacuum. The residue was taken up in water and extracted with dichloromethane (×2) and ethyl acetate (×2). The combined organic layers were washed with brine, dried (Na$_2$SO$_4$), filtered and concentrated. The resulting residue was purified by flash column chromatography on silica gel using ethyl acetate/hexane as eluent to afford the corresponding dicarbonyl compound.

The following intermediates were synthesized according to General procedure h.

Intermediate h1: Methyl 4-methoxy-3-oxobutanoate

Colorless oil (0.9 g, 93%).
$^1$H-NMR (300 MHz, CDCl$_3$) δ=4.10 (s, 2H), 3.75 (s, 3H), 3.50 (s, 2H), 3.40 (s, 3H).

Intermediate h2: Methyl 4-(dimethylamino)-3-oxobutanoate

Light-yellow oil (0.37 g, 35%).
$^1$H-NMR (300 MHz, CDCl$_3$) δ=3.73 (s, 3H), 3.51 (s, 2H), 3.20 (s, 2H), 2.28 (s, 6H).

Intermediate h3: Methyl 4-morpholino-3-oxobutanoate

Light-yellow oil (0.5 g, 37%).
$^1$H-NMR (300 MHz, CDCl$_3$) δ=3.76-3.78 (m, 7H), 3.51 (s, 2H), 3.25 (s, 2H), 2.55-2.43 (m, 4H).

Preparation of Enamine Intermediates

General Procedure i

Intermediate i1: Dimethyl (Z)-3-aminopent-2-enedioate

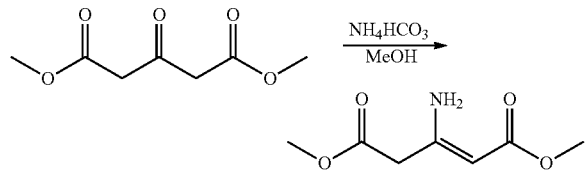

To a round bottom flask containing a dimethyl 3-oxopentanedioate (0.83 ml, 5.74 mmol, 1 eq.) in MeOH (10 ml) at room temperature was added ammonium bicarbonate (1.13 g, 14.35 mmol, 2.5 eq). The mixture was stirred at room temperature overnight and then concentrated. The resulting residue was purified by flash column chromatography on silica gel using ethyl acetate/hexane (1:3) as eluent to afford dimethyl (Z)-3-aminopent-2-enedioate as a yellow oil (0.8 g, 81%).

$^1$H-NMR (300 MHz, CDCl$_3$) δ=7.81 (bs, 1H), 5.50 (bs, 1H). 4.58 (s, 1H), 3.73 (s, 3H), 3.65 (s, 3H), 3.15 (s, 2H).

The following intermediates were synthesized according to General procedure i.

Intermediate i2: Cyclopropylmethyl (Z)-3-aminobut-2-enoate

White solid (0.45 g, 53%).
$^1$H-NMR (300 MHz, CDCl$_3$) δ=7.91 (bs, 2H), 4.56 (s, 1H), 3.88 (d, J=7.2 Hz, 2H), 1.90 (s, 3H), 1.19-1.07 (m, 1H), 0.58-0.50 (m, 2H), 0.32-0.23 (m, 2H).

Intermediate i3: Methyl (Z)-3-amino-5-methoxypent-2-enoate

Light-yellow oil (0.93 g, 94%).
$^1$H-NMR (300 MHz, CDCl$_3$) δ=7.83 (bs, 1H), 5.50 (bs, 1H), 4.49 (s, 1H), 3.63 (s, 3H), 3.59-3.54 (m, 2H), 3.36 (s, 3H), 2.37 (t, J=5.7 Hz, 2H).

Intermediate i4: Methyl (Z)-3-amino-4-(benzyloxy)but-2-enoate

Orange oil (0.55 g, 76%).
$^1$H-NMR (300 MHz, CDCl$_3$) δ=7.41-7.36 (m, 1H), 7.36-7.30 (m, 4H), 6.61 (bs, 1H), 5.27 (bs, 1H), 4.58-4.54 (m, 1H), 4.52 (s, 2H), 4.07 (d, J=0.7 Hz, 2H), 3.66 (s, 3H).

Intermediate i5: Methyl (Z)-3-amino-4-phenoxybut-2-enoate

Yellow solid (0.11 g, 65%).
$^1$H-NMR (300 MHz, CDCl$_3$) δ=7.35-7.27 (m, 2H), 7.05-6.87 (m, 3H), 5.86 (bs, 2H), 4.74-4.67 (m, 1H), 4.59 (d, J=0.8 Hz, 2H), 3.68 (s, 3H).

Intermediate i6: 5-Amino-2H-thiopyran-3(6H)-one

Brown solid (0.05 g, 35%).
$^1$H-NMR (300 MHz, CDCl$_3$) δ=6.97 (bs, 2H), 4.94 (s, 1H), 3.31 (s, 2H), 3.03 (s, 2H).

Intermediates i7 and i8: (Z)-4-amino-1-methoxypent-3-en-2-one and (Z)-4-amino-5-methoxypent-3-en-2-one General procedure i yielded a mixture of the title compounds that were separated by flash chromatography.

i7: (Z)-4-amino-1-methoxypent-3-en-2-one; light yellow oil, 0.703 g, 74%.
$^1$H-NMR (300 MHz, CDCl$_3$) δ=9.56 (bs, 1H), 5.72 (bs, 1H), 5.00 (s, 1H), 3.97 (s, 2H), 3.38 (s, 3H), 2.05 (s, 3H).

i8: (Z)-4-amino-5-methoxypent-3-en-2-one; light yellow oil, 0.25 g, 26%.
$^1$H-NMR (300 MHz, CDCl$_3$) δ=9.85 (bs, 1H), 5.31 (s, 1H), 5.12 (bs, 1H), 3.89 (s, 2H), 3.41 (s, 3H), 1.97 (s, 3H).

Intermediate i9: Methyl (Z)-3-amino-4-fluorobut-2-enoate

Yellowish solid (0.22 g, 55%).
$^1$H-NMR (300 MHz, CDCl$_3$) δ=6.35 (bs, 2H), 4.89 (d, J=46.9 Hz, 2H), 4.59 (s, 1H), 3.67 (s, 3H). $^{19}$F NMR (282 MHz, CDCl$_3$) δ=122.24 (t, J=46.9 Hz).

Intermediate i10: Cyclohexylmethyl (Z)-3-aminobut-2-enoate

Yellowish oil (0.8 g, 73%).
$^1$H-NMR (300 MHz, CDCl$_3$) δ=7.88 (s, 2H), 4.53 (s, 1H), 3.86 (d, J=6.6 Hz, 2H), 1.90 (s, 3H), 1.87-1.47 (m, 6H), 1.38-1.12 (m, 3H), 1.08-0.76 (m, 2H).

Intermediate i11: Cyclopentylmethyl (Z)-3-aminobut-2-enoate

Yellowish oil (0.3 g, 55%).
$^1$H-NMR (300 MHz, CDCl$_3$) δ=7.92 (s, 2H), 4.54 (s, 1H), 3.93 (d, J=7.1 Hz, 2H), 2.20 (p, J=7.5 Hz, 1H), 1.90 (s, 3H), 1.74 (dtdd, J=13.6, 7.5, 5.2, 3.4 Hz, 2H), 1.67-1.46 (m, 4H), 1.34-1.18 (m, 2H).

Intermediate i12: Cyclohexyl (Z)-3-aminobut-2-enoate

Yellowish oil (0.75 g, 63%).
$^1$H-NMR (300 MHz, CDCl$_3$) δ=7.90 (s, 2H), 4.73 (tt, J=8.8, 4.3 Hz, 1H), 4.52 (s, 1H), 2.27 (s, 3H), 1.72 (d, J=10.3 Hz, 4H), 1.61-1.49 (m, 4H), 1.49-1.35 (m, 2H).

Intermediate i13: Cyclopentyl (Z)-3-aminobut-2-enoate

Yellowish oil (0.17 g, 24%).
$^1$H-NMR (300 MHz, CDCl$_3$) δ=7.90 (s, 2H), 4.73 (tt, J=8.8, 4.3 Hz, 1H), 4.52 (s, 1H), 2.27 (s, 3H), 1.72 (d, J=10.3 Hz, 2H), 1.61-1.49 (m, 4H), 1.49-1.35 (m, 2H).

Intermediate i14: Benzyl (Z)-3-aminobut-2-enoate

Yellowish oil (0.203 g, 68%).
$^1$H-NMR (300 MHz, CDCl$_3$) δ=7.91 (s, 2H), 7.36-7.28 (m, 5H), 5.12 (s, 2H), 4.61 (s, 1H), 1.91 (s, 3H).

Intermediate i15: (Tetrahydro-2H-pyran-4-yl)methyl (Z)-3-aminobut-2-enoate

Yellowish oil (0.23 g, 77%).
$^1$H-NMR (300 MHz, CDCl$_3$) δ=7.85 (s, 2H), 4.51 (s, 1H), 4.05-3.85 (m, 4H), 3.37 (td, J=11.8, 2.2 Hz, 2H), 1.96-1.86 (m, 4H), 1.62 (ddt, J=10.8, 4.3, 2.2 Hz, 2H), 1.35 (dtd, J=13.3, 11.8, 4.5 Hz, 2H).

Intermediate i16: (Tetrahydro-2H-pyran-4-yl)methyl (Z)-3-aminobut-2-enoate

Yellowish oil (0.23 g, 77%).
$^1$H-NMR (300 MHz, CDCl$_3$) δ=7.85 (s, 2H), 4.51 (s, 1H), 4.05-3.85 (m, 4H), 3.37 (td, J=11.8, 2.2 Hz, 2H), 1.96-1.86 (m, 4H), 1.62 (ddt, J=10.8, 4.3, 2.2 Hz, 2H), 1.35 (dtd, J=13.3, 11.8, 4.5 Hz, 2H).

Intermediate i17: Pyridin-4-ylmethyl (Z)-3-aminobut-2-enoate

Yellow oil (0.19 g, 69%).
$^1$H-NMR (300 MHz, CDCl$_3$) δ=8.71-8.39 (m, 2H), 7.89 (s, 2H), 7.29-7.23 (m, 2H), 5.13 (s, 2H), 4.64 (s, 1H), 1.94 (s, 3H).

Intermediate i18: 4-Fluorobenzyl (Z)-3-aminobut-2-enoate

Yellow oil (0.72 g, 96%).
$^1$H-NMR (300 MHz, CDCl$_3$) δ=7.96 (s, 2H), 7.40-7.30 (m, 2H), 7.11-6.89 (m, 2H), 5.07 (s, 2H), 4.58 (s, 1H), 1.97-1.81 (m, 3H).

Intermediate i19: tert-Butyl (Z)-4-(((3-aminobut-2-enoyl)oxy)methyl)benzoate Yellow oil (0.40 g, 89%).
$^1$H-NMR (300 MHz, CDCl$_3$) δ=7.98-7.92 (m, 2H), 7.42-7.33 (m, 2H), 5.15 (s, 2H), 4.61 (s, 1H), 1.92 (s, 3H), 1.58 (s, 9H) 1.28 (s, 2H).

Intermediate i20: Pyridin-3-ylmethyl (Z)-3-aminobut-2-enoate

Yellowish oil (0.50 g, 71%).
$^1$H-NMR (300 MHz, CDCl$_3$) δ=8.62 (d, J=1.7 Hz, 1H), 8.54 (dd, J=4.8, 1.6 Hz, 1H), 7.94 (s, 2H), 7.70 (dt, J=7.8, 1.9 Hz, 1H), 7.31-7.27 (m, 1H), 5.12 (s, 2H), 4.58 (s, 1H), 1.92 (s, 3H).

Intermediate i21: 4-Bromobenzyl (Z)-3-aminobut-2-enoate

Light-yellow oil (0.48 g, 95%).
$^1$H-NMR (300 MHz, CDCl$_3$) δ=7.85 (s, 2H), 7.46 (d, J=8.4 Hz, 2H), 7.23 (d, J=8.4 Hz, 2H), 5.05 (s, 2H), 4.58 (s, 1H), 1.91 (s, 3H).

Intermediate i22: 3-Bromobenzyl (Z)-3-aminobut-2-enoate

Light-yellow oil (0.2 g, 69%).
$^1$H-NMR (300 MHz, CDCl$_3$) δ=7.92 (s, 2H), 7.51 (s, 1H), 7.44 (m, 2H), 7.24-7.18 (m, 1H), 5.07 (s, 2H), 3.52 (s, 1H), 1.92 (s, 3H).

Intermediate i23: 2-Bromobenzyl (Z)-3-aminobut-2-enoate

Light-yellow oil (0.45 g, 90%).
$^1$H-NMR (300 MHz, CDCl$_3$) δ=7.95 (bs, 2H), 7.61-7.44 (m, 1H), 7.41 (d, J=7.6 Hz, 1H), 7.33-7.22 (m, 1H), 7.22-7.06 (m, 1H), 5.19 (s, 2H), 4.64 (s, 1H), 1.93 (s, 3H).

Intermediate i24: (3-Fluoropyridin-4-yl)methyl (Z)-3-aminobut-2-enoate

Light-yellow oil (0.207 g, 69%).
$^1$H-NMR (300 MHz, CDCl$_3$) δ=8.55-8.30 (m, 2H), 7.92 (bs, 2H), 7.35 (t, J=5.6 Hz, 1H), 5.22 (s, 2H), 4.64 (s, 1H), 1.95 (s, 3H). $^{19}$F NMR (282 MHz, CDCl$_3$) δ=−132.71 (s, F).

Intermediate i25: Pyrimidin-5-ylmethyl(Z)-3-aminobut-2-enoate

Light-yellow oil (0.415 g, 64%).
$^1$H-NMR (300 MHz, CDCl$_3$) δ=9.16 (s, 1H), 8.77 (d, J=4.8 Hz, 2H), 7.94 (bs, 2H), 5.12 (s, 2H), 3.53 (s, 1H), 1.93 (s, 3H).

Intermediate i26: (5-Bromopyridin-3-yl)methyl (Z)-3-aminobut-2-enoate

Light-yellow oil (0.364 g, 73%).
$^1$H-NMR (300 MHz, CDCl$_3$) δ=9.16 (d, J=4.8 Hz, 1H), 8.77 (d, J=4.8 Hz, 1H), 7.94 (s, 3H), 5.12 (s, 2H), 3.53 (s, 1H), 1.93 (s, 3H).

Intermediate i27: 2-Phenylpropan-2-yl (Z)-3-aminobut-2-enoate

Light-yellow oil (0.20 g, 69%).
$^1$H-NMR (300 MHz, CDCl$_3$) δ=7.74 (bs, 1H), 7.41-7.29 (m, 5H), 4.61 (s, 1H), 4.34 (bs, 2H), 1.88 (s, 3H), 1.76 (s, 6H).

Intermediate i28: 3-cyanobenzyl (Z)-3-aminobut-2-enoate

Light-yellow oil (0.52 g, 93%).
$^1$H-NMR (300 MHz, CDCl$_3$) δ=7.92 (bs, 2H), 7.66 (s, 1H), 7.57 (d, J=7.9 Hz, 2H), 7.51-7.36 (m, 1H), 5.12 (s, 2H), 4.60 (s, 1H), 1.93 (s, 3H).

Intermediate i29: 4-cyanobenzyl (Z)-3-aminobut-2-enoate

Light-yellow oil (0.56 g, 90%).
$^1$H-NMR (300 MHz, CDCl$_3$) δ=7.92 (bs, 2H), 7.67-7.61 (m, 2H), 7.44 (d, J=7.9 Hz, 2H), 5.15 (s, 2H), 4.61 (s, 1H), 1.93 (s, 3H).

Intermediate i30: 4-cyanobenzyl (Z)-3-aminobut-2-enoate

Light-yellow oil (0.22 g, 75%).
$^1$H-NMR (300 MHz, CDCl$_3$) δ=8.37 (s, 1H), 7.90 (s, 2H), 7.65 (dd, J=8.2, 2.4 Hz, 1H), 7.30 (dd, J=12.8, 8.2 Hz, 1H), 5.07 (s, 2H), 4.54 (s, 1H), 1.90 (s, 3H).

Intermediate i31: 3-Morpholinobenzyl (Z)-3-aminobut-2-enoate

Light-yellow oil (0.69 g, 97%).
$^1$H-NMR (300 MHz, CDCl$_3$) δ=7.92 (s, 2H), 7.31-7.20 (m, 1H), 6.88 (dd, J=16.4, 8.5 Hz, 3H), 5.07 (s, 2H), 4.60 (s, 1H), 3.86 (t, J=4.8 Hz, 4H), 3.16 (t, J=4.8 Hz, 4H), 1.91 (s, 3H).

Intermediate i32: 4,4-Dimethylcyclohexyl (Z)-3-aminobut-2-enoate

Light-yellow oil (0.55 g, 81%).
$^1$H-NMR (300 MHz, CDCl$_3$) δ=7.85 (bs, 2H), 4.71 (tt, J=8.9, 4.2 Hz, 1H), 4.52 (s, 1H), 1.90 (s, 3H), 1.82-1.70 (m, 2H), 1.58 (dt, J=9.3, 5.8 Hz, 2H), 1.49-1.39 (m, 2H), 1.26 (ddd, J=13.7, 10.8, 4.1 Hz, 2H), 0.93 (s, 3H), 0.91 (s, 3H).

Intermediate i33: (2-chloropyridin-4-yl)methyl (Z)-3-aminobut-2-enoate

Light-yellow oil (0.25 g, 83%).
$^1$H-NMR (300 MHz, CDCl$_3$) δ=8.33 (d, J=5.4 Hz, 1H), 7.92 (bs, 2H), 7.30 (s, 1H), 7.17 (d, J=5.4 Hz, 1H), 5.10 (s, 2H), 4.64 (s, 1H), 1.95 (s, 3H).

Intermediate i34: 4,4-difluorocyclohexyl (Z)-3-aminobut-2-enoate

Light-yellow oil (0.30 g, 94%).
$^1$H-NMR (300 MHz, CDCl$_3$) δ=7.86 (bs, 2H), 5.16-4.75 (m, 1H), 4.53 (s, 1H), 2.16-1.98 (m, 3H), 2-1.78 (m, 8H). $^{19}$F NMR (282 MHz, CDCl$_3$) δ=−94.48 (d, J=252.2 Hz), −100.51 (d, J=235.8 Hz).

Intermediate i35: (Z)-3-Amino-N-benzyl-N-methylbut-2-enamide

Light-yellow oil (0.70 g, 71%).
$^1$H-NMR (300 MHz, CDCl$_3$) δ=7.54-6.96 (m, 7H), 4.72 (s, 1H), 4.56 (m, 2H), 2.92 (s, 3H), 1.90 (s, 3H).

Intermediate i36: oxetan-3-yl (Z)-3-aminobut-2-enoate

Light-yellow oil (0.04 g, 17%).
$^1$H-NMR (300 MHz, CDCl$_3$) δ=6.33 (s, 2H), 5.42 (tt, J=6.4, 5.6 Hz, 1H), 4.87 (td, J=6.8, 1.0 Hz, 2H), 4.66 (ddd, J=6.9, 5.6, 1.0 Hz, 2H), 4.50 (s, 1H), 1.48-1.38 (m, 1H), 0.98-0.83 (m, 2H), 0.83-0.70 (m, 2H).

Intermediate i37: 3-Chlorobenzyl (Z)-3-aminobut-2-enoate

Light-yellow oil (0.198 g, 99%).
$^1$H-NMR (300 MHz, CDCl$_3$-d) δ (ppm): 7.93 (bs, 1H), 7.36 (s, 1H), 7.33-7.26 (m, 1H), 7.24 (s, 2H), 5.08 (s, 2H), 4.89-4.39 (m, 2H), 1.93 (s, 3H).

Intermediate i38: 2-Phenylpropan-2-yl (Z)-3-amino-3-cyclopropylacrylate

Light-yellow solid (0.38 g, 93%).
$^1$H-NMR (300 MHz, CDCl$_3$-d) δ (ppm): 7.40-7.31 (m, 4H), 7.24-7.17 (m, 1H), 6.19 (s, 2H), 4.56 (s, 1H), 1.76 (s, 6H), 1.47-1.31 (m, 1H), 0.87-0.79 (m, 2H), 0.78-0.70 (m, 2H).

Intermediate i39: Cyclohexyl (Z)-3-amino-3-cyclopropylacrylate

Light-yellow solid (0.22 g, 43%).
$^1$H-NMR (300 MHz, CDCl$_3$-d) δ (ppm): 6.22 (bs, 2H), 4.80-4.58 (m, 1H), 4.46 (s, 1H), 1.97-1.77 (m, 2H), 1.80-1.61 (m, 2H), 1.56-1.18 (m, 7H), 0.90-0.78 (m, 2H), 0.78-0.68 (m, 2H).

Intermediate i40: (Z)-3-Amino-1,3-dicyclopropylprop-2-en-1-one

Light-yellow solid (0.22 g, 44%).
$^1$H-NMR (300 MHz, CDCl$_3$-d) δ (ppm): 9.82 (bs, 1H), 5.12 (s, 1H), 4.83 (bs, 1H), 1.75-1.59 (m, 1H), 1.49-1.32 (m, 1H), 1.01-0.84 (m, 4H), 0.84-0.76 (m, 2H), 0.76-0.63 (m, 2H).

Intermediate i41: 3-Chlorobenzyl (Z)-3-amino-3-cyclopropylacrylate

Light-yellow solid (0.14 g, 70%).
$^1$H-NMR (300 MHz, CDCl$_3$-d) δ (ppm): 7.37-7.29 (m, 1H), 7.23-7.17 (m, 3H), 6.25 (bs, 2H), 5.03 (s, 1H), 4.65 (s, 2H), 1.19-1.03 (m, 1H), 0.92-0.75 (m, 2H), 0.78-0.63 (m, 2H).

Intermediate i42: 2-(4-Fluorophenyl)propan-2-yl (Z)-3-aminobut-2-enoate

Light-yellow solid (0.20 g, 80%).
$^1$H-NMR (300 MHz, CDCl$_3$-d) δ (ppm): 7.77 (bs, 1H), 7.39-7.27 (m, 2H), 7.08-6.93 (m, 2H), 4.58 (s, 1H), 4.36 (bs, 1H), 1.88 (s, 3H), 1.74 (s, 6H).
$^{19}$F NMR (282 MHz, CDCl$_3$-d) δ (ppm): −117.11 (CF).

Intermediate i43: 2-(4-Fluorophenyl)propan-2-yl (Z)-3-amino-3-cyclopropylacrylate Yellow solid (0.43 g, 96%)

$^1$H-NMR (300 MHz, CDCl$_3$-d) δ (ppm): 7.41-7.28 (m, 2H), 7.09-6.89 (m, 2H), 6.11 (bs, 2H), 4.54 (s, 1H), 1.73 (s, 6H), 1.40 (qt, J=8.1, 5.0 Hz, 1H), 0.89-0.81 (m, 2H), 0.73 (dt, J=8.1, 5.0 Hz, 2H).
$^{19}$F NMR (282 MHz, CDCl$_3$-d) δ (ppm): −117.14 (CF).

Intermediate i44: 3-Bromobenzyl (Z)-3-amino-3-cyclopropylacrylate

Light-yellow solid (0.15 g, 54%).
$^1$H-NMR (300 MHz, CDCl$_3$-d) δ (ppm): 7.57-7.48 (m, 1H), 7.46-7.37 (m, 1H), 7.33-7.24 (m, 1H), 7.25-7.18 (m, 1H), 6.10 (bs, 2H), 5.06 (s, 1H), 3.75 (s, 2H), 2.10-1.93 (m, 1H), 1.18-1.03 (m, 2H), 1.03-0.92 (m, 2H).

Intermediate i45: Methyl (Z)-3-amino-3-cyclobutylacrylate

Light-yellow solid (0.35 g, 70%).
$^1$H-NMR (300 MHz, CDCl$_3$-d) δ (ppm): 6.98 (bs, 2H), 4.53 (s, 1H), 3.64 (s, 3H), 3.05 (p, J=8.4 Hz, 1H), 2.22-1.95 (m, 4H), 1.94-1.57 (m, 2H).

Intermediate i46: Methyl (Z)-3-amino-3-cyclopentylacrylate

Light-yellow solid (0.42 g, 83%).
$^1$H-NMR (300 MHz, CDCl$_3$-d) δ (ppm): 7.52 (bs, 2H), 4.59 (s, 1H), 3.63 (s, 3H), 2.49 (p, J=8.5 Hz, 1H), 2.07-1.85 (m, 2H), 1.85-1.40 (m, 6H).

Intermediate i47: Methyl (Z)-3-amino-3-cyclohexylacrylate

Light-yellow solid (0.45 g, 92%).
$^1$H-NMR (300 MHz, CDCl$_3$-d) δ (ppm): 17.57 (bs, 2H), 4.54 (s, 1H), 3.63 (s, 3H), 1.98-1.60 (m, 6H), 1.35-1.13 (m, 5H).

Intermediate i48: 3-((4-Methylpiperazin-1-yl)methyl)benzyl (Z)-3-aminobut-2-enoate Yellow solid (0.54 g, 98%).
$^1$H-NMR (300 MHz, CDCl$_3$-d) δ (ppm): 7.91 (s, 2H), 7.29 (s, 4H), 5.09 (s, 2H), 4.60 (s, 1H), 3.51 (s, 2H), 2.52 (bs, 8H), 2.33 (s, 3H), 1.91 (s, 3H).
Other Methods of Enamine Preparation:
The following enamines have been prepared by alternative procedures:

Intermediate i49: 2,2,2-trifluoroethyl (Z)-3-aminobut-2-enoate

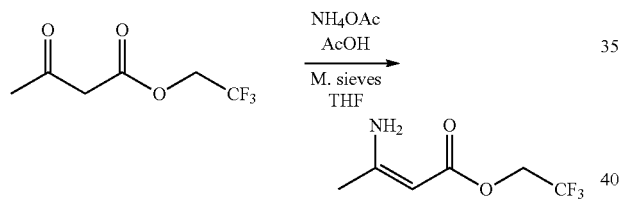

2,2,2-trifluoroethyl 3-oxobutanoate (1 g, 5.43 mmol, 1 eq) was dissolved in THF (1.2 M) at RT, and molecular sieves (2 g), ammonium acetate (0.83 g, 10.87 mmol, 2 eq) and acetic acid (0,310 ml, 5.43 mmol, 1 eq) were added. The reaction mixture was heated at 110° C. for 6 hours and then allowed to cool to RT. Water was added, and the mixture was extracted with ethyl acetate (×3). The combined organic layers were washed with brine, dried (Na$_2$SO$_4$), filtered and concentrated. The residue was purified by flash column chromatography on silica gel using ethyl acetate/hexane (1:3) as eluent to afford 2,2,2-trifluoroethyl (Z)-3-aminobut-2-enoate (0.5 g, 56%).
$^1$H-NMR (300 MHz, CDCl$_3$) δ=7.89 (bs, 1H), 4.84 (bs, 1H), 4.59 (s, 1H), 4.44 (q, J=8.7 Hz, 2H), 1.93 (s, 3H). $^{19}$F NMR (282 MHz, CDCl$_3$) δ=−73.40 (t, J=8.6 Hz, 3F).

Intermediate i50: Methyl (Z)-3-amino-3-(pyridin-3-yl)acrylate

The procedure described for 2,2,2-trifluoroethyl (Z)-3-aminobut-2-enoate (see above) was followed to obtain the title compound (0.7 g, 72%).
$^1$H-NMR (300 MHz, CDCl$_3$) δ=8.80 (s, 1H), 8.66 (s, 1H), 7.82 (d, J=7.8 Hz, 1H), 7.40-7.30 (m, 1H), 4.96 (s, 1H), 3.72 (s, 3H).

Intermediate i51: Mixture of (Z)-4-amino-5-phenyl-pent-3-en-2-one and (Z)-4-amino-1-phenylpent-3-en-2-one The procedure described for 2,2,2-trifluoroethyl (Z)-3-aminobut-2-enoate (see above) was followed to obtain a mixture of (Z)-4-amino-5-phenylpent-3-en-2-one and (Z)-4-amino-1-phenylpent-3-en-2-one as a yellow oil (0.5 g, 79%) that was used as such in the subsequent step.

Intermediate i52: (Z)-4-Aminopent-3-en-2-one

Prepared according to the process described in U.S. Pat. No. 8,030,302 (3.7 g, 74%).
$^1$H-NMR (300 MHz, CDCl$_3$) δ=9.70 (bs, 1H), 5.04 (bs, 1H), 4.92 (s, 1H), 2.03 (s, 3H), 1.91 (s, 3H).

Intermediate i53: 5-Amino-2H-pyran-3(6H)-one

Literature procedure Synth. Comm. 2004, 34, 557-565 yielded the title compound as a dark orange solid (0.35 g, 90%).
$^1$H-NMR (300 MHz, CDCl$_3$) δ=7.03 (bs, 2H), 5.01 (s, 1H), 4.18 (s, 2H), 3.80 (s, 2H).

Preparation of Amidine Intermediates

General Procedure y

Intermediate y1: Cyclopentyl 3-amino-3-iminopropanoate hydrochloride

Step 1: Synthesis of cyclopentyl 3-imino-3-phenoxypropanoate hydrochloride

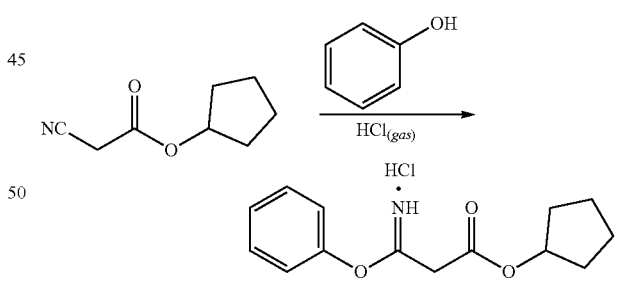

A mixture of cyclopentyl 2-cyanoacetate (2.81 g, 18.34 mmol, 1.15 eq) and phenol (1.50 g, 15.95 mmol, 1.3 eq) was stirred at −20° C., when HCl gas was bubbled into the mixture for 90 min. Then, the mixture was left at 4° C. for two days without stirring. Cold ether was added, and the mixture was stirred at 0° C. The solid formed and was filtered off and washed with cold ether to afford cyclopentyl 3-imino-3-phenoxypropanoate hydrochloride as a white solid (2.76 g, 61%).
$^1$H-NMR (300 MHz, DMSO-d$_6$) δ (ppm): 7.55-7.41 (m, 1H), 7.20-7.09 (m, 2H), 6.80-6.70 (m, 2H), 5.10-5.01 (m, 1H), 3.95 (s, 4H), 1.94-1.69 (m, 2H), 1.68-1.47 (m, 6H).

Step 2: Synthesis of cyclopentyl 3-imino-3-phenoxypropanoate

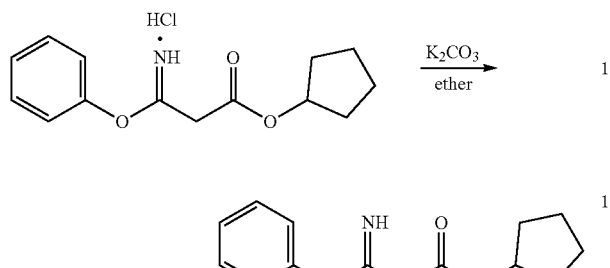

To a suspension of cyclopentyl 3-imino-3-phenoxypropanoate hydrochloride (1.0 g, 3.53 mmol, 1.0 eq.) in ether (25 ml) was added a solution of potassium carbonate (0.73 g, 5.30 mmol, 1.5 eq) in water (11 mL) at 0° C. The resultant mixture was stirred until the solid had dissolved and was then washed with ether, dried ($Na_2SO_4$) and concentrated to afford cyclopentyl 3-imino-3-phenoxypropanoate as light yellow oil (0.86 g, 99%).

$^1$H-NMR (300 MHz, DMSO-$d_6$) δ (ppm): 7.66 (bs, 2H), 7.51-7.39 (m, 2H), 7.35-7.23 (m, 1H), 7.20-7.10 (m, 2H), 4.97 (dq, J=5.7, 3.1 Hz, 1H), 3.46 (s, 1H), 1.89-1.65 (m, 2H), 1.64-1.25 (m, 6H).

Step 3: Synthesis of cyclopentyl 3-amino-3-iminopropanoate hydrochloride

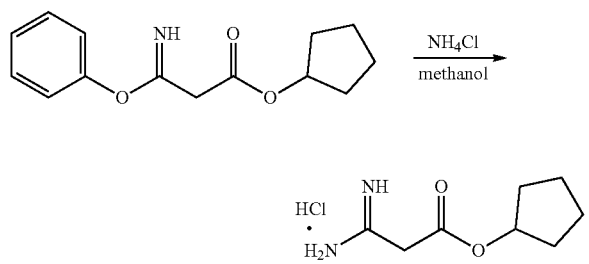

To a solution of cyclopentyl 3-imino-3-phenoxypropanoate (0.86 g, 3.49 mmol, 1.0 eq.) in methanol (5 ml) was added ammonium chloride (0.21 g, 3.84 mmol, 1.1 eq). The mixture was stirred at room temperature overnight and concentrated. The remaining solid was triturated with diethyl ether and filtered off to afford cyclopentyl 3-amino-3-iminopropanoate hydrochloride as a white solid (0.61 g, 84%).

$^1$H-NMR (300 MHz, DMSO-$d_6$) δ (ppm): 9.12 (bs, 2H), 8.82 (bs, 2H), 5.12 (tt, J=4.9, 2.2 Hz, 1H), 3.55 (s, 2H), 1.81 (t, J=7.5 Hz, 2H), 1.76-1.47 (m, 6H).

The cyclopentyl 2-cyanoacetate precursor used in Step 1 of the synthesis of Intermediate y1 was purchased from commercial vendors. Other alkyl 2-cyanoacetates were synthesized using the following ester formation method (Step 0), as shown for 3-fluorobenzyl 2-cyanoacetate, a precursor of Intermediate y2:

Step 0: Synthesis of 3-fluorobenzyl 2-cyanoacetate

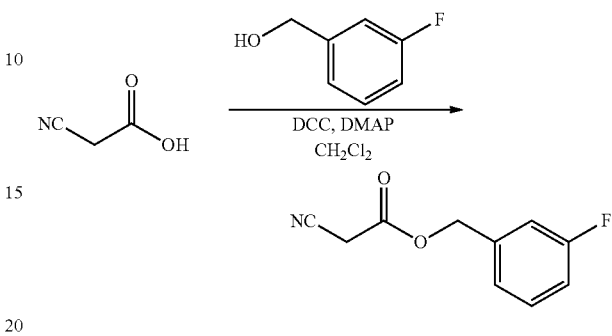

To a solution of 2-cyanoacetic acid (4.45 g, 52.32 mmol, 1.0 eq.) in DCM (34 ml) was added (3-fluorophenyl)methanol (5.67 mL, 52.32 mmol, 1.0 eq) and cooled at 0° C. Then, a solution of N,N-dicylohexylcarbodiimide (10.79 g, 52.32 mmol, 1.0 eq) and dimethylaminopyridine (0.32 g, 2.62 mmol, 0.05 eq) in DCM (16 mL) was dropwise added, and the mixture was stirred at RT overnight. The solid was filtered off and washed with DCM. The filtrate was concentrated and purified by flash column chromatography on silica gel using ethyl acetate/hexane (1:3) as eluent to afford 3-fluorobenzyl 2-cyanoacetate as a light-yellow oil (7.2 g, 66%).

$^1$H-NMR (300 MHz, DMSO-$d_6$) δ (ppm): 7.45-7.27 (m, 1H), 7.20-7.01 (m, 3H), 5.22 (s, 2H), 3.51 (s, 2H).

The following amidine intermediates were prepared according to General Procedure y (Steps 0 to 3).

Intermediate y2: 3-Fluorobenzyl 3,3-diaminoacrylate hydrochloride

White solid (0.550 g).
$^1$H-NMR (300 MHz, DMSO-$d_6$) δ (ppm): 9.36 (bs, 2H), 9.05 (bs, 2H), 7.64-7.43 (m, 4H), 5.21 (s, 2H), 3.78 (s, 2H).

Intermediate y3: Cyclobutylmethyl 3,3-diaminoacrylate hydrochloride

White solid (0.542 g).
$^1$H-NMR (300 MHz, DMSO-$d_6$) δ (ppm): 9.27 (bs, 2H), 8.99 (bs, 2H), 4.19-3.85 (m, 2H), 3.67 (s, 2H), 2.67-2.53 (m, 1H), 2.11-1.54 (m, 6H).

Intermediate y4: 3,3-Difluorocyclobutyl)methyl 3,3-diaminoacrylate

White solid (0.450 g).
$^1$H-NMR (300 MHz, DMSO-$d_6$) δ (ppm): 9.33 (bs, 2H), 9.01 (bs, 2H), 4.17 (d, J=5.1 Hz, 2H), 3.71 (s, 2H), 2.79-2.53 (m, 3H), 2.44-2.29 (m, 2H).

Intermediate y5: 2,2-Difluorocyclopropyl)methyl 3,3-diaminoacrylate hydrochloride White solid (0.36 g).
$^1$H-NMR (300 MHz, DMSO-$d_6$) δ (ppm): 9.33 (bs, 2H), 9.05 (bs, 2H), 4.42-4.21 (m, 1H), 4.14-3.90 (m, 1H), 3.73 (s, 2H), 2.20-2.00 (m, 1H), 1.82-1.61 (m, 1H), 1.61-1.36 (m, 1H).

Intermediate y6: Isopropyl 3,3-diaminoacrylate hydrochloride

White solid (0.47 g).
$^1$H-NMR (300 MHz, DMSO-$d_6$) δ (ppm): 9.28 (bs, 2H), 9.00 (bs, 2H), 4.95 (pd, J=6.3, 1.5 Hz, 1H), 3.62 (s, 2H), 1.22 (d, J=6.3 Hz, 6H).

Intermediate y7: 2,2-Difluoro-3,3-dimethylcyclopropyl)methyl 3,3-diaminoacrylate hydrochloride White solid (0.132 g).
$^1$H-NMR (300 MHz, DMSO-$d_6$) δ (ppm): 9.31 (s, 2H), 9.03 (s, 2H), 4.21 (d, J=8.8 Hz, 2H), 3.70 (s, 2H), 1.82-1.56 (m, 1H), 1.34-0.94 (m, 6H).

Intermediate y8: Neopentyl 3,3-diaminoacrylate hydrochloride

White solid (0.791 g).
$^1$H-NMR (300 MHz, DMSO-$d_6$) δ (ppm): 9.25 (s, 2H), 8.97 (s, 2H), 3.79 (s, 2H), 3.66 (s, 2H), 0.89 (s, 9H).

Intermediate y9: 2,2,2-Trifluoroethyl (E)-3-amino-3-(2,2,2-trifluoroethoxy)acrylate The title compound was prepared following Step 0 of General Procedure y and a slightly modified version of Steps 1 and 2, as outlined below.

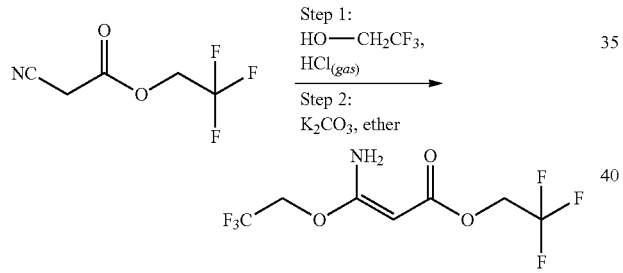

Step 1: Into a mixture of 2,2,2-trifluoroethyl 2-cyanoacetate (3.5 g, 20.94 mmol, 1.15 eq) and 2,2,2-trifluoroethyl-1-ol (1.32 mL, 18.21 mmol, 1 eq) that was stirred at −20° C., HCl gas was bubbled for 60 min. Then, the mixture was left at 4° C. for two days without stirring. After that time the mixture was stirred again, and cold ether was added at 0° C. The solid was filtered off and washed with cold ether to afford 2,2,2-trifluoroethyl (E)-3-amino-3-(2,2,2-trifluoroethoxy)acrylate hydrochloride as a white solid (2.5 g, 40%).
$^1$H-NMR (300 MHz, DMSO-$d_6$) δ (ppm): 7.70 (s, 1H), 5.83 (s, 2H), 4.73 (ddq, J=37.4, 18.4, 9.0 Hz, 4H), 3.89 (s, 1H).

Step 2: To a mixture of 2,2,2-trifluoroethyl (E)-3-amino-3-(2,2,2-trifluoroethoxy) acrylate hydrochloride (0.13 g, 0.43 mmol, 1.0 eq.) and ether (5 ml) was added a solution of potassium carbonate (0.088 g, 0.64 mmol, 1.5 eq) in water (1.5 mL) at 0° C. The resultant mixture was stirred until the solid dissolved. The mixture was extracted with ether, and the organic phase was dried ($Na_2SO_4$) and concentrated to afford 2,2,2-trifluoroethyl (E)-3-amino-3-(2,2,2-trifluoroethoxy) acrylate as colorless oil (0.12 g, 98%) which was used as such in the next step.

Intermediate y10: 2-Fluoro-2-methylpropyl 3-amino-3-iminopropanoate hydrochloride General Procedure y (Steps 0 to 3) afforded the title compound as white solid (0.28 g).
$^1$H-NMR (300 MHz, DMSO-$d_6$) δ (ppm): 9.33 (s, 2H), 9.04 (s, 2H), 4.19 (d, J=21.1 Hz, 2H), 3.76 (s, 2H), 1.41-1.34 (m, 6H).

Intermediate y11: Cyclopropylmethyl 3,3-diaminoacrylate hydrochloride

General Procedure y (Steps 0 to 3) afforded the title compound as white solid (0.48 g).
$^1$H-NMR (300 MHz, DMSO-$d_6$) δ (ppm): 9.13 (bs, 3H), 8.83 (bs, 2H), 5.13 (t, J=6.0 Hz, 1H), 3.57 (s, 2H), 1.86-1.80 (m, 1H), 1.68-1.58 (m, 4H).

Intermediate y12: 4,4-Difluorocyclohexyl 3-amino-3-iminopropanoate hydrochloride General Procedure y (Steps 0 to 3) afforded title compound as white solid (0.098 g).
$^1$H-NMR (300 MHz, DMSO-$d_6$) δ (ppm): δ 9.32 (s, 2H), 9.02 (s, 2H), 4.96-4.66 (m, 1H), 3.41 (s, 2H), 2.10-1.76 (m, 8H).

Intermediate y13: 4-Fluorobenzyl 3-amino-3-iminopropanoate hydrochloride

General Procedure y (Steps 0 to 3) afforded title compound as white solid (0.45 g).
$^1$H-NMR (300 MHz, DMSO-$d_6$) δ (ppm): 9.30 (bs, 2H), 9.01 (bs, 2H), 7.49-7.43 (m, 2H), 7.26-7.17 (m, 2H), 5.17 (s, 2H), 3.73 (s, 2H).

Intermediate y14: Cyclopentylmethyl 3-amino-3-iminopropanoate hydrochloride

General Procedure y (Steps 0 to 3) afforded title compound as white solid (0.22 g).
$^1$H-NMR (300 MHz, DMSO-$d_6$) δ (ppm): 9.31 (bs, 2H), 9.03 (bs, 2H), 3.96 (d, 2H), 3.76 (s, 2H), 2.2-2.1 (m, 1H), 1.8-1.6 (m, 2H), 1.6-1.4 (m, 4H), 1.4-1.1 (m, 2H).

Preparation of Knoevenagel Intermediates

General Procedure j (Adapted from Lu Liu et al, Chem. Int. Ed. 2009, 48, 6093-6096)

Intermediate j1: 3-(benzo[b]thiophen-3-ylmethylene)pentane-2,4-dione

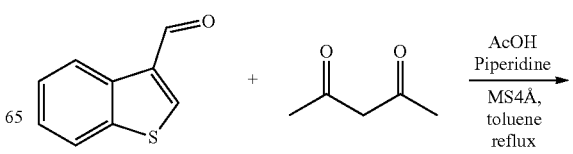

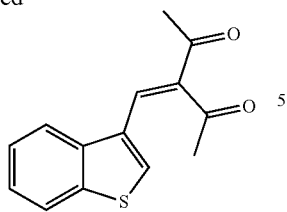

Benzo[b]thiophene-3-carbaldehyde (1 g, 6.16 mmol, 1 eq) was dissolved in toluene (0.5 M) at RT, and acetic acid (0.176 ml, 3.08 mmol, 0.5 eq), piperidine (0.061 ml, 0.61 mmol, 0.1 eq), molecular sieves (6 g) and 2,4-pentanedione (0.95 ml, 9.24 mmol, 1.5 eq) were added. The reaction mixture was heated in a microwave oven at 111° C. until the disappearance of starting material (4 h). The mixture was allowed to cool to RT and then concentrated. The resulting residue was purified by flash column chromatography on silica gel using ethyl acetate/hexane (1:6) as eluent to afford the Knoevenagel product as a yellow solid (1.8 g, 60%).

$^1$H-NMR (300 MHz, CDCl$_3$) δ=7.89 (t, J=7.5 Hz, 2H), 7.76 (s, 1H), 7.72 (s, 1H), 7.48 (p, J=7.4 Hz, 2H), 2.49 (s, 3H), 2.30 (s, 3H).

The following intermediates were synthesized according to General procedure j.

Intermediate j2: (E)-2-(benzo[b]thiophen-3-ylmethylene)-1-(pyridin-3-yl)butane-1,3-dione Yellow solid (0.25 g, 33%).
$^1$H-NMR (300 MHz, CDCl$_3$) δ=9.03 (s, 1H), 8.72 (d, J=3.6 Hz, 1H), 8.20 (ddd, J=8.0, 2.3, 1.7 Hz, 1H), 8.14 (d, J=0.9 Hz, 1H), 7.96 (dt, J=8.1, 1.0 Hz, 1H), 7.83 (ddd, J=7.9, 1.2, 0.7 Hz, 1H), 7.53 (s, 1H), 7.52-7.32 (m, 3H), 2.52 (s, 3H).

Intermediate j3: Methyl (Z)-2-(benzo[b]thiophen-3-ylmethylene)-4-chloro-3-oxobutanoate Yellow solid (0.4 g, 32%).
$^1$H-NMR (300 MHz, CDCl$_3$) δ=8.16 (s, 1H), 8.03-7.86 (m, 2H), 7.82 (s, 1H), 7.60-7.39 (m, 2H), 4.34 (s, 2H), 3.90 (s, 3H).

Intermediate j4: (E)-2-(Benzo[b]thiophen-3-ylmethylene)-1-cyclopropylbutane-1,3-dione Yellow oil (0.4 g, 63%).
$^1$H-NMR (300 MHz, CDCl$_3$) δ=7.96-7.84 (m, 3H), 7.75 (d, J=1.1 Hz, 1H), 7.56-7.38 (m, 2H), 2.45 (s, 3H), 2.03 (dt, J=7.9, 3.6 Hz, 1H), 1.28-1.08 (m, 2H), 1.04-0.83 (m, 2H).

Intermediate j5: Tetrahydro-2H-pyran-4-yl (Z)-3-oxo-2-(thieno[2,3-b]pyridin-3-ylmethylene)butanoate Yellow oil (0.04 g, 25%).
$^1$H-NMR (300 MHz, CDCl$_3$) δ=8.63 (d, J=4.6 Hz, 1H), 8.14 (d, J=8.1 Hz, 1H), 7.94 (s, 1H), 7.76 (s, 1H), 7.40 (dd, J=8.1, 4.6 Hz, 1H), 5.16 (tt, J=8.6, 4.1 Hz, 1H), 3.81 (dt, J=11.8, 4.6 Hz, 2H), 3.49 (ddd, J=11.8, 8.8, 3.0 Hz, 2H), 2.46 (s, 3H), 1.91 (dp, J=8.5, 4.1 Hz, 2H), 1.63 (dtd, J=13.0, 8.5, 4.1 Hz, 2H).

Intermediate j6: Isopropyl (Z)-3-(7-bromobenzo[b]thiophen-3-yl)-2-(cyclopropanecarbonyl)acrylate Yellow oil (0.13 g, 32%).
$^1$H-NMR (300 MHz, CDCl$_3$) δ=7.88 (s, 2H), 7.85 (s, 1H), 7.57-7.53 (m, 1H), 7.38-7.31 (m, 1H), 5.19 (p, J=6.3 Hz, 1H), 2.08 (tt, J=7.8, 4.6 Hz, 1H), 1.35 (s, 3H), 1.32 (s, 3H), 1.21-1.11 (m, 2H), 1.02-0.91 (m, 2H).

Intermediate j7: Methyl (Z)-2-((7-bromobenzo[b]thiophen-3-yl)methylene)-4,4,4-trifluoro-3-oxobutanoate Yellow solid (0.040 g, 10%).
$^1$H-NMR (300 MHz, CDCl$_3$) δ=8.22 (d, J=1.0 Hz, 1H), 7.87 (t, J=1.3 Hz, 1H), 7.78-7.75 (m, 1H), 7.69 (d, J=5.0 Hz, 1H), 7.38-7.34 (m, 1H), 3.92 (s, 3H). $^{19}$F NMR (282 MHz, CDCl$_3$) δ=−75.69 (s, CF$_3$).

Intermediate j8: Cyclopropylmethyl (Z)-3-(7-bromobenzo[b]thiophen-3-yl)-2-(cyclopropanecarbonyl)acrylate Yellow solid (0.25 g, 59%).
$^1$H-NMR (300 MHz, CDCl$_3$) δ=7.96-7.84 (m, 3H), 7.58 (d, J=7.6 Hz, 1H), 7.40-7.33 (m, 1H), 4.13 (d, J=7.5 Hz, 2H), 2.10 (tt, J=7.5, 4.6 Hz, 1H), 1.25-1.18 (m, 3H), 0.99 (dt, J=7.9, 3.5 Hz, 2H), 0.71-0.46 (m, 2H), 0.41-0.23 (m, 2H).

Intermediate j9: Cyclopropylmethyl (Z)-3-(7-bromobenzo[b]thiophen-3-yl)-2-(cyclopropanecarbonyl)acrylate Yellow solid (0.13 g, 50%).
$^1$H-NMR (300 MHz, CDCl$_3$) δ=8.33-8.24 (m, 2H), 7.93 (s, 1H), 7.78 (s, 1H), 7.72 (t, J=7.8 Hz, 1H), 2.50 (s, 3H), 2.30 (s, 3H). $^{19}$F NMR (282 MHz, CDCl$_3$) δ=−69.81 (s, CF$_3$).

Intermediate j10: 3-((7-Chlorobenzo[b]thiophen-3-yl)methylene)pentane-2,4-dione

Yellow solid (0.158 g, 56%).
$^1$H-NMR (300 MHz, CDCl$_3$-d) δ (ppm): 7.77 (d, J=7.1 Hz, 2H), 7.69 (s, 1H), 7.45 (d, J=5.0 Hz, 2H), 2.48 (s, 3H), 2.29 (s, 3H).

Intermediate j11: 3-((7-(Trifluoromethyl)benzo[b]thiophen-3-yl)methylene)pentane-2,4-dione Yellow solid (0.052 g, 50%).
$^1$H-NMR (300 MHz, CDCl$_3$-d) δ (ppm): 8.06 (d, J=8.0 Hz, 1H), 7.82 (s, 1H), 7.80-7.73 (m, 2H), 7.61 (t, J=8.0 Hz, 1H), 2.50 (s, 3H), 2.30 (s, 3H).
$^{19}$F NMR (282 MHz, CDCl$_3$-d) δ (ppm): −62.87 (CF$_3$).

Intermediate j12: 3-(2-Acetyl-3-oxobut-1-en-1-yl)benzo[b]thiophene-7-carbonitrile Dark-yellow solid (0.132 g, 68%).
$^1$H-NMR (300 MHz, CDCl$_3$-d) δ (ppm): 8.10 (d, J=8.1 Hz, 1H), 7.85 (s, 1H), 7.81 (d, J=7.5 Hz, 1H), 7.69 (s, 1H), 7.60 (td, J=8.1, 7.4, 1.0 Hz, 1H), 2.49 (s, 3H), 2.31 (s, 3H).

Intermediate j13: Cyclopropylmethyl (Z)-2-(cyclopropanecarbonyl)-3-(thieno[2,3-b]pyridin-3-yl)acrylate Yellow solid (0.146 g, 61%).
$^1$H-NMR (300 MHz, CDCl$_3$-d) δ (ppm): 8.63 (d, J=4.6 Hz, 1H), 8.20 (d, J=8.4 Hz, 1H), 7.91 (s, 1H), 7.90 (s, 1H), 7.40 (ddd, J=8.4, 4.6, 0.8 Hz, 1H), 4.12 (d, J=7.2 Hz, 2H), 2.21-2.04 (m, 1H), 1.29-1.13 (m, 3H), 1.11-0.93 (m, 2H), 0.67-0.54 (m, 2H), 0.43-0.27 (m, 2H).

Intermediate j14: Cyclopentyl (Z)-2-(cyclopropanecarbonyl)-3-(thieno[2,3-b]pyridin-3-yl)acrylate Light-yellow solid (0.21 g, 90%).
$^1$H-NMR (300 MHz, CDCl$_3$-d) δ (ppm): 8.63 (dd, J=4.6, 1.4 Hz, 1H), 8.19 (dd, J=8.2, 1.4 Hz, 1H), 7.89 (s, 1H), 7.86 (s, 1H), 7.40 (dd, J=8.2, 4.6 Hz, 1H), 5.36 (tt, J=5.7, 2.5 Hz, 1H), 2.10 (tt, J=8.0, 4.6 Hz, 1H), 1.98-1.86 (m, 2H), 1.86-1.70 (m, 4H), 1.69-1.57 (m, 2H), 1.19 (dt, J=6.9, 3.5 Hz, 2H), 0.99 (dt, J=8.0, 3.5 Hz, 2H).

Intermediate j15: Cyclopropylmethyl (Z)-3-(7-cyanobenzo[b]thiophen-3-yl)-2-(cyclopropanecarbonyl)acrylate Yellow solid (0.23 g, 69%).
$^1$H-NMR (300 MHz, CDCl$_3$-d) δ (ppm): 8.19-8.09 (m, 1H), 7.95 (s, 1H), 7.92 (s, 1H), 7.81-7.74 (m, 1H), 7.62-7.53 (m, 1H), 4.13 (d, J=7.2 Hz, 2H), 2.12 (tt, J=7.8, 4.6 Hz, 1H), 1.29-1.13 (m, 3H), 1.07-0.93 (m, 2H), 0.67-0.55 (m, 2H), 0.35 (dt, J=6.2, 4.6 Hz, 2H).

Intermediate j16: Methyl (Z)-3-(7-cyanobenzo[b]thiophen-3-yl)-2-(cyclopropanecarbonyl)acrylate Yellow solid (0.21 g, 80%).
$^1$H-NMR (300 MHz, CDCl$_3$-d) δ (ppm): 8.13 (t, J=9.1 Hz, 1H), 8.02-7.86 (m, 2H), 7.79 (d, J=7.7 Hz, 1H), 7.57 (td, J=7.7, 2.7 Hz, 1H), 3.89 (s, 3H), 2.13-2.01 (m, 1H), 1.28-1.16 (m, 2H), 1.14-0.93 (m, 2H).

Intermediate j17: Methyl (Z)-2-((7-cyanobenzo[b]thiophen-3-yl)methylene)-3-oxobutanoate Yellow solid (0.11 g, 60%).
$^1$H-NMR (300 MHz, CDCl$_3$-d) δ (ppm): 8.11 (d, J=8.2 Hz, 1H), 7.99 (s, 1H), 7.84 (s, 1H), 7.80 (d, J=7.4 Hz, 1H), 7.62-7.54 (m, 1H), 3.87 (s, 3H), 2.47 (s, 3H).

Intermediate j18: (E)-2-((7-cyanobenzo[b]thiophen-3-yl)methylene)-3-oxobutanamide Yellow solid (0.17 g, 58%).
$^1$H-NMR (300 MHz, CDCl$_3$-d) δ (ppm): 8.35 (s, 1H), 8.14-8.07 (m, 1H), 7.88-7.73 (m, 2H), 7.63-7.54 (m, 1H), 6.08 (bs, 1H), 5.87 (bs, 1H), 2.55 (s, 3H).

Intermediate j19: Cyclopropyl (E)-2-((7-cyanobenzo[b]thiophen-3-yl)methylene)-3-oxobutanoate Yellow solid (0.104 g, 30%).
$^1$H-NMR (300 MHz, CDCl$_3$-d) δ (ppm): 8.09 (d, J=8.2 Hz, 1H), 8.02 (s, 1H), 7.80 (d, J=7.3 Hz, 2H), 7.63-7.51 (m, 1H), 4.43-4.31 (m, 1H), 2.46 (s, 3H), 0.85-0.74 (m, 2H), 0.73-0.61 (m, 2H).

Intermediate j20: Methyl (E)-2-((7-cyano-5-fluorobenzo[b]thiophen-3-yl)methylene)-3-oxobutanoate Yellow solid (0.136 g, 60%).
$^1$H-NMR (300 MHz, CDCl$_3$-d) δ (ppm): 8.07 (s, 1H), 7.79 (d, J=8.7 Hz, 1H), 7.72 (d, J=0.9 Hz, 1H), 7.56 (d, J=7.7 Hz, 1H), 3.87 (s, 3H), 2.47 (s, 3H).

Intermediate j21: Methyl (E)-2-((7-cyano-4-fluorobenzo[b]thiophen-3-yl)methylene)-3-oxobutanoate Yellow solid (0.116 g, 63%).
$^1$H-NMR (300 MHz, CDCl$_3$-d) δ (ppm): 8.11 (s, 1H), 7.85 (s, 1H), 7.76 (dd, J=8.2, 4.3 Hz, 1H), 7.24-7.16 (m, 1H), 3.89 (s, 3H), 2.35 (s, 3H).

Intermediate j22: Methyl (E)-2-((7-cyanothieno[3,2-b]pyridin-3-yl)methylene)-3-oxobutanoate Yellow solid (0.77 g, 40%).
$^1$H-NMR (300 MHz, CDCl$_3$-d) δ (ppm): 8.91 (d, J=4.7 Hz, 1H), 8.32 (s, 1H), 8.15 (s, 1H), 7.63 (d, J=4.7 Hz, 1H), 3.90 (s, 3H), 2.53 (s, 3H).

Intermediate j23: Cyclopropylmethyl (E)-2-((7-cyanobenzo[b]thiophen-3-yl)methylene)-3-oxobutanoate Yellow solid (0.45 g, 52%).
$^1$H-NMR (300 MHz, CDCl$_3$-d) δ (ppm): 8.11 (dd, J=8.2, 0.9 Hz, 1H), 8.06 (s, 1H), 7.83 (d, J=0.9 Hz, 1H), 7.79 (d, J=7.5 Hz, 1H), 7.57 (dd, J=8.2, 7.5 Hz, 1H), 4.13 (d, J=7.4 Hz, 2H), 2.48 (s, 3H), 1.26-1.04 (m, 1H), 0.66-0.51 (m, 2H), 0.38-0.21 (m, 2H).

Intermediate j24: Prop-2-yn-1-yl (E)-2-((7-cyanobenzo[b]thiophen-3-yl)methylene)-3-oxobutanoate Yellow solid (0.7 g, 85%).
$^1$H-NMR (300 MHz, CDCl$_3$-d) δ (ppm): 8.13 (dd, J=8.2, 0.9 Hz, 1H), 7.99 (s, 1H), 7.96 (s, 1H), 7.80 (d, J=7.1 Hz, 1H), 7.62-7.55 (m, 1H), 4.89 (d, J=2.5 Hz, 2H), 2.55 (t, J=2.5 Hz, 1H), 2.40 (s, 3H).

Intermediate j25: Methyl (E)-2-((5,7-dicyanobenzo[b]thiophen-3-yl)methylene)-3-oxobutanoate Yellow solid (0.135 g, 59%).
$^1$H-NMR (300 MHz, CDCl$_3$-d) δ (ppm): 8.31 (d, J=1.4 Hz, 1H), 7.96-7.87 (m, 2H), 7.49 (s, 1H), 4.13 (d, J=1.0 Hz, 3H), 2.04 (d, J=1.0 Hz, 3H).

Intermediate j26: But-2-yn-1-yl (E)-2-((7-cyanobenzo[b]thiophen-3-yl) methylene)-3-oxobutanoate Yellow solid (0.125 g, 36%).
$^1$H-NMR (300 MHz, CDCl$_3$-d) δ (ppm): 8.11 (td, J=4.4, 0.8 Hz, 2H), 7.86 (d, J=0.8 Hz, 1H), 7.80 (d, J=7.4 Hz, 1H), 7.58 (dd, J=8.2, 7.4 Hz, 1H), 4.86 (q, J=2.3 Hz, 2H), 2.48 (s, 3H), 1.89 (t, J=2.3 Hz, 3H).

Intermediate j27: (2,2,2-Trifluoroethyl)-2-((7-cyanobenzo[b]thiophen-3-yl) methylene)-3-oxobutanoate Yellow solid (0.079 g, 38%).
$^1$H-NMR (300 MHz, CDCl$_3$-d) δ (ppm): 8.15-7.98 (m, 2H), 7.95-7.88 (m, 1H), 7.86-7.72 (m, 2H), 4.66 (dq, J=11.7, 8.3 Hz, 2H), 2.53-2.40 (m, 3H).

Intermediate j28: Methyl (E)-2-((6-chloro-7-cyanobenzo[b]thiophen-3-yl) methylene)-3-oxobutanoate Yellow solid (0.24 g, 56%).
$^1$H-NMR (300 MHz, CDCl$_3$-d) δ (ppm): 8.01 (d, J=8.7 Hz, 1H), 7.91 (d, J=0.9 Hz, 1H), 7.84 (d, J=0.9 Hz, 1H), 7.58 (d, J=8.7 Hz, 1H), 3.90 (s, 3H), 2.36 (s, 3H).

Intermediate j29: (E)-3-(2-Cyano-3-oxobut-1-en-1-yl)benzo[b]thiophene-7-carbonitrile General procedure j using 3-oxobutanenitrile gave title compound as yellow solid (0.23 g, 69%).

$^1$H-NMR (300 MHz, DMSO-d$_6$) δ (ppm): 9.07 (s, 1H), 8.47 (s, 1H), 8.22 (d, J=8.2 Hz, 1H), 7.85 (d, J=7.4 Hz, 1H), 7.64 (t, J=7.8 Hz, 1H), 2.63 (s, 3H).

Intermediate j30: 3-((5-Fluorothieno[2,3-b]pyridin-3-yl)methylene)pentane-2,4-dione General procedure j gave title compound as yellow solid (0.132 g, 61%).

$^1$H-NMR (300 MHz, DMSO-d$_6$) δ (ppm): 8.56 (d, J=2.4 Hz, 1H), 7.90 (s, 1H), 7.83 (dd, J=8.7, 2.4 Hz, 1H), 7.55 (s, 1H), 2.48 (s, 3H), 2.32 (s, 3H).

EXAMPLES

Preparation of Dihydropyridines

Method A (Rampa, A et al, Forsch. 1992, 42, 1284)

Example A1: Methyl 5-acetyl-4-(benzo[b]thiophen-3-yl)-2,6-dimethyl-1,4-dihydro-pyridine-3-carboxylate

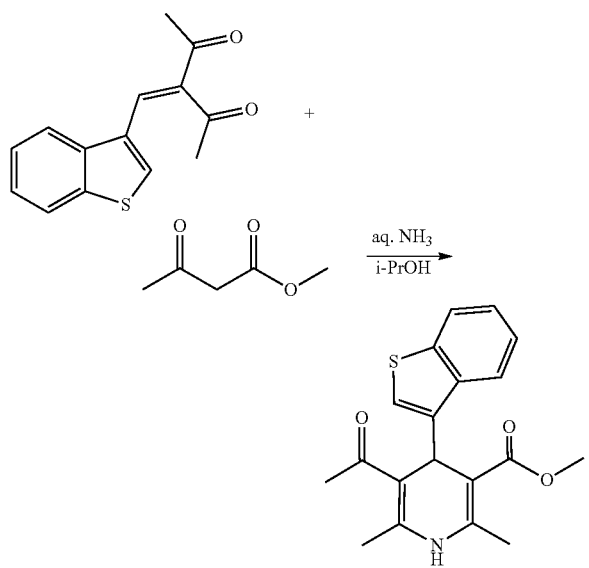

A mixture of 3-(benzo[b]thiophen-3-ylmethylene)pentane-2,4-dione (0.24 g, 0.98 mmol, 1 eq), methyl 3-oxobutanoate (0.158 ml, 1.47 mmol, 1.5 eq) and 30% aqueous ammonium (0.62 ml, 9.8 mmol, 10 eq) in i-PrOH (2 ml) was heated at reflux temperature for 12 h. The solvent was removed under reduced pressure. The residue was taken up in water and extracted with dichloromethane and ethyl acetate. The combined organic layers were washed with brine, dried (Na$_2$SO$_4$), filtered and concentrated, and the crude product was purified by flash column chromatography on silica gel using CH$_2$Cl$_2$/MeOH (1%) as eluent to afford the title compound as a yellow solid (114 mg, 25%).

$^1$H-NMR (300 MHz, CDCl$_3$) δ=8.10 (d, J=8.0 Hz, 1H), 7.79 (d, J=7.9 Hz, 1H), 7.34 (dt, J=24.0, 7.1 Hz, 2H), 7.13 (s, 1H), 6.27 (bs, 1H), 5.47 (s, 1H), 3.64 (s, 3H), 2.34 (s, 3H), 2.27 (s, 3H), 2.14 (s, 3H).

HRMS (IE) m/z calculated C$_{19}$H$_{19}$NO$_3$S [M$^+$]: 341.1086, found: 341.1069.

Example A1 is a racemic mixture of two stereoisomers that have been separated by semi-preparative chiral HPLC (column: ChiralPak IA, 5 µm, 4.6×250 mm, eluent: n-hexane/iPrOH 95:5) affording Example A2 (Enantiomer 1, Tr=22.54 min, 95.60% ee; 96.46% purity) and Example A3 (Enantiomer 2, Tr=18.10 min, 99.88% ee; 92.87% purity). Purity has been determined on a RP-C18 analytical column (Gemini-NX C18 5 µm, 4.6×150 mm; eluents: ACN/water/100 mM ammonium acetate, pH 7). The absolute stereochemistry has not been determined.

Example A4: 5-acetyl-4-(benzo[b]thiophen-3-yl)-2,6-dimethyl-1,4-dihydropyridine-3-carboxamide Method A yielded the title compound as a yellow solid (73 mg, 22%).

$^1$H-NMR (300 MHz, CDCl$_3$) δ=8.05 (d, J=7.7 Hz, 1H), 7.76 (d, J=7.6 Hz, 1H), 7.29 (dt, J=15.0, 7.0 Hz, 2H), 7.09 (s, 1H), 6.76 (s, 1H), 5.65 (bs, 2H), 5.34 (s, 1H), 2.25 (s, 3H), 2.08 (s, 6H).

HRMS (IE) m/z calculated C$_{18}$H$_{18}$N$_2$O$_2$S: 326.0910, found: 326.1011.

Example A5: 1-(4-(benzo[b]thiophen-3-yl)-5-benzoyl-2,6-dimethyl-1,4-dihydropyridin-3-yl)ethan-1-one Method A yielded the title compound as a dark yellow solid (63 mg, 16%).

$^1$H-NMR (300 MHz, CDCl$_3$) δ=7.79-7.70 (m, 1H), 7.65-7.56 (m, 1H), 7.53-7.31 (m, 5H), 7.25-7.18 (m, 2H), 7.06 (s, 1H), 5.72 (bs, 1H), 5.56 (s, 1H), 2.48 (s, 3H), 2.07 (s, 3H), 1.77 (s, 3H).

HRMS (IE): m/z calculated C$_{24}$H$_{21}$NO$_2$S [M$^+$]: 387.1293, found: 387.1286.

Example A6: Methyl 5-acetyl-4-(benzo[b]thiophen-3-yl)-6-methyl-2-phenyl-1,4-dihydropyridine-3-carboxylate Method A in MeOH yielded the title compound as a dark yellow solid (15 mg, 5%).

$^1$H-NMR (300 MHz, CDCl$_3$) δ=8.21 (d, J=8.2 Hz, 1H), 7.83 (d, J=7.9 Hz, 1H), 7.45-7.31 (m, 5H), 7.30-7.24 (m, 3H), 6.02 (bs, 1H), 5.59 (s, 1H), 3.38 (s, 3H), 2.41 (s, 3H), 2.17 (s, 3H).

HRMS (IE): m/z calculated C$_{24}$H$_{21}$NO$_3$S [M$^+$]: 403.1242, found: 403.1252.

In the Hantzsch synthesis of the following examples, preformed enamines have been used instead of mixtures of 1,3-dicarbonyl compounds and ammonia:

Example A8: 1-(4-(benzo[b]thiophen-3-yl)-2,6-dimethyl-5-nicotinoyl-1,4-dihydro pyridin-3-yl)ethan-1-one Method A using (E)-4-aminopent-3-en-2-one in EtOH yielded the title compound as a dark yellow solid (60 mg, 19%).

$^1$H-NMR (300 MHz, CDCl$_3$) δ=8.64 (d, J=11.7 Hz, 2H), 7.84-7.60 (m, 3H), 7.35-7.21 (m, 3H), 7.08 (s, 1H), 5.97 (bs, 1H), 5.56 (s, 1H), 2.45 (s, 3H), 2.10 (s, 3H), 1.77 (s, 3H).

HRMS (IE): m/z calculated C$_{23}$H$_{20}$N$_2$O$_2$S [M$^+$]: 388.1245, found: 388.1229.

Example A9: Methyl 5-acetyl-4-(benzo[b]thiophen-3-yl)-6-methyl-1,4-dihydro-[2,3'-bipyridine]-3-carboxylate Method A using methyl (Z)-3-amino-3-(pyridin-3-yl)acrylate in acetic acid yielded the title compound as a yellow solid (31 mg, 16%).

$^1$H-NMR (300 MHz, CDCl$_3$) δ=8.49 (s, 1H), 8.42 (s, 1H), 8.18 (d, J=8.0 Hz, 1H), 7.83 (d, J=8.0 Hz, 1H), 7.55 (d, J=7.9 Hz, 1H), 7.41 (t, J=7.5 Hz, 1H), 7.33 (t, J=7.2 Hz, 1H), 7.26-7.16 (m, 2H), 6.68 (bs, 1H), 5.59 (s, 1H), 3.37 (s, 3H), 2.41 (s, 3H), 2.15 (s, 3H).

HRMS (IE) m/z calculated C$_{23}$H$_{20}$N$_2$O$_3$S [M$^+$]: 404.1195, found: 404.1179.

Example A10: 2,2,2-trifluoroethyl 5-acetyl-4-(benzo[b]thiophen-3-yl)-2,6-dimethyl-1,4-dihydropyridine-3-carboxylate Method A using 2,2,2-trifluoroethyl (E)-3-aminobut-2-enoate in 2,2,2-trifluoroethanol yielded the title compound as a yellow solid (190 mg, 58%).

$^1$H-NMR (300 MHz, CDCl$_3$) δ=8.08 (d, J=7.9 Hz, 1H), 7.81 (d, J=8.0 Hz, 1H), 7.35 (dt, J=21.4, 7.1 Hz, 2H), 7.17 (s, 1H), 6.10 (bs, 1H), 5.47 (s, 1H), 4.58-4.27 (m, 2H), 2.37 (s, 3H), 2.31 (s, 3H), 2.16 (s, 2H). $^{19}$F-NMR (300 MHz, CDCl$_3$) δ=−73.39 (t, J=8.1 Hz).

HRMS (IE) m/z calculated C$_{20}$H$_{18}$F$_3$NO$_3$S [M$^+$]: 409.0960, found: 409.0943.

Example A10 was hydrolyzed to afford the carboxylic acid Example A11:

Example A11: 5-Acetyl-4-(benzo[b]thiophen-3-yl)-2,6-dimethyl-1,4-dihydropyridine-3-carboxylic acid 2,2,2-trifluoroethyl 5-acetyl-4-(benzo[b]thiophen-3-yl)-2,6-dimethyl-1,4-dihydropyridine-3-carboxylate (0.05 g, 0.14 mmol, 1 eq.) was dissolved in dioxane (3 ml) at room temperature. Sodium hydroxide (0.42 ml, 0.84 mmol, 6 eq) was added, and the reaction mixture was heated at 130° C. for 4 hours. The solvent was removed under reduced pressure, and water and 2N HCl was added (pH 6-7). The mixture was extracted with dichloromethane and ethyl acetate, and the combined organic layers were washed with brine, dried (Na$_2$SO$_4$), filtered and concentrated. The crude product was purified by flash column chromatography on silica gel using CH$_2$Cl$_2$/MeOH (4%) as eluent to afford the title compound (15 mg, 38%).

$^1$H-NMR (300 MHz, CDCl$_3$) δ=11.82 (s, 1H), 8.95 (s, 1H), 8.14 (dd, J=6.9, 1.3 Hz, 1H), 7.89 (dd, J=7.0, 1.6 Hz, 1H), 7.32 (td, J=7.6, 1.5 Hz, 2H), 7.18 (s, 1H), 5.40 (s, 1H), 2.32 (s, 3H), 2.24 (s, 3H), 2.10 (s, 3H).

HRMS (IE) m/z calculated C$_{18}$H$_{17}$NO$_3$S [M$^+$]: 327.0929, found: 327.0937.

Method B (Adapted from WO2006047537)

Example B1: 1-(4-(Benzo[b]thiophen-3-yl)-2,6-dimethyl-5-(4-methylpiperazine-1-carbonyl)-1,4-dihydropyridin-3-yl)ethan-1-one

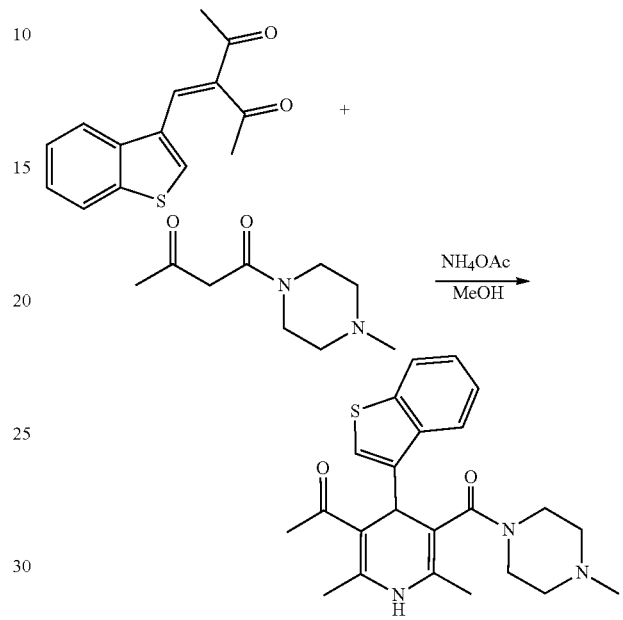

A mixture of 3-(benzo[b]thiophen-3-ylmethylene)pentane-2,4-dione (0.12 g, 0.49 mmol, 1 eq), 1-(4-methylpiperazin-1-yl)butane-1,3-dione (0.1 g, 0.54 mmol, 1.1 eq), ammonium acetate (0.06 g, 0.73 mmol, 1.5 eq) in MeOH (2 ml) was heated in a microwave reactor at 130° C. for 15 min. The reaction mixture was allowed to cool to RT and then concentrated. The residue was purified by flash column chromatography on silica gel using CH$_2$Cl$_2$/MeOH (5%) as eluent to afford the title compound as a yellow solid (30 mg, 16%).

$^1$H-NMR (300 MHz, CDCl$_3$) δ=7.87 (d, J=7.6 Hz, 1H), 7.80 (d, J=7.3 Hz, 1H), 7.34 (dt, J=14.8, 6.7 Hz, 2H), 7.09 (s, 1H), 5.91 (bs, 1H), 5.38 (s, 1H), 3.90 (d, J=11.6 Hz, 1H), 3.11-2.92 (m, 1H), 2.91-2.73 (m, 1H), 2.68-2.55 (m, 1H), 2.37 (s, 3H), 2.33-2.19 (m, 2H), 1.90 (s, 3H), 1.85 (s, 3H), 1.69 (s, 3H), 1.55-1.36 (m, 1H), 0.40-0.17 (m, 1H).

HRMS (IE): m/z calculated C$_{23}$H$_{27}$N$_3$O$_2$S [M$^+$]: 409.1824, found: 409.1834.

Example B2: 5-Acetyl-4-(benzo[b]thiophen-3-yl)-N,N-diethyl-2,6-dimethyl-1,4-dihydropyridine-3-carboxamide Method B yielded the title compound as a yellow solid (30 mg, 16%).

$^1$H-NMR (300 MHz, CDCl$_3$) δ=7.86 (d, J=7.3 Hz, 1H), 7.78 (d, J=7.8 Hz, 1H), 7.35-7.28 (m, 2H), 7.11 (s, 1H), 5.68 (bs, 1H), 5.37 (s, 1H), 3.50-3.28 (m, 1H), 3.23-2.94 (m, 1H), 2.86-2.75 (m, 1H), 2.70-2.45 (m, 1H), 2.37 (s, 3H), 1.93 (s, 3H), 1.71 (s, 3H), 0.94 (t, J=6.0 Hz, 3H), 0.20 (s, 3H).

HRMS (IE) m/z calculated C$_{22}$H$_{26}$N$_2$O$_2$S [M$^+$]: 382.1715, found: 382.1724.

Example B3: 1-(4-(Benzo[b]thiophen-3-yl)-2,6-dimethyl-5-(morpholine-4-carbonyl)-1,4-dihydro-pyridin-3-yl)ethan-1-one Method B yielded the title compound as a yellow solid (18 mg, 12%).

$^1$H-NMR (300 MHz, CDCl$_3$) δ=7.89 (d, J=7.3 Hz, 1H), 7.83 (d, J=7.9 Hz, 1H), 7.45-7.28 (m, 2H), 7.11 (s, 1H), 5.66 (bs, 1H), 5.39 (s, 1H), 3.84 (d, J=11.8 Hz, 1H), 3.54-3.36 (m, 2H), 3.14-2.97 (m, 2H), 2.90-2.79 (m, 2H), 2.66-2.45 (m, 1H), 2.38 (s, 3H), 1.93 (s, 3H), 1.70 (s, 3H).

HRMS (IE): m/z calculated C$_{22}$H$_{24}$N$_2$O$_3$S [M$^+$]: 396.1508, found: 396.1494.

Example B4: 2-Methoxyethyl 5-acetyl-4-(benzo[b]thiophen-3-yl)-2,6-dimethyl-1,4-dihydropyridine-3-carboxylate Method B yielded the title compound as a yellow solid (30 mg, 16%).

$^1$H-NMR (300 MHz, CDCl$_3$) δ=8.13 (d, J=8.0 Hz, 1H), 7.80 (d, J=7.9 Hz, 1H), 7.45-7.29 (m, 2H), 7.17 (s, 1H), 5.90 (bs, 1H), 5.49 (s, 1H), 4.20 (t, J=4.8 Hz, 2H), 3.57-3.50 (m, 2H), 3.33 (s, 3H), 2.37 (s, 3H), 2.30 (s, 3H), 2.14 (s, 3H).

HRMS (IE): m/z calculated C$_{21}$H$_{23}$NO$_4$S [M$^+$]: 385.1348, found: 385.1335.

Example B5: 3-Acetamidopropyl 5-acetyl-4-(benzo[b]thiophen-3-yl)-2,6-dimethyl-1,4-dihydropyridine-3-carboxylate Method B yielded the title compound as a yellow solid (22 mg, 11%).

$^1$H-NMR (300 MHz, CDCl$_3$) δ=8.14 (d, J=8.0 Hz, 1H), 7.79 (d, J=8.0 Hz, 1H), 7.38 (t, J=7.6 Hz, 1H), 7.34-7.25 (m, 1H), 7.14 (s, 1H), 5.56 (bs, 1H), 5.46 (s, 1H), 4.24-3.95 (m, 2H), 3.06-2.71 (m, 2H), 2.32 (s, 3H), 2.30 (s, 3H), 2.16 (s, 3H), 2.04-1.94 (m, 1H), 1.85 (s, 3H), 1.81-1.43 (m, 2H).

HRMS (IE): m/z calculated C$_{23}$H$_{26}$N$_2$O$_4$S [M$^+$]: 426.1613, found: 426.1603.

Example B6: Benzyl 5-acetyl-4-(benzo[b]thiophen-3-yl)-2,6-dimethyl-1,4-dihydro-pyridine-3-carboxylate Method B yielded the title compound as a yellow solid (19 mg, 10%).

$^1$H-NMR (300 MHz, CDCl$_3$)=8.01 (d, J=8.7 Hz, 1H), 7.79 (d, J=8.5 Hz, 1H), 7.41-7.26 (m, 5H), 7.26-7.19 (m, 2H), 7.09 (s, 1H), 5.87 (bs, 1H), 5.49 (s, 1H), 5.19-5.01 (m, 2H), 2.36 (s, 3H), 2.30 (s, 3H), 2.12 (s, 3H).

HRMS (IE): m/z calculated C$_{25}$H$_{23}$NO$_3$S [M$^+$]: 417.1399, found: 417.1399.

Example B7: 2-Morpholinoethyl 5-acetyl-4-(benzo[b]thiophen-3-yl)-2,6-dimethyl-1,4-dihydropyridine-3-carboxylate Method B yielded the title compound as a yellow solid (30 mg, 11%).

$^1$H-NMR (300 MHz, CDCl$_3$) δ=8.11 (d, J=9.1 Hz, 1H), 7.79 (d, J=7.1 Hz, 1H), 7.42-7.25 (m, 2H), 7.15 (s, 1H), 6.07 (bs, 1H), 5.49 (s, 1H), 4.29-4.07 (m, 2H), 3.59 (t, J=4.6 Hz, 4H), 2.51 (t, J=5.7 Hz, 2H), 2.38-2.33 (m, 7H), 2.31 (s, 3H), 2.16 (s, 3H).

HRMS (IE) m/z calculated C$_{24}$H$_{28}$N$_2$O$_4$S [M$^+$]: 440.1770, found: 440.1783.

Example B8: 2-(Dimethylamino)ethyl 5-acetyl-4-(benzo[b]thiophen-3-yl)-2,6-dimethyl-1,4-dihydropyridine-3-carboxylate Method B yielded the title compound as a yellow solid (15 mg, 7%).

$^1$H-NMR (300 MHz, CDCl$_3$) δ=8.12 (d, J=8.0 Hz, 1H), 7.79 (d, J=7.9 Hz, 1H), 7.43-7.23 (m, 2H), 7.15 (s, 1H), 5.97 (bs, 1H), 5.48 (s, 1H), 4.19 (h, J=5.8 Hz, 2H), 2.59 (q, J=6.2 Hz, 2H), 2.36 (s, 3H), 2.30 (s, 3H), 2.23 (s, 6H), 2.15 (s, 3H).

HRMS (IE): m/z calculated C$_{22}$H$_{26}$N$_2$O$_3$S [M$^+$]: 398.1664, found: 398.1663.

Example B9: 2-Acetamidoethyl 5-acetyl-4-(benzo[b]thiophen-3-yl)-2,6-dimethyl-1,4-dihydropyridine-3-carboxylate Method B yielded the title compound as a yellow solid (34 mg, 14%).

$^1$H-NMR (300 MHz, CDCl$_3$) δ=8.19 (d, J=8.0 Hz, 1H), 7.82 (d, J=7.9 Hz, 1H), 7.43 (t, J=7.4 Hz, 1H), 7.34 (t, J=7.4 Hz, 1H), 7.20 (s, 1H), 5.84 (bs, 1H), 5.47 (s, 1H), 4.86 (bs, 1H), 4.25-4.09 (m, 1H), 4.07-3.86 (m, 1H), 3.60-3.38 (m, 1H), 3.24-3.08 (m, 1H), 2.37 (s, 3H), 2.34 (s, 3H), 2.20 (s, 3H), 1.61 (s, 3H).

HRMS (IE): m/z calculated C$_{22}$H$_{24}$N$_2$O$_4$S [M$^+$]: 412.1457, found: 412.1458.

Example B10: Methyl 5-acetyl-4-(benzo[b]thiophen-3-yl)-2-(methoxymethyl)-6-methyl-1,4-dihydropyridine-3-carboxylate Method B yielded the title compound as a light-yellow solid (25 mg, 14%).

$^1$H-NMR (300 MHz, CDCl$_3$) δ=8.10 (d, J=8.0 Hz, 1H), 7.80 (d, J=7.9 Hz, 1H), 7.42-7.27 (m, 3H), 7.15 (s, 1H), 5.46 (s, 1H), 4.59 (dd, J=26.8 Hz, 2H), 3.63 (s, 3H), 3.47 (s, 3H), 2.41 (s, 3H), 2.14 (s, 3H).

HRMS (IE): m/z calculated C$_{20}$H$_{21}$NO$_4$S [M$^+$]: 371.1191, found: 371.1176.

Example B11: Methyl 5-acetyl-4-(benzo[b]thiophen-3-yl)-2-((dimethylamino)methyl)-6-methyl-1,4-dihydropyridine-3-carboxylate Method B yielded the title compound as a yellow solid (25 mg, 11%).

$^1$H-NMR (300 MHz, CDCl$_3$) δ=8.18 (s, 1H), 8.10 (d, J=8.2 Hz, 1H), 7.80 (d, J=7.6 Hz, 1H), 7.43-7.28 (m, 2H), 7.14 (s, 1H), 5.47 (s, 1H), 3.73-3.50 (m, 5H), 2.42 (s, 3H), 2.29 (s, 6H), 2.14 (s, 3H).

HRMS (IE) m/z calculated C$_{21}$H$_{24}$N$_2$OS [M$^+$]: 384.1508, found: 384.1506.

Example B12: Pyridin-4-ylmethyl 5-acetyl-4-(benzo[b]thiophen-3-yl)-2,6-dimethyl-1,4-dihydropyridine-3-carboxylate Method B yielded the title compound as a yellow solid (25 mg, 13%).

$^1$H-NMR (300 MHz, CDCl$_3$) δ=8.49-8.34 (m, 2H), 8.03 (d, J=6.8 Hz, 1H), 7.80 (d, J=8.5 Hz, 1H), 7.35-7.20 (m, 2H), 7.14 (s, 1H), 6.93 (s, 1H), 6.91 (s, 1H), 6.33 (s, 1H), 5.52 (s, 1H), 5.08 (q, J=13.7 Hz, 2H), 2.35 (s, 3H), 2.33 (s, 3H), 2.16 (s, 3H).

HRMS (IE): m/z calculated $C_{24}H_{22}N_2O_3S$ [M$^+$]: 418.1351, found: 418.1360.

Example B13: 4-Methoxybenzyl 5-acetyl-4-(benzo[b]thiophen-3-yl)-2,6-dimethyl-1,4-dihydropyridine-3-carboxylate Method B yielded the title compound as a yellow solid (28 mg, 13%).

$^1$H-NMR (300 MHz, CDCl$_3$) δ=8.00 (d, J=8.6 Hz, 1H), 7.78 (d, J=8.5 Hz, 1H), 7.32-7.20 (m, 2H), 7.16 (d, J=8.5 Hz, 2H), 7.08 (s, 1H), 6.83 (d, J=8.6 Hz, 2H), 5.93 (s, 1H), 5.47 (s, 1H), 5.02 (d, J=2.8 Hz, 2H), 3.81 (s, 3H), 2.35 (s, 3H), 2.28 (s, 3H), 2.11 (s, 3H).

HRMS (IE): m/z calculated $C_{26}H_{25}NO_4S$ [M$^+$]: 447.1504, found: 447.1506.

Example B15: Pyridin-2-ylmethyl 5-acetyl-4-(benzo[b]thiophen-3-yl)-2,6-dimethyl-1,4-dihydropyridine-3-carboxylate Method B yielded the title compound as a yellow solid (35 mg, 14%).

$^1$H-NMR (300 MHz, CDCl$_3$) δ=8.53 (d, J=4.0 Hz, 1H), 8.04 (d, J=8.5 Hz, 1H), 7.78 (d, J=8.5 Hz, 1H), 7.52-7.43 (m, 1H), 7.31-7.21 (m, 2H), 7.15 (d, J=5.4 Hz, 2H), 6.91 (d, J=7.8 Hz, 1H), 6.22 (s, 1H), 5.55 (s, 1H), 5.22 (d, J=3.8 Hz, 2H), 2.34 (s, 3H), 2.31 (s, 3H), 2.14 (s, 3H).

HRMS (IQ) m/z calculated $C_{24}H_{23}N_2O_3S$ [M$^-$]: 419.1429, found: 419.1436.

Example B16: Methyl 5-acetyl-4-(benzo[b]thiophen-3-yl)-6-methyl-2-(morpholino-methyl)-1,4-dihydropyridine-3-carboxylate Method B yielded the title compound as a yellow solid (25 mg, 10%).

$^1$H-NMR (300 MHz, CDCl$_3$) δ=8.16-7.97 (m, 2H), 7.80 (d, J=8.0 Hz, 1H), 7.42-7.17 (m, 2H), 7.11 (s, 1H), 5.47 (s, 1H), 3.82-3.69 (m, 5H), 3.64 (s, 4H), 2.52 (t, J=4.6 Hz, 4H), 2.42 (s, 3H), 2.13 (s, 3H).

HRMS (IE) m/z calculated $C_{23}H_{26}N_2O_4S$ [M$^+$]: 426.1613, found: 426.1604.

Example B16-a: Dimethyl 4-(benzo[b]thiophen-3-yl)-2,6-bis(morpholinomethyl)-1,4-dihydropyridine-3,5-dicarboxylate $^1$H-NMR (300 MHz, CDCl$_3$) δ=9.52 (s, 1H), 8.06 (d, J=8.4 Hz, 1H), 7.79 (d, J=7.8 Hz, 1H), 7.47-7.14 (m, 2H), 7.05 (s, 1H), 5.48 (s, 1H), 3.80 (d, J=4.6 Hz, 12H), 3.55 (d, J=1.7 Hz, 6H), 2.56 (tq, J=11.7, 5.9, 4.9 Hz, 8H).

HRMS (IE) m/z calculated $C_{27}H_{33}N_3O_6S$ [M$^+$]: 527.2090, found: 527.2064.

Example B17: 2-Hydroxyethyl 5-acetyl-4-(benzo[b]thiophen-3-yl)-2,6-dimethyl-1,4-dihydropyridine-3-carboxylate Method B yielded the title compound as a yellow solid (25 mg, 10%).

$^1$H-NMR (300 MHz, CDCl$_3$) δ=8.14 (d, J=8.1 Hz, 1H), 7.81 (d, J=7.9 Hz, 1H), 7.35 (dt, J=25.8, 7.3 Hz, 2H), 7.17 (s, 1H), 6.07 (s, 1H), 5.48 (s, 1H), 4.25-4.05 (m, 2H), 3.68 (s, 2H), 2.34 (s, 3H), 2.32 (s, 3H), 2.16 (s, 3H), 1.83 (bs, 1H).

HRMS (IE): m/z calculated $C_{20}H_{21}NO_4S$ [M$^+$]: 371.1191, found: 371.1190.

Example B18: 1-(4-(Benzo[b]thiophen-3-yl)-5-(cyclopropanecarbonyl)-6-cyclopropyl-2-methyl-1,4-dihydropyridin-3-yl)ethan-1-one Method B yielded the title compound as a yellow solid (15 mg, 10%).

$^1$H-NMR (300 MHz, CDCl$_3$) δ=8.07 (d, J=8.0 Hz, 1H), 7.78 (d, J=8.0 Hz, 1H), 7.45-7.26 (m, 2H), 7.04 (s, 1H), 5.78 (s, 1H), 5.57 (s, 1H), 2.39 (s, 3H), 2.37-2.23 (m, 1H), 2.13 (s, 4H), 1.27 (s, 1H), 1.11 (tdd, J=5.6, 4.3, 2.7 Hz, 1H), 1.05-0.88 (m, 3H), 0.86-0.75 (m, 1H), 0.70 (d, J=5.5 Hz, 2H).

HRMS (IE) m/z calculated $C_{23}H_{23}NO_2S$ [M$^+$]: 377.1424, found: 377.1428.

Example B19: Methyl 5-acetyl-4-(benzo[b]thiophen-3-yl)-2-(1-(tert-butoxycarbonyl) azetidin-3-yl)-6-methyl-1,4-dihydropyridine-3-carboxylate Method B yielded the title compound as a light-yellow solid (0.065 mg, 19%).

$^1$H-NMR (300 MHz, CDCl$_3$) δ=8.06 (d, J=8.1 Hz, 1H), 7.80 (d, J=7.8 Hz, 1H), 7.50-7.22 (m, 2H), 7.14 (s, 1H), 6.69 (s, 1H), 5.48 (s, 1H), 4.68 (tt, J=8.8, 4.6 Hz, 1H), 4.22 (td, J=8.9, 3.6 Hz, 2H), 3.82 (ddd, J=14.7, 9.0, 5.0 Hz, 2H), 3.63 (s, 3H), 2.45 (s, 3H), 2.14 (s, 3H), 1.46 (s, 9H).

HRMS (IE): m/z calculated $C_{26}H_{30}N_2O_5S$ [M$^+$]: 482.1875, found: 482.1874.

Example B20: (1-(tert-Butoxycarbonyl)piperidin-4-yl)methyl 5-acetyl-4-(benzo[b]thiophen-3-yl)-2,6-dimethyl-1,4-dihydropyridine-3-carboxylate Method B yielded the title compound as a yellow solid (0.06 mg, 26%).

$^1$H-NMR (300 MHz, CDCl$_3$) δ=8.12 (d, J=7.9 Hz, 1H), 7.78 (d, J=7.9 Hz, 1H), 7.32 (ddd, J=23.7, 11.3, 4.4 Hz, 2H), 7.12 (s, 1H), 6.23 (s, 1H), 5.47 (s, 1H), 4.11-3.79 (m, 4H), 2.72-2.44 (m, 2H), 2.34 (s, 3H), 2.30 (s, 3H), 2.17 (s, 3H), 1.71-1.58 (m, 1H), 1.44 (s, 10H), 1.38-1.21 (m, 1H), 0.99 (td, J=11.8, 4.2 Hz, 2H).

HRMS (IE) m/z calculated $C_{29}H_{36}N_2O_5S$ [M$^+$]: 524.2345, found: 524.2349.

Example B21: Cyclohexylmethyl 5-acetyl-4-(benzo[b]thiophen-3-yl)-2,6-dimethyl-1,4-dihydropyridine-3-carboxylate Method B yielded the title compound as a light-yellow solid (35 mg, 17%).

$^1$H-NMR (300 MHz, CDCl$_3$) δ=8.13 (d, J=7.9 Hz, 1H), 7.79 (d, J=8.0 Hz, 1H), 7.43-7.19 (m, 2H), 7.12 (s, 1H), 5.96 (s, 1H), 5.49 (s, 1H), 3.87 (d, J=6.2 Hz, 2H), 2.36 (s, 3H), 2.30 (s, 3H), 2.16 (s, 3H), 1.70-1.46 (m, 6H), 1.27-1.01 (m, 4H), 1.01-0.75 (m, 1H).

HRMS (IE) m/z calculated $C_{25}H_{29}NO_3S$ [M$^+$]: 423.1868, found: 423.1876.

Example B22: Methyl 4-(benzo[b]thiophen-3-yl)-5-(cyclopropanecarbonyl)-2,6-dicyclopropyl-1,4-dihydropyridine-3-carboxylate Method B yielded the title compound as a light-yellow solid (0.030 g, 11%).

$^1$H-NMR (300 MHz, CDCl$_3$) δ=8.09 (ddd, J=8.1, 1.1, 0.7 Hz, 1H), 7.78 (ddd, J=7.8, 1.1, 0.7 Hz, 1H), 7.45-7.27 (m, 2H), 7.03 (s, 1H), 5.66 (bs, 1H), 5.59 (s, 1H), 3.64 (s, 3H), 2.73 (tt, J=8.5, 5.5 Hz, 1H), 2.37 (tt, J=8.5, 5.5 Hz, 1H), 2.22 (tt, J=7.8, 4.6 Hz, 1H), 1.13-0.86 (m, 6H), 0.80-0.52 (m, 6H).

HRMS (IE) m/z calculated $C_{25}H_{25}NO_3S$ [M$^+$]: 419.1555, found: 419.1543.

HPLC (98.4%): Rt 11.68 min.

Example B23: 5-acetyl-4-(benzo[b]thiophen-3-yl)-2,6-dimethyl-N-phenyl-1,4-dihydropyridine-3-carboxamide Method B yielded the title compound as a yellow solid (0.04 g, 23%).

$^1$H-NMR (300 MHz, CDCl$_3$) δ=8.11-8.04 (m, 1H), 7.89-7.81 (m, 1H), 7.41-7.27 (m, 3H), 7.25-6.98 (m, 6H), 5.66 (bs, 1H), 5.44 (s, 1H), 2.38 (s, 3H), 2.22 (s, 3H), 2.16 (s, 3H).

HRMS (IE) m/z calculated $C_{24}H_{22}N_2O_2S$ [M$^+$]: 402.1402, found: 402.1403.

HPLC (96.5%): Rt 24.12 min.

Method C

Example C1: Tetrahydro-2H-pyran-4-yl 5-acetyl-4-(benzo[b]thiophen-3-yl)-2,6-dimethyl-1,4-dihydropyridine-3-carboxylate

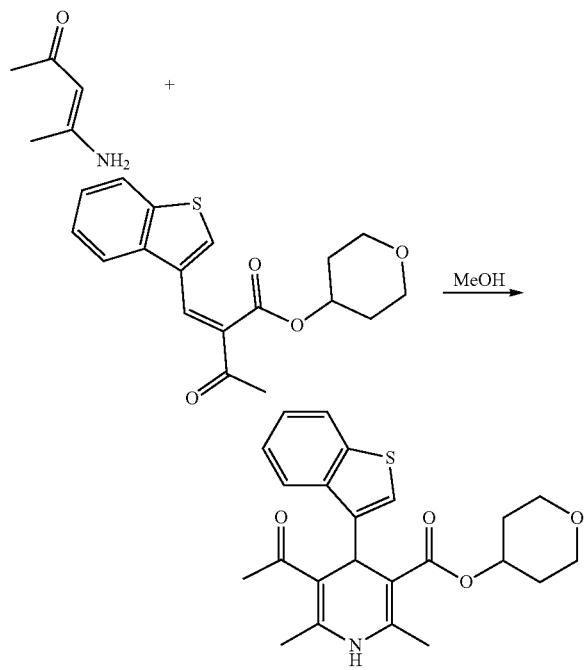

A mixture of tetrahydro-2H-pyran-4-yl (Z)-2-(benzo[b]thiophen-3-ylmethylene)-3-oxobutanoate (0.056 g, 0.17 mmol) and (E)-4-aminopent-3-en-2-one (0.017 g, 0.17 mmol) in methanol (1 mL) was heated in a microwave reactor at 130° C. for 60 min. The mixture was allowed to cool to RT and the solvent was removed under reduced pressure. The residue was purified by column chromatography (2:1 hexane:ethyl acetate) affording a light yellow solid (0.07 g, 43%).

$^1$H-NMR (300 MHz, CDCl$_3$) δ=8.13 (d, J=7.8 Hz, 1H), 7.80 (d, J=7.8 Hz, 1H), 7.42-7.26 (m, 2H), 7.13 (s, 1H), 5.77 (bs, 1H), 5.49 (s, 1H), 4.94 (tt, J=8.9, 4.5 Hz, 1H), 3.84 (ddd, J=15.8, 12.0, 4.5 Hz, 2H), 3.46 (dddd, J=12.0, 8.9, 6.2, 3.0 Hz, 2H), 2.38 (s, 3H), 2.32 (s, 3H), 2.16 (s, 3H), 1.96-1.56 (m, 4H).

HRMS (IE) m/z calculated $C_{23}H_{25}NO_4S$ [M$^+$]: 411.1504, found: 411.1503.

HPLC (99.4%): Rt 22.96 min.

The following examples have been prepared according to Method C:

Example C2: (Tetrahydro-2H-pyran-4-yl)methyl 5-acetyl-4-(benzo[b]thiophen-3-yl)-2,6-dimethyl-1,4-dihydropyridine-3-carboxylate Light-yellow solid (0.018 g, 28%).

$^1$H-NMR (300 MHz, CDCl$_3$) δ=8.12 (d, J=8.1 Hz, 1H), 7.79 (d, J=8.1 Hz, 1H), 7.44-7.23 (m, 2H), 7.13 (s, 1H), 5.87 (bs, 1H), 5.48 (s, 1H), 4.09-3.57 (m, 4H), 3.53-3.08 (m, 2H), 2.36 (s, 3H), 2.32 (s, 3H), 2.16 (s, 3H), 1.88-1.52 (m, 1H), 1.52-1.08 (m, 4H).

HRMS (IE) m/z calculated $C_{24}H_{27}NO_4S$ [M$^+$]: 425.1661, found: 425.1661.

HPLC (98.8%): Rt 17.86 min.

Example C3: Cyclohexyl 5-acetyl-4-(benzo[b]thiophen-3-yl)-2,6-dimethyl-1,4-dihydropyridine-3-carboxylate Light-yellow solid (0.07 g, 36%).

$^1$H-NMR (300 MHz, CDCl$_3$) δ=8.19-8.11 (m, 1H), 7.85-7.72 (m, 1H), 7.40-7.28 (m, 2H), 7.12 (s, 1H), 5.77 (bs, 1H), 5.49 (s, 1H), 4.77 (dt, J=9.2, 5.0 Hz, 1H), 2.38 (s, 3H), 2.30 (s, 3H), 2.16 (s, 3H), 1.92-1.61 (m, 4H), 1.47-1.13 (m, 6H).

HRMS (IE) m/z calculated $C_{24}H_{27}NO_3S$ [M$^+$]: 409.1712, found: 409.1714.

HPLC (98.4%): Rt 20.63 min.

Example C4: Methyl 5-acetyl-4-(benzo[b]thiophen-3-yl)-2-(2-methoxy-2-oxoethyl)-6-methyl-1,4-dihydropyridine-3-carboxylate Light-yellow solid (0.148 g, 45%).

$^1$H-NMR (300 MHz, CDCl$_3$) δ=8.08 (d, J=8.1 Hz, 1H), 7.80 (d, J=8.1 Hz, 1H), 7.42-7.26 (m, 2H), 7.21 (s, 1H), 6.96 (bs, 1H), 5.50 (s, 1H), 4.02-3.76 (m, 2H), 3.73 (s, 3H), 3.63 (s, 3H), 2.39 (s, 3H), 2.15 (s, 3H).

HRMS (IE) m/z calculated $C_{21}H_{21}NO_5S$ [M$^+$]: 399.1140, found: 399.1148.

HPLC (95.2%): Rt 20.91 min.

Example C5: Methyl 5-acetyl-2,6-dimethyl-4-(2-methylbenzo[b]thiophen-3-yl)-1,4-dihydropyridine-3-carboxylate Light-yellow solid (0.065 g, 25%).

$^1$H-NMR (300 MHz, CDCl$_3$) δ=7.83 (d, J=8.1 Hz, 1H), 7.67 (d, J=8.1 Hz, 1H), 7.35-7.14 (m, 2H), 5.63 (bs, 1H), 5.59 (s, 1H), 3.49 (s, 3H), 2.50 (s, 3H), 2.29 (s, 3H), 2.25 (s, 3H), 2.07 (s, 3H).

HRMS (IE) m/z calculated $C_{20}H_{21}NO_3S$ [M$^+$]: 355.1242, found: 355.1241.

HPLC (98.43%): Rt 18.11 min.

Example C6: Cyclopropylmethyl 5-acetyl-4-(benzo[b]thiophen-3-yl)-2,6-dimethyl-1,4-dihydropyridine-3-carboxylate Light-yellow solid (0.065 g, 25%).
$^1$H-NMR (300 MHz, CDCl$_3$) δ=8.15 (d, J=8.0 Hz, 1H), 7.79 (d, J=8.0 Hz, 1H), 7.34 (dt, J=13.1, 7.4 Hz, 2H), 7.16 (s, 1H), 5.78 (bs, 1H), 5.51 (s, 1H), 3.88 (dd, J=7.6, 3.9 Hz, 2H), 2.39 (s, 3H), 2.32 (s, 3H), 2.15 (s, 3H), 1.08 (ddt, J=10.9, 7.6, 3.9 Hz, 1H), 0.51 (d, J=7.6 Hz, 2H), 0.20 (d, J=4.9 Hz, 2H).
HRMS (IE) m/z calculated C$_{22}$H$_{23}$NO$_3$S [M$^+$]: 381.1399, found: 381.1399.
HPLC (98.9%): Rt 17.72 min.

Example C7: Methyl 5-acetyl-4-(benzo[b]thiophen-3-yl)-2-(2-methoxyethyl)-6-methyl-1,4-dihydropyridine-3-carboxylate Light-yellow solid (0.16 g, 64%).
$^1$H-NMR (300 MHz, CDCl$_3$) δ=8.09 (d, J=8.0 Hz, 1H), 7.80 (d, J=8.0 Hz, 1H), 7.43-7.27 (m, 2H), 7.21 (bs, 1H), 7.16 (s, 1H), 5.49 (s, 1H), 3.63 (s, 3H), 3.61 (d, J=5.1 Hz, 2H), 3.40 (s, 3H), 3.26-3.11 (m, 1H), 3.10-2.97 (m, 1H), 2.36 (s, 3H), 2.15 (s, 3H).
HRMS (IE) m/z calculated C$_{21}$H$_{23}$NO$_4$S [M$^+$]: 385.1348, found: 385.1347.
HPLC (99.7%): Rt 19.65 min.

Example C8: Methyl 5-acetyl-4-(benzo[b]thiophen-3-yl)-2-((benzyloxy)methyl)-6-methyl-1,4-dihydropyridine-3-carboxylate Yellow solid (0.18 g, 64%).
$^1$H-NMR (300 MHz, CDCl$_3$) δ=8.09 (d, J=8.0 Hz, 1H), 7.85-7.76 (m, 1H), 7.45-7.24 (m, 8H), 7.13 (s, 1H), 5.45 (s, 1H), 4.85-4.66 (m, 2H), 4.62 (s, 2H), 3.61 (s, 3H), 2.37 (s, 3H), 2.13 (s, 3H).
HRMS (IE) m/z calculated C$_{26}$H$_{25}$NO$_4$S [M$^+$]: 447.1504, found: 447.1490.
HPLC (95.6%): Rt 11.55 min.

Example C9: Methyl 5-acetyl-4-(benzo[b]thiophen-3-yl)-6-methyl-2-(phenoxymethyl)-1,4-dihydropyridine-3-carboxylate Yellow solid (0.11 g, 52%).
$^1$H-NMR (300 MHz, CDCl$_3$) δ=8.15-8.07 (m, 1H), 7.86-7.76 (m, 1H), 7.43-7.27 (m, 4H), 7.17 (s, 1H), 7.14 (bs, 1H), 7.07-6.93 (m, 3H), 5.50 (s, 1H), 5.36-5.12 (m, 2H), 3.67 (d, J=0.6 Hz, 3H), 2.40 (s, 3H), 2.15 (d, 3H).
HRMS (IE) m/z calculated C$_{25}$H$_{23}$NO$_4$S [M$^+$]: 433.1348, found: 433.1346.
HPLC (96.0%): Rt 10.20 min.

Example C10: Phenethyl 5-acetyl-4-(benzo[b]thiophen-3-yl)-2,6-dimethyl-1,4-dihydropyridine-3-carboxylate Yellow solid (0.075 g, 21%).
$^1$H-NMR (300 MHz, CDCl$_3$) δ=7.98-7.89 (m, 1H), 7.81-7.75 (m, 1H), 7.35-7.26 (m, 3H), 7.24-7.13 (m, 4H), 7.00 (s, 1H), 5.75 (bs, 1H), 5.40 (s, 1H), 4.38 (dt, J=10.9, 6.6 Hz, 1H), 4.21 (dt, J=10.9, 7.2 Hz, 1H), 2.88 (t, J=6.6 Hz, 2H), 2.37 (s, 3H), 2.23 (s, 3H), 2.10 (s, 3H).
HRMS (IE) m/z calculated C$_{26}$H$_{25}$NO$_3$S [M$^+$]: 431.1555, found: 431.1549.
HPLC (97.6%): Rt 17.80 min.

Example C11: Methyl 4-(benzo[b]thiophen-3-yl)-5-(cyclopropanecarbonyl)-6-cyclopropyl-2-methyl-1,4-dihydropyridine-3-carboxylate Yellow solid (0.080 g, 40%).
$^1$H-NMR (300 MHz, CDCl$_3$) δ=8.53 (s, 1H), 8.09-7.91 (m, 1H), 7.91-7.79 (m, 1H), 7.37-7.16 (m, 2H), 7.03 (s, 1H), 5.28 (s, 1H), 3.51 (s, 3H), 2.47-2.39 (m, 1H), 2.28 (s, 3H), 2.28-2.20 (m, 1H), 1.00-0.59 (m, 8H).
HRMS (IE) m/z calculated C$_{23}$H$_{23}$NO$_3$S [M$^+$]: 393.1399, found: 393.1403.
HPLC (98.3%): Rt 16.05 min.

Example C14: Methyl 5-acetyl-4-(benzo[b]thiophen-3-yl)-6-methyl-2-(trifluoromethyl)-1,4-dihydropyridine-3-carboxylate Yellow solid (0.012 g, 6%).
$^1$H-NMR (300 MHz, CDCl$_3$) δ=8.00 (ddd, J=8.1, 1.3, 0.7 Hz, 1H), 7.83 (ddd, J=7.8, 1.3, 0.7 Hz, 1H), 7.46-7.30 (m, 2H), 7.17 (s, 1H), 6.22 (bs, 1H), 5.51 (s, 1H), 3.65 (s, 3H), 2.43 (s, 3H), 2.11 (s, 3H). $^{19}$F-NMR (300 MHz, CDCl$_3$) δ=−63.89 (3F).
HRMS (IE) m/z calculated C$_{19}$H$_{16}$F$_3$NO$_3$S [M$^+$]: 395.0803, found: 395.0792.
HPLC (99.5%): Rt 12.57 min.

Example C15 and Example C16: Methyl 5-acetyl-4-(benzo[b]thiophen-3-yl)-6-benzyl-2-methyl-1,4-dihydropyridine-3-carboxylate and methyl 4-(benzo[b]thiophen-3-yl)-2,6-dimethyl-5-(2-phenylacetyl)-1,4-dihydropyridine-3-carboxylate Method C afforded Examples C15 and C16 which were separated by column chromatography.
Example C15: Yellow solid (0.02 g, 6%).
$^1$H-NMR (500 MHz, CDCl$_3$) δ=8.07 (d, J=8.2 Hz, 1H), 7.81 (d, J=8.2 Hz, 1H), 7.41-7.26 (m, 7H), 7.14 (s, 1H), 5.70 (bs, 1H), 5.53 (s, 1H), 4.35 (d, J=16.1 Hz, 1H), 4.11 (d, J=16.1 Hz, 1H), 3.64 (s, 3H), 2.20 (s, 3H), 2.14 (s, 3H).
HRMS (IE) m/z calculated C$_{25}$H$_{23}$NO$_3$S [M$^+$]: 417.1399, found: 417.1400.
HPLC (98.6%): Rt 12.86 min.
Example C16: Yellow solid (0.078 g, 24%).
$^1$H-NMR (500 MHz, CDCl$_3$) δ=8.13 (d, J=8.0 Hz, 1H), 7.84 (d, J=8.0 Hz, 1H), 7.40 (ddd, J=8.2, 7.0, 1.3 Hz, 1H), 7.33 (ddd, J=8.2, 7.0, 1.3 Hz, 1H), 7.26-7.20 (m, 2H), 7.20-7.15 (m, 2H), 7.00 (s, 1H), 6.99 (s, 1H), 5.82 (bs, 1H), 5.60 (s, 1H), 3.91 (d, J=15.9 Hz, 1H), 3.67 (s, 3H), 3.58 (d, J=15.9 Hz, 1H), 2.40 (s, 3H), 2.29 (s, 3H).
HRMS (IE) m/z calculated C$_{25}$H$_{23}$NO$_3$S [M$^+$]: 417.1399, found: 417.1396.
HPLC (95.4%): Rt 15.69 min.

Example C18: Methyl 4-(benzo[b]thiophen-3-yl)-5-(2-methoxyacetyl)-2,6-dimethyl-1,4-dihydropyridine-3-carboxylate Yellow solid (0.03 g, 23%).
$^1$H-NMR (300 MHz, CDCl$_3$) δ=8.10 (d, J=8.7 Hz, 1H), 7.82 (d, J=8.7 Hz, 1H), 7.41 (t, J=7.6 Hz, 1H), 7.33 (t, J=7.6 Hz, 1H), 7.16 (s, 1H), 5.96 (s, 1H), 5.44 (s, 1H), 4.32 (d, J=16.1 Hz, 1H), 3.92 (d, J=16.6 Hz, 1H), 3.66 (s, 3H), 3.28 (s, 3H), 2.43 (s, 3H), 2.31 (s, 3H).

HRMS (IE) m/z calculated C$_{20}$H$_{21}$NO$_4$S [M$^+$]: 371.1191, found: 371.1183.
HPLC (97.4%): Rt 22.72 min.

Example C19: Methyl 5-acetyl-4-(benzo[b]thiophen-3-yl)-6-(methoxymethyl)-2-methyl-1,4-dihydropyridine-3-carboxylate Yellow solid (0.062 g, 36%).
$^1$H-NMR (300 MHz, CDCl$_3$) δ=8.08 (d, J=8.0 Hz, 1H), 7.81 (d, J=8.0 Hz, 1H), 7.42-7.36 (m, 2H), 7.31 (t, J=7.5 Hz, 1H), 7.17 (s, 1H), 5.47 (s, 1H), 4.71 (s, 2H), 3.65 (s, 3H), 3.52 (s, 3H), 2.32 (s, 3H), 2.07 (s, 3H).
HRMS (IE) m/z calculated C$_{20}$H$_{21}$NO$_4$S [M$^+$]: 371.1191, found: 371.1187.
HPLC (96.0%): Rt 26.61 min.

Example C20: Methyl 5-acetyl-4-(benzo[b]thiophen-3-yl)-2-(fluoromethyl)-6-methyl-1,4-dihydropyridine-3-carboxylate Yellow solid (0.015 g, 7%).
$^1$H-NMR (300 MHz, CDCl$_3$) δ=8.09 (d, J=8.0 Hz, 1H), 7.81 (d, J=8.0 Hz, 1H), 7.36 (dt, J=24.7, 7.3 Hz, 2H), 7.18 (s, 1H), 6.72 (d, J=6.5 Hz, 1H), 5.65 (dd, J=47.7, 16.3 Hz, 2H), 5.44 (s, 1H), 3.63 (s, 3H), 2.43 (s, 3H), 2.14 (s, 3H). $^{19}$F NMR (282 MHz, CDCl$_3$) δ=122.68 (td, J=47.7, 6.5 Hz).
HRMS (IE) m/z calculated C$_{19}$H$_{18}$FNO$_3$S [M$^+$]: 359.0991, found: 359.0977.
HPLC (96.8%): Rt 13.25 min.

Example C21: Cyclopropylmethyl 5-acetyl-4-(5-fluorobenzo[b]thiophen-3-yl)-2,6-dimethyl-1,4-dihydropyridine-3-carboxylate Yellow solid (0.055 g, 52%).
$^1$H-NMR (300 MHz, CDCl$_3$) δ=7.82 (dd, J=10.5, 2.3 Hz, 1H), 7.70 (dd, J=8.7, 5.0 Hz, 1H), 7.24 (s, 1H), 7.06 (td, J=8.7, 2.3 Hz, 1H), 5.95 (s, 1H), 5.43 (s, 1H), 3.97-3.80 (m, 2H), 2.37 (s, 3H), 2.32 (s, 3H), 2.16 (s, 3H), 1.19-1.02 (m, 1H), 0.62-0.43 (m, 2H), 0.28-0.15 (m, 2H). $^{19}$F NMR (282 MHz, CDCl$_3$) δ=−118.91 (s).
HRMS (IE) m/z calculated C$_{22}$H$_{22}$FNO$_3$S [M$^+$]: 399.1304, found: 399.1318.
HPLC (98.9%): Rt 17.97 min.

Example C22: 1-(tert-Butoxycarbonyl)piperidin-4-yl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a yellow solid (0.085 g, 21%).
$^1$H-NMR (300 MHz, CDCl$_3$) δ=8.12 (d, J=7.8 Hz, 1H), 7.79 (d, J=7.8 Hz, 1H), 7.34 (dt, J=12.9, 7.2 Hz, 2H), 7.12 (s, 1H), 5.80 (s, 1H), 5.48 (s, 1H), 4.91 (dt, J=8.6, 4.4 Hz, 1H), 3.67 (dd, J=15.3, 7.8 Hz, 2H), 3.07 (dt, J=10.2, 5.2 Hz, 2H), 2.38 (s, 3H), 2.31 (s, 3H), 2.16 (s, 3H), 1.62-1.52 (m, 4H), 1.45 (s, 9H).
HRMS (IE) m/z calculated C$_{28}$H$_{34}$N$_2$O$_5$S [M$^+$]: 510.2188, found: 510.2182. HPLC (99.0%): Rt 21.85 min.

Example C23: Cyclopentylmethyl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a yellow solid (0.035 g, 14%).

$^1$H-NMR (300 MHz, CDCl$_3$) δ=8.13 (d, J=7.9 Hz, 1H), 7.79 (d, J=7.4 Hz, 1H), 7.43-7.29 (m, 2H), 7.13 (s, 1H), 5.84 (bs, 1H), 5.50 (s, 1H), 3.95 (d, J=7.3 Hz, 2H), 2.38 (s, 3H), 2.31 (s, 3H), 2.22-2.09 (m, 4H), 1.77-1.45 (m, 6H), 1.18-1.11 (m, 2H).
HRMS (IE) m/z calculated C$_{24}$H$_{27}$NO$_3$S [M$^+$]: 409.1712, found: 409.1712.
HPLC (99.4%): Rt 16.93 min.

Example C24 Cyclopropylmethyl 5-acetyl-2,6-dimethyl-4-(thieno[2,3-b]pyridin-3-yl)-1,4-dihydropyridine-3-carboxylate Yellow solid (0.035 g, 43%).
$^1$H-NMR (300 MHz, CDCl$_3$) δ=8.53-8.46 (m, 2H), 7.30 (dd, J=7.9, 4.6 Hz, 1H), 7.23 (s, 1H), 6.53 (s, 1H), 5.47 (s, 1H), 3.95-3.73 (m, 2H), 2.37 (s, 3H), 2.32 (s, 3H), 2.17 (s, 3H), 1.03 (ddd, J=12.7, 8.0, 5.0 Hz, 1H), 0.48 (d, J=8.0 Hz, 2H), 0.17 (d, J=4.4 Hz, 2H).
HRMS (IE) m/z calculated C$_{21}$H$_{22}$N$_2$O$_3$S [M$^+$]: 382.1351, found: 382.1346.
HPLC (97.9%): Rt 25.95 min.

Example C25: 1-methylpiperidin-4-yl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a yellow solid (0.025 g, 10%).
$^1$H-NMR (300 MHz, CDCl$_3$) δ=8.13 (d, J=8.0 Hz, 1H), 7.78 (d, J=8.0 Hz, 1H), 7.34 (dt, J=15.9, 7.3 Hz, 2H), 7.11 (s, 1H), 6.03 (s, 1H), 5.49 (s, 1H), 4.78 (tt, J=8.5, 4.1 Hz, 1H), 2.67-2.50 (d, J=17.6 Hz, 2H), 2.35 (s, 3H), 2.30 (s, 3H), 2.27 (d, J=2.3 Hz, 1H), 2.20 (s, 3H), 2.16 (s, 3H), 2.12 (bs, 1H), 1.96-1.83 (m, 2H), 1.80-1.59 (m, 2H).
HRMS (IE) m/z calculated C$_{24}$H$_{28}$N$_2$O$_3$S [M$^+$]: 424.1821, found: 424.1827.
HPLC (96.8%): Rt 33.18 min.

Example C26: Cyclopentyl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a yellow solid (0.04 g, 17%).
$^1$H-NMR (300 MHz, CDCl$_3$) δ=8.14 (d, J=8.2 Hz, 1H), 7.79 (d, J=7.7 Hz, 1H), 7.42-7.28 (m, 2H), 7.11 (s, 1H), 5.81 (s, 1H), 5.48 (s, 1H), 5.27-5.11 (m, 1H), 2.38 (s, 3H), 2.29 (s, 3H), 2.16 (s, 3H), 1.90-1.47 (m, 8H).
HRMS (IE) m/z calculated C$_{23}$H$_{25}$NO$_3$S [M$^+$]: 395.1555, found: 395.1558.
HPLC (97.1%): Rt 17.56 min.

Example C27: 4,4-dimethylcyclohexyl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a light yellow solid (0.03 g, 11%).
$^1$H-NMR (300 MHz, CDCl$_3$) δ=8.15 (ddd, J=8.1, 1.3, 0.7 Hz, 1H), 7.79 (ddd, J=7.8, 1.3, 0.7 Hz, 1H), 7.40-7.28 (m, 2H), 7.13 (s, 1H), 5.78 (bs, 1H), 5.50 (s, 1H), 4.74 (tt, J=8.8, 4.2 Hz, 1H), 2.37 (s, 3H), 2.31 (s, 3H), 2.16 (s, 3H), 1.80-1.66 (m, 1H), 1.66-1.50 (m, 3H), 1.46-1.27 (m, 3H), 1.27-1.16 (m, 1H), 0.88 (s, 3H), 0.88 (s, 3H).

HRMS (IE) m/z calculated $C_{26}H_{31}NO_3S$ [M$^+$]: 437.2025, found: 437.2028.

HPLC (98.3%): Rt 16.78 min.

Example C28: Cyclobutyl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a light yellow solid (0.02 g, 9%).

$^1$H-NMR (300 MHz, CDCl$_3$) δ=8.14 (d, J=7.9 Hz, 1H), 7.79 (d, J=7.9 Hz, 1H), 7.35-7.31 (m, 2H), 7.13 (s, 1H), 6.09 (s, 1H), 5.47 (s, 1H), 5.00-4.89 (m, 1H), 2.36 (s, 3H), 2.32-2.23 (m, 5H), 2.15 (s, 3H), 2.12-1.99 (m, 1H), 1.99-1.85 (m, 1H), 1.82-1.66 (m, 1H), 1.66-1.51 (m, 1H).

HRMS (IE) m/z calculated $C_{22}H_{23}NO_3S$ [M$^+$]: 381.1399, found: 381.1408.

HPLC (99.0%): Rt 17.42 min.

Example C29: Methyl 5-acetyl-4-(5-fluorobenzo[b]thiophen-3-yl)-6-methyl-2-(trifluoromethyl)-1,4-dihydropyridine-3-carboxylate Method C using trifluoroacetic acid (1.5 eq) in methanol afforded the title compound as a yellow solid (0.035 g, 37%).

$^1$H-NMR (300 MHz, CDCl$_3$) δ=7.71 (dd, J=9.6, 3.6 Hz, 2H), 7.24 (s, 1H), 7.11 (td, J=8.7, 2.4 Hz, 1H), 6.30 (s, 1H), 5.43 (s, 1H), 3.69 (s, 3H), 2.43 (s, 3H), 2.13 (s, 3H). $^{19}$F-NMR (282 MHz, CDCl$_3$) δ=−63.84 (s, CF$_3$), −118.19 (td, J=9.6, 4.9 Hz, F).

HRMS (IE) m/z calculated $C_{19}H_{15}NO_3SF_4$ [M$^+$]: 413.0709, found: 413.0702.

HPLC (99.1%): Rt 13.51 min.

Example C30: Methyl 5-acetyl-2,6-dimethyl-4-(thieno[3,2-b]pyridin-3-yl)-1,4-dihydropyridine-3-carboxylate Yellow solid (0.015 g, 24%).

$^1$H-NMR (300 MHz, CDCl$_3$) δ=8.66 (dd, J=4.5, 1.5 Hz, 1H), 8.07 (dd, J=8.2, 1.5 Hz, 1H), 7.29 (s, 1H), 7.18 (dd, J=8.2, 4.5 Hz, 1H), 5.97 (s, 1H), 5.72 (s, 1H), 3.63 (s, 3H), 2.45 (s, 3H), 2.36 (s, 3H), 2.24 (s, 3H).

HRMS (IE) m/z calculated $C_{18}H_{18}N_2O_3S$ [M$^+$]: 342.1038, found: 342.1034.

HPLC (98.8%): Rt 22.75 min.

Example C31: Methyl 5-acetyl-4-(benzo[b]thiophen-3-yl)-2-methyl-6-(trifluoromethyl)-1,4-dihydropyridine-3-carboxylate Method C using trifluoroacetic acid (1.5 eq) in methanol afforded the title compound as a yellow solid (0.035 g, 24%).

$^1$H-NMR (300 MHz, CDCl$_3$) δ=7.97-7.91 (m, 1H), 7.83 (ddd, J=7.7, 1.4, 0.7 Hz, 1H), 7.44-7.30 (m, 2H), 7.24 (s, 1H), 5.94 (s, 1H), 5.40 (s, 1H), 3.58 (s, 3H), 2.39 (s, 3H), 1.99 (q, J=0.7 Hz, 3H). $^{19}$F-NMR (282 MHz, CDCl$_3$) δ=−63.65. (s, CF3).

HRMS (IE) m/z calculated $C_{19}H_{16}NO_3SF_3$ [M$^+$]: 395.0803, found: 395.0810. HPLC (98.5%): Rt 10.44 min.

Example C32: Cyclopropylmethyl 5-acetyl-4-(5-chlorobenzo[b]thiophen-3-yl)-2,6-dimethyl-1,4-dihydropyridine-3-carboxylate Yellow solid (0.075 g, 50%).

$^1$H-NMR (300 MHz, CDCl$_3$) δ=8.12 (d, J=2.0 Hz, 1H), 7.70 (d, J=9.0 Hz, 1H), 7.28 (d, J=2.5 Hz, 1H), 7.21 (s, 1H), 5.78 (s, 1H), 5.44 (s, 1H), 3.90 (d, J=7.3 Hz, 2H), 2.39 (s, 3H), 2.33 (s, 3H), 2.16 (s, 3H), 1.29-1.13 (m, 1H), 0.59-0.46 (m, 2H), 0.21 (dd, J=4.8, 1.8 Hz, 2H).

HRMS (IE) m/z calculated $C_{22}H_{22}NO_3SCl$ [M$^+$]: 415.1009, found: 415.0997.

HPLC (99.6%): Rt 18.43 min.

Example C33: Cyclohexylmethyl 5-acetyl-4-(5-chlorobenzo[b]thiophen-3-yl)-2,6-dimethyl-1,4-dihydropyridine-3-carboxylate Yellow solid (0.080 g, 61%).

$^1$H-NMR (300 MHz, CDCl$_3$) δ=8.10 (bs, 1H), 7.68 (d, J=8.5 Hz, 1H), 7.31-7.21 (m, 1H), 7.17 (s, 1H), 6.05 (bs, 1H), 5.42 (s, 1H), 3.90 (ddd, J=27.5, 10.8, 6.6 Hz, 2H), 2.36 (s, 3H), 2.30 (s, 3H), 2.17 (s, 3H), 1.85-1.43 (m, 6H), 1.32-1.01 (m, 3H), 1.01-0.78 (m, 2H).

HRMS (IE) m/z calculated $C_{25}H_{28}NO_3SCl$ [M$^+$]: 457.1478, found: 457.1477.

HPLC (99.1%): Rt 18.16 min.

Example C34: Cyclohexylmethyl 5-acetyl-2,6-dimethyl-4-(thieno[2,3-b]pyridin-3-yl)-1,4-dihydropyridine-3-carboxylate Yellow solid (0.075 g, 58%).

$^1$H-NMR (300 MHz, CDCl$_3$) δ=8.57-8.44 (m, 2H), 7.32 (dd, J=8.2, 4.6 Hz, 1H), 7.20 (s, 1H), 6.40 (s, 1H), 5.46 (s, 1H), 3.86 (dd, J=6.1, 3.5 Hz, 2H), 2.37 (s, 3H), 2.33 (s, 3H), 2.18 (s, 3H), 1.70-1.44 (m, 6H), 1.16 (d, J=40.3 Hz, 3H), 0.91-0.74 (m, 2H).

HRMS (IE) m/z calculated $C_{24}H_{28}N_2O_3S$ [M$^+$]: 424.1821, found: 424.1833.

HPLC (98.9%): Rt 25.30 min.

Example C35: Cyclopentylmethyl 5-acetyl-2,6-dimethyl-4-(thieno[2,3-b]pyridin-3-yl)-1,4-dihydropyridine-3-carboxylate Yellow solid (0.095 g, 75%).

$^1$H-NMR (300 MHz, CDCl$_3$) δ=8.49 (d, J=8.2 Hz, 2H), 7.31 (dd, J=8.1, 4.6 Hz, 1H), 7.20 (s, 1H), 6.44 (s, 1H), 5.46 (s, 1H), 4.01-3.86 (m, 2H), 2.37 (s, 3H), 2.32 (s, 3H), 2.17 (s, 3H), 2.14-2.02 (m, 1H), 1.67-1.44 (m, 6H), 1.21-1.05 (m, 2H).

HRMS (IE) m/z calculated $C_{23}H_{26}N_2O_3S$ [M$^+$]: 410.1664, found: 410.1665.

HPLC (98.4%): Rt 25.14 min.

Example C36: Cyclohexyl 5-acetyl-2,6-dimethyl-4-(thieno[2,3-b]pyridin-3-yl)-1,4-dihydropyridine-3-carboxylate Yellow solid (0.028 g, 48%).

$^1$H-NMR (300 MHz, CDCl$_3$) δ=8.59-8.40 (m, 2H), 7.31 (dd, J=8.2, 4.6 Hz, 1H), 7.19 (s, 1H), 6.47 (s, 1H), 5.46 (s, 1H), 4.75 (tt, J=8.8, 3.9 Hz, 1H), 2.37 (s, 3H), 2.31 (s, 3H), 2.17 (s, 3H), 1.87-1.74 (m, 1H), 1.75-1.55 (m, 3H), 1.56-1.45 (m, 1H), 1.45-1.13 (m, 5H).

HRMS (IE) m/z calculated $C_{23}H_{26}N_2O_3S$ [M+]: 410.1664, found: 410.1665.

HPLC (98.2%): Rt 24.87 min.

Example C37: Cyclopentyl 5-acetyl-2,6-dimethyl-4-(thieno[2,3-b]pyridin-3-yl)-1,4-dihydropyridine-3-carboxylate Yellow solid (0.034 g, 59%).

$^1$H-NMR (300 MHz, CDCl$_3$) δ=8.53-8.42 (m, 2H), 7.31 (dd, J=8.2, 4.6 Hz, 1H), 7.17 (s, 1H), 5.85 (s, 1H), 5.44 (s, 1H), 5.16 (dq, J=6.1, 3.0 Hz, 1H), 2.38 (s, 3H), 2.31 (s, 3H), 2.17 (s, 3H), 1.80 (td, J=15.9, 14.5, 6.1 Hz, 2H), 1.67-1.46 (m, 6H).

HRMS (IE) m/z calculated $C_{22}H_{24}N_2O_3S$ [M+]: 396.1508, found: 396.1505.

HPLC (98.9%): Rt 25.70 min.

Example C38: Methyl 5-acetyl-4-(5-chlorobenzo[b]thiophen-3-yl)-6-methyl-2-(trifluoromethyl)-1,4-dihydropyridine-3-carboxylate Method C using trifluoroacetic acid (1.5 eq) in methanol afforded the title compound as a yellow solid (0.022 g, 51%).

$^1$H-NMR (300 MHz, CDCl$_3$) δ=8.00 (d, J=1.6 Hz, 1H), 7.73 (d, J=8.6 Hz, 1H), 7.31 (dd, J=8.6, 1.6 Hz, 1H), 7.20 (s, 1H), 6.29 (s, 1H), 5.45 (s, 1H), 3.71 (s, 3H), 2.44 (s, 3H), 2.13 (s, 3H). $^{19}$F-NMR (282 MHz, CDCl$_3$) δ=−63.85 (s, CF$_3$).

HRMS (IE) m/z calculated $C_{19}H_{15}NO_3SF_3Cl$ [M+]: 429.0413, found: 429.0413.

HPLC (95.7%): Rt 13.94 min.

Example C39: Benzyl 5-acetyl-2,6-dimethyl-4-(thieno[2,3-b]pyridin-3-yl)-1,4-dihydropyridine-3-carboxylate Yellow solid (0.070 g, 69%).

$^1$H-NMR (300 MHz, CDCl$_3$) δ=8.50-8.44 (m, 1H), 8.26 (dd, J=8.2, 1.5 Hz, 1H), 7.34-7.24 (m, 2H), 7.26 (d, J=0.8 Hz, 1H), 7.20-7.16 (m, 2H), 7.16-7.10 (m, 2H), 5.95 (s, 1H), 5.44 (s, 1H), 5.07 (s, 2H), 2.37 (s, 3H), 2.33 (s, 3H), 2.13 (s, 3H).

HRMS (IE) m/z calculated $C_{24}H_{22}N_2O_3S$ [M+]: 418.1351, found: 418.1358.

HPLC (99.4%): Rt 26.38 min.

Example C40: (Tetrahydro-2H-pyran-4-yl)methyl 5-acetyl-2,6-dimethyl-4-(thieno[2,3-b]pyridin-3-yl)-1,4-dihydropyridine-3-carboxylate Yellow solid (0.029 g, 45%).

$^1$H-NMR (300 MHz, CDCl$_3$) δ=8.55-8.43 (m, 2H), 7.32 (dd, J=8.1, 4.6 Hz, 1H), 7.19 (s, 1H), 6.18 (s, 1H), 5.45 (s, 1H), 3.99-3.77 (m, 4H), 3.24 (dtd, J=20.2, 11.6, 2.5 Hz, 2H), 2.37 (s, 3H), 2.34 (s, 3H), 2.18 (s, 3H), 1.47-1.15 (m, 5H).

HRMS (IE) m/z calculated $C_{23}H_{26}N_2O_4S$ [M+]: 426.1613, found: 426.1600.

HPLC (99.5%): Rt 32.56 min.

Example C41: Benzyl 5-acetyl-4-(5-fluorobenzo[b]thiophen-3-yl)-2,6-dimethyl-1,4-dihydropyridine-3-carboxylate Yellow solid (0.018 g, 11%).

$^1$H-NMR (300 MHz, CDCl$_3$) δ=7.75-7.63 (m, 2H), 7.33-7.17 (m, 5H), 7.16 (s, 1H), 7.04 (td, J=8.9, 8.5, 2.0 Hz, 1H), 5.92 (s, 1H), 5.42 (s, 1H), 5.10 (q, J=12.3 Hz, 2H), 2.35 (s, 3H), 2.31 (s, 3H), 2.13 (s, 3H). $^{19}$F-NMR (282 MHz, CDCl$_3$) δ=−118.53 (s, CF).

HRMS (IE) m/z calculated $C_{25}H_{22}NO_3SF$ [M+]: 435.1304, found: 435.1307.

HPLC (97.1%): Rt 18.43 min.

Example C42: Benzyl 5-acetyl-4-(5-chlorobenzo[b]thiophen-3-yl)-2,6-dimethyl-1,4-dihydropyridine-3-carboxylate Yellow solid (0.065 g, 60%).

$^1$H-NMR (300 MHz, CDCl$_3$) δ=8.06 (d, J=1.7 Hz, 1H), 7.68 (d, J=8.6 Hz, 1H), 7.39-7.18 (m, 6H), 7.13 (s, 1H), 6.00 (s, 1H), 5.44 (s, 1H), 5.27-4.96 (m, 2H), 2.35 (s, 3H), 2.30 (s, 3H), 2.13 (s, 3H).

HRMS (IE) m/z calculated $C_{25}H_{22}NO_3SCl$ [M+]: 451.1011, found: 451.1011.

HPLC (97.4%): Rt 18.38 min.

Example C43: (Tetrahydro-2H-pyran-4-yl)methyl 5-acetyl-4-(5-chlorobenzo[b]thiophen-3-yl)-2,6-dimethyl-1,4-dihydropyridine-3-carboxylate Yellow solid (0.076 g, 46%).

$^1$H-NMR (300 MHz, CDCl$_3$) δ=8.10 (d, J=1.8 Hz, 1H), 7.68 (d, J=8.1 Hz, 1H), 7.27-7.24 (m, 1H), 7.18 (s, 1H), 6.15 (bs, 1H), 5.39 (s, 1H), 3.93-3.82 (m, 4H), 3.50-3.19 (m, 2H), 2.35 (s, 3H), 2.17 (s, 3H), 2.03 (s, 3H), 1.89-1.63 (m, 2H), 1.51-1.47 (m, 1H), 1.35-1.17 (m, 2H).

HRMS (IE) m/z calculated $C_{24}H_{26}NO_4SCl$ [M+]: 459.1271, found: 459.1272.

HPLC (99.4%): Rt 24.50 min.

Example C44: (Tetrahydro-2H-pyran-4-yl)methyl 5-acetyl-4-(5-fluorobenzo[b]thiophen-3-yl)-2,6-dimethyl-1,4-dihydropyridine-3-carboxylate Yellow solid (0.097 g, 57%).

$^1$H-NMR (300 MHz, CDCl$_3$) δ=7.79 (d, J=9.7 Hz, 1H), 7.70 (dd, J=8.3, 5.1 Hz, 1H), 7.21 (s, 1H), 7.06 (t, J=8.3 Hz, 1H), 6.02 (s, 1H), 5.40 (s, 1H), 3.99-3.73 (m, 4H), 3.28 (dt, J=25.5, 12.5 Hz, 2H), 2.36 (s, 3H), 2.32 (s, 3H), 2.17 (s, 3H), 1.81 (s, 1H), 1.54-1.13 (m, 4H). $^{19}$F-NMR (282 MHz, CDCl$_3$) δ=−118.74 (s, CF).

HRMS (IE) m/z calculated $C_{24}H_{26}NO_4SF$ [M+]: 443.1567, found: 443.1574.

HPLC (99.6%): Rt 24.69 min

Example C45: Benzyl 5-acetyl-4-(benzo[b]thiophen-3-yl)-6-methyl-2-(trifluoromethyl)-1,4-dihydropyridine-3-carboxylate Method C using trifluoroacetic acid (1.5 eq) in methanol afforded the title compound as a yellow solid (0.015 g, 27%).

$^1$H-NMR (300 MHz, CDCl$_3$) δ=7.97-7.90 (m, 1H), 7.85-7.77 (m, 1H), 7.35-7.29 (m, 2H), 7.29-7.22 (m, 3H), 7.16-

7.07 (m, 3H), 6.18 (s, 1H), 5.53 (s, 1H), 5.07 (q, J=12.2 Hz, 2H), 2.42 (s, 3H), 2.10 (s, 3H). $^{19}$F-NMR (282 MHz, CDCl$_3$) δ=−63.64 (s, CF$_3$).

HRMS (IE) m/z calculated C$_{25}$H$_{20}$NO$_3$SF$_3$ [M$^+$]: 471.1116, found: 471.1117.

HPLC (99.3%): Rt 12.46 min

Example C46: Pyridin-4-ylmethyl 5-acetyl-4-(5-fluorobenzo[b]thiophen-3-yl)-2,6-dimethyl-1,4-dihydropyridine-3-carboxylate Yellow solid (0.091 g, 55%).

$^1$H-NMR (300 MHz, CDCl$_3$) δ=8.50-8.42 (m, 2H), 7.76-7.63 (m, 2H), 7.21 (s, 1H), 7.04 (td, J=8.7, 2.5 Hz, 1H), 6.96 (d, J=5.2 Hz, 2H), 6.13 (s, 1H), 5.45 (s, 1H), 5.11 (q, J=13.7 Hz, 2H), 2.36 (s, 3H), 2.35 (s, 3H), 2.17 (s, 3H). $^{19}$F-NMR (282 MHz, CDCl$_3$) δ=−118.54 (s, CF).

HRMS (IE) m/z calculated C$_{24}$H$_{21}$N$_2$O$_3$SF [M$^+$]: 436.1257, found: 436.1255.

HPLC (99.5%): Rt 26.10 min.

Example C47: 4-Fluorobenzyl 5-acetyl-2,6-dimethyl-4-(thieno[2,3-b]pyridin-3-yl)-1,4-dihydropyridine-3-carboxylate Yellow solid (0.050 g, 43%).

$^1$H-NMR (300 MHz, CDCl$_3$) δ=8.49 (d, J=4.5 Hz, 1H), 8.28 (dd, J=8.2, 1.6 Hz, 1H), 7.21-7.07 (m, 4H), 6.95 (t, J=8.6 Hz, 2H), 6.06 (s, 1H), 5.43 (s, 1H), 5.11-4.93 (m, 2H), 2.37 (s, 3H), 2.33 (s, 3H), 2.14 (s, 3H). $^{19}$F-NMR (282 MHz, CDCl$_3$) δ=−113.87 (s, CF).

HRMS (IE) m/z calculated C$_{24}$H$_{21}$N$_2$O$_3$SF [M$^+$]: 436.1257, found: 436.1259.

HPLC (98.5%): Rt 20.40 min.

Example C48: Pyridin-3-ylmethyl 5-acetyl-4-(benzo[b]thiophen-3-yl)-2,6-dimethyl-1,4-dihydropyridine-3-carboxylate Method C using ammonium acetate (1.5 eq) in methanol afforded the title compound as a yellow solid (0.025 g, 15%).

$^1$H-NMR (300 MHz, CDCl$_3$) δ=8.50 (d, J=11.7 Hz, 2H), 8.01-7.96 (m, 1H), 7.85-7.66 (m, 1H), 7.40 (d, J=7.9 Hz, 1H), 7.32-7.21 (m, 2H), 7.17 (t, J=6.5 Hz, 1H), 7.10 (s, 1H), 6.14 (s, 1H), 5.46 (s, 1H), 5.08 (d, J=3.1 Hz, 2H), 2.34 (s, 3H), 2.30 (s, 3H), 2.12 (s, 3H).

HRMS (IE) m/z calculated C$_{24}$H$_{22}$N$_2$O$_3$S [M$^+$]: 418.1351, found: 418.1346.

HPLC (98.0%): Rt 24.79 min.

Example C51: 1,1'-(4-(benzo[b]thiophen-3-yl)-2-benzyl-6-methyl-1,4-dihydropyridine-3,5-diyl)bis(ethan-1-one)

Yield: 8% (18 mg, yellow solid).

$^1$H-NMR (300 MHz, CDCl$_3$) δ=8.12 (d, J=7.8 Hz, 1H), 7.80 (d, J=8.5 Hz, 1H), 7.45-7.28 (m, 5H), 7.32-7.19 (m, 2H), 7.09 (s, 1H), 5.85 (s, 1H), 5.66 (s, 1H), 4.15 (dd, J=16.5 Hz, J=41.8 Hz, 1H), 2.26 (s, 3H), 2.24 (s, 3H), 2.17 (s, 3H).

HRMS (IE) m/z calculated C$_{25}$H$_{23}$NO$_2$S [M$^+$]: 401.1450, found: 401.1442.

Example C52: 1-(5-acetyl-4-(benzo[b]thiophen-3-yl)-2,6-dimethyl-1,4-dihydropyridin-3-yl)-2-phenylethan-1-one Light-yellow solid (35 mg, 15%).

$^1$H-NMR (300 MHz, CDCl$_3$) δ=8.12 (d, J=8.1 Hz, 1H), 7.80 (d, J=7.9 Hz, 1H), 7.47-7.25 (m, 5H), 7.22 (d, J=8.3 Hz, 2H), 7.09 (s, 1H), 5.85 (s, 1H), 5.66 (s, 1H), 4.15 (dd, J=94.6, 16.2 Hz, 2H), 2.26 (s, 3H), 2.24 (s, 3H), 2.17 (s, 3H).

HRMS (IE) m/z calculated C$_{25}$H$_{23}$NO$_2$S [M$^+$]: 401.1450, found: 401.1437.

Example C53: Methyl 5-acetyl-6-methyl-4-(thieno[2,3-b]pyridin-3-yl)-2-(trifluoromethyl)-1,4-dihydropyridine-3-carboxylate Method C using 1.5 eq of TFA yielded the title compound as a yellow solid (30 mg, 26%).

$^1$H-NMR (300 MHz, CDCl$_3$) δ=8.56 (bs, 1H), 8.36 (dd, J=8.2, 1.3 Hz, 1H), 7.36 (dd, J=8.2, 4.5 Hz, 1H), 7.23 (s, 1H), 6.52 (bs, 1H), 5.49 (s, 1H), 3.66 (s, 3H), 2.44 (s, 3H), 2.16 (s, 3H). $^{19}$F-NMR (282 MHz, CDCl$_3$) δ=−63.72 (CF$_3$).

HRMS (IE) m/z calculated C$_{18}$H$_{15}$N$_2$O$_3$SF$_3$ [M$^+$]: 396.0755, found: 396.0768.

Example C54: 1-(2-methyl-5-(piperidine-1-carbonyl)-4-(thieno[2,3-b]pyridin-3-yl)-6-(trifluoromethyl)-1,4-dihydropyridin-3-yl)ethan-1-one Method C using 1.5 eq of TFA yielded the title compound as a yellow solid (10 mg, 15%).

$^1$H-NMR (300 MHz, CDCl$_3$) δ=8.60 (dd, J=4.6, 1.6 Hz, 1H), 8.13 (dd, J=8.2, 1.6 Hz, 1H), 7.42-7.31 (m, 2H), 5.65 (s, 1H), 5.47 (s, 1H), 3.35-3.14 (m, 2H), 2.80-2.65 (m, 1H), 2.41 (s, 3H), 2.26-2.12 (m, 1H), 1.93 (s, 3H), 1.39-1.22 (m, 2H), 1.23-1.04 (m, 2H), 1.06-0.82 (m, 2H). $^{19}$F-NMR (282 MHz, CDCl$_3$) δ=−67.14 (CF$_3$).

HRMS (IE) m/z calculated C$_{22}$H$_{22}$N$_3$O$_2$SF$_3$ [M$^+$]: 449.1385, found: 449.1378.

Example C55: 4-(((5-acetyl-4-(benzo[b]thiophen-3-yl)-2,6-dimethyl-1,4-dihydro-pyridine-3-carbonyl)oxy)methyl)benzoic acid Method C gave 4-(tert-butoxycarbonyl)benzyl 5-acetyl-4-(benzo[b]thiophen-3-yl)-2,6-dimethyl-1,4-dihydropyridine-3-carboxylate (yellow solid, 30 mg, 66%).

$^1$H-NMR (300 MHz, CDCl$_3$) δ=8.00 (d, J=8.1 Hz, 1H), 7.88 (d, J=8.6 Hz, 2H), 7.79 (d, J=8.1 Hz, 1H), 7.32-7.22 (m, 3H), 7.19 (d, J=7.9 Hz, 2H), 5.86 (s, 1H), 5.49 (s, 1H), 5.11 (s, 2H), 2.37 (s, 3H), 2.31 (s, 3H), 2.13 (s, 3H), 1.60 (s, 9H).

Hydrolysis of the ester: A mixture of 4-(tert-butoxycarbonyl)benzyl 5-acetyl-4-(benzo[b]thiophen-3-yl)-2,6-dimethyl-1,4-dihydropyridine-3-carboxylate (0.05 g, 0.09 mmol) in dichloromethane (3 mL) was stirred at 0° C. Trifluoroacetic acid (0.5 mL) in dichloromethane (2 mL) was dropwise added at the same temperature during 60 min. The mixture was allowed to warm up to RT and the solvent was removed under reduced pressure. The residue was purified by column chromatography (5% DCM in methanol) affording a yellow solid (0.012 g, 27%).

$^1$H-NMR (300 MHz, CDCl$_3$) δ=17.14 (s, 1H), 9.14 (s, 1H), 8.02 (dd, J=4.8, 3.0 Hz, 1H), 7.89 (dd, J=6.2, 3.0 Hz,

1H), 7.81 (d, J=7.9 Hz, 2H), 7.30-7.24 (m, 2H), 7.20 (s, 1H), 7.12 (d, J=7.9 Hz, 2H), 5.46 (s, 1H), 5.05 (s, 2H), 2.31 (s, 3H), 2.27 (s, 3H), 2.11 (s, 3H).

HRMS (IE) m/z calculated $C_{26}H_{23}NO_5SNa$ [M$^{+Na}$]: 484.1189, found: 484.1188.

Example C56: Benzyl 5-acetyl-6-methyl-4-(thieno[2,3-b]pyridin-3-yl)-2-(trifluoromethyl)-1,4-dihydropyridine-3-carboxylate Method C using 1.5 eq of TFA in dioxane yielded the title compound as a yellow solid (35 mg, 12%).

$^1$H-NMR (300 MHz, CDCl$_3$) δ=8.51 (s, 1H), 8.23 (d, J=8.1 Hz, 1H), 7.32-7.07 (m, 7H), 6.45 (s, 1H), 5.49 (s, 1H), 5.09 (d, J=2.6 Hz, 2H), 2.43 (s, 3H), 2.14 (s, 3H). $^{19}$F-NMR (282 MHz, CDCl$_3$) δ=−63.44 (CF$_3$).

HRMS (IE) m/z calculated $C_{24}H_{19}N_2O_3SF_3$ [M$^+$]: 472.1068, found: 472.1067.

Example C57: Pyridin-3-ylmethyl 5-acetyl-4-(5-fluorobenzo[b]thiophen-3-yl)-2,6-dimethyl-1,4-dihydropyridine-3-carboxylate Method C yielded the title compound as a yellow solid (60 mg, 50%).

$^1$H-NMR (300 MHz, CDCl$_3$) δ=8.52 (d, J=4.3 Hz, 1H), 8.48 (s, 1H), 7.72-7.63 (m, 2H), 7.46 (d, J=7.8 Hz, 1H), 7.24-7.18 (m, 1H), 7.17 (s, 1H), 7.04 (td, J=8.7, 2.5 Hz, 1H), 6.27 (s, 1H), 5.39 (s, 1H), 5.11 (s, 2H), 2.34 (s, 3H), 2.30 (s, 3H), 2.14 (s, 3H).

$^{19}$F-NMR (282 MHz, CDCl$_3$) δ=−118.51 (q, J=9.2 Hz, CF).

HRMS (IE) m/z calculated $C_{24}H_{21}N_2O_3SF$ [M$^+$]: 436.1257, found: 436.1252.

Example C58: Pyridin-3-ylmethyl 5-acetyl-4-(7-bromobenzo[b]thiophen-3-yl)-2,6-dimethyl-1,4-dihydropyridine-3-carboxylate Method C yielded the title compound as a yellow solid (68 mg, 49%).

$^1$H-NMR (300 MHz, CDCl$_3$) δ=8.52 (s, 2H), 7.98 (d, J=7.9 Hz, 1H), 7.44 (d, J=7.5 Hz, 1H), 7.36 (d, J=7.1 Hz, 1H), 7.23-7.10 (m, 3H), 5.93 (s, 1H), 5.41 (s, 1H), 5.08 (q, J=12.8 Hz, 2H), 2.36 (s, 3H), 2.32 (s, 3H), 2.13 (s, 3H).

HRMS (IE) m/z calculated $C_{24}H_{21}N_2O_3SBr$ [M$^+$]: 496.0456, found: 496.0462.

Example C59: Pyridin-3-ylmethyl 5-acetyl-4-(7-cyanobenzo[b]thiophen-3-yl)-2,6-dimethyl-1,4-dihydropyridine-3-carboxylate Method C yielded the title compound as a yellow solid (30 mg, 31%).

$^1$H-NMR (300 MHz, CDCl$_3$) δ=8.52 (d, J=15.9 Hz, 2H), 8.29 (d, J=8.2 Hz, 1H), 7.64 (d, J=8.2 Hz, 1H), 7.43-7.29 (m, 2H), 7.25-7.14 (m, 2H), 6.00 (s, 1H), 5.48 (s, 1H), 5.07 (q, J=13.7, 13.0 Hz, 2H), 2.38 (s, 3H), 2.36 (s, 3H), 2.15 (s, 3H).

HRMS (IE) m/z calculated $C_{25}H_{21}N_3O_3S$ [M$^+$]: 443.1304, found: 443.1288.

Example C60: Pyridin-3-ylmethyl 5-acetyl-4-(5-chlorobenzo[b]thiophen-3-yl)-2,6-dimethyl-1,4-dihydropyridine-3-carboxylate Method C yielded the title compound as a yellow solid (68 mg, 35%).

$^1$H-NMR (300 MHz, CDCl$_3$) δ=8.52 (s, 2H), 8.04 (s, 1H), 7.69 (d, J=8.6 Hz, 1H), 7.49 (d, J=7.8 Hz, 1H), 7.29-7.19 (m, 2H), 7.15 (s, 1H), 6.00 (s, 1H), 5.41 (s, 1H), 5.13 (s, 2H), 2.36 (s, 3H), 2.32 (s, 3H), 2.14 (s, 3H).

HRMS (IE) m/z calculated $C_{24}H_{21}N_2O_3SCl$ [M$^+$]: 452.0961, found: 452.0959.

Example C61: Pyridin-3-ylmethyl 5-acetyl-2,6-dimethyl-4-(thieno[2,3-b]pyridin-3-yl)-1,4-dihydropyridine-3-carboxylate Method C yielded the title compound as a yellow solid (35 mg, 34%).

$^1$H-NMR (300 MHz, CDCl$_3$) δ=8.62-8.40 (m, 3H), 8.29 (d, J=8.0 Hz, 1H), 7.40 (d, J=8.0 Hz, 1H), 7.23-7.14 (m, 3H), 6.05 (s, 1H), 5.43 (s, 1H), 5.09 (q, J=12.6 Hz, 2H), 2.38 (s, 3H), 2.35 (s, 3H), 2.15 (s, 3H).

HRMS (IE) m/z calculated $C_{23}H_{21}N_3O_3S$ [M$^+$]: 419.1304, found: 419.1306.

Example C62: Pyridin-4-ylmethyl 5-acetyl-4-(5-chlorobenzo[b]thiophen-3-yl)-2,6-dimethyl-1,4-dihydropyridine-3-carboxylate Method C yielded the title compound as a yellow solid (35 mg, 48%).

$^1$H-NMR (300 MHz, CDCl$_3$) δ=8.46 (d, J=4.7 Hz, 2H), 8.04 (s, 1H), 7.70 (d, J=8.5 Hz, 1H), 7.23-7.16 (m, 2H), 6.99 (d, J=5.0 Hz, 2H), 6.00 (s, 1H), 5.46 (s, 1H), 5.22-5.03 (m, 2H), 2.38 (s, 3H), 2.35 (s, 3H), 2.17 (s, 3H).

HRMS (IE) m/z calculated $C_{24}H_{21}N_2O_3SCl$ [M$^+$]: 452.0961, found: 452.0954.

Example C63: 4-(cyclopropylcarbamoyl)benzyl 5-acetyl-4-(benzo[b]thiophen-3-yl)-2,6-dimethyl-1,4-dihydropyridine-3-carboxylate Method C yielded the title compound as a yellow solid (30 mg, 13%).

$^1$H-NMR (300 MHz, CDCl$_3$) δ=8.00 (dd, J=6.9, 2.4 Hz, 1H), 7.84-7.75 (m, 1H), 7.61 (d, J=8.2 Hz, 2H), 7.34-7.24 (m, 1H), 7.28-7.20 (m, 1H), 7.18 (d, J=8.2 Hz, 2H), 7.10 (s, 1H), 6.18 (bs, 1H), 5.87 (bs, 1H), 5.49 (s, 1H), 5.10 (s, 2H), 2.90 (dt, J=6.9, 3.6 Hz, 1H), 2.37 (s, 3H), 2.31 (s, 3H), 2.13 (s, 3H), 0.93-0.82 (m, 2H), 0.67-0.57 (m, 2H).

HRMS (IE) m/z calculated $C_{29}H_{29}N_2O_4S$ [M$^+$]: 501.1843, found: 501.1841.

Example C64: Pyridin-4-ylmethyl 5-acetyl-2,6-dimethyl-4-(thieno[2,3-b]pyridin-3-yl)-1,4dihydropyridine-3-carboxylate Method C yielded the title compound as a yellow solid (28 mg, 40%).

$^1$H-NMR (300 MHz, CDCl$_3$) δ=8.51-8.41 (m, 3H), 8.37 (dd, J=8.2, 1.6 Hz, 1H), 7.22-7.15 (m, 2H), 6.96 (d, J=5.5 Hz, 2H), 5.49 (s, 1H), 5.28 (s, 1H), 5.04 (q, J=15.0 Hz, 2H), 2.35 (s, 6H), 2.18 (s, 3H).

HRMS (IE) m/z calculated $C_{23}H_{21}N_{30}O_3S$ [M$^+$]: 419.1304, found: 419.1304.

Example C65: 4-bromobenzyl 5-acetyl-2,6-dimethyl-4-(thieno[2,3-b]pyridin-3-yl)-1,4-dihydropyridine-3-carboxylate Method C yielded the title compound as a yellow solid (131 mg, 72%).

$^1$H-NMR (300 MHz, CDCl$_3$) δ=8.50 (d, J=4.7 Hz, 1H), 8.34 (s, 1H), 7.38 (d, J=8.0 Hz, 2H), 7.18 (s, 2H), 6.99 (d, J=8.0 Hz, 2H), 6.00 (s, 1H), 5.43 (s, 1H), 4.99 (q, J=12.5 Hz, 2H), 2.39 (s, 3H), 2.36 (s, 3H), 2.16 (s, 3H).

HRMS (IE) m/z calculated C$_{24}$H$_{21}$N$_2$O$_3$SBr [M$^+$]: 496.0456, found: 496.0441.

Example C66: 3-bromobenzyl 5-acetyl-2,6-dimethyl-4-(thieno[2,3-b]pyridin-3-yl)-1,4-dihydropyridine-3-carboxylate Method C yielded the title compound as a yellow solid (115 mg, 54%).

$^1$H-NMR (300 MHz, CDCl$_3$) δ=8.50 (dd, J=4.6, 1.5 Hz, 1H), 8.31 (d, J=8.1 Hz, 1H), 7.48-7.37 (m, 1H), 7.33 (t, J=1.5 Hz, 1H), 7.23-7.01 (m, 4H), 5.97 (s, 1H), 5.44 (s, 1H), 5.02 (q, J=12 Hz, 2H), 2.38 (s, 3), 2.36 (s, 3H), 2.15 (s, 3H).

HRMS (IE) m/z calculated C$_{24}$H$_{21}$N$_2$O$_3$SBr [M$^+$]: 496.0456, found: 496.0456.

Example C67: 2-bromobenzyl 5-acetyl-2,6-dimethyl-4-(thieno[2,3-b]pyridin-3-yl)-1,4-dihydropyridine-3-carboxylate Method C yielded the title compound as a yellow solid (127 mg, 74%).

$^1$H-NMR (300 MHz, CDCl$_3$) δ=8.46 (dd, J=4.7, 1.6 Hz, 1H), 8.32 (d, J=8.2 Hz, 1H), 7.57-7.48 (m, 1H), 7.23-7.05 (m, 5H), 6.04 (s, 1H), 5.47 (s, 1H), 5.14 (q, J=15 Hz, 2H), 2.39 (s, 3H), 2.38 (s, 3H), 2.16 (s, 3H).

HRMS (IE) m/z calculated C$_{24}$H$_{21}$N$_2$O$_3$SBr [M$^+$]: 496.0456, found: 496.0446.

Example C68: (3-fluoropyridin-4-yl)methyl 5-acetyl-2,6-dimethyl-4-(thieno[2,3-b]pyridin-3-yl)-1,4-dihydropyridine-3-carboxylate Method C yielded the title compound as a yellow solid (30 mg, 47%).

$^1$H-NMR (300 MHz, CDCl$_3$) δ=8.50 (d, J=4.6 Hz, 1H), 8.44-8.30 (m, 2H), 8.23 (s, 1H), 7.20 (q, J=4.9 Hz, 2H), 6.88 (t, J=5.4 Hz, 1H), 6.18 (s, 1H), 5.47 (s, 1H), 5.24-5.09 (m, 2H), 2.38 (s, 3H), 2.37 (s, 3H), 2.18 (s, 3H). $^{19}$F-NMR (282 MHz, CDCl$_3$) δ=−132.30 (s, CF).

HRMS (IE) m/z calculated C$_{23}$H$_{20}$N$_3$O$_3$SF [M$^+$]: 437.1209, found: 437.1215.

Example C69: Pyrimidin-5-ylmethyl 5-acetyl-2,6-dimethyl-4-(thieno[2,3-b]pyridin-3-yl)-1,4-dihydropyridine-3-carboxylate Method C yielded the title compound as a yellow solid (35 mg, 58%).

$^1$H-NMR (300 MHz, CDCl$_3$) δ=9.13 (s, 1H), 8.56 (s, 2H), 8.50 (dd, J=4.6, 1.6 Hz, 1H), 8.33 (dd, J=8.2, 1.6 Hz, 1H), 7.23 (dd, J=8.3, 4.6 Hz, 1H), 7.18 (s, 1H), 6.51 (s, 1H), 5.42 (s, 1H), 5.08 (q, J=12 Hz, 2H), 2.36 (s, 3H), 2.33 (s, 3H), 2.16 (s, 3H).

HRMS (IE) m/z calculated C$_{22}$H$_{20}$N$_4$O$_3$S [M$^+$]: 420.1256, found: 420.1262.

Example C70: (5-bromopyridin-3-yl)methyl 5-acetyl-2,6-dimethyl-4-(thieno[2,3-b]pyridin-3-yl)-1,4-dihydropyridine-3-carboxylate Method C yielded the title compound as a yellow solid (84 mg, 63%).

$^1$H-NMR (300 MHz, CDCl$_3$) δ=8.58 (s, 1H), 8.50 (d, J=4.3 Hz, 1H), 8.38 (s, 1H), 8.32 (d, J=7.8 Hz, 1H), 7.54 (s, 1H), 7.22 (dd, J=4.3, 7.8 Hz, 1H), 7.18 (s, 1H), 6.32 (bs, 1H), 5.43 (s, 1H), 5.04 (q, J=13 Hz, 2H), 2.37 (s, 3H), 2.35 (s, 3H), 2.16 (s, 3H).

HRMS (IE) m/z calculated C$_{23}$H$_{20}$N$_3$O$_3$SBr [M$^+$]: 497.0409, found: 497.0412.

Example C71: 2-phenylpropan-2-yl 5-acetyl-2,6-dimethyl-4-(thieno[2,3-b]pyridin-3-yl)-1,4-dihydropyridine-3-carboxylate Method C yielded the title compound as a yellow solid (17 mg, 27%).

$^1$H-NMR (300 MHz, CDCl$_3$) δ=8.60-8.47 (m, 1H), 8.36 (dd, J=8.2, 1.6 Hz, 1H), 7.23-7.09 (m, 5H), 7.08-6.99 (m, 2H), 6.02 (s, 1H), 5.49 (s, 1H), 2.38 (s, 3H), 2.31 (s, 3H), 2.15 (s, 3H), 1.70 (s, 3H), 1.64 (s, 3H).

HRMS (IE) m/z calculated C$_{26}$H$_{27}$N$_2$O$_3$S [M$^+$]: 447.1737, found: 447.1736.

Example C72: 3-Cyanobenzyl 5-acetyl-2,6-dimethyl-4-(thieno[2,3-b]pyridin-3-yl)-1,4-dihydropyridine-3-carboxylate Method C yielded the title compound as a yellow solid (38 mg, 58%).

$^1$H-NMR (300 MHz, CDCl$_3$) δ=8.55-8.45 (m, 1H), 8.34 (dd, J=8.2, 1.5 Hz, 1H), 7.54 (dt, J=7.4, 1.5 Hz, 1H), 7.45 (s, 1H), 7.37-7.27 (m, 2H), 7.24-7.20 (m, 1H), 7.19 (s, 1H), 6.40 (s, 1H), 5.45 (s, 1H), 5.06 (q, J=12 Hz, 2H), 2.37 (s, 3H), 2.35 (s, 3H), 2.17 (s, 3H).

HRMS (IE) m/z calculated C$_{25}$H$_{21}$N$_3$O$_3$S [M$^+$]: 443.1304, found: 443.1310.

Example C73: 4-cyanobenzyl 5-acetyl-2,6-dimethyl-4-(thieno[2,3-b]pyridin-3-yl)-1,4-dihydropyridine-3-carboxylate Method C yielded the title compound as a yellow solid (25 mg, 40%).

$^1$H-NMR (300 MHz, CDCl$_3$) δ=8.55-8.45 (m, 1H), 8.34 (dd, J=8.2, 1.5 Hz, 1H), 7.54 (dt, J=7.4, 1.5 Hz, 1H), 7.45 (s, 1H), 7.37-7.27 (m, 2H), 7.24-7.20 (m, 1H), 7.19 (s, 1H), 6.40 (s, 1H), 5.45 (s, 1H), 5.19-4.93 (q, J=12 Hz, 2H), 2.37 (s, 3H), 2.35 (s, 3H), 2.17 (s, 3H).

HRMS (IE) m/z calculated C$_{25}$H$_{21}$N$_3$O$_3$S [M$^+$]: 443.1304, found: 443.1306.

Example C74: (6-chloropyridin-3-yl)methyl 5-acetyl-2,6-dimethyl-4-(thieno[2,3-b]pyridin-3-yl)-1,4-dihydropyridine-3-carboxylate Method C yielded the title compound as a yellow solid (80 mg, 54%).

$^1$H-NMR (300 MHz, CDCl$_3$) δ=8.57-8.46 (m, 1H), 8.37 (d, J=8.2 Hz, 1H), 8.26 (d, J=2.4 Hz, 1H), 7.28 (d, J=2.7 Hz,

1H), 7.22 (d, J=4.6 Hz, 1H), 7.20-7.12 (m, 2H), 6.16 (s, 1H), 5.41 (s, 1H), 5.13-4.93 (q, J=12 Hz, 2H), 2.38 (s, 3H), 2.36 (s, 3H), 2.17 (s, 3H).

HRMS (IE) m/z calculated $C_{23}H_{20}N_3O_3SCl$ [M$^+$]: 453.0914, found: 453.0894.

Example C75: 3-morpholinobenzyl 5-acetyl-2,6-dimethyl-4-(thieno[2,3-b]pyridin-3-yl)-1,4-dihydropyridine-3-carboxylate Method C yielded the title compound as a yellow solid (50 mg, 69%).

$^1$H-NMR (300 MHz, CDCl$_3$) δ=8.51-8.45 (m, 1H), 8.32 (d, J=8.1 Hz, 1H), 7.24-7.11 (m, 3H), 6.89 (d, J=8.1 Hz, 1H), 6.74 (d, J=6.9 Hz, 2H), 5.92 (s, 1H), 5.45 (s, 1H), 5.04 (d, J=3.0 Hz, 2H), 3.88 (d, J=4.8 Hz, 4H), 3.09 (t, J=4.8 Hz, 4H), 2.39 (s, 3H), 2.35 (s, 3H), 2.14 (s, 3H).

HRMS (IE) m/z calculated $C_2H_{29}N_3O_4S$ [M$^+$]: 503.1879, found: 503.1878.

Example C76: 4,4-dimethylcyclohexyl 5-acetyl-2,6-dimethyl-4-(thieno[2,3-b]pyridin-3-yl)-1,4-dihydropyridine-3-carboxylate Method C yielded the title compound as a yellow solid (45 mg, 73%).

$^1$H-NMR (300 MHz, CDCl$_3$) δ=8.57-8.45 (m, 2H), 7.31 (dd, J=8.1, 4.7 Hz, 1H), 7.20 (s, 1H), 6.90 (s, 1H), 5.46 (s, 1H), 4.71 (tt, J=8.8, 4.1 Hz, 1H), 2.35 (s, 3H), 2.31 (s, 3H), 2.17 (s, 3H), 1.70-1.49 (m, 3H), 1.35-1.17 (m, 5H), 0.86 (s, 3H), 0.83 (s, 3H).

HRMS (IE) m/z calculated $C_{25}H_{30}N_2O_3S$ [M$^+$]: 438.1977, found: 438.1967.

Example C77: (2-chloropyridin-4-yl)methyl 5-acetyl-2,6-dimethyl-4-(thieno[2,3-b]pyridin-3-yl)-1,4-dihydropyridine-3-carboxylate Method C yielded the title compound as a yellow solid (117 mg, 75%).

$^1$H-NMR (300 MHz, CDCl$_3$) δ=8.53 (s, 1H), 8.41 (d, J=8.2 Hz, 1H), 8.22 (d, J=5.1 Hz, 1H), 7.22 (s, 2H), 7.01 (d, J=7.4 Hz, 1H), 6.85 (d, J=5.1 Hz, 1H), 6.14 (s, 1H), 5.49 (s, 1H), 5.13-4.96 (q, J=12 Hz, 2H), 2.40 (s, 6H), 2.19 (s, 3H).

HRMS (IE) m/z calculated $C_{23}H_{20}N_3O_3SCl$ [M$^+$]: 453.0914, found: 453.0927.

Example C78: Tetrahydro-2H-pyran-4-yl 5-acetyl-2,6-dimethyl-4-(thieno[2,3-b]pyridin-3-yl)-1,4-dihydropyridine-3-carboxylate Method C yielded the title compound as a yellow solid (25 mg, 51%).

$^1$H-NMR (300 MHz, CDCl$_3$) δ=8.50 (d, J=8.1 Hz, 2H), 7.33 (dd, J=8.1, 4.7 Hz, 1H), 7.24-7.17 (m, 1H), 6.70 (s, 1H), 5.46 (s, 1H), 4.92 (tt, J=8.9, 4.2 Hz, 1H), 3.81 (ddt, J=16.6, 11.5, 4.2 Hz, 2H), 3.46 (ddt, J=12.0, 5.3, 2.9 Hz, 2H), 2.36 (s, 3H), 2.33 (s, 3H), 2.18 (s, 3H), 1.92-1.83 (m, 1H), 1.80-1.71 (m, 1H), 1.69-1.57 (m, 1H), 1.53-1.40 (m, 1H).

HRMS (IE) m/z calculated $C_{22}H_{24}N_2O_4S$ [M$^+$]: 412.1457, found: 412.1457.

Example C79: 4,4-difluorocyclohexyl 5-acetyl-2,6-dimethyl-4-(thieno[2,3-b]pyridin-3-yl)-1,4-dihydropyridine-3-carboxylate Method C yielded the title compound as a yellow solid (45 mg, 83%).

$^1$H-NMR (300 MHz, CDCl$_3$) δ=8.57-8.48 (m, 2H), 7.33 (dd, J=7.9, 4.8 Hz, 1H), 7.20 (s, 1H), 6.96 (s, 1H), 5.46 (s, 1H), 4.90 (s, 1H), 2.35 (s, 3H), 2.32 (s, 3H), 2.19 (s, 3H), 1.96-1.58 (m, 8H). $^{19}$F-NMR (282 MHz, CDCl$_3$) δ=−95.77 (d, J=247.3 Hz CF).

HRMS (IE) m/z calculated $C_{23}H_{24}N_2O_3SF_2$ [M$^+$]: 446.1476, found: 446.1475.

Example C80: 5-Acetyl-N-benzyl-N,2,6-trimethyl-4-(thieno[2,3-b]pyridin-3-yl)-1,4-dihydropyridine-3-carboxamide Method C yielded the title compound as a yellow solid (37 mg, 67%).

$^1$H-NMR (300 MHz, CDCl$_3$) δ=8.51 (d, J=4.6 Hz, 1H), 8.16-8.06 (m, 1H), 7.25-7.15 (m, 5H), 7.08-6.98 (m, 2H), 6.12 (s, 1H), 5.37 (s, 1H), 4.65 (d, J=14.1 Hz, 1H), 4.07 (d, J=14.1 Hz, 1H), 2.36 (s, 3H), 2.13 (s, 3H), 1.98 (s, 3H), 1.68 (s, 3H).

HRMS (IE) m/z calculated $C_{25}H_{25}N_3O_2S$ [M$^+$]: 431.1667, found: 431.1675.

Example C81: Oxetan-3-yl 5-acetyl-4-(7-bromobenzo[b]thiophen-3-yl)-2-cyclopropyl-6-methyl-1,4-dihydropyridine-3-carboxylate Method C yielded the title compound as a yellow solid (5.2 mg, 6%).

$^1$H-NMR (300 MHz, CDCl$_3$) δ=8.12 (d, J=8.0 Hz, 1H), 7.48 (d, J=7.9 Hz, 1H), 7.30 (d, J=7.9 Hz, 1H), 7.18 (s, 1H), 5.73 (s, 1H), 5.45 (s, 1H), 5.40 (q, J=5.9 Hz, 1H), 4.89-4.80 (m, 2H), 4.61-4.49 (m, 2H), 2.55 (tt, J=8.6, 5.7 Hz, 1H), 2.36 (s, 3H), 2.16 (s, 3H), 1.01 (ddp, J=18.2, 8.6, 4.6 Hz, 2H), 0.69 (dq, J=7.4, 4.6, 4.0 Hz, 2H).

HRMS (IE) m/z calculated $C_{23}H_{22}NO_4SBr$ [M$^+$]: 487.0453, found: 487.0439.

Example C82: Isopropyl 5-acetyl-4-(7-bromobenzo[b]thiophen-3-yl)-2-cyclopropyl-6-methyl-1,4-dihydropyridine-3-carboxylate Method C yielded the title compound as a yellow solid (21 mg, 14%).

$^1$H-NMR (300 MHz, CDCl$_3$) δ=8.14 (d, J=8.1 Hz, 1H), 7.46 (d, J=7.6 Hz, 1H), 7.30 (s, 1H), 7.24 (s, 1H), 7.15 (s, 1H), 5.68 (s, 1H), 5.44 (s, 1H), 5.03 (p, J=6.2 Hz, 1H), 2.53 (ddd, J=8.8, 5.7, 3.4 Hz, 1H), 2.36 (s, 3H), 2.14 (s, 3H), 1.21 (d, J=6.2 Hz, 3H), 1.12 (d, J=6.2 Hz, 3H), 1.01-0.88 (m, 2H), 0.67 (dqd, J=11.1, 5.7, 3.4 Hz, 2H).

HRMS (IE) m/z calculated $C_{23}H_{24}NO_3SBr$ [M$^+$]: 473.0660, found: 473.0677.

Example C83: Methyl 5-acetyl-4-(7-bromobenzo[b]thiophen-3-yl)-6-methyl-2-(trifluoromethyl)-1,4-dihydropyridine-3-carboxylate Method C using 1.5 eq of TFA in MeOH yielded the title compound as a yellow solid (8 mg, 18%).

$^1$H-NMR (300 MHz, CDCl$_3$) δ=8.00 (d, J=8.1 Hz, 1H), 7.51 (d, J=7.5 Hz, 1H), 7.35-7.28 (m, 1H), 7.24 (s, 1H), 6.20

(bs, 1H), 5.47 (s, 1H), 3.65 (s, 3H), 2.44 (s, 3H), 2.12 (s, 3H).
$^{19}$F-NMR (282 MHz, CDCl$_3$) δ=63.85 (s, CF$_3$).
HRMS (IE) m/z calculated C$_{19}$H$_{15}$NO$_3$SF$_3$Br [M$^+$]: 472.9908, found: 472.9915.

Example C84: Cyclopropylmethyl 5-acetyl-4-(7-bromobenzo[b]thiophen-3-yl)-2-cyclopropyl-6-methyl-1,4-dihydropyridine-3-carboxylate Method C in dioxane yielded the title compound as a yellow solid (20 mg, 13%).
$^1$H-NMR (300 MHz, CDCl$_3$) δ=8.15 (d, J=8.1 Hz, 1H), 7.46 (d, J=7.6 Hz, 1H), 7.29-7.23 (m, 1H), 7.17 (s, 1H), 5.70 (bs, 1H), 5.47 (bs, 1H), 3.95-3.86 (m, 2H), 2.59 (tt, J=8.7, 5.7 Hz, 1H), 2.36 (s, 3H), 2.14 (s, 3H), 1.12-0.87 (m, 3H), 0.73-0.59 (m, 2H), 0.57-0.44 (m, 2H), 0.26-0.14 (m, 2H).
HRMS (IE) m/z calculated C$_{24}$H$_{24}$NO$_3$SBr [M$^+$]: 485.0660, found: 485.0676.

Example C85: Methyl 5-acetyl-2-cyclopropyl-6-methyl-4-(7-(2,2,2-trifluoroacetyl)benzo[b]thiophen-3-yl)-1,4-dihydropyridine-3-carboxylate Method C yielded the title compound as a yellow solid (42 mg, 44%).
$^1$H-NMR (300 MHz, CDCl$_3$) δ=8.64 (d, J=8.1 Hz, 1H), 8.17 (d, J=7.4 Hz, 1H), 7.62 (t, J=7.8 Hz, 1H), 7.32 (s, 1H), 5.89 (bs, 1H), 5.54 (s, 1H), 3.64 (s, 3H), 2.59 (tt, J=8.7, 5.6 Hz, 1H), 2.36 (s, 3H), 2.14 (s, 3H), 1.06-0.85 (m, 2H), 0.81-0.58 (m, 2H).
HRMS (IE) m/z calculated C$_{23}$H$_{20}$NO$_4$SF$_3$ [M$^+$]: 463.1065, found: 463.1054.

Example C86: 2-phenylpropan-2-yl 5-acetyl-4-(7-bromobenzo[b]thiophen-3-yl)-2,6-dimethyl-1,4-dihydropyridine-3-carboxylate Method C yielded the title compound as a yellow solid (18 mg, 18%).
$^1$H-NMR (300 MHz, CDCl$_3$) δ=8.06 (d, J=8.1 Hz, 1H), 7.46 (d, J=7.6 Hz, 1H), 7.21-7.10 (m, 5H), 7.07-6.98 (m, 2H), 5.87 (bs, 1H), 5.49 (s, 1H), 2.36 (s, 3H), 2.28 (s, 3H), 2.14 (s, 3H), 1.72 (s, 3H), 1.64 (s, 3H).
HRMS (ESI) m/z calculated C$_{27}$H$_{26}$NO$_3$SBr [M$^+$]: 546.0709, found: 546.0711.
HPLC (98.2%): Rt 18.30 min.

Example C87: Methyl 5-acetyl-4-(7-chlorobenzo[b]thiophen-3-yl)-2-cyclopropyl-6-methyl-1,4-dihydropyridine-3-carboxylate Method C yielded the title compound as a yellow solid (80 mg, 69%).
$^1$H-NMR (300 MHz, CDCl$_3$) δ=8.07-7.99 (m, 1H), 7.39-7.28 (m, 2H), 7.15 (d, J=1.7 Hz, 1H), 5.67 (s, 1H), 5.45 (s, 1H), 3.66 (s, 3H), 2.59 (tt, J=8.4, 5.7 Hz, 1H), 2.35 (s, 3H), 2.13 (s, 3H), 1.04-0.90 (m, 2H), 0.66 (dtt, J=9.0, 5.7, 3.4 Hz, 2H).
HRMS (IE) m/z calculated C$_{21}$H$_{20}$NO$_3$SCl [M$^+$]: 401.0852, found: 401.0855.
HPLC (99.1%): Rt 18.66 min.

Example C88: methyl 5-acetyl-2-cyclopropyl-6-methyl-4-(7-(trifluoromethyl)benzo[b]thiophen-3-yl)-1,4-dihydropyridine-3-carboxylate Method C yielded the title compound as a yellow solid (55 mg, 80%).
$^1$H-NMR (300 MHz, CDCl$_3$) δ=8.35 (d, J=8.2 Hz, 1H), 7.62 (d, J=7.5 Hz, 1H), 7.49 (t, J=7.9 Hz, 1H), 7.20 (s, 1H), 5.66 (bs, 1H), 5.51 (s, 1H), 3.65 (s, 3H), 2.59 (h, J=6.9, 6.2 Hz, 1H), 2.36 (s, 3H), 2.13 (s, 3H), 1.09-0.84 (m, 2H), 0.7509-0.57 (m, 2H).
$^{19}$F-NMR (282 MHz, CDCl$_3$) δ (ppm): −62.96 (s, CF$_3$).
HRMS (IE) m/z calculated C$_{22}$H$_{20}$NO$_3$SF$_3$ [M$^+$]: 435.1116, found: 435.1129.
HPLC (99.4%): Rt 19.68 min.

Example C89: 3-chlorobenzyl 5-acetyl-2,6-dimethyl-4-(thieno[2,3-b]pyridin-3-yl)-1,4-dihydropyridine-3-carboxylate Method C yielded the title compound as a yellow solid (78 mg, 53%).
$^1$H-NMR (300 MHz, CDCl$_3$) δ=8.49 (dd, J=4.6, 1.6 Hz, 1H), 8.29 (dd, J=8.2, 1.6 Hz, 1H), 7.28-7.23 (m, 1H), 7.22-7.13 (m, 4H), 7.01 (dt, J=7.6, 1.6 Hz, 1H), 6.26 (s, 1H), 5.44 (s, 1H), 5.09-4.97 (m, 2H), 2.37 (s, 3H), 2.34 (s, 6H), 2.15 (s, 3H).
HRMS (IE) m/z calculated C$_{24}$H$_{21}$N$_2$O$_3$SCl [M$^+$]: 452.0961, found: 452.0966.
HPLC (98.6%): Rt 19.83 min.

Example C90: 2-phenylpropan-2-yl 5-acetyl-4-(7-bromobenzo[b]thiophen-3-yl)-2-cyclopropyl-6-methyl-1,4-dihydropyridine-3-carboxylate Method C yielded the title compound as a yellow solid (20 mg, 17%).
$^1$H-NMR (300 MHz, CDCl$_3$) δ=8.05 (d, J=8.0 Hz, 1H), 7.52-7.40 (m, 1H), 7.22-7.13 (m, 4H), 7.12 (s, 1H), 7.10-7.04 (m, 2H), 5.67 (bs, 1H), 5.50 (s, 1H), 2.63-2.47 (m, 1H), 2.35 (s, 3H), 2.13 (s, 3H), 1.72 (s, 3H), 1.67 (s, 3H), 1.03-0.77 (m, 2H), 0.76-0.57 (m, 2H).
HRMS (ESI) m/z calculated C$_{29}$H$_{28}$NO$_3$SBrNa [M$^{+Na}$]: 572.0865, found: 572.0865.
HPLC (98.82%): Rt 17.16 min.

Example C91: Cyclohexyl 5-acetyl-2-cyclopropyl-6-methyl-4-(thieno[2,3-b]pyridin-3-yl)-1,4-dihydropyridine-3-carboxylate Method C yielded the title compound as a yellow solid (70 mg, 79%).
$^1$H-NMR (300 MHz, CDCl$_3$) δ=8.52 (s, 1H), 8.46 (d, J=8.1 Hz, 1H), 7.31 (dd, J=8.1, 4.7 Hz, 1H), 7.13 (s, 1H), 5.69 (bs, 1H), 5.47 (s, 1H), 4.83-4.71 (m, 1H), 2.64-2.47 (m, 1H), 2.36 (s, 3H), 2.16 (s, 3H), 1.90-1.70 (m, 2H), 1.68-1.50 (m, 4H), 1.35-1.19 (m, 4H), 1.08-0.87 (m, 2H), 0.78-0.58 (m, 2H).
HRMS (IE) m/z calculated C$_{25}$H$_{28}$N$_2$O$_3$S [M$^+$]: 436.1821, found: 436.1841.
HPLC (99.3%): Rt 18.47 min.

Example C92: 2-phenylpropan-2-yl 5-acetyl-2-cyclopropyl-6-methyl-4-(thieno[2,3-b]pyridin-3-yl)-1,4-dihydropyridine-3-carboxylate Method C yielded the title compound as a yellow solid (15 mg, 16%).
$^1$H-NMR (300 MHz, CDCl$_3$) δ=8.50 (dd, J=4.6, 1.6 Hz, 1H), 8.33 (dd, J=8.2, 1.6 Hz, 1H), 7.23-7.12 (m, 4H), 7.11 (s, 1H), 7.12-7.02 (m, 2H), 5.71 (s, 1H), 5.49 (s, 1H), 2.65-2.49 (m, 1H), 2.36 (s, 3H), 2.13 (s, 3H), 1.70 (s, 3H), 1.67 (s, 3H), 1.03-0.83 (m, 2H), 0.76-0.58 (m, 2H).

HRMS (ESI) m/z calculated $C_{28}H_{29}N_2O_3S$ [M+]: 473.1893, found: 473.1891.
HPLC (95.7%): Rt 25.13 min.

Example C93: 1-(4-(7-Bromobenzo[b]thiophen-3-yl)-5-(cyclopropanecarbonyl)-6-cyclopropyl-2-methyl-1,4-dihydropyridin-3-yl)ethan-1-one Method C yielded the title compound as a yellow solid (80 mg, 56%).
$^1$H-NMR (300 MHz, CDCl$_3$) δ=8.09 (d, J=8.1 Hz, 1H), 7.46 (d, J=7.6 Hz, 1H), 7.28 (d, J=8.1 Hz, 1H), 7.10 (s, 1H), 5.84 (bs, 1H), 5.50 (s, 1H), 2.41 (s, 3H), 2.38-2.27 (m, 1H), 2.20-2.01 (m, 4H), 1.41-1.22 (m, 1H), 1.20-1.06 (m, 1H), 1.07-0.90 (m, 3H), 0.84-0.65 (m, 3H).
HRMS (IE) m/z calculated $C_{23}H_{22}NO_2SBr$ [M+]: 455.0555, found: 455.0540.
HPLC (99.1%): Rt 22.48 min

Example C94: 3-chlorobenzyl 5-acetyl-2-cyclopropyl-6-methyl-4-(thieno[2,3-b]pyridin-3-yl)-1,4-dihydropyridine-3-carboxylate Method C yielded the title compound as a yellow solid (16 mg, 13%).
$^1$H-NMR (300 MHz, CDCl$_3$) δ=8.53 (d, J=4.6 Hz, 1H), 8.32 (d, J=8.1 Hz, 1H), 7.32-7.28 (m, 1H), 7.25-7.18 (m, 3H), 7.16 (s, 1H), 7.07 (d, J=7.4 Hz, 1H), 5.79 (bs, 1H), 5.50 (s, 1H), 5.16-5.04 (m, 2H), 2.73-2.51 (m, 1H), 2.39 (s, 3H), 2.19 (s, 3H), 1.08-0.87 (m, 2H), 0.83-0.61 (m, 2H).
HRMS (IE) m/z calculated $C_{26}H_{23}N_2O_3SCl$ [M+]: 478.1118, found: 478.1118.
HPLC (96.7%): Rt 19.79 min.

Example C95: 2-(4-fluorophenyl)propan-2-yl 5-acetyl-2,6-dimethyl-4-(thieno[2,3-b]pyridin-3-yl)-1,4-dihydropyridine-3-carboxylate Method C yielded the title compound as a yellow solid (10 mg, 7%).
$^1$H-NMR (300 MHz, CDCl$_3$) δ (ppm): 8.52 (d, J=3.9 Hz, 1H), 8.35 (dd, J=8.3, 1.6 Hz, 1H), 7.21 (dd, J=8.2, 4.6 Hz, 1H), 7.16 (s, 1H), 7.00-6.91 (m, 2H), 6.87-6.75 (m, 2H), 5.90 (s, 1H), 5.48 (s, 1H), 2.38 (s, 3H), 2.30 (s, 3H), 2.15 (s, 3H), 1.68 (s, 3H), 1.61 (s, 3H). $^{19}$F-NMR (282 MHz, CDCl$_3$) δ (ppm): −116.44 (CF).
HRMS (IE) m/z calculated $C_{26}H_{25}N_2O_3SF$ [M+]: 464.1570, found: 464.1570.
HPLC (98.2%): Rt 19.52 min.

Example C96: 2-(4-fluorophenyl)propan-2-yl 5-acetyl-4-(7-bromobenzo[b]thiophen-3-yl)-2-cyclopropyl-6-methyl-1,4-dihydropyridine-3-carboxylate Method C yielded the title compound as a yellow solid (30 mg, 17%).
$^1$H-NMR (300 MHz, CDCl$_3$) δ=8.03 (d, J=8.1 Hz, 1H), 7.47 (d, J=7.6 Hz, 1H), 7.17 (t, J=7.9 Hz, 1H), 7.12 (s, 1H), 6.98 (dd, J=8.7, 5.4 Hz, 2H), 6.80 (t, J=8.7 Hz, 2H), 5.61 (s, 1H), 5.48 (s, 1H), 2.62-2.45 (m, 1H), 2.35 (s, 3H), 2.13 (s, 3H), 1.69 (s, 3H), 1.65 (s, 3H), 1.04-0.82 (m, 2H), 0.76-0.59 (m, 2H). $^{19}$F-NMR (282 MHz, CDCl$_3$) δ (ppm): −116.65 (CF).
HRMS (IE) m/z calculated $C_{29}H_{27}N_2O_3SBrFNa$ [M$^{+Na}$]: 590.0771, found: 590.0772.
HPLC (98.0%): Rt 18.52 min.

Example C97: 2-(4-fluorophenyl)propan-2-yl 5-acetyl-2-cyclopropyl-6-methyl-4-(thieno[2,3-b]pyridin-3-yl)-1,4-dihydropyridine-3-carboxylate Method C yielded the title compound as a yellow solid (38 mg, 24%).
$^1$H-NMR (300 MHz, CDCl$_3$) δ (ppm): 8.55-8.44 (m, 1H), 8.33 (dd, J=8.2, 1.3 Hz, 1H), 7.19 (dd, J=8.2, 4.6 Hz, 1H), 7.10 (s, 1H), 7.03-6.93 (m, 2H), 6.79 (t, J=8.7 Hz, 2H), 5.97 (bs, 1H), 5.46 (s, 1H), 2.60-2.43 (m, 1H), 2.34 (s, 3H), 2.12 (s, 3H), 1.66 (s, 3H), 1.63 (s, 3H), 1.00-0.80 (m, 2H), 0.78-0.56 (m, 2H). $^{19}$F-NMR (282 MHz, CDCl$_3$) δ (ppm): −116.53 (CF).
HRMS (IE) m/z calculated $C_{28}H_{28}N_2O_3SF$ [M+]: 491.1799, found: 491.1800.
HPLC (98.9%): Rt 19.26 min.

Example C98: Methyl 5-acetyl-2-cyclopropyl-4-(7-fluorobenzo[b]thiophen-3-yl)-6-methyl-1,4-dihydropyridine-3-carboxylate Method C yielded the title compound as a yellow solid (94 mg, 71%).
$^1$H-NMR (300 MHz, CDCl$_3$) δ (ppm): 7.89 (d, J=8.2 Hz, 1H), 7.35 (td, J=8.0, 5.2 Hz, 1H), 7.13 (s, 1H), 7.01 (dd, J=9.7, 8.0 Hz, 1H), 5.63 (bs, 1H), 5.47 (s, 1H), 3.67 (s, 3H), 2.60 (tt, J=8.7, 5.7 Hz, 1H), 2.36 (s, 3H), 2.14 (s, 3H), 1.08-0.85 (m, 2H), 0.74-0.56 (m, 2H). $^{19}$F-NMR (282 MHz, CDCl$_3$) δ (ppm): −116.08 (CF).
HRMS (IE) m/z calculated $C_{21}H_{20}NO_3SF$ [M+]: 385.1148, found: 385.1132.
HPLC (99.3%): Rt 22.58 min.

Example C99: Cyclopropylmethyl 5-acetyl-2-cyclopropyl-6-methyl-4-(thieno[2,3-b]pyridin-3-yl)-1,4-dihydropyridine-3-carboxylate Method C in dioxane yielded the title compound as a yellow solid (12 mg, 26%).
$^1$H-NMR (300 MHz, CDCl$_3$) δ (ppm): 8.53-8.50 (m, 1H), 8.46 (dd, J=8.2, 1.6 Hz, 1H), 7.29 (dd, J=8.2, 4.6 Hz, 1H), 7.17 (s, 1H), 5.71 (bs, 1H), 5.48 (s, 1H), 3.90 (dd, J=7.3, 2.7 Hz, 2H), 2.60 (tt, J=8.6, 5.7 Hz, 1H), 2.37 (s, 3H), 2.16 (s, 3H), 1.05-0.91 (m, 3H), 0.72-0.61 (m, 2H), 0.55-0.43 (m, 2H), 0.27-0.12 (m, 2H).
HRMS (IE) m/z calculated $C_{23}H_{24}N_2O_3S$ [M+]: 408.1508, found: 408.1509.
HPLC (99.7%): Rt 30.16 min.

Example C100: Cyclopentyl 5-acetyl-2-cyclopropyl-6-methyl-4-(thieno[2,3-b]pyridin-3-yl)-1,4-dihydropyridine-3-carboxylate Method C in dioxane yielded the title compound as a yellow solid (27 mg, 14 $^1$H-NMR (300 MHz, CDCl$_3$) δ (ppm): 8.52 (dd, J=4.6, 1.5 Hz, 1H), 8.46 (dd, J=8.2, 1.5 Hz, 1H), 7.30 (dd, J=8.2, 4.6 Hz, 1H), 7.12 (s, 1H), 5.71 (bs, 1H), 5.45 (s, 1H), 5.24-5.11 (m, 1H), 2.62-2.45 (m, 1H), 2.36 (s, 3H), 2.16 (s, 3H), 1.92-1.72 (m, 2H), 1.64-1.44 (m, 6H), 1.07-0.85 (m, 2H), 0.76-0.56 (m, 2H).
HRMS (IE) m/z calculated $C_{24}H_{26}N_2O_3S$ [M+]: 422.1664, found: 422.1662.
HPLC (99.7%): Rt 30.24 min.

Example C101: Cyclopropylmethyl 5-acetyl-4-(7-cyanobenzo[b]thiophen-3-yl)-2-cyclopropyl-6-methyl-1,4-dihydropyridine-3-carboxylate Method C in dioxane yielded the title compound as a yellow solid (9 mg, 26%).

$^1$H-NMR (300 MHz, CDCl$_3$) δ (ppm): 8.56-8.41 (m, 1H), 7.66 (d, J=7.5 Hz, 1H), 7.46 (t, J=7.5 Hz, 1H), 7.24 (s, 1H), 5.71 (bs, 1H), 5.53 (s, 1H), 3.98-3.77 (m, 2H), 2.70-2.52 (m, 1H), 2.37 (s, 3H), 2.16 (s, 3H), 1.09-0.92 (m, 3H), 0.77-0.58 (m, 2H), 0.53-0.39 (m, 2H), 0.27-0.10 (m, 2H).

HRMS (IE) m/z calculated C$_{25}$H$_{24}$N$_2$O$_3$S [M$^+$]: 432.1508, found: 432.1516.

HPLC (97.8%): Rt 22.16 min.

Example C102: Methyl 5-acetyl-4-(7-bromobenzo[b]thiophen-3-yl)-2-cyclobutyl-6-methyl-1,4-dihydropyridine-3-carboxylate Method C yielded the title compound as a yellow solid (41 mg, 29%).

$^1$H-NMR (300 MHz, CDCl$_3$) δ (ppm): 8.09 (d, J=8.8 Hz, 1H), 7.47 (d, J=7.5 Hz, 1H), 7.29 (d, J=8.0 Hz, 1H), 7.18 (s, 1H), 6.10 (bs, 1H), 5.41 (s, 1H), 3.63 (s, 3H), 2.42 (s, 3H), 2.33-2.17 (m, 2H), 2.14 (s, 3H), 2.06-1.78 (m, 5H).

HRMS (IE) m/z calculated C$_{22}$H$_{22}$NO$_3$SBr [M$^+$]: 459.0504, found: 459.0505.

HPLC (95.2%): Rt 18.21 min.

Example C103: Dimethyl 4-(7-cyanobenzo[b]thiophen-3-yl)-2-cyclopropyl-6-methyl-1,4-dihydropyridine-3,5-dicarboxylate Method C yielded the title compound as a yellow solid (80 mg, 65%).

$^1$H-NMR (300 MHz, CDCl$_3$) δ (ppm): 8.36 (d, J=9.2 Hz, 1H), 7.66 (d, J=7.3 Hz, 1H), 7.46 (dd, J=9.2, 7.3 Hz, 1H), 7.24 (s, 1H), 5.64 (bs, 1H), 5.47 (s, 1H), 3.56 (s, 3H), 3.54 (s, 3H), 2.77-2.67 (m, 1H), 2.34 (s, 3H), 1.07-0.96 (m, 2H), 0.77-0.65 (m, 2H).

HRMS (IE) m/z calculated C$_{22}$H$_{20}$N$_2$O$_4$S [M$^+$]: 408.1144, found: 408.1153.

HPLC (99.2%): Rt 12.64 min.

Example C104: Methyl 5-cyano-4-(7-cyanobenzo[b]thiophen-3-yl)-2-cyclopropyl-6-methyl-1,4-dihydropyridine-3-carboxylate Method C yielded the title compound as a yellow solid (40 mg, 48%).

$^1$H-NMR (300 MHz, CDCl$_3$) δ (ppm): 8.24 (d, J=9.1 Hz, 1H), 7.71 (d, J=7.3 Hz, 1H), 7.56-7.44 (m, 1H), 7.23 (s, 1H), 5.73 (bs, 1H), 5.14 (s, 1H), 3.55 (s, 3H), 2.87-2.71 (m, 1H), 2.09 (s, 3H), 1.13-0.99 (m, 2H), 0.82-0.65 (m, 2H).

HRMS (IE) m/z calculated C$_{21}$H$_{17}$N$_3$O$_2$S [M$^+$]: 375.1041, found: 375.1046.

HPLC (99.0%): Rt 21.27 min.

Example C105: Methyl 5-acetyl-4-(7-bromobenzo[b]thiophen-3-yl)-2-cyclopentyl-6-methyl-1,4-dihydropyridine-3-carboxylate Method C yielded the title compound as a yellow solid (59 mg, 40%).

$^1$H-NMR (300 MHz, CDCl$_3$) δ (ppm): 8.06 (d, J=8.0 Hz, 1H), 7.47 (d, J=7.4 Hz, 1H), 7.29 (d, J=8.0 Hz, 1H), 7.19 (s, 1H), 5.88 (bs, 1H), 5.45 (s, 1H), 4.26-4.02 (m, 1H), 3.63 (s, 3H), 2.38 (s, 3H), 2.15 (s, 3H), 2.04-1.90 (m, 2H), 1.78-1.69 (m, 4H), 1.53-1.38 (m, 2H).

HRMS (IE) m/z calculated C$_{23}$H$_{24}$NO$_3$SBr [M$^+$]: 473.0660, found: 473.0647.

HPLC (97.4%): Rt 12.81 min.

Example C106: Methyl 5-acetyl-4-(7-bromobenzo[b]thiophen-3-yl)-2-cyclohexyl-6-methyl-1,4-dihydropyridine-3-carboxylate Method C yielded the title compound as a yellow solid (89 mg, 59%).

$^1$H-NMR (300 MHz, CDCl$_3$) δ (ppm): 8.05 (d, J=8.8 Hz, 1H), 7.46 (d, J=7.5 Hz, 1H), 7.28 (d, J=7.5 Hz, 1H), 7.18 (s, 1H), 6.00 (bs, 1H), 5.44 (s, 1H), 3.80-3.66 (m, 1H), 3.62 (s, 3H), 2.38 (s, 3H), 2.15 (s, 3H), 1.92-1.69 (m, 5H), 1.44-1.20 (m, 5H).

HRMS (IE) m/z calculated C$_{24}$H$_{26}$NO$_3$SBr [M$^+$]: 487.0817, found: 487.0801.

HPLC (96.7%): Rt 11.94 min.

Example C107: Methyl 5-cyano-4-(7-cyanobenzo[b]thiophen-3-yl)-2,6-dicyclopropyl-1,4-dihydropyridine-3-carboxylate Method C yielded the title compound as a yellow solid (15 mg, 13%).

$^1$H-NMR (300 MHz, CDCl$_3$) δ (ppm): 8.25 (dd, J=8.2, 0.9 Hz, 1H), 7.71 (d, J=7.3 Hz, 1H), 7.55-7.45 (m, 1H), 7.20 (s, 1H), 5.57 (bs, 1H), 5.14 (s, 1H), 3.56 (s, 3H), 2.87-2.70 (m, 1H), 1.93-1.78 (m, 1H), 1.16-0.83 (m, 5H), 0.80-0.63 (m, 3H).

HRMS (IE) m/z calculated C$_{23}$H$_{19}$N$_3$O$_2$S [M$^+$]: 401.1198, found: 401.1199.

HPLC (96.5%): Rt 15.42 min.

Example C108: 3-((4-methylpiperazin-1-yl)methyl)benzyl 5-acetyl-4-(7-bromobenzo[b]thiophen-3-yl)-2,6-dimethyl-1,4-dihydropyridine-3-carboxylate Method C yielded the title compound as a yellow solid (33 mg, 18%).

$^1$H-NMR (300 MHz, CDCl$_3$) δ (ppm): 7.98 (d, J=8.2 Hz, 1H), 7.43 (d, J=7.6 Hz, 1H), 7.27-7.04 (m, 6H), 5.80 (bs, 1H), 5.44 (s, 1H), 5.07 (s, 2H), 3.44 (s, 2H), 2.48-2.41 (m, 4H), 2.37 (s, 3H), 2.32 (s, 3H), 2.28 (s, 3H), 2.12 (s, 3H), 1.73-1.60 (m, 4H).

HRMS (IE) m/z calculated C$_{31}$H$_{34}$N$_3$O$_3$SBr [M$^+$]: 607.1504, found: 607.1491.

HPLC (98.4%): Rt 9.94 min.

Example C109: 3-(cyclopropylmethyl) 5-methyl 4-(7-cyanobenzo[b]thiophen-3-yl)-2-cyclopropyl-6-methyl-1,4-dihydropyridine-3,5-dicarboxylate The title compound was prepared using a variation of Method C by heating in dioxane in a sealed tube at 130° C. overnight yielding a yellow solid (35 mg, 28%).

$^1$H-NMR (300 MHz, CDCl$_3$) δ (ppm): 8.40 (d, J=8.2 Hz, 1H), 7.65 (d, J=7.0 Hz, 1H), 7.44 (t, J=7.7 Hz, 1H), 7.26 (s, 1H), 5.61 (bs, 1H), 5.49 (s, 1H), 3.84-3.73 (m, 2H), 3.55 (s, 3H), 2.81-2.65 (m, 1H), 2.34 (s, 3H), 1.02 (dd, J=8.9, 5.5 Hz, 2H), 0.95-0.80 (m, 1H), 0.72 (d, J=6.1 Hz, 2H), 0.38 (t, J=9.7 Hz, 2H), 0.06 (s, 2H).

Example C110: 3-(cyclopropylmethyl) 5-methyl 4-(7-cyanobenzo[b]thiophen-3-yl)-2,6-dicyclopropyl-1,4-dihydropyridine-3,5-dicarboxylate The title compound was prepared using a variation of Method C by heating in dioxane in a sealed tube at 130° C. overnight yielding a yellow solid (20 mg, 15%).

$^1$H-NMR (300 MHz, CDCl$_3$) δ (ppm): 8.41 (d, J=8.3 Hz, 1H), 7.65 (d, J=7.4 Hz, 1H), 7.44 (t, J=7.8 Hz, 1H), 7.23 (s, 1H), 5.56 (bs, 1H), 5.51 (s, 1H), 3.79 (d, J=7.3 Hz, 2H), 3.57 (s, 3H), 2.85-2.61 (m, 2H), 1.09-0.84 (m, 5H), 0.75-0.55 (m, 4H), 0.47-0.29 (m, 2H), 0.15--0.02 (m, 2H).

HRMS (IE) m/z calculated C$_{27}$H$_{26}$N$_2$NaO$_4$S [M$^{+Na}$]: 497.1505, found: 497.1503.

Example C111: Cyclopropylmethyl 5-cyano-4-(7-cyanobenzo[b]thiophen-3-yl)-2-cyclopropyl-6-methyl-1,4-dihydropyridine-3-carboxylate The title compound was prepared using a variation of Method C by heating the reaction mixture in MeOH in a sealed tube at 130° C. for 7 h yielding a yellow solid (8 mg, 7%).

$^1$H-NMR (300 MHz, CDCl$_3$) δ (ppm): 8.24 (d, J=8.3 Hz, 1H), 7.70 (d, J=7.4 Hz, 1H), 7.48 (t, J=7.8 Hz, 1H), 7.27 (s, 1H), 5.73 (bs, 1H), 5.19 (s, 1H), 3.75 (d, J=7.3 Hz, 2H), 2.92-2.70 (m, 1H), 2.09 (s, 3H), 1.14-0.97 (m, 2H), 0.88-0.66 (m, 3H), 0.40-0.12 (m, 2H), 0.08--0.17 (m, 2H)

HRMS (IE) m/z calculated C$_{24}$H$_{21}$N$_3$NaO$_2$S [M$^{+Na}$]: 438.1247, found: 438.1245.

Example C112: Dimethyl 2-cyano-4-(7-cyanobenzo[b]thiophen-3-yl)-6-cyclopropyl-1,4-dihydropyridine-3,5-dicarboxylate The title compound was prepared in three steps following Y. Satoh et al., *Chem. Pharm. Bull.* 1991, 39, 3189-3201.

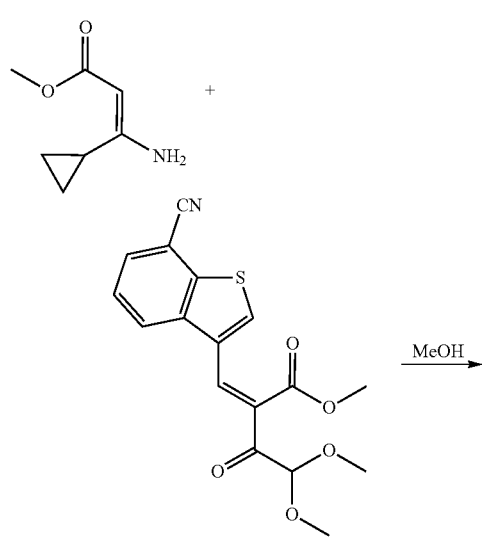

In a first step, dimethyl 4-(7-cyanobenzo[b]thiophen-3-yl)-2-cyclopropyl-6-(dimethoxymethyl)-1,4-dihydropyridine-3,5-dicarboxylate was prepared using a variation of Method C by heating the reaction mixture in methanol in a sealed tube at 130° C. for 90 min yielding a yellow solid (130 mg, 48%).

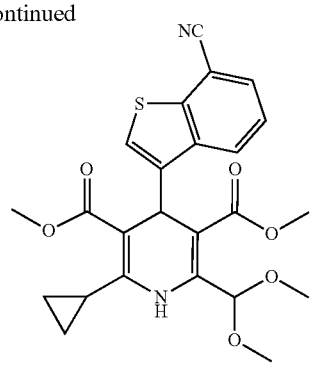

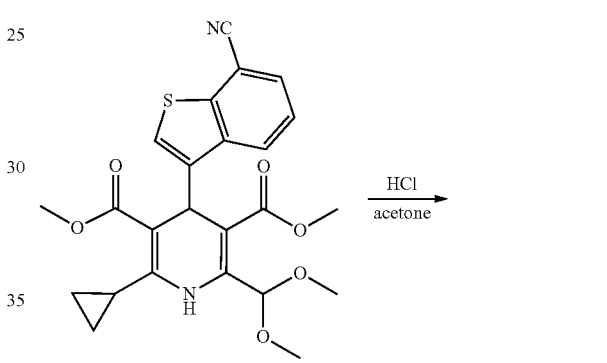

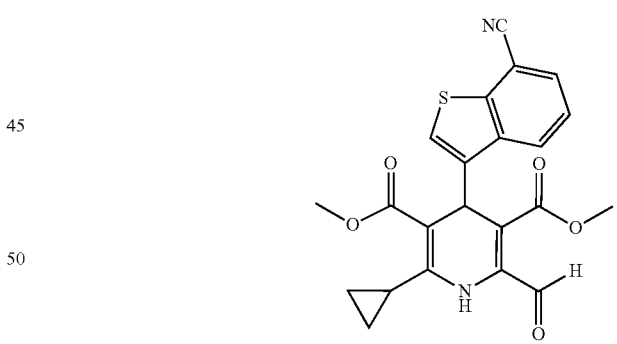

In a second step, dimethyl 4-(7-cyanobenzo[b]thiophen-3-yl)-2-cyclopropyl-6-(dimethoxymethyl)-1,4-dihydropyridine-3,5-dicarboxylate (0.100 g, 0.21 mmol) was stirred in acetone (4 mL) and hydrochloride acid 4N (0.53 mL, 2.13 mmol) at room temperature for 60 minutes. The solvent was removed under reduced pressure, and the residue was dissolved in ethyl acetate and washed with toluene, saturated bicarbonate solution and brine. The organic phase was dried (Na$_2$SO$_4$), filtered and concentrated yielding dimethyl 4-(7-cyanobenzo[b]thiophen-3-yl)-2-cyclopropyl-6-formyl-1,4-dihydropyridine-3,5-dicarboxylate that was used in the next step without further purification.

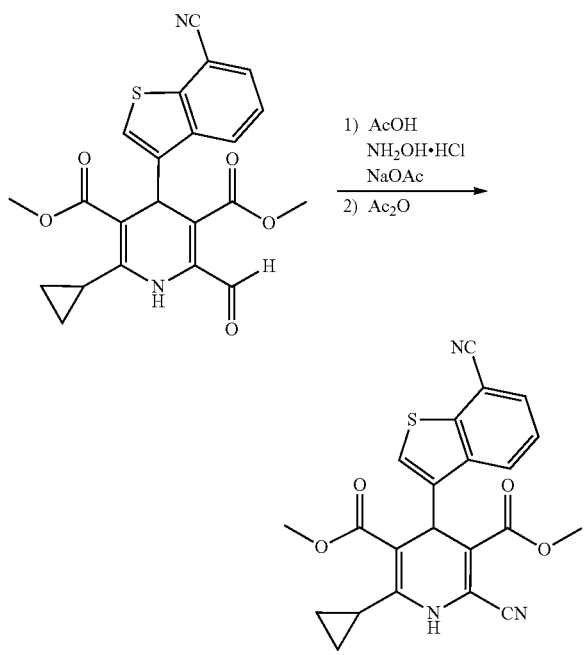

In a third step, a mixture of dimethyl 4-(7-cyanobenzo[b]thiophen-3-yl)-2-cyclopropyl-6-formyl-1,4-dihydropyridine-3,5-dicarboxylate, sodium acetate (0.026 g, 0.32 mmol) and hydroxylamine hydrochloride (0.018 g, 0.25 mmol) in acetic acid (1 mL) was stirred at room temperature for 60 minutes. Acetic anhydride (0.142 mL, 1.48 mmol) was added and stirred at room temperature for 60 minutes and then at 95° C. for 120 minutes. The solvent was removed under reduced pressure, and the residue was taken up in ethyl acetate and washed with toluene, saturated bicarbonate solution and brine. The organic phase was dried ($Na_2SO_4$), filtered and concentrated and the residue purified by column chromatography (4:1 hexane:ethyl acetate) affording the title compound dimethyl 2-cyano-4-(7-cyanobenzo[b]thiophen-3-yl)-6-cyclopropyl-1,4-dihydropyridine-3,5-dicarboxylate as a yellow solid (0.030 g, 34%).

$^1$H-NMR (300 MHz, $CDCl_3$) δ (ppm): 8.33 (d, J=8.3 Hz, 1H), 7.72 (d, J=7.3 Hz, 1H), 7.58-7.49 (m, 1H), 7.35 (s, 1H), 6.73 (bs, 1H), 5.52 (s, 1H), 3.69 (s, 3H), 3.64 (s, 1H), 3.55 (s, 3H), 3.03-2.86 (m, 2H), 2.21-2.07 (m, 2H).

HRMS (IE) m/z calculated $C_{22}H_{18}N_3O_4S$ [M$^+$]: 420.1013, found: 420.1012.

Example C113: Dimethyl 2-cyano-4-(7-cyanobenzo[b]thiophen-3-yl)-6-methyl-1,4-dihydropyridine-3,5-dicarboxylate Following the 3-step procedure described above for the synthesis of Example C112, the title compound was obtained as a yellow solid (0.046 g, 41%).

$^1$H-NMR (300 MHz, $CDCl_3$) δ (ppm): 8.35 (d, J=8.3 Hz, 1H), 7.71 (d, J=7.3 Hz, 1H), 7.58-7.47 (m, 1H), 7.36 (s, 1H), 6.70 (bs, 1H), 5.52 (s, 1H), 3.69 (s, 3H), 3.56 (s, 3H), 2.42 (s, 3H).

HRMS (IE) m/z calculated $C_{20}H_{14}N_3O_4S$ [M$^+$]: 392.0700, found: 392.0698.

Example C114: Methyl 5-acetyl-2-((2-aminoethoxy)methyl)-4-(benzo[b]thiophen-3-yl)-6-methyl-1,4-dihydropyridine-3-carboxylate In a first step, methyl 5-acetyl-4-(benzo[b]thiophen-3-yl)-2-((2-(1,3-dioxoisoindolin-2-yl)ethoxy)methyl)-6-methyl-1,4-dihydropyridine-3-carboxylate was prepared using a variation of Method C by heating in methanol in a sealed tube at 130° C. for 7 h yielding a yellow solid (120 mg, 60%).

Deprotection: In a second step, methyl 5-acetyl-4-(benzo[b]thiophen-3-yl)-2-((2-(1,3-dioxoisoindolin-2-yl)ethoxy)methyl)-6-methyl-1,4-dihydropyridine-3-carboxylate (0.060 g, 0.11 mmol) and hydrazine monohydrate (0.018 g, 0.56 mmol) were heated in ethanol (3 mL) at 78° C. for 5 minutes. The mixture was allowed to cool to RT and after addition of hydrazine monohydrate (0.018 g, 0.56 mmol) was stirred at room temperature overnight. The mixture was filtered, concentrated and the residue purified by column chromatography (dichloromethane: methanol 10%) affording a yellow solid (0.020 g, 44%).

$^1$H-NMR (300 MHz, $CDCl_3$) δ (ppm): 8.15-8.01 (m, 2H), 7.80 (d, J=7.6 Hz, 1H), 7.34 (dt, J=24.5, 6.8 Hz, 2H), 7.15 (bs, 1H), 5.45 (bs, 1H), 4.85-4.49 (m, 2H), 3.62 (s, 3H), 3.57 (t, J=5.0 Hz, 2H), 2.97 (bs, 2H), 2.42 (s, 3H), 2.13 (s, 3H), 1.78 (bs, 3H).

Example C115: Methyl 5-acetyl-2-((2-aminoethoxy)methyl)-4-(7-bromobenzo[b]thiophen-3-yl)-6-methyl-1,4-dihydropyridine-3-carboxylate Following the 2-step procedure described above for the synthesis of Example C114, the title compound was obtained as a yellow solid (0.030 g, 33%).

$^1$H-NMR (300 MHz, $CDCl_3$) δ (ppm): 8.10 (d, J=7.5 Hz, 2H), 7.46 (d, J=7.3 Hz, 1H), 7.31-7.25 (m, 1H), 7.22 (s, 1H), 5.40 (s, 1H), 4.85-4.56 (m, 2H), 3.60 (s, 5H), 2.99 (s, 2H), 2.42 (s, 5H), 2.13 (s, 3H).

Example C116: Methyl 5-acetyl-2-((2-aminoethoxy)methyl)-4-(7-cyanobenzo[b]thiophen-3-yl)-6-methyl-1,4-dihydropyridine-3-carboxylate Following the 2-step procedure described above for the synthesis of Example C114, the title compound was obtained as a yellow solid (0.035 g, 51%).

$^1$H-NMR (300 MHz, $CDCl_3$) δ (ppm): 8.41 (d, J=8.2 Hz, 1H), 8.27 (bs, 1H), 7.66 (d, J=7.2 Hz, 1H), 7.47 (t, J=7.8 Hz, 1H), 7.27 (s, 1H), 5.47 (s, 1H), 4.85-4.56 (m, 2H), 3.59 (s, 5H), 2.98 (s, 2H), 2.42 (s, 3H), 2.15 (s, 3H), 1.83 (s, 2H).

HRMS (IE) m/z calculated $C_{22}H_{24}N_3O_4S$ [M$^+$]: 426.1482, found: 426.1480.

Examples C117 and C118 have been prepared according to the following 3-step synthesis:

Example C117: Dimethyl 4-(7-cyanobenzo[b]thiophen-3-yl)-2-cyclopropyl-6-formyl-1,4-dihydropyridine-3,5-dicarboxylate In a first step, dimethyl 4-(7-cyanobenzo[b]thiophen-3-yl)-2-cyclopropyl-6-(dimethoxymethyl)-1,4-dihydropyridine-3,5-dicarboxylate was prepared using a variation of Method C by heating in methanol in a sealed tube at 130° C. for 1.5 h yielding a yellow solid (0.130 g, 48%).

$^1$H-NMR (300 MHz, $CDCl_3$) δ (ppm): 8.36 (d, J=8.3 Hz, 1H), 7.67 (d, J=7.4 Hz, 1H), 7.47 (t, J=7.8 Hz, 1H), 7.30 (s, 1H), 6.80 (s, 1H), 5.98 (s, 1H), 5.52 (s, 1H), 3.59 (s, 3H), 3.58 (s, 3H), 3.44 (s, 3H), 3.43 (s, 3H), 2.89-2.79 (m, 1H), 1.11-0.89 (m, 2H), 0.91-0.58 (m, 2H).

Deprotection: In a second step, a mixture of dimethyl 4-(7-cyanobenzo[b]thiophen-3-yl)-2-cyclopropyl-6-(dimethoxymethyl)-1,4-dihydropyridine-3,5-dicarboxylate (0.100 g, 0.21 mmol) and hydrochloride acid 4N (0.53 mL, 2.13 mmol) in acetone (4 mL) was stirred at room temperature for 60 minutes. The solvent was removed under reduced pressure and the residue was taken up in ethyl acetate, washed with toluene, saturated bicarbonate solution and brine and then dried (Na$_2$SO$_4$) and concentrated yielding the title compound that was used without further purification.

$^1$H-NMR (300 MHz, CDCl$_3$) δ (ppm): 10.50 (s, 1H), 8.33 (d, J=8.3 Hz, 1H), 7.71 (d, J=7.0 Hz, 1H), 7.51 (t, J=7.8 Hz, 1H), 7.32 (s, 1H), 7.26 (s, 1H), 5.59 (s, 1H), 3.68 (s, 3H), 3.62 (d, J=6.2 Hz, 1H), 3.57 (s, 3H), 2.98 (t, J=7.6 Hz, 2H), 2.17-2.05 (m, 2H).

HRMS (APCI) m/z calculated C$_{22}$H$_{19}$N$_2$O$_5$S [M$^{+1}$]: 423.1009, found: 423.1007.

Example C118: Dimethyl 4-(7-cyanobenzo[b]thiophen-3-yl)-2-cyclopropyl-6-(hydroxymethyl)-1,4-dihydropyridine-3,5-dicarboxylate Reduction: In a third step, sodium borohydride (0.005 g, 0.13 mmol) was added to a mixture of dimethyl 4-(7-cyanobenzo[b]thiophen-3-yl)-2-cyclopropyl-6-formyl-1,4-dihydropyridine-3,5-dicarboxylate (0.047 g, 0.11 mmol) in ethanol (3 mL) at 0° C. which was stirred at same temperature for 1 h. Then water was added, and the mixture was extracted with ethyl acetate. The organic phase was separated, dried (Na$_2$SO$_4$), filtered and concentrated, and the resulting residue was purified by column chromatography (2:1 hexane:ethyl acetate) affording the title compound as a yellow solid (0.026 g, 56%).

$^1$H-NMR (300 MHz, CDCl$_3$) δ (ppm): 8.33 (d, J=7.9 Hz, 1H), 7.67 (d, J=7.2 Hz, 1H), 7.52-7.45 (m, 2H), 7.30 (s, 1H), 5.46 (s, 1H), 4.82 (bs, 2H), 3.61 (t, J=6.2 Hz, 2H), 3.54 (s, 3H), 3.53 (s, 3H), 2.93 (t, J=7.4 Hz, 2H), 2.86 (bs, 1H), 2.17-2.05 (m, 2H).

Example C119: Dimethyl 4-(7-cyanobenzo[b]thiophen-3-yl)-2-formyl-6-methyl-1,4-dihydropyridine-3,5-dicarboxylate The title compound was prepared following the synthesis described for Example C117 yielding a solid that was used without further purification.

$^1$H-NMR (300 MHz, CDCl$_3$) δ (ppm): 10.50 (s, 1H), 8.35 (d, J=8.3 Hz, 1H), 7.70 (d, J=7.3 Hz, 1H), 7.55-7.46 (m, 1H), 7.33 (s, 1H), 7.10 (bs, 1H), 5.58 (s, 1H), 3.67 (s, 3H), 3.57 (s, 3H), 2.45 (s, 3H).

HRMS (APCI) m/z calculated C$_{20}$H$_{17}$N$_2$O$_5$S [M$^+$]: 397.0853, found: 397.0853.

Example C120: Dimethyl 4-(7-cyanobenzo[b]thiophen-3-yl)-2-(hydroxymethyl)-6-methyl-1,4-dihydropyridine-3,5-dicarboxylate The title compound was prepared following the synthesis described for Example C118 yielding a yellow solid (0.007 g, 16%).

$^1$H-NMR (300 MHz, CDCl$_3$) δ (ppm): 8.35 (d, J=8.5 Hz, 1H), 7.66 (d, J=7.2 Hz, 1H), 7.47 (t, J=7.7 Hz, 1H), 7.30 (s, 1H), 7.24 (bs, 1H), 5.45 (s, 1H), 4.83 (d, J=2.1 Hz, 2H), 3.54 (s, 3H), 3.53 (s, 3H), 2.41 (s, 3H), 1.61 (s, 1H).

HRMS (APCI) m/z calculated C$_{20}$H$_{19}$N$_2$O$_5$S [M$^+$]: 399.1009, found: 399.1010.

Example C121: Dimethyl 2-cyano-6-methyl-4-(thieno[2,3-b]pyridin-3-yl)-1,4-dihydropyridine-3,5-dicarboxylate The title compound was prepared from methyl (Z)-4,4-dimethoxy-3-oxo-2-(thieno[2,3-b]pyridin-3-ylmethylene) butanoate following the 3-step synthesis described for Examples C117 and C118 yielding a yellow solid (0.025 g).

$^1$H-NMR (300 MHz, CDCl$_3$) δ (ppm): 8.33 (d, J=8.3 Hz, 1H), 7.72 (d, J=7.3 Hz, 1H), 7.58-7.49 (m, 1H), 7.35 (s, 1H), 6.73 (bs, 1H), 5.52 (s, 1H), 3.69 (s, 3H), 3.64 (s, 1H), 3.55 (s, 3H), 3.03-2.86 (m, 2H), 2.21-2.07 (m, 2H).

HRMS (APCI) m/z calculated C$_{22}$H$_{18}$N$_3$O$_4$S [M$^+$]: 420.1013, found: 420.1012.

Example C122: Cyclopropylmethyl 5-acetyl-4-(6-cyanobenzo[b]thiophen-3-yl)-2-cyclopropyl-6-methyl-1,4-dihydropyridine-3-carboxylate The title compound was prepared using a variation of Method C by heating in dioxane in a sealed tube at 130° C. for 2 h yielding a yellow solid (0.010 g, 10%).

$^1$H-NMR (300 MHz, CDCl$_3$) δ (ppm): 8.30 (d, J=9.1 Hz, 1H), 8.11 (s, 1H), 7.59 (d, J=9.1 Hz, 1H), 7.36 (s, 1H), 5.71 (bs, 1H), 5.54 (s, 1H), 3.88 (dd, J=7.3, 2.1 Hz, 2H), 2.68-2.54 (m, 1H), 2.36 (s, 3H), 2.15 (s, 3H), 1.08-0.93 (m, 3H), 0.74-0.64 (m, 2H), 0.54-0.42 (m, 2H), 0.22-0.12 (m, 2H).

HRMS (APCI) m/z calculated C$_{25}$H$_{25}$N$_2$O$_3$S [M$^+$]: 433.1580, found: 433.1581.

Example C123: Cyclopropylmethyl 2,5-diacetyl-4-(7-cyanobenzo[b]thiophen-3-yl)-6-methyl-1,4-dihydropyridine-3-carboxylate The title compound was prepared using a variation of Method C by heating in dioxane in a sealed tube at 130° C. for 2 h yielding a yellow solid (0.006 g, 11%).

$^1$H-NMR (300 MHz, CDCl$_3$) δ (ppm): 8.47 (d, J=8.2 Hz, 1H), 7.66 (d, J=7.3 Hz, 1H), 7.46 (t, J=7.6 Hz, 1H), 7.29 (s, 1H), 5.86 (bs, 1H), 5.52 (s, 1H), 3.91-3.78 (m, 2H), 2.40 (s, 3H), 2.35 (s, 3H), 2.16 (s, 3H), 0.26-0.07 (m, 1H), 1.09-0.95 (m, 2H), 0.57-0.38 (m, 2H).

Method D

Example D1: Methyl 5-acetyl-2-amino-4-(benzo[b]thiophen-3-yl)-6-methyl-1,4-dihydropyridine-3-carboxylate

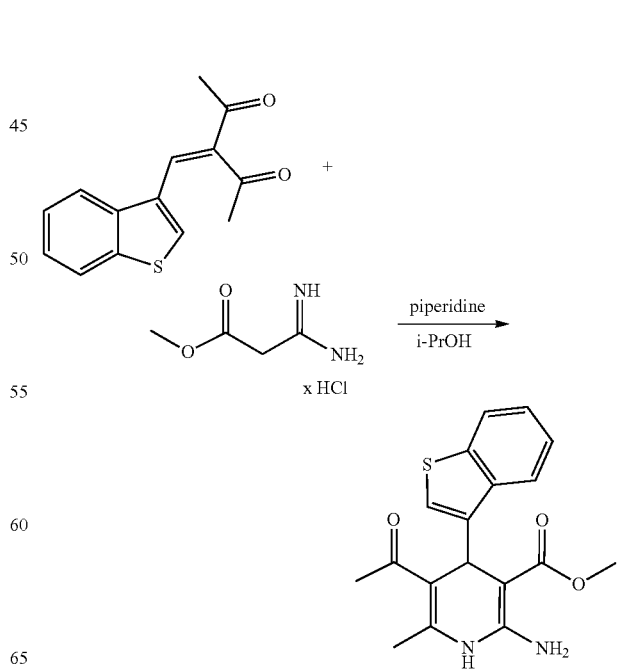

A mixture of 3-(benzo[b]thiophen-3-ylmethylene)pentane-2,4-dione (0.15 g, 0.61 mmol, 1 eq), methyl 3-amino-3-iminopropanoate (0.093 g, 0.61 mmol, 1 eq) and piperidine (0.073 g, 0.74 mmol, 1.2 eq) in i-PrOH (5 ml) was stirred at reflux temperature for 4 hours. The reaction mixture was concentrated in vacuum, and the precipitate that formed was filtered off, washed with methanol, dichloromethane and ether and dried affording the title compound as a yellow solid (65 mg, 31%).

$^1$H-NMR (300 MHz, CDCl$_3$) δ=8.00 (s, 1H), 7.22 (d, J=7.8 Hz, 1H), 7.06 (d, J=7.9 Hz, 1H), 6.63-6.43 (m, 2H), 6.40 (s, 1H), 5.80 (s, 2H), 4.46 (s, 1H), 2.66 (s, 3H), 1.46 (s, 3H), 1.24 (s, 3H).

HRMS (IE) m/z calculated C$_{18}$H$_{18}$N$_2$O$_3$S [M$^+$]: 342.1038, found: 342.1044.

Example D2: Methyl 2-amino-4-(benzo[b]thiophen-3-yl)-5-(cyclopropanecarbonyl)-6-methyl-1,4-dihydropyridine-3-carboxylate Method D yielded the title compound as a light-yellow solid (40 mg, 48%).

$^1$H-NMR (300 MHz, CDCl$_3$) δ=8.02 (d, J=7.7 Hz, 1H), 7.78 (d, J=7.5 Hz, 1H), 7.40-7.19 (m, 3H), 7.10 (s, 1H), 6.23 (s, 2H), 5.51 (s, 1H), 3.61 (s, 3H), 2.23-1.97 (m, 4H), 0.96 (dq, J=6.9, 2.1 Hz, 1H), 0.82 (td, J=7.2, 6.3, 3.5 Hz, 2H), 0.68 (dt, J=8.6, 4.2 Hz, 1H).

HRMS (IE) m/z calculated C$_{20}$H$_{20}$N$_2$O$_3$S [M$^+$]: 368.1195, found: 368.1183.

Example D3: Methyl 5-acetyl-2-amino-4-(5-fluorobenzo[b]thiophen-3-yl)-6-methyl-1,4-dihydropyridine-3-carboxylate Method D yielded the title compound as a yellow solid (0.075 g, 44%).

$^1$H-NMR (300 MHz, CDCl$_3$) δ=7.75-7.67 (m, 2H), 7.48 (s, 1H), 7.19 (s, 1H), 7.05 (t, J=7.7 Hz, 1H), 6.27 (s, 2H), 5.29 (s, 1H), 3.66 (s, 3H), 2.20 (s, 3H), 2.17 (s, 3H).

$^{19}$F-NMR (282 MHz, CDCl$_3$) δ=−119.10 (s).

HRMS (IE) m/z calculated C$_{18}$H$_{17}$FN$_2$O$_3$S [M$^+$]: 360.0944, found: 360.0943.

Example D4: Methyl 5-acetyl-2-amino-4-(7-bromobenzo[b]thiophen-3-yl)-6-methyl-1,4-dihydropyridine-3-carboxylate Method D in methanol yielded the title compound as a yellow solid (0.031 g, 24%).

$^1$H-NMR (300 MHz, CDCl$_3$) δ=8.82 (s, 1H), 8.06 (d, J=8.0 Hz, 1H), 7.54 (d, J=7.5 Hz, 1H), 7.39-7.27 (m, 2H), 6.61 (bs, 2H), 5.22 (s, 1H), 3.45 (s, 3H), 2.27 (s, 3H), 2.05 (s, 3H).

HRMS (IE) m/z calculated C$_{18}$H$_{17}$N$_2$O$_3$SBr [M$^+$]: 420.0143, found: 420.0130.

HPLC (98.4%): Rt 16.46 min.

Example D5: Methyl 5-acetyl-2-amino-4-(7-cyanobenzo[b]thiophen-3-yl)-6-methyl-1,4-dihydropyridine-3-carboxylate Method D in methanol yielded the title compound as a yellow solid (0.075 g, 64%).

$^1$H-NMR (300 MHz, CDCl$_3$) δ (ppm): 8.35 (d, J=8.2 Hz, 1H), 7.66 (d, J=7.3 Hz, 1H), 7.46 (t, J=7.8 Hz, 1H), 7.27 (s, 1H), 6.33 (bs, 1H), 6.03 (bs, 2H), 5.39 (s, 1H), 3.61 (s, 3H), 2.35 (s, 3H), 2.14 (s, 3H).

HRMS (IE) m/z calculated C$_{19}$H$_{18}$N$_3$O$_3$S [M$^+$]: 368.1063, found: 368.1064.

HPLC (98.4%): Rt 20.05 min.

Example D6: Cyclopentyl 5-acetyl-2-amino-4-(7-bromobenzo[b]thiophen-3-yl)-6-methyl-1,4-dihydropyridine-3-carboxylate Method D in methanol yielded the title compound as a yellow solid (0.070 g, 46%).

$^1$H-NMR (300 MHz, DMSO) δ (ppm): 8.83 (bs, 1H), 8.11-8.01 (m, 1H), 7.55 (d, J=7.5 Hz, 1H), 7.39-7.26 (m, 2H), 6.65 (bs, 2H), 5.21 (s, 1H), 5.03-4.89 (m, 1H), 2.26 (s, 3H), 2.11 (s, 3H), 1.86-1.71 (m, 1H), 1.69-1.52 (m, 3H), 1.54-1.33 (m, 3H), 1.33-1.19 (m, 1H).

HRMS (IE) m/z calculated C$_{22}$H$_{23}$N$_2$O$_3$SBr [M$^+$]: 474.0613, found: 474.0605.

HPLC (95.5%): Rt 13.81 min.

Example D7: Dimethyl 2-amino-4-(7-cyanobenzo[b]thiophen-3-yl)-6-methyl-1,4-dihydropyridine-3,5-dicarboxylate Method D in methanol yielded the title compound as a yellow solid (0.045 g, 34%).

$^1$H-NMR (300 MHz, DMSO) δ (ppm): 8.33 (d, J=8.0 Hz, 1H), 7.65 (d, J=7.3 Hz, 1H), 7.43 (t, J=8.0 Hz, 1H), 7.27 (s, 1H), 6.91 (bs, 1H), 6.20 (bs, 2H), 5.37 (s, 1H), 3.53 (s, 3H), 3.51 (s, 3H), 2.27 (s, 3H).

HRMS (IE) m/z calculated C$_{19}$H$_{17}$N$_3$O$_4$S [M$^+$]: 383.0940, found: 383.0947.

HPLC (97.5%): Rt 14.58 min.

Example D8: Cyclopentyl 5-acetyl-2-amino-4-(7-cyanobenzo[b]thiophen-3-yl)-6-methyl-1,4-dihydropyridine-3-carboxylate Method D in methanol yielded the title compound as a yellow solid (0.048 g, 31 $^1$H-NMR (300 MHz, DMSO) δ (ppm): 8.35-8.20 (m, 1H), 7.57 (d, J=7.8 Hz, 1H), 7.35 (t, J=7.8 Hz, 1H), 7.18 (bs, 2H), 6.16 (bs, 2H), 5.30 (s, 1H), 5.11-4.95 (m, 1H), 2.17 (s, 3H), 2.12 (s, 3H), 1.86-1.73 (m, 1H), 1.71-1.51 (m, 3H), 1.52-1.36 (m, 3H), 1.35-1.24 (m, 1H).

HRMS (IE) m/z calculated C$_{23}$H$_{23}$N$_3$O$_3$S [M$^+$]: 421.1460, found: 421.1453.

HPLC (98.4%): Rt 17.10 min.

Example D9: Dimethyl 2,6-diamino-4-(benzo[b]thiophen-3-yl)-1,4-dihydropyridine-3,5-dicarboxylate Method D using benzo[b]thiophene-3-carbaldehyde and methyl 3-amino-3-iminopropanoate (2 eq) yielded the title compound as a yellow solid (0.115 g, 53%).

$^1$H-NMR (300 MHz, CDCl$_3$) δ=8.13-7.90 (m, 2H), 7.86 (d, J=8.0 Hz, 1H), 7.58-7.34 (m, 3H), 7.19 (s, 1H), 6.98 (s, 1H), 6.54 (s, 1H), 4.74 (s, 1H), 3.72 (s, 3H), 3.60 (s, 1H), 3.37 (s, 3H).

Example D10: Cyclopropylmethyl 5-acetyl-2-amino-4-(7-cyanobenzo[b]thiophen-3-yl)-6-methyl-1,4-dihydropyridine-3-carboxylate Method D using morpholine (1.2 eq.) in isopropanol yielded the title compound as a yellow solid (0.038 g, 51%).

¹H-NMR (300 MHz, CDCl₃) δ=8.43 (d, J=8.3 Hz, 1H), 7.66 (d, J=7.3 Hz, 1H), 7.43 (t, J=7.8 Hz, 1H), 7.30 (s, 1H), 6.51 (bs, 1H), 6.08 (bs, 2H), 5.43 (s, 1H), 3.83 (d, J=7.3 Hz, 2H), 2.33 (s, 3H), 2.17 (s, 3H), 1.10-0.95 (m, 1H), 0.60-0.40 (m, 2H), 0.27-0.03 (m, 2H).

Example D11: 4,4-difluorocyclohexyl 5-acetyl-2-amino-4-(7-cyanobenzo[b]thiophen-3-yl)-6-methyl-1,4-dihydropyridine-3-carboxylate Method D using morpholine (1.2 eq.) in isopropanol yielded the title compound as a yellow solid (0.053 g, 30%).
¹H-NMR (300 MHz, CDCl₃) δ=8.35 (d, J=8.2 Hz, 1H), 7.67 (d, J=7.3 Hz, 1H), 7.45 (t, J=7.8 Hz, 1H), 7.28 (s, 1H), 6.05 (bs, 2H), 5.42 (s, 1H), 4.82 (bs, 1H), 2.32 (s, 3H), 2.20 (s, 3H), 2.02-1.80 (m, 3H), 1.76-1.58 (m, 5H), 1.53-1.38 (m, 1H). ¹⁹F-NMR (282 MHz, CDCl₃) δ (ppm): −97.60 (CF), −98.46 (CF).

Example D12: Methyl 2-amino-5-cyano-4-(7-cyanobenzo[b]thiophen-3-yl)-6-methyl-1,4-dihydropyridine-3-carboxylate Method D using morpholine (1.2 eq.) in isopropanol yielded the title compound as a yellow solid (0.022 g, 15%).
¹H-NMR (300 MHz, CDCl₃) δ=8.24-8.16 (m, 1H), 7.74-7.67 (m, 1H), 7.47 (t, J=7.8 Hz, 1H), 7.31 (s, 1H), 6.89 (bs, 1H), 6.26 (bs, 2H), 5.03 (s, 1H), 3.49 (s, 3H), 2.04 (s, 3H).

Example D13: 4-fluorobenzyl 5-acetyl-2-amino-4-(7-cyanobenzo[b]thiophen-3-yl)-6-methyl-1,4-dihydropyridine-3-carboxylate Method D using morpholine (1.2 eq.) in isopropanol yielded the title compound as a yellow solid (0.074 g, 43%).
¹H-NMR (300 MHz, CDCl₃) δ=8.14 (d, J=7.9 Hz, 1H), 7.60 (d, J=7.0 Hz, 1H), 7.20 (s, 2H), 7.13-7.02 (m, 2H), 6.95 (t, J=8.2 Hz, 2H), 6.48 (bs, 1H), 6.12 (bs, 2H), 5.37 (s, 1H), 4.98 (s, 2H), 2.31 (s, 3H), 2.12 (s, 3H). ¹⁹F-NMR (282 MHz, CDCl₃) δ (ppm): −113.91 (CF).

Example D14: Methyl 5-acetyl-2-amino-4-(5-fluorothieno[2,3-b]pyridin-3-yl)-6-methyl-1,4-dihydropyridine-3-carboxylate Method D in methanol yielded the title compound as a yellow solid (0.012 g, 67%).
¹H-NMR (300 MHz, CDCl₃) δ=8.90 (s, 1H), 8.55 (d, J=2.6 Hz, 1H), 8.16 (dd, J=10.5, 2.6 Hz, 1H), 7.48 (s, 1H), 6.65 (bs, 2H), 5.20 (s, 1H), 3.48 (s, 3H), 2.30 (s, 3H), 2.11 (s, 3H). ¹⁹F-NMR (282 MHz, CDCl₃) δ (ppm): −129.28 (d, J=10.4 Hz).

Example D14 was further modified to render Example D15:

Example D15: Methyl 2-acetamido-5-acetyl-4-(5-fluorothieno[2,3-b]pyridin-3-yl)-6-methyl-1,4-dihydropyridine-3-carboxylate A mixture of methyl 5-acetyl-2-amino-4-(5-fluorothieno[2,3-b]pyridin-3-yl)-6-methyl-1,4-dihydropyridine-3-carboxylate (0.025 g, 0.07 mmol) and acetyl chloride (0.005 mL, 0.07 mmol) in pyridine (1 mL) was stirred at 75° C. for 3 hours. The mixture was allowed to cool to RT and the solvent was removed under reduced pressure. The residue was purified by column chromatography (DCM:MeOH 2%) affording a yellow solid (0.017 g, 61%).

¹H-NMR (300 MHz, CDCl₃) δ=11.71 (bs, 1H), 10.50 (s, 1H), 8.43 (d, J=2.4 Hz, 1H), 8.02 (dd, J=9.8, 2.7 Hz, 1H), 7.34 (s, 1H), 5.33 (s, 1H), 3.66 (s, 3H), 2.39 (s, 3H), 2.21 (s, 3H), 2.18 (s, 3H). ¹⁹F-NMR (282 MHz, CDCl₃) δ (ppm): −133.66 (d, J=9.5 Hz).

Example D16: Cyclopentylmethyl 5-acetyl-2-amino-4-(7-cyanobenzo[b]thiophen-3-yl)-6-methyl-1,4-dihydropyridine-3-carboxylate Method D using morpholine (1.2 eq.) in isopropanol yielded the title compound as a yellow solid (0.066 g, 51%).
¹H-NMR (300 MHz, CDCl₃) δ=8.36 (d, J=8.2 Hz, 1H), 7.65 (d, J=7.4 Hz, 1H), 7.43 (t, J=7.8 Hz, 1H), 7.26 (s, 1H), 6.25 (bs, 1H), 6.02 (bs, 2H), 5.42 (s, 1H), 3.90 (dd, J=7.2, 1.8 Hz, 2H), 2.32 (s, 3H), 2.18 (s, 3H), 1.58 (d, J=34.3 Hz, 7H), 1.28-1.04 (m, 2H).

Example D17: 3-(cyclopropylmethyl) 5-methyl 2-amino-4-(7-cyanobenzo[b]thiophen-3-yl)-6-methyl-1,4-dihydropyridine-3,5-dicarboxylate Method D using morpholine (1.2 eq.) in isopropanol yielded the title compound as a yellow solid (0.070 g, 47%).
¹H-NMR (300 MHz, CDCl₃) δ=8.36 (d, J=8.7 Hz, 1H), 7.64 (d, J=7.1 Hz, 1H), 7.47-7.37 (m, 1H), 7.32 (s, 1H), 5.99 (bs, 2H), 5.87 (bs, 1H), 5.41 (s, 1H), 3.71 (d, J=7.2 Hz, 2H), 3.52 (s, 3H), 2.35 (s, 3H), 0.91-0.75 (m, 1H), 0.44-0.24 (m, 2H), 0.13--0.10 (m, 2H).

Example D18: Dimethyl 2-amino-4-(7-cyanobenzo[b]thiophen-3-yl)-6-cyclopropyl-1,4-dihydropyridine-3,5-dicarboxylate Method D in methanol yielded the title compound as a yellow solid (0.054 g, 41%).
¹H-NMR (300 MHz, CDCl₃) δ=8.32 (d, J=8.2 Hz, 1H), 7.65 (d, J=7.3 Hz, 1H), 7.44 (t, J=7.8 Hz, 1H), 7.24 (s, 1H), 6.18 (bs, 2H), 6.15 (bs, 1H), 5.39 (s, 1H), 3.56 (s, 3H), 3.52 (s, 3H), 2.81-2.64 (m, 1H), 1.01-0.84 (m, 2H), 0.83-0.60 (m, 2H).

Example D19: 3-(cyclopropylmethyl) 5-methyl 2-amino-4-(7-cyanobenzo[b]thiophen-3-yl)-6-cyclopropyl-1,4-dihydropyridine-3,5-dicarboxylate Method D yielded the title compound as a yellow solid (0.017 g, 12%).
¹H-NMR (300 MHz, CDCl₃) δ=8.37 (d, J=8.2 Hz, 1H), 7.64 (d, J=7.3 Hz, 1H), 7.42 (t, J=7.8 Hz, 1H), 7.28 (s, 1H), 6.15 (bs, 2H), 6.02 (bs, 1H), 5.42 (s, 1H), 3.72 (d, J=7.2 Hz, 2H), 3.55 (s, 3H), 2.78-2.62 (m, 1H), 1.01-0.77 (m, 3H), 0.79-0.62 (m, 2H), 0.47-0.24 (m, 2H), 0.12--0.09 (m, 2H).

Example D20: dimethyl 2,6-diamino-4-(7-cyanobenzo[b]thiophen-3-yl)-1,4-dihydropyridine-3,5-dicarboxylate Method D in methanol yielded the title compound as a yellow solid (0.135 g, 66%).
¹H-NMR (300 MHz, CDCl₃) δ=8.14 (d, J=7.9 Hz, 1H), 7.98 (d, J=7.2 Hz, 1H), 7.69 (t, J=7.9 Hz, 1H), 7.47 (bs, 1H), 7.21 (s, 1H), 7.16 (bs, 1H), 6.60 (bs, 2H), 4.74 (s, 1H), 3.70 (s, 3H), 3.56 (s, 1H), 3.35 (s, 3H).

HRMS (APCI) m/z calculated $C_{24}H_{18}N_4O_2S$ [M$^{+1}$]: 445.1129, found: 445.1126.

Example D21: 5-(cyclopropylmethyl) 3-methyl 2-amino-4-(7-cyanobenzo[b]thiophen-3-yl)-6-cyclopropyl-1,4-dihydropyridine-3,5-dicarboxylate Method D using morpholine in isopropanol yielded the title compound as a yellow solid (0.040 g, 31%).
$^1$H-NMR (300 MHz, CDCl$_3$) δ=8.35 (d, J=8.2 Hz, 1H), 7.64 (d, J=7.2 Hz, 1H), 7.42 (t, J=7.7 Hz, 1H), 7.26 (s, 1H), 6.26 (bs, 3H), 5.41 (s, 1H), 3.77 (d, J=7.2 Hz, 2H), 3.52 (s, 3H), 2.84-2.66 (m, 1H), 0.97-0.80 (m, 3H), 0.81-0.61 (m, 2H), 0.48-0.25 (m, 2H), 0.15--0.08 (m, 2H).

Example D22: 3-(4-fluorobenzyl) 5-methyl 2-amino-4-(7-cyanobenzo[b]thiophen-3-yl)-6-methyl-1,4-dihydropyridine-3,5-dicarboxylate Method D using morpholine in isopropanol yielded the title compound as a yellow solid (0.035 g, 25%).
$^1$H-NMR (300 MHz, CDCl$_3$) δ=8.11 (d, J=8.3 Hz, 1H), 7.59 (d, J=7.3 Hz, 1H), 7.30-7.15 (m, 2H), 6.97-6.77 (m, 4H), 6.68 (s, 1H), 6.22 (bs, 2H), 5.34 (s, 1H), 5.04-4.75 (m, 2H), 3.50 (s, 3H), 2.26 (s, 3H). $^{19}$F-NMR (282 MHz, CDCl$_3$) δ (ppm): −114.23 (CF).

Example D23: 3-(4-fluorobenzyl) 5-methyl 2-amino-4-(7-cyanobenzo[b]thiophen-3-yl)-6-cyclopropyl-1,4-dihydropyridine-3,5-dicarboxylate Method D using morpholine in isopropanol yielded the title compound as a yellow solid (0.035 g, 25%).
$^1$H-NMR (300 MHz, CDCl$_3$) δ=8.10 (d, J=8.2 Hz, 1H), 7.60 (d, J=7.3 Hz, 1H), 7.25-7.13 (m, 2H), 6.87 (q, J=8.7, 7.6 Hz, 4H), 6.29 (s, 2H), 6.20 (s, 1H), 5.36 (s, 1H), 5.00-4.77 (m, 2H), 3.52 (s, 3H), 2.83-2.53 (m, 1H), 0.99-0.82 (m, 2H), 0.79-0.62 (m, 2H). $^{19}$F-NMR (282 MHz, CDCl$_3$) δ (ppm): −114.26 (CF).

Example D24: cyclopropylmethyl 2-amino-5-cyano-4-(7-cyanobenzo[b]thiophen-3-yl)-6-methyl-1,4-dihydropyridine-3-carboxylate Method D using piperidine in dioxane yielded the title compound as a yellow solid (0.035 g, 23%).
$^1$H-NMR (300 MHz, CDCl$_3$) δ=8.20 (d, J=8.3 Hz, 1H), 7.69 (d, J=7.4 Hz, 1H), 7.45 (t, J=7.8 Hz, 1H), 7.35 (s, 1H), 7.04 (bs, 1H), 6.27 (bs, 2H), 5.08 (s, 1H), 3.69 (dt, J=7.2, 3.8 Hz, 2H), 2.02 (s, 3H), 0.83-0.64 (m, 1H), 0.35-0.11 (m, 2H), 0.06--0.29 (m, 2H).
HRMS (APCI) m/z calculated $C_{21}H_{19}N_4O_2S$ [M$^{+1}$]: 391.1223, found: 391.1223.

Example D25: 4-Fluorobenzyl 2-amino-5-cyano-4-(7-cyanobenzo[b]thiophen-3-yl)-6-methyl-1,4-dihydropyridine-3-carboxylate Method D using morpholine in dioxane yielded the title compound as a yellow solid (0.010 g, 8%).
$^1$H-NMR (300 MHz, CDCl$_3$) δ=8.08 (d, J=8.2 Hz, 1H), 7.69 (d, J=7.1 Hz, 1H), 7.38 (t, J=7.8 Hz, 1H), 7.28 (s, 1H), 6.79 (s, 2H), 6.77 (s, 2H), 6.46 (bs, 1H), 6.28 (s, 2H), 5.05 (s, 1H), 4.98-4.75 (m, 2H), 2.09 (s, 3H). $^{19}$F-NMR (282 MHz, CDCl$_3$) δ (ppm): −114.12 (CF).

Example D26: Cyclopropylmethyl 6-amino-5-cyano-4-(7-cyanobenzo[b]thiophen-3-yl)-2-cyclopropyl-1,4-dihydropyridine-3-carboxylate Method D run at room temperature overnight yielded the title compound as a yellow solid (0.060 g, 51%).
$^1$H-NMR (300 MHz, DMSO-d$_6$) δ=8.20 (d, J=8.3 Hz, 1H), 7.95 (d, J=7.3 Hz, 1H), 7.76 (bs, 1H), 7.61 (t, J=7.8 Hz, 1H), 6.77 (s, 1H), 5.51 (bs, 2H), 5.21 (s, 1H), 4.60-4.35 (m, 1H), 3.56 (d, J=7.2 Hz, 2H), 1.23-1.10 (m, 1H), 0.81-0.64 (m, 1H), 0.64-0.47 (m, 1H), 0.39-0.29 (m, 2H), 0.27-0.12 (m, 2H), 0.04--0.20 (m, 2H).
HRMS (APCI) m/z calculated $C_{23}H_{21}N_4O_2S$ [M$^{+1}$]: 417.1380, found: 417.1382.

Example D27: 3-Cyclopentyl 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.082 g, 51%).
$^1$H-NMR (300 MHz, CDCl$_3$) δ=8.30 (d, J=8.7 Hz, 1H), 7.65 (d, J=7.3 Hz, 1H), 7.43 (t, J=7.8 Hz, 1H), 7.30 (s, 1H), 6.07 (s, 2H), 6.03 (s, 1H), 5.32 (s, 1H), 5.07-4.92 (m, 1H), 3.54 (s, 3H), 2.32 (s, 3H), 1.87-1.74 (m, 1H), 1.71-1.57 (m, 2H), 1.54-1.40 (m, 3H), 1.39-1.29 (m, 1H), 1.24-1.11 (m, 1H).
HRMS (APCI) m/z calculated $C_{23}H_{24}N_3O_4S$ [M$^{+1}$]: 438.1482, found: 438.1481.

Example D28: Cyclopropylmethyl 5-acetyl-2-amino-4-(6-cyanobenzo[b]thiophen-3-yl)-6-methyl-1,4-dihydropyridine-3-carboxylate Method D using morpholine at room temperature overnight yielded the title compound as a yellow solid (0.062 g, 45%).
$^1$H-NMR (300 MHz, CDCl$_3$) δ=8.93 (bs, 1H), 8.53 (s, 1H), 8.25 (d, J=8.4 Hz, 1H), 7.75 (d, J=8.4 Hz, 1H), 7.59 (s, 1H), 6.69 (bs, 2H), 5.32 (s, 1H), 3.79-3.62 (m, 2H), 2.30 (s, 3H), 2.09 (s, 3H), 1.06-0.87 (m, 1H), 0.40 (d, J=8.0 Hz, 2H), 0.20-0.02 (m, 2H).
HRMS (APCI) m/z calculated $C_{22}H_{22}N_3O_3S$ [M$^+$]: 408.1376, found: 408.1378.

Example D29: Cyclohexyl 5-acetyl-2-amino-4-(7-cyanobenzo[b]thiophen-3-yl)-6-methyl-1,4-dihydropyridine-3-carboxylate Method D using morpholine at room temperature overnight yielded the title compound as a yellow solid (0.066 g, 43%).
$^1$H-NMR (300 MHz, CDCl$_3$) δ=8.37 (d, J=8.0 Hz, 1H), 7.66 (d, J=7.1 Hz, 1H), 7.43 (t, J=7.8 Hz, 1H), 7.27 (s, 1H), 6.25 (bs, 1H), 6.03 (bs, 2H), 5.40 (s, 1H), 4.77-4.56 (m, 1H), 2.32 (s, 3H), 2.17 (s, 3H), 1.99-1.86 (m, 1H), 1.78-1.67 (m, 1H), 1.63-1.49 (m, 3H), 1.39-1.07 (m, 5H).
HRMS (APCI) m/z calculated $C_{24}H_{26}N_3O_3S$ [M$^+$]: 436.1689, found: 436.1690.

Example D30: Cyclohexylmethyl 5-acetyl-2-amino-4-(7-cyanobenzo[b]thiophen-3-yl)-6-methyl-1,4-dihydropyridine-3-carboxylate Method D using morpholine at room temperature overnight yielded the title compound as a yellow solid (0.077 g, 46%).

$^1$H-NMR (300 MHz, CDCl$_3$) δ=8.37 (d, J=8.1 Hz, 1H), 7.66 (d, J=7.3 Hz, 1H), 7.45 (t, J=7.8 Hz, 1H), 7.28 (s, 1H), 6.38 (bs, 1H), 6.06 (bs, 2H), 5.41 (s, 1H), 3.81 (d, J=6.6 Hz, 2H), 2.31 (s, 3H), 2.18 (s, 3H), 1.69-1.53 (m, 4H), 1.51-1.37 (m, 2H), 1.16-0.96 (m, 3H), 0.87-0.73 (m, 2H).

HRMS (APCI) m/z calculated C$_{25}$H$_{28}$N$_3$O$_3$S [M$^+$]: 450.1846, found: 450.1849.

Example D31: Cyclopropylmethyl 2-amino-4-(7-cyanobenzo[b]thiophen-3-yl)-5-(cyclopropanecarbonyl)-6-methyl-1,4-dihydropyridine-3-carboxylate Method D using morpholine at room temperature overnight yielded the title compound as a yellow solid (0.120 g, 40%).

$^1$H-NMR (300 MHz, CDCl$_3$) δ=8.38 (d, J=8.2 Hz, 1H), 7.66 (d, J=7.3 Hz, 1H), 7.42 (t, J=7.8 Hz, 1H), 7.32 (s, 1H), 6.54 (bs, 1H), 6.14 (bs, 2H), 5.56 (s, 1H), 3.82 (d, J=7.3 Hz, 2H), 2.25 (s, 3H), 2.13-1.98 (m, 1H), 1.04-0.94 (m, 2H), 0.91-0.69 (m, 3H), 0.50-0.38 (m, 2H), 0.21-0.05 (m, 2H).

HRMS (APCI) m/z calculated C$_{24}$H$_{24}$N$_3$O$_3$S [M$^+$]: 434.1533, found: 421.1537.

Example D32: 3-Fluorobenzyl 5-acetyl-2-amino-4-(7-cyanobenzo[b]thiophen-3-yl)-6-methyl-1,4-dihydropyridine-3-carboxylate Method D using morpholine at room temperature overnight yielded the title compound as a yellow solid (0.058 g, 34%).

$^1$H-NMR (300 MHz, CDCl$_3$) δ=8.17 (d, J=8.5 Hz, 1H), 7.60 (d, J=7.3 Hz, 1H), 7.23 (s, 3H), 6.96 (t, J=8.5 Hz, 1H), 6.86 (d, J=7.3 Hz, 1H), 6.74 (d, J=11.4 Hz, 1H), 6.41 (bs, 1H), 6.12 (bs, 2H), 5.39 (s, 1H), 5.06-4.92 (m, 2H), 2.32 (s, 3H), 2.13 (s, 3H). $^{19}$F-NMR (282 MHz, CDCl$_3$) δ (ppm): −112.76 (s, CF).

HRMS (APCI) m/z calculated C$_{25}$H$_{21}$N$_3$O$_3$SF [M$^{+1}$]: 462.1282, found: 462.1278.

Example D33: 3-(Cyclobutylmethyl) 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.040 g, 33%).

$^1$H-NMR (300 MHz, CDCl$_3$) δ=8.31 (d, J=8.1 Hz, 1H), 7.66 (d, J=7.2 Hz, 1H), 7.44 (t, J=7.8 Hz, 1H), 7.29 (s, 1H), 6.82 (s, 1H), 6.22 (bs, 2H), 5.35 (s, 1H), 3.89 (t, J=7.2 Hz, 2H), 3.54 (s, 3H), 2.41-2.29 (m, 1H), 2.26 (s, 3H), 1.93-1.63 (m, 4H), 1.58-1.27 (m, 2H).

HRMS (APCI) m/z calculated C$_{23}$H$_{24}$N$_3$O$_4$S [M$^+$]: 438.1482, found: 438.1483.

Example D34: 3-((3,3-Difluorocyclobutyl)methyl) 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.035 g, 22%).

$^1$H-NMR (300 MHz, CDCl$_3$) δ=8.28 (d, J=8.2 Hz, 1H), 7.67 (d, J=7.2 Hz, 1H), 7.46 (t, J=7.8 Hz, 1H), 7.31 (s, 1H), 6.19 (s, 1H), 6.14 (bs, 2H), 5.35 (s, 1H), 4.00-3.81 (m, 2H), 3.55 (s, 3H), 2.35 (m, 1H), 2.32 (s, 3H), 2.26-1.93 (m, 4H).

$^{19}$F-NMR (282 MHz, CDCl$_3$) δ (ppm): −83.87 (d, J=193.0 Hz), −93.31 (d, J=193.0 Hz).

HRMS (APCI) m/z calculated C$_{23}$H$_{22}$N$_3$O$_4$SF$_2$ [M$^+$]: 474.1294, found: 474.1295.

Example D35: Cyclopropylmethyl 2-amino-5-carbamoyl-4-(7-cyanobenzo[b]thiophen-3-yl)-6-methyl-1,4-dihydropyridine-3-carboxylate Method D using morpholine at room temperature overnight yielded the title compound as a yellow solid (0.011 g, 11%).

$^1$H-NMR (300 MHz, CDCl$_3$) δ=8.28 (d, J=8.2 Hz, 1H), 7.66 (d, J=7.3 Hz, 1H), 7.46-7.33 (m, 2H), 6.93 (bs, 1H), 6.28 (bs, 2H), 5.37 (bs, 2H), 5.21 (s, 1H), 3.76 (d, J=7.2 Hz, 2H), 2.16 (s, 3H), 0.95-0.85 (m, 1H), 0.53-0.27 (m, 2H), 0.23-−0.06 (m, 2H).

HRMS (APCI) m/z calculated C$_{21}$H$_{21}$N$_4$O$_3$S [M$^{+1}$]: 409.1329, found: 409.1324.

Example D36: 3-((2,2-Difluorocyclopropyl)methyl) 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.065 g, 40%).

$^1$H-NMR (300 MHz, CDCl$_3$) δ=8.31 (dd, J=7.7, 2.8 Hz, 1H), 7.65 (d, J=7.0 Hz, 1H), 7.52-7.38 (m, 1H), 7.31 (d, J=3.3 Hz, 1H), 6.07 (bs, 3H), 5.37 (s, 1H), 4.16-3.95 (m, 1H), 3.91-3.71 (m, 1H), 3.52 (s, 3H), 2.35 (s, 3H), 1.71-1.60 (m, 1H), 1.29-1.16 (m, 1H), 0.90 (s, 1H). $^{19}$F-NMR (282 MHz, CDCl$_3$) δ (ppm): −129.21 (ddt, J=160.2, 70.2, 10.9 Hz), −143.62 (ddd, J=160.2, 51.3, 10.9 Hz).

HRMS (APCI) m/z calculated C$_{22}$H$_{20}$N$_3$O$_4$SF$_2$ [M$^+$]: 460.1137, found: 460.1137.

Example D37: 5-Cyclopropyl 3-(cyclopropylmethyl) 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.008 g, 5%).

$^1$H-NMR (300 MHz, CDCl$_3$) δ=8.32 (d, J=8.2 Hz, 1H), 7.65 (d, J=7.2 Hz, 1H), 7.47-7.36 (m, 1H), 7.28 (s, 1H), 6.35 (bs, 1H), 6.11 (bs, 2H), 5.31 (s, 1H), 4.03-3.89 (m, 1H), 3.71 (d, J=7.2 Hz, 2H), 2.33 (s, 3H), 1.25 (s, 1H), 1.00-0.69 (m, 2H), 0.60-0.28 (m, 4H), 0.22-−0.03 (m, 2H).

HRMS (APCI) m/z calculated C$_{24}$H$_{24}$N$_3$O$_4$S [M$^{+1}$]: 450.1482, found: 450.1481.

Example D38: 3-((2,2-Difluorocyclopropyl)methyl) 5-methyl 2-amino-4-(7-cyanobenzo[b]thiophen-3-yl)-6-cyclopropyl-1,4-dihydropyridine-3,5-dicarboxylate Method D using morpholine at room temperature overnight yielded the title compound as a yellow solid (0.004 g, 26%).

$^1$H-NMR (300 MHz, CDCl$_3$) δ=8.32 (d, J=8.3 Hz, 1H), 7.65 (d, J=7.2 Hz, 1H), 7.44 (t, J=7.8 Hz, 1H), 7.27 (s, 1H), 6.30 (bs, 3H), 5.38 (s, 1H), 4.15-3.95 (m, 1H), 3.91-3.73 (m,

1H), 3.55 (s, 3H), 2.77-2.62 (m, 1H), 1.84-1.40 (m, 1H), 1.28-1.17 (m, 2H), 1.03-0.52 (m, 4H). $^{19}$F-NMR (282 MHz, CDCl$_3$) δ (ppm): −129.11 (ddt, J=160.0, 62.6, 11.7 Hz), −143.52 (ddd, J=160.0, 35.4, 11.7 Hz).

HRMS (APCI) m/z calculated C$_{24}$H$_{22}$N$_3$O$_4$SF$_2$ [M$^{+1}$]: 486.1294, found: 486.1292.

Example D39: 3-(Cyclopropylmethyl) 5-methyl 2-amino-4-(7-cyano-5-fluorobenzo[b]thiophen-3-yl)-6-methyl-1,4-dihydropyridine-3,5-dicarboxylate Method D using morpholine at room temperature overnight yielded the title compound as a yellow solid (0.020 g, 28%).

$^1$H-NMR (300 MHz, CDCl$_3$) δ=8.05 (dd, J=10.0, 2.3 Hz, 1H), 7.46-7.36 (m, 2H), 6.14 (s, 1H), 6.08 (bs, 2H), 5.32 (s, 1H), 3.73 (d, J=7.3 Hz, 2H), 3.55 (s, 3H), 2.35 (s, 3H), 0.94-0.78 (m, 1H), 0.53-0.25 (m, 2H), 0.17-−0.11 (m, 2H). $^{19}$F-NMR (282 MHz, CDCl$_3$) δ (ppm): −117.83 (d, J=7.7 Hz).

HRMS (APCI) m/z calculated C$_{22}$H$_{21}$N$_3$O$_4$SF [M$^{+1}$]: 442.1231, found: 442.1231.

Example D40: 3-(cyclopropylmethyl) 5-methyl 2-amino-4-(7-cyano-4-fluorobenzo[b]thiophen-3-yl)-6-methyl-1,4-dihydropyridine-3,5-dicarboxylate Method D using morpholine at room temperature overnight yielded the title compound as a yellow solid (0.015 g, 16%).

$^1$H-NMR (300 MHz, CDCl$_3$) δ=7.62 (dd, J=8.2, 4.0 Hz, 1H), 7.33 (s, 1H), 7.09 (dd, J=11.0, 8.2 Hz, 1H), 6.15-6.01 (m, 3H), 5.66 (d, J=4.0 Hz, 1H), 3.76-3.57 (m, 2H), 3.48 (s, 3H), 2.32 (s, 3H), 0.91-0.59 (m, 1H), 0.39-0.02 (m, 2H), 0.02-−0.25 (m, 2H). $^{19}$F-NMR (282 MHz, CDCl$_3$) δ (ppm): −104.35 (d, J=11.0 Hz).

HRMS (APCI) m/z calculated C$_{22}$H$_{21}$N$_3$O$_4$SF [M$^{+1}$]: 442.1231, found: 442.1229.

Example D41: 3-Isopropyl 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.045 g, 26%).

$^1$H-NMR (300 MHz, CDCl$_3$) δ=8.34 (d, J=8.2 Hz, 1H), 7.65 (d, J=7.2 Hz, 1H), 7.43 (t, J=7.8 Hz, 1H), 7.29 (s, 1H), 6.91 (bs, 1H), 6.25 (bs, 2H), 5.34 (s, 1H), 4.95-4.76 (m, 1H), 3.53 (s, 3H), 2.26 (s, 3H), 1.18 (d, J=6.1 Hz, 3H), 0.70 (d, J=6.1 Hz, 3H).

HRMS (APCI) m/z calculated C$_{21}$H$_{22}$N$_3$O$_4$S [M$^{+1}$]: 412.1326, found: 412.1335.

Example D42: 3-((2,2-Difluoro-3,3-dimethylcyclopropyl)methyl) 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.052 g, 31%).

$^1$H-NMR (300 MHz, CDCl$_3$) δ=8.32 (ddd, J=8.3, 5.3, 1.0 Hz, 1H), 7.65 (d, J=7.4 Hz, 1H), 7.50-7.39 (m, 1H), 7.31 (s, 1H), 6.12 (d, J=3.4 Hz, 1H), 6.08 (d, J=2.2 Hz, 2H), 5.37 (s, 1H), 4.16-4.02 (m, 1H), 3.97-3.81 (m, 1H), 3.55 (d, J=1.5 Hz, 3H), 2.33 (d, J=2.9 Hz, 3H), 1.40-1.21 (m, 1H), 1.15 (dd, J=2.4, 1.5 Hz, 2H), 1.01-0.92 (m, 3H), 0.90 (dd, J=2.9, 1.4 Hz, 1H). $^{19}$F-NMR (282 MHz, CDCl$_3$) δ (ppm): −137.08 (ddd, J=156.1, 65.1, 13.6 Hz), −148.04 (dd, J=155.7, 19.2 Hz)

HRMS (APCI) m/z calculated C$_{24}$H$_{24}$N$_3$O$_4$SF$_2$ [M$^{+1}$]: 488.1450, found: 488.1468.

Example D43: 5-Methyl 3-neopentyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.061 g, 40%).

$^1$H-NMR (300 MHz, CDCl$_3$) δ=8.34 (d, J=8.2 Hz, 1H), 7.63 (d, J=7.1 Hz, 1H), 7.45-7.36 (m, 1H), 7.32 (s, 1H), 6.10 (bs, 3H), 5.44 (s, 1H), 3.80-3.53 (m, 5H), 2.30 (s, 3H), 0.74 (s, 9H).

HRMS (APCI) m/z calculated C$_{23}$H$_{26}$N$_3$O$_4$S [M$^{+1}$]: 440.1639, found: 440.1638.

Example D44: 3-(Cyclopropylmethyl) 5-methyl 2-amino-4-(7-cyanothieno[3,2-b]pyridin-3-yl)-6-methyl-1,4-dihydropyridine-3,5-dicarboxylate Method D using morpholine at room temperature overnight yielded the title compound as a yellow solid (0.048 g, 42%).

$^1$H-NMR (300 MHz, CDCl$_3$) δ=8.77 (d, J=4.7 Hz, 1H), 7.64 (s, 1H), 7.42 (d, J=4.7 Hz, 1H), 6.34 (s, 1H), 6.13 (s, 2H), 5.54 (s, 1H), 3.83-3.62 (m, 2H), 3.56 (s, 3H), 2.26 (s, 3H), 0.92-0.75 (m, 1H), 0.39-0.17 (m, 2H), 0.10-−0.13 (m, 2H).

HRMS (APCI) m/z calculated C$_{21}$H$_{21}$N$_4$O$_4$S [M$^+$]: 425.1278, found: 425.1280.

Example D45: 5-Methyl 3-neopentyl 2-amino-4-(7-cyanobenzo[b]thiophen-3-yl)-6-cyclopropyl-1,4-dihydropyridine-3,5-dicarboxylate Method D using morpholine at room temperature overnight yielded the title compound as a yellow solid (0.063 g, 35%).

$^1$H-NMR (300 MHz, CDCl$_3$) δ=8.33 (dd, J=8.3, 1.0 Hz, 1H), 7.64 (dd, J=7.6, 0.8 Hz, 1H), 7.41 (dd, J=8.3, 7.4 Hz, 1H), 7.28 (s, 1H), 6.13 (bs, 2H), 5.91 (bs, 1H), 5.46 (s, 1H), 3.75-3.56 (m, 5H), 2.68-2.51 (m, 1H), 0.94-0.84 (m, 2H), 0.75 (s, 9H), 0.72-0.64 (m, 2H).

HRMS (APCI) m/z calculated C$_{25}$H$_{28}$N$_3$O$_4$S [M$^+$]: 466.1795, found: 466.1798.

Example D46: Bis(cyclopropylmethyl) 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.120 g, 56%).

$^1$H-NMR (300 MHz, CDCl$_3$) δ=8.40 (d, J=7.3 Hz, 1H), 7.63 (d, J=8.4 Hz, 1H), 7.39 (dd, J=8.2, 7.4 Hz, 1H), 7.34 (s, 1H), 6.02 (bs, 3H), 5.44 (s, 1H), 3.83-3.64 (m, 4H), 2.36 (s, 3H), 0.97-0.75 (m, 2H), 0.51-0.23 (m, 4H), 0.16-−0.07 (m, 4H).

HRMS (APCI) m/z calculated C$_{25}$H$_{26}$N$_3$O$_4$S [M$^+$]: 464.1639, found: 464.11638.

Example D47: 3-(Cyclopropylmethyl) 5-(prop-2-yn-1-yl) 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.112 g, 52%).

$^1$H-NMR (300 MHz, CDCl$_3$) δ=8.39 (dd, J=8.3, 1.0 Hz, 1H), 7.64 (dd, J=7.1, 1.2 Hz, 1H), 7.41 (dd, J=8.2, 7.4 Hz, 1H), 7.34 (s, 1H), 6.02 (bs, 3H), 5.44 (s, 1H), 4.63-4.42 (m, 2H), 3.71 (d, J=7.3 Hz, 2H), 2.46-2.26 (m, 4H), 0.91-0.73 (m, 1H), 0.49-0.20 (m, 2H), 0.12--0.14 (m, 2H).

HRMS (APCI) m/z calculated C$_{24}$H$_{22}$N$_3$O$_4$S [M$^+$]: 448.1326, found: 448.1327.

Example D48: 3-(Cyclopropylmethyl) 5-methyl 2-amino-4-(5,7-dicyanobenzo[b]thiophen-3-yl)-6-methyl-1,4-dihydropyridine-3,5-dicarboxylate Method D using morpholine at room temperature overnight yielded the title compound as a yellow solid (0.005 g, 8%).

$^1$H-NMR (300 MHz, CDCl$_3$) δ=8.64 (s, 1H), 7.85 (s, 1H), 7.49 (s, 1H), 6.07 (bs, 2H), 5.97 (bs, 1H), 5.40 (s, 1H), 3.72 (d, J=7.3 Hz, 2H), 3.55 (s, 3H), 2.37 (s, 3H), 0.87-0.82 (m, 1H), 0.58-0.29 (m, 2H), 0.16-0.11 (m, 2H).

HRMS (APCI) m/z calculated C$_{23}$H$_{21}$N$_4$O$_4$S [M$^+$]: 449.1278, found: 449.1277.

Example D49: 5-(But-2-yn-1-yl) 3-(cyclopropylmethyl) 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.007 g, 4%).

$^1$H-NMR (300 MHz, CDCl$_3$) δ=8.39 (dd, J=8.3, 1.0 Hz, 1H), 7.64 (dd, J=7.1, 1.2 Hz, 1H), 7.41 (dd, J=8.2, 7.4 Hz, 1H), 7.34 (s, 1H), 6.02 (bs, 3H), 5.44 (s, 1H), 4.63-4.42 (m, 2H), 3.71 (d, J=7.3 Hz, 2H), 2.46-2.26 (m, 4H), 0.91-0.73 (m, 1H), 0.49-0.20 (m, 2H), 0.12--0.14 (m, 2H).

HRMS (APCI) m/z calculated C$_{25}$H$_{24}$N$_3$O$_4$S [M$^+$]: 462.1482, found: 462.1480.

Example D50: 5-Methyl 3-(2,2,2-trifluoroethyl) 2-amino-4-(7-cyanobenzo[b]thiophen-3-yl)-6-methyl-1,4-dihydropyridine-3,5-dicarboxylate The title compound was prepared using a variation of Method D: A mixture of methyl(Z)-2-((7-cyanobenzo[b]thiophen-3-yl)methylene)-3-oxobutanoate (0.123 g, 0.43 mmol), 2,2,2-trifluoroethyl 3-amino-3-iminopropanoate (0.115 g, 0.43 mmol), ammonium acetate (0.033 g, 0.43 mmol) in trifluoroethanol (3 mL) was stirred at room temperature overnight and then concentrated. The residue was purified by column chromatography (1:1 hexane:ethyl acetate) affording a yellow solid (0.019 g, 10%).

$^1$H-NMR (300 MHz, CDCl$_3$) δ=8.30 (d, J=8.3 Hz, 1H), 7.68 (d, J=7.2 Hz, 1H), 7.46 (t, J=7.7 Hz, 1H), 7.34 (s, 1H), 6.55 (bs, 1H), 6.24 (bs, 2H), 5.41 (s, 1H), 4.54-4.38 (m, 1H), 4.23-4.07 (m, 1H), 3.57 (s, 3H), 2.35 (s, 3H). $^{19}$F-NMR (282 MHz, CDCl$_3$) δ (ppm): −73.93 (t, J=9.8 Hz).

HRMS (APCI) m/z calculated C$_{20}$H$_{17}$N$_3$O$_4$SF$_3$ [M$^+$]: 452.0886, found: 452.0885.

Example D51: 3-(Cyclopropylmethyl) 5-(2,2,2-trifluoroethyl) 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.0065 g, 7%).

$^1$H-NMR (300 MHz, CDCl$_3$) δ=8.34 (d, J=8.3 Hz, 1H), 7.65 (d, J=7.2 Hz, 1H), 7.44-7.38 (m, 1H), 7.34 (s, 1H), 6.16 (bs, 1H), 6.04 (bs, 2H), 5.42 (s, 1H), 4.41 (dq, J=12.7, 8.5 Hz, 1H), 4.20 (dt, J=12.7, 8.5 Hz, 1H), 3.73 (d, J=7.3 Hz, 2H), 2.38 (s, 3H), 0.90-0.82 (m, 1H), 0.47-0.29 (m, 2H), 0.10--0.04 (m, 2H). $^{19}$F-NMR (282 MHz, CDCl$_3$) δ (ppm): −73.88 (t, J=9.1 Hz).

HRMS (APCI) m/z calculated C$_{23}$H$_{21}$N$_3$O$_4$SF$_3$ [M$^{+1}$]: 492.1199, found: 492.1197.

Example D52: 3-(Cyclopropylmethyl) 5-methyl 2-amino-4-(6-chloro-7-cyanobenzo[b]thiophen-3-yl)-6-methyl-1,4-dihydropyridine-3,5-dicarboxylate Method D using morpholine at room temperature overnight yielded the title compound as a yellow solid (0.060 g, 39%).

$^1$H-NMR (300 MHz, CDCl$_3$) δ=8.27 (d, J=8.8 Hz, 1H), 7.44 (d, J=8.8 Hz, 1H), 7.29 (s, 1H), 6.14-5.94 (m, 3H), 5.35 (s, 1H), 3.76-3.67 (m, 2H), 3.54 (s, 3H), 2.34 (s, 3H), 0.93-0.75 (m, 1H), 0.48-0.24 (m, 2H), 0.12--0.09 (m, 2H)

HRMS (APCI) m/z calculated C$_{22}$H$_{21}$N$_3$O$_4$SCl [M$^{+1}$]: 458.0936, found: 458.0938.

Example D53: 3-(2-Fluoro-2-methylpropyl) 5-methyl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.060 g, 39%).

$^1$H-NMR (300 MHz, CDCl$_3$) δ=8.34 (d, J=9.0 Hz, 1H), 7.64 (d, J=7.4 Hz, 1H), 7.47-7.37 (m, 1H), 7.32 (s, 1H), 6.63 (bs, 1H), 6.20 (bs, 2H), 5.43 (s, 1H), 4.12-3.79 (m, 2H), 3.56 (s, 3H), 2.30 (s, 3H), 1.27-1.03 (m, 6H). $^{19}$F-NMR (282 MHz, CDCl$_3$) δ (ppm): (−142.28)-(−148.26) (m, CF).

HRMS (APCI) m/z calculated C$_{22}$H$_{23}$N$_3$O$_4$SF [M$^{+1}$]: 444.1388, found: 444.1388.

Example D54: 3-(Cyclopropylmethyl) 5-methyl 2-amino-4-(7-cyano-6-(trifluoromethyl)benzo[b]thiophen-3-yl)-6-methyl-1,4-dihydropyridine-3,5-dicarboxylate Method D using morpholine at room temperature overnight yielded the title compound as a yellow solid (0.003 g, 3%).

$^1$H-NMR (300 MHz, CDCl$_3$) δ=8.09 (d, J=8.4 Hz, 1H), 7.44 (d, J=8.2 Hz, 1H), 7.35 (s, 1H), 6.03-5.91 (m, 3H), 5.24 (s, 1H), 3.84 (d, J=7.0 Hz, 2H), 3.58 (s, 3H), 2.22 (s, 3H), 0.88-0.77 (m, 1H), 0.50-0.22 (m, 2H), 0.14--0.10 (m, 2H).

Example D55: 5-Methyl 3-prop-2-yn-1-yl 2-amino-4-(7-cyanobenzo[b]thiophen-3-yl)-6-methyl-1,4-dihydropyridine-3,5-dicarboxylate Method D using morpholine at room temperature overnight yielded the title compound as a yellow solid (0.005 g, 4%).

$^1$H-NMR (300 MHz, CDCl$_3$) δ=8.34 (d, 1H), 7.63 (d, 1H), 7.49 (t, 1H), 7.31 (s, 1H), 6.1 (bs, 3H), 5.44 (s, 1H), 4.44-4.26 (m, 2H), 3.59 (s, 3H), 2.42-2.24 (m, 4H).

Example D56: 3-(Cyclopropylmethyl) 5-methyl 2-amino-4-(7-cyanobenzo[b]thiophen-3-yl)-6-(trifluoromethyl)-1,4-dihydropyridine-3,5-dicarboxylate Method D using morpholine at room temperature overnight yielded the title compound as a yellow solid (0.007 g, 5%).

$^1$H-NMR (300 MHz, CDCl$_3$) δ=8.33 (d, 1H), 7.65 (d, 1H), 7.44-7.35 (m, 1H), 7.31 (s, 1H), 6.09 (bs, 2H), 5.96 (bs, 1H), 5.48 (s, 1H), 3.76 (d, 2H), 2.38 (s, 3H), 0.98-0.81 (m, 1H), 0.46-0.26 (m, 2H), 0.14--0.11 (m, 2H).

Method E

Example E1: 4-(Benzo[b]thiophen-3-yl)-2,6-dimethyl-1,4-dihydropyridine-3,5-dicarbonitrile

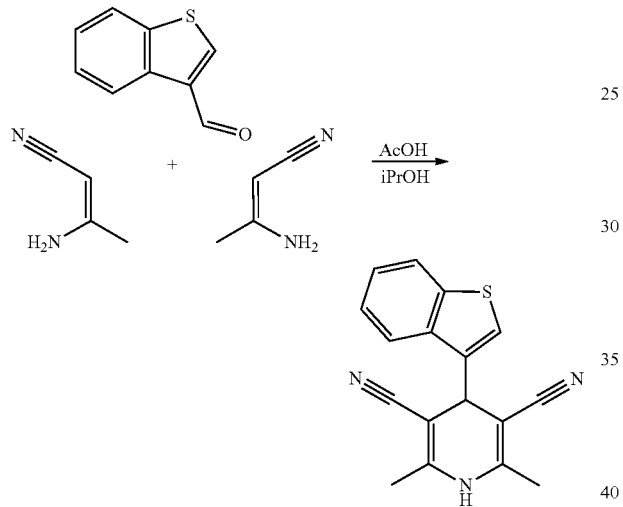

A mixture of thianaphthene-3-carboxaldehyde (0.5 g, 3.08 mmol), 3-aminocrotonitrile (0.554 mL, 6.74 mmol) and acetic acid (0.076 mL, 3.08 mmol) in isopropyl alcohol (10 mL) was stirred at 100° C. for 18 hours. The mixture was allowed to cool to RT and concentrated. The residue was basified with aq. sodium bicarbonate, and the resulting solid was filtered off and washed with cold water and ethyl ether. The desired product was obtained as a light-yellow solid (0.738 g, 82%).

$^1$H-NMR (400 MHz, DMSO-d$_6$) δ=2.06 (s, 6H), 5.00 (s, 1H), 7.36-7.46 (m, 1H), 7.65 (s, 1H), 7.89 (d, 1H), 8.03 (d, 1H), 9.67 (s, 1H).

HPLC-MS: Rt 3.878 min, m/z 292.0 (MH$^+$).

The following examples were synthesized according to Method E:

Example E2: 4-(6-hydroxybenzo[b]thiophen-3-yl)-2,6-dimethyl-1,4-dihydropyridine-3,5-dicarbonitrile $^1$H-NMR (400 MHz, DMSO-d$_6$) δ=2.05 (s, 6H), 4.80 (s, 1H), 6.86 (dd, 1H), 7.13 (s, 1H), 7.24 (d, 1H), 7.61 (d, 1H), 9.64 (s, 2H).

HPLC-MS: Rt 3.285 min, m/z 308.0 (MH$^+$).

Example E3: 4-(6-methoxybenzo[b]thiophen-3-yl)-2,6-dimethyl-1,4-dihydropyridine-3,5-dicarbonitrile $^1$H-NMR (400 MHz, DMSO-d$_6$) δ=2.06 (s, 6H), 3.81 (s, 3H), 4.84 (s, 1H), 7.00 (d, 1H), 7.20 (s, 1H), 7.50 (d, 1H), 7.71 (d, 1H), 9.69 (s, 1H).

HPLC-MS: Rt 3.962 min, m/z 322.0 (MH$^+$).

Example E4: 2,6-dimethyl-4-(thieno[2,3-b]pyridin-3-yl)-1,4-dihydropyridine-3,5-dicarbonitrile $^1$H-NMR (400 MHz, DMSO-d$_6$) δ=8.90 (s, 1H), 8.47 (s, 1H), 7.78 (s, 1H), 7.72 (d, 1H), 6.91 (t, 1H), 6.17 (s, 1H), 2.65 (s, 6H).

HPLC-MS: Rt 2.735; m/z 229.9 (MH$^+$).

Method F

Example F1: 4-(benzo[b]thiophen-3-yl)-2-methyl-6-phenyl-1,4-dihydropyridine-3,5-dicarbonitrile

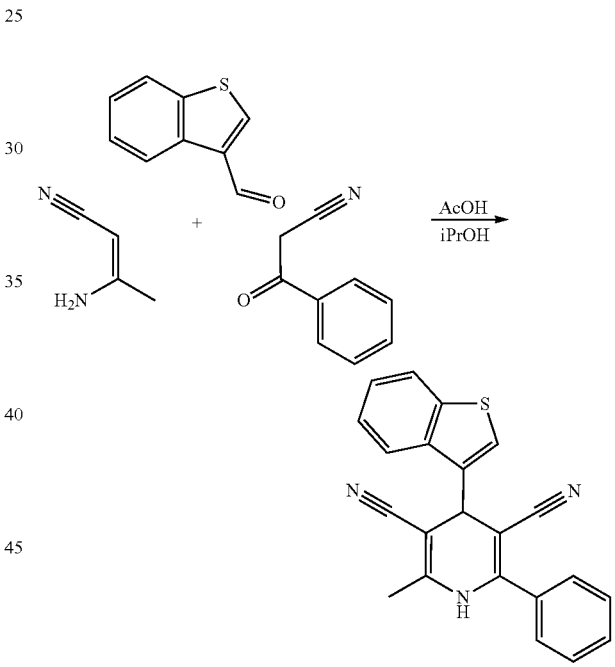

A mixture of thianaphthene-3-carboxaldehyde (0.104 g, 0.64 mmol), 3-aminocrotonitrile (0.052 g, 0.64 mmol), benzoylacetonitrile (0.0897 g, 0.62 mmol) and acetic acid (0.035 mL, 0.64 mmol) in isopropyl alcohol (3.5 mL) was heated to 100° C. and left to stir for 16 hours. The mixture was allowed to cool to RT and concentrated. The residue was basified with aq. sodium bicarbonate, and the resulting solid was filtered off and purified by column chromatography (3:1 Hexane: Ethyl acetate) rendering a light-yellow solid (0.0162 g, 7%).

$^1$H-NMR (400 MHz, DMSO-d$_6$) δ=2.12 (s, 3H), 5.17 (s, 1H), 7.39-7.49 (m, 2H), 7.50-7.59 (m, 5H), 7.78 (s, 1H), 8.01 (dd, 1H), 8.06 (dd, 1H), 9.92 (s, 1H).

HPLC-MS: Rt 4.329 min, m/z 354.1 (MH$^+$).

The following examples were synthesized according to Method F.

Example F2: 4-(benzo[b]thiophen-3-yl)-2-cyclopropyl-6-methyl-1,4-dihydropyridine-3,5-dicarbonitrile ¹H-NMR (400 MHz, DMSO-d₆) δ=0.95 (s, 4H), 2.06 (s, 3H), 4.98 (s, 1H), 7.41 (s, 2H), 7.64 (s 1H), 7.84 (s, 1H), 8.03 (s, 1H), 8.82 (s, 1H).

HPLC-MS: Rt 4.138 min, m/z 318.0 (MH⁺).

Example F3: 5-acetyl-4-(benzo[b]thiophen-3-yl)-2,6-dimethyl-1,4-dihydropyridine-3-carbonitrile ¹H-NMR (400 MHz, DMSO-d₆) δ=2.00 (s, 6H), 2.31 (s, 3H), 5.16 (s, 1H), 7.30-7.48 (m, 3H), 7.97 (d 1H), 8.04 (d, 1H), 9.30 (s, 1H).

HPLC-MS: Rt 3.816 min, m/z 175.1 (MH⁺-134).

Example F4: Ethyl 4-(benzo[b]thiophen-3-yl)-5-cyano-2,6-dimethyl-1,4-dihydropyridine-3-carboxylate ¹H-NMR (400 MHz, DMSO-d₆) δ=0.90 (t, 3H), 2.02 (s, 3H), 2.30 (s, 3H), 3.85 (dd, 2H), 5.02 (s, 1H), 7.31-7.45 (m, 3H), 7.91 (d, 1H), 7.96 (d, 1H), 9.30 (s, 1H).

HPLC-MS: Rt 4.418 min, m/z 205.1 (MH⁺-134).

Example F5: Ethyl 4-(benzo[b]thiophen-3-yl)-5-cyano-2-methyl-6-phenyl-1,4-dihydropyridine-3-carboxylate ¹H-NMR (400 MHz, DMSO-d₆) δ=0.98 (t, 3H), 2.37 (s, 3H), 3.92 (q, 2H), 5.17 (s, 1H), 7.41 (ddd 2H), 7.49 (d, 5H), 8.00 (t, 2H), 9.60 (s, 1H).

HPLC-MS: Rt 4.946 min, m/z 267.1 (MH⁺-134).

Example F6: Ethyl 4-(benzo[b]thiophen-3-yl)-5-cyano-2-cyclopropyl-6-methyl-1,4-dihydropyridine-3-carboxylate ¹H-NMR (400 MHz, DMSO-d₆) δ=0.80-0.98 (m, 6H), 0.96-1.06 (m, 1H), 2.03 (s, 3H), 2.73-2.84 (m, 1H), 3.82-3.95 (m, 2H), 5.02 (s, 1H), 7.32 (s, 1H), 7.33-7.44 (m, 2H), 7.90 (d, 1H), 7.96 (d, 1H), 8.23 (s, 1H).

HPLC-MS: Rt 4.693 min, m/z 231.1 (MH⁺-134).

Example F7: Methyl 4-(benzo[b]thiophen-3-yl)-5-cyano-2-cyclopropyl-6-methyl-1,4-dihydropyridine-3-carboxylate ¹H-NMR (400 MHz, DMSO-d₆) δ=0.79-0.95 (m, 3H), 1.02 (ddd, 1H), 2.03 (s, 3H), 2.78 (dq, 1H), 3.45 (s, 3H), 5.01 (s, 1H), 7.30 (s, 1H), 7.39 (dt, 2H), 7.90 (d, 1H), 7.96 (dd, 1H), 8.28 (s, 1H).

HPLC-MS: Rt 4.438 min, m/z 217.1 (MH⁺-134).

Method G

Example G1: 1,1'-(4-(benzo[b]thiophen-3-yl)-2,6-dimethyl-1,4-dihydropyridine-3,5-diyl)diethanone

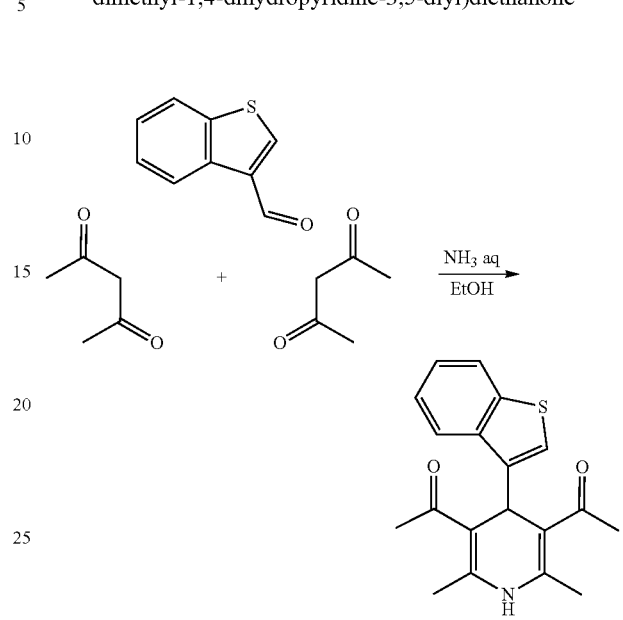

A mixture of thianaphthene-3-carboxaldehyde (0.2 g, 1.23 mmol), acetylacetone (0.25 mL, 2.47 mmol) and aqueous ammonium hydroxide solution (38-40%, 0.12 mL) in ethanol (1 mL) was heated to 90° C. and left to stir for 16 hours. The mixture was allowed to cool to RT and was then poured into 10 ml of cold water. The precipitate formed was filtered off, dried and washed with cold diethyl ether. The desired product was obtained as a strongly yellow solid (0.193 g, 48%).

¹H-NMR (400 MHz, DMSO-d₆) δ=2.17 (s, 6H), 2.29 (s, 6H), 5.52 (s, 1H), 7.23 (s, 1H), 7.33 (dt 2H), 7.88 (d, 1H), 8.12 (d, 1H), 9.08 (s, 1H).

HPLC-MS: Rt 3.668 min, m/z 192.1 (MH⁺-134).

The following examples were synthesized according to Method G.

Example G2: 1,1'-(4-(6-hydroxybenzo[b]thiophen-3-yl)-2,6-dimethyl-1,4-dihydropyridine-3,5-diyl)bis(ethan-1-one)

¹H-NMR (400 MHz, DMSO-d₆) δ=2.28 (s, 12H), 5.29 (s, 1H), 6.76 (d, 2H), 7.10 (s 1H), 7.45 (d, 1H), 9.10 (s, 1H), 9.40 (s, 1H).

HPLC-MS: Rt 2.950 min, m/z 192.1 (MH⁺-150).

Example G3: 1,1'-(4-(6-Methoxybenzo[b]thiophen-3-yl)-2,6-dimethyl-1,4-dihydropyridine-3,5-diyl)diethanone ¹H-NMR (400 MHz, DMSO-d₆) δ=2.29 (d, 12H), 3.75 (s, 3H), 5.32 (s, 1H), 6.86 (d 1H), 6.89 (dd, 1H), 7.36 (d, 1H), 7.55 (d, 1H), 9.12 (s, 1H).

HPLC-MS: Rt 3.676 min, m/z 192 (MH⁺-164).

Example G4: 1,1'-(4-(Benzo[b]thiophen-3-yl)-2,6-dicyclopropyl-1,4-dihydropyridine-3,5-diyl)diethanone ¹H-NMR (400 MHz, DMSO-d₆) δ=0.69 (dd, 2H), 0.74 (dd, 4H), 0.78-0.84 (m, 2H), 2.18-2.25 (m, 2H), 2.27 (s, 6H), 5.69 (s, 1H), 7.21 (s 1H), 7.26-7.36 (m, 2H), 7.89 (d, 1H), 7.97 (d, 1H), 83.99 (s, 1H).

Method H

Example H1: 1,1'-(4-(5-chlorobenzo[b]thiophen-3-yl)-2,6-dimethyl-1,4-dihydropyridine-3,5-diyl)diethanone

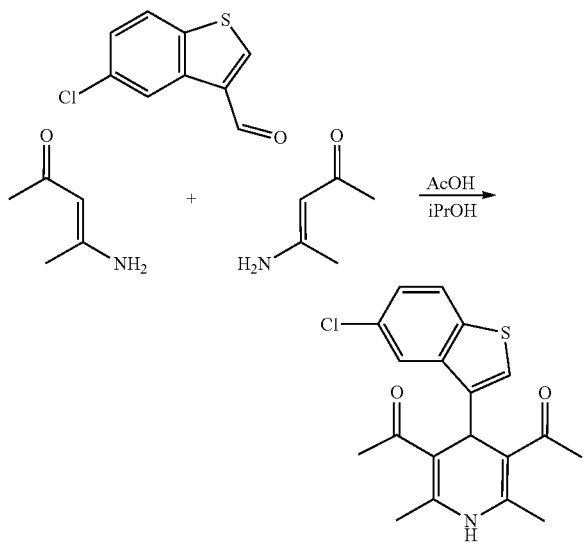

A mixture of 5-chlorobenzo[b]thiophene-3-carbaldehyde (0.05 g, 0.26 mmol), 4-amino-3-penten-2-one (0.60 g, 0.52 mmol) and acetic acid (0.015 mL) in isopropanol (1.5 mL) was heated to 100° C. and left to stir for 16 hours. The mixture was allowed to cool to RT and was then treated with saturated aqueous sodium bicarbonate solution (10 mL). The solid was filtered off, washed with water, dried and purified by column chromatography (3:1 hexane:ethyl acetate) affording a fine yellow solid (8.8 mg, 9.5%).

¹H-NMR (400 MHz, DMSO-d₆) δ=2.17 (s, 6H), 2.31 (s, 6H), 5.44 (s, 1H), 7.33 (d, 2H), 7.92 (d, 1H), 8.23 (s, 1H), 9.15 (s, 1H).

HPLC-MS: Rt 4.072 min. m/z 192.1 (MH⁺-168).

The following examples were synthesized according to Method H.

Example H2: 1,1'-(4-(5-bromobenzo[b]thiophen-3-yl)-2,6-dimethyl-1,4-dihydropyridine-3,5-diyl)diethanone ¹H-NMR (400 MHz, DMSO-d₆) δ=2.17 (s, 6H), 2.31 (s, 6H), 5.44 (s, 1H), 7.30 (d, 1H), 7.44 (d, 1H), 7.86 (d, 1H), 8.38 (s, 1H), 9.16 (s, 1H).

Example H3: 1,1'-(4-(5-fluorobenzo[b]thiophen-3-yl)-2,6-dimethyl-1,4-dihydropyridine-3,5-diyl)bis(ethan-1-one)

¹H-NMR (400 MHz, DMSO-d₆) δ=9.15 (s, 1H), 7.92 (dd, J=8.1, 4.2 Hz, 2H), 7.34 (s, 1H), 7.20 (td, J=8.8, 2.3 Hz, 1H), 5.44 (s, 1H), 2.32 (s, 6H), 2.18 (s, 6H).

Example H4: 1,1'-(2,6-dimethyl-4-(5-morpholinobenzo[b]thiophen-3-yl)-1,4-dihydropyridine-3,5-diyl)bis(ethan-1-one)

¹H-NMR (400 MHz, DMSO-d₆) δ=9.11 (s, 1H), 7.70 (d, 1H), 7.49 (d, 1H), 7.20 (s, 1H), 7.09 (dd, 1H), 5.48 (s, 1H), 3.80 (t, 4H), 3.12 (t, 4H), 2.27 (s, 6H), 2.19 (s, 6H).

Example H5: 1,1'-(2,6-dimethyl-4-(5-(4-methylpiperazin-1-yl)benzo[b]thiophen-3-yl)-1,4-dihydropyridine-3,5-diyl)bis(ethan-1-one)

¹H-NMR (400 MHz, DMSO-d₆) δ=9.12 (s, 1H), 7.67 (d, 1H), 7.48 (d, 1H), 7.19 (s, 1H), 5.48 (s, 1H), 3.80 (t, 4H), 3.12 (t, 4H), 2.27 (s, 6H), 2.19 (s, 6H).

Example H6: 1,1'-(4-(5-(benzylamino)benzo[b]thiophen-3-yl)-2,6-dimethyl-1,4-dihydropyridine-3,5-diyl)bis(ethan-1-one)

¹H-NMR (400 MHz, DMSO-d₆) δ=8.98 (s, 1H), 7.50 (d, 1H), 7.43 (d, 2H), 7.32 (t, 2H), 7.23 (t, 1H), 7.14 (d, 1H), 7.08 (s, 1H), 6.77 (dd, 1H), 6.21 (t, 1H), 5.33 (s, 1H), 4.30 (d, 2H), 2.22 (s, 6H), 2.09 (s, 6H).

Example H7: 3-(3,5-diacetyl-2,6-dimethyl-1,4-dihydropyridin-4-yl)benzo[b]thiophene-5-carbonitrile ¹H-NMR (400 MHz, DMSO-d₆) δ=2.17 (s, 6H), 2.33 (s, 6H), 5.49 (s, 1H), 7.43 (s, 1H), 7.67 (dd, 1H), 8.13 (d, 1H), 8.66 (s, 1H), 9.20 (s, 1H).
HPLC-MS: Rt 3.563; m/z 351.1 (MH⁺).

Example H8: 3-(3,5-diacetyl-2,6-dimethyl-1,4-dihydropyridin-4-yl)benzo[b]thiophene-5-carboxylic acid ¹H-NMR (400 MHz, DMSO-d₆) δ=9.13 (s, 1H), 8.82 (s, 1H), 7.96 (d, 1H), 7.85 (d, 1H), 7.33 (s, 1H), 5.54 (s, 1H), 2.30 (s, 6H), 2.18 (s, 6H).

Example H9: N-cyclopropyl-3-(3,5-diacetyl-2,6-dimethyl-1,4-dihydropyridin-4-yl)benzo[b]thiophene-5-carboxamide ¹H-NMR (400 MHz, DMSO-d₆) δ=9.13 (s, 1H), 8.64 (s, 1H), 8.42 (d, 1H), 7.93 (d, 1H), 7.72 (d, 1H), 7.32 (s, 1H), 5.53 (s, 1H), 2.89 (m, 1H), 2.29 (s, 6H), 2.18 (s, 6H), 0.73 (m, 2H), 0.61 (m, 2H).

Example H10: N-(cyclopropylmethyl)-3-(3,5-diacetyl-2,6-dimethyl-1,4-dihydropyridin-4-yl)benzo[b]thiophene-5-carboxamide ¹H-NMR (400 MHz, DMSO-d₆) δ=9.12 (s, 1H), 8.68 (s, 1H), 8.50 (d, 1H), 7.95 (d, 1H), 7.78 (d, 1H), 7.32 (s, 1H), 5.53 (s, 1H), 3.26 (t, 2H), 2.29 (s, 6H), 2.18 (s, 6H), 1.08 (m, 1H), 0.45 (m, 2H), 0.28 (m, 2H).

Example H11: 1,1'-(2,6-Dimethyl-4-(5-(4-methylpiperazine-1-carbonyl)benzo[b]thiophen-3-yl)-1,4-dihydropyridine-3,5-diyl)bis(ethan-1-one)

$^1$H-NMR (400 MHz, CDCl$_3$) δ=8.21 (s, 1H), 7.82 (d, 1H), 7.42 (d, 1H), 7.21 (d, 1H), 6.17 (s, 1H), 5.61 (s, 1H), 3.77 (d, 4H), 2.54 (m, 4H), 2.38 (s, 3H), 2.34 (s, 3H), 2.22 (s, 3H), 2.08 (s, 3H).

Example H12: 1,1'-(2,6-Dimethyl-4-(5-(morpholine-4-carbonyl)benzo[b]thiophen-3-yl)-1,4-dihydropyridine-3,5-diyl)bis(ethan-1-one)

$^1$H-NMR (400 MHz, DMSO-d$_6$) δ=9.15 (s, 1H), 8.21 (s, 1H), 7.97 (d, 1H), 7.35 (dd, 1H), 7.32 (s, 1H), 5.50 (s, 1H), 3.67 (m, 8H), 2.31 (s, 6H), 2.16 (s, 6H).

Example H13: 1,1'-(2,6-Dimethyl-4-(thieno[3,2-c]pyridin-3-yl)-1,4-dihydropyridine-3,5-diyl)bis(ethan-1-one)

$^1$H-NMR (400 MHz, DMSO-d$_6$) δ=9.35 (s, 1H), 9.18 (s, 1H), 8.36 (d, 1H), 7.95 (d, 1H), 7.34 (s, 1H), 5.58 (s, 1H), 2.31 (s, 6H), 2.19 (s, 6H).

Example H14: 1,1'-(2,6-Dimethyl-4-(thieno[2,3-c]pyridin-3-yl)-1,4-dihydropyridine-3,5-diyl)bis(ethan-1-one)

$^1$H-NMR (400 MHz, DMSO-d$_6$) δ=9.17 (s, 1H), 9.13 (d, 1H), 8.44 (d, 1H), 8.05 (dd, 1H), 7.57 (s, 1H), 5.51 (s, 1H), 2.31 (s, 6H), 2.17 (s, 6H).

Example H15: 1,1'-(2,6-Dimethyl-4-(thieno[2,3-b]pyridin-3-yl)-1,4-dihydropyridine-3,5-diyl)bis(ethan-1-one)

$^1$H-NMR (400 MHz, DMSO-d$_6$) δ=9.15 (s, 1H), 8.49 (d, 2H), 7.43 (s, 1H), 7.33 (s, 1H), 5.47 (s, 1H), 2.32 (s, 6H), 2.18 (s, 6H).

Method I

Example 11: Dimethyl 5-acetyl-4-(benzo[b]thiophen-3-yl)-6-methyl-1,4-dihydropyridine-2,3-dicarboxylate

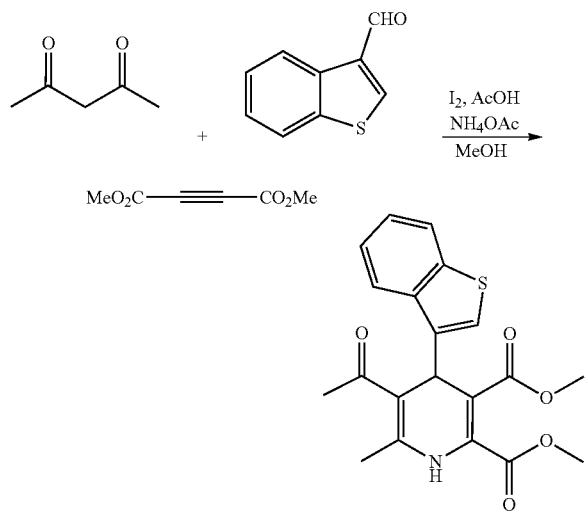

A mixture of benzo[b]thiophene-3-carbaldehyde (0.20 g, 1.23 mmol), pentane-2,4-dione (0.123 g, 1.23 mmol), dimethyl but-2-ynedioate (0.182 mL, 1.48 mmol), ammonium acetate (0.143 g, 1.85 mmol), iodine (0.094 g, 0.37 mmol) and two drops of acetic acid were stirred in methanol (3 mL) at 60° C. for 12 h. The solvent was removed under reduced pressure. The residue was dissolved in ethyl acetate and the organic layer was washed twice with saturated NaS$_2$O$_3$ solution and brine, dried (Na$_2$SO$_4$), filtered and concentrated. The residue was purified by column chromatography (2:1 hexane:ethyl acetate) affording a yellow solid (0.028 g, 6%).

$^1$H-NMR (300 MHz, CDCl$_3$) δ=7.94-7.80 (m, 2H), 7.46-7.29 (m, 2H), 7.19 (s, 1H), 6.38 (bs, 1H), 5.38 (s, 1H), 3.81 (s, 3H), 3.52 (s, 3H), 2.43 (s, 3H), 2.04 (s, 3H).

HRMS (APCI) m/z calculated C$_{20}$H$_{20}$NO$_5$S [M$^{+1}$]: 386.1056, found: 386.1058.

Example 12: Dimethyl 5-acetyl-4-(7-cyanobenzo[b]thiophen-3-yl)-6-methyl-1,4-dihydropyridine-2,3-dicarboxylate The title compound was prepared according to Method I affording a yellow solid (0.04 g, 2%).

$^1$H-NMR (300 MHz, CDCl$_3$) δ=8.24 (d, J=7.9 Hz, 1H), 7.70 (d, J=7.2 Hz, 1H), 7.50 (t, J=7.9 Hz, 1H), 7.34 (s, 1H), 6.43 (bs, 1H), 5.41 (s, 1H), 3.84 (s, 3H), 3.55 (s, 3H), 2.44 (s, 3H), 2.11 (s, 3H).

HRMS (APCI) m/z calculated C$_{21}$H$_{19}$N$_2$O$_5$S [M$^{+1}$]: 411.1009, found: 411.1006.

Method J

Example J1: Methyl 5-acetyl-4-(benzo[b]thiophen-3-yl)-2-cyclopropyl-6-methyl-1,4-dihydropyridine-3-carboxylate

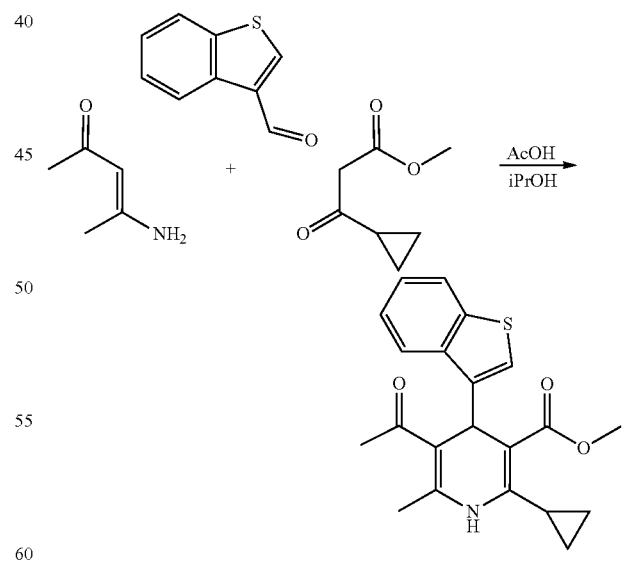

A mixture of thianaphthene-3-carboxaldehyde (0.106 g, 0.65 mmol), methyl 3-cyclopropyl-3-oxopropanoate (0.071 g, 0.72 mmol) and 4-amino-3-penten-2-one (0.088 g, 0.61 mmol) and acetic acid (0.035 mL) in isopropylalcohol (1.5 mL) was heated to 100° C. and left to stir for 19 hours. The mixture was allowed to cool to RT and was then treated with saturated aqueous sodium bicarbonate solution (10 mL). The solid was filtered off, washed with water, dried and purified by column chromatography (4:1 hexane:ethyl acetate) affording a fine yellow solid (0.075 g, 44%).

$^1$H-NMR (400 MHz, DMSO-d$_6$) δ=0.76 (s, 2H), 0.96 (d, 2H), 2.12 (s, 3H), 2.33 (s, 3H), 2.69 (s, 1H), 3.58 (s, 3H), 5.43 (s, 1H), 7.15 (s, 1H), 7.31 (s, 1H), 7.38 (s, 1H), 7.90 (s, 2H), 8.05 (d, 1H).

HPLC-MS: Rt 4.302 min, m/z 234.1 (MH$^+$-133).

A second reaction product was isolated by column chromatography:

Example J1-a: Dimethyl 4-(benzo[b]thiophen-3-yl)-2,6-dicyclopropyl-1,4-dihydropyridine-3,5-dicarboxylate $^1$H-NMR (400 MHz, DMSO-d$_6$) δ=0.56 (s, 2H), 0.82 (s, 2H), 0.90 (d, 2H), 1.04 (s, 2H), 2.56 (m, 2H), 3.55 (s, 5H), 5.37 (s, 1H), 7.05 (s, 1H), 7.11 (s 1H), 7.32 (t, 1H), 7.39 (t, 1H), 7.90 (d, 1H), 7.98 (s, 1H).

HPLC-MS: Rt 4.935; m/z 276.1 (MH$^+$).

The following examples were synthesized according to Method J.

Example J2: Ethyl 5-acetyl-4-(benzo[b]thiophen-3-yl)-2,6-dimethyl-1,4-dihydropyridine-3-carboxylate $^1$H-NMR (400 MHz, DMSO-d$_6$) δ=1.1 (t, 3H), 2.11 (s, 3H), 2.25 (s, 3H), 2.31 (s, 3H), 3.99 (d, 2H), 5.40 (s, 1H), 7.23 (s, 1H), 7.31 (t 1H), 7.37 (m, 1H), 7.89 (d, 1H), 8.08 (d, 1H), 9.02 (s, 1H).

HPLC-MS: Rt 4.284 min, m/z 222.1 (MH$^+$-134).

Example J3: Methyl 5-acetyl-4-(5-chlorobenzo[b]thiophen-3-yl)-2,6-dimethyl-1,4-dihydropyridine-3-carboxylate $^1$H-NMR (400 MHz, DMSO-d$_6$) δ=2.13 (s, 3H), 2.25 (s, 3H), 2.33 (s, 3H), 3.54 (s, 3H), 5.33 (s, 1H), 7.33 (s, 1H), 7.93 (d, 1H), 8.11 (d, 1H), 8.52 (s, 1H), 9.11 (s, 1H).

HPLC-MS: Rt 4.431 min, m/z 208.1 (MH$^+$-168).

Example J6: 1,1'-(4-(benzo[b]thiophen-3-yl)-2-cyclopropyl-6-methyl-1,4-dihydro-pyridine-3,5-diyl)diethanone $^1$H-NMR (400 MHz, DMSO-d$_6$) δ=0.72 (m, 2H), 0.80 (m, 2H), 2.16 (s, 3H), 2.26 (d, 1H), 2.33 (s, 6H), 5.60 (s, 1H), 7.21 (s, 1H), 7.32 (dd, 2H), 7.89 (d, 1H), 8.04 (d, 1H), 9.02 (s, 1H).

HPLC-MS: Rt 4.692; m/z 352.0 (MH$^+$).

Example J10: 1-(4-(benzo[b]thiophen-3-yl)-2,6-dimethyl-5-(methylsulfonyl)-1,4-dihydro-pyridin-3-yl)ethanone $^1$H-NMR (400 MHz, DMSO-d$_6$) δ=2.16 (s, 3H), 2.29 (d, 6H), 2.47 (s, 3H), 5.47 (s, 1H), 7.33 (t, 1H), 7.43-7.37 (m, 2H), 7.93 (d, 1H), 8.07 (d, 1H), 9.26 (s, 1H).

HPLC-MS: Rt 3.395 min, m/z 228.0 (MH$^+$-134).

Example J11: Methyl 5-acetyl-4-(5-fluorobenzo[b]thiophen-3-yl)-2,6-dimethyl-1,4-dihydropyridine-3-carboxylate $^1$H-NMR (400 MHz, DMSO-d$_6$) δ=9.10 (s, 1H), 7.93 (dd, J=8.8, 5.2 Hz, 1H), 7.81 (dd, J=11.0, 2.5 Hz, 1H), 7.35 (s, 1H), 7.20 (td, J=8.8, 2.6 Hz, 1H), 5.33 (s, 1H), 3.54 (s, 3H), 2.32 (s, 3H), 2.26 (s, 3H), 2.12 (s, 3H).

HPLC-MS: Rt 4.345; m/z 360.0 (MH$^+$).

Example J12: Methyl 5-acetyl-4-(5-bromobenzo[b]thiophen-3-yl)-2,6-dimethyl-1,4-dihydropyridine-3-carboxylate $^1$H-NMR (400 MHz, DMSO-d$_6$) δ=9.11 (s, 1H), 8.26 (d, 1H), 7.88 (d, 1H), 7.45 (d, 1H), 7.31 (s, 1H), 5.34 (s, 1H), 3.58 (s, 3H), 2.34 (s, 3H), 2.25 (s, 3H), 2.16 (s, 3H).

Example J13: Methyl 5-acetyl-4-(5-cyanobenzo[b]thiophen-3-yl)-2,6-dimethyl-1,4-dihydropyridine-3-carboxylate $^1$H-NMR (400 MHz, DMSO-d$_6$) δ=9.16 (s, 1H), 8.53 (s, 1H), 8.15 (d, 1H), 7.67 (d, 1H), 7.46 (s, 1H), 5.40 (s, 1H), 3.55 (s, 3H), 2.35 (s, 3H), 2.27 (s, 3H), 2.17 (s, 3H).

Example J14: 3-(3-acetyl-5-(methoxycarbonyl)-2,6-dimethyl-1,4-dihydropyridin-4-yl)benzo[b]thiophene-5-carboxylic acid $^1$H-NMR (400 MHz, DMSO-d$_6$) δ=12.94 (s, 1H), 9.12 (s, 1H), 8.77 (s, 1H), 8.00 (d, 1H), 7.85 (d, 1H), 7.32 (s, 1H), 5.52 (s, 1H), 3.56 (s, 3H), 2.35 (s, 3H), 2.24 (s, 3H), 2.12 (s, 3H).

Example J15: Methyl 5-acetyl-4-(5-(cyclopropylcarbamoyl)benzo[b]thiophen-3-yl)-2,6-dimethyl-1,4-dihydropyridine-3-carboxylate $^1$H-NMR (400 MHz, DMSO-d$_6$) δ=9.06 (s, 1H), 8.59 (s, 1H), 8.45 (d, 1H), 7.91 (d, 1H), 7.72 (dd, 1H), 7.26 (s, 1H), 5.39 (s, 1H), 3.53 (s, 3H), 2.85 (m, 1H), 2.37 (s, 3H), 2.19 (s, 3H), 2.06 (s, 3H), 0.69 (m, 2H), 0.58 (m, 2H).

Example J16: Methyl 5-acetyl-4-(5-((cyclopropylmethyl)carbamoyl)benzo[b]thiophen-3-yl)-2,6-dimethyl-1,4-dihydropyridine-3-carboxylate $^1$H-NMR (400 MHz, DMSO-d$_6$) δ=9.10 (s, 1H), 8.66 (s, 1H), 8.60 (d, 1H), 7.97 (d, 1H), 7.81 (d, 1H), 7.30 (s, 1H), 5.43 (s, 1H), 3.57 (s, 3H), 3.20 (m, 2H), 2.85 (m, 1H), 2.34 (s, 3H), 2.22 (s, 3H), 2.10 (s, 3H), 0.45 (m, 2H), 0.26 (m, 2H).

Example J17: Methyl 5-acetyl-2,6-dimethyl-4-(5-(4-methylpiperazine-1-carbonyl)benzo[b]thiophen-3-yl)-1,4-dihydropyridine-3-carboxylate $^1$H-NMR (400 MHz, CDCl$_3$) δ=8.22 (s, 1H), 7.82 (d, 1H), 7.36 (dd, 1H), 7.22 (d, 1H), 5.94 (s, 1H), 5.46 (s, 1H), 3.77 (d, 4H), 3.65 (s, 3H), 2.53 (m, 4H), 2.38 (s, 3H), 2.36 (s, 3H), 2.32 (s, 3H), 2.12 (s, 3H).

Example J18: Methyl 5-acetyl-2,6-dimethyl-4-(5-(morpholine-4-carbonyl)benzo[b]thiophen-3-yl)-1,4-dihydropyridine-3-carboxylate $^1$H-NMR (400 MHz, DMSO-d$_6$) δ=9.11 (s, 1H), 8.13 (s, 1H), 7.97 (d, 1H), 7.35 (d, 1H), 7.32 (s, 1H), 5.39 (s, 1H), 3.64 (m, 8H), 3.36 (s, 3H), 2.32 (s, 3H), 2.25 (s, 3H), 2.12 (s, 3H).

Example J19: Methyl 5-acetyl-2,6-dimethyl-4-(thieno[3,2-c]pyridin-3-yl)-1,4-dihydropyridine-3-carboxylate ¹H-NMR (400 MHz, DMSO-d$_6$) δ=9.27 (d, 1H), 9.13 (s, 1H), 8.36 (d, 1H), 7.97 (dd, 1H), 7.35 (s, 1H), 5.48 (s, 1H), 3.52 (s, 3H), 2.32 (s, 3H), 2.27 (s, 3H), 2.14 (s, 3H).

Example J20: Methyl 5-acetyl-2,6-dimethyl-4-(thieno[2,3-c]pyridin-3-yl)-1,4-dihydropyridine-3-carboxylate ¹H-NMR (400 MHz, DMSO-d$_6$) δ=9.15 (s, 1H), 9.12 (s, 1H), 8.46 (d, 1H), 7.97 (dd, 1H), 7.59 (s, 1H), 5.41 (s, 1H), 3.52 (s, 3H), 2.32 (s, 3H), 2.27 (s, 3H), 2.12 (s, 3H).

Example J21: Methyl 5-acetyl-2,6-dimethyl-4-(thieno[2,3-b]pyridin-3-yl)-1,4-dihydropyridine-3-carboxylate ¹H-NMR (400 MHz, DMSO-d$_6$) δ=9.10 (s, 1H), 8.50 (dd, 1H), 8.40 (dd, 1H), 7.45 (dd, 1H), 7.35 (s, 1H), 5.36 (s, 1H), 3.52 (s, 3H), 2.32 (s, 3H), 2.27 (s, 3H), 2.13 (s, 3H).

Example J22: Methyl 5-acetyl-2-cyclopropyl-4-(5-fluorobenzo[b]thiophen-3-yl)-6-methyl-1,4-dihydropyridine-3-carboxylate ¹H-NMR (400 MHz, DMSO-d$_6$) δ=0.76 (m, 1H), 0.87 (m, 2H), 1.05 (m, 1H), 2.14 (s, 3H), 2.33 (s, 3H), 2.70 (m, 1H), 3.57 (s, 3H), 5.34 (s, 1H), 7.21 (t, 1H), 7.27 (s, 1H), 7.80 (s, 1H), 7.93 (dd, 1H), 7.96 (s, 1H).
HPLC-MS: Rt 4.645 m/z 234.1 (MH$^+$).

A second reaction product was isolated by column chromatography:

Example J22-a: Dimethyl 2,6-dicyclopropyl-4-(5-fluorobenzo[b]thiophen-3-yl)-1,4-dihydropyridine-3,5-dicarboxylate ¹H-NMR (400 MHz, DMSO-d$_6$) δ=0.60 (m, 2H), 0.68 (m, 2H), 1.00 (m, 4H), 2.76 (m, 2H), 3.61 (s, 6H), 5.42 (s, 1H), 5.54 (s, 1H), 7.05 (t, 1H), 7.14 (s, 1H), 7.71 (m, 1H).
HPLC-MS: Rt 5.256; m/z 428.1 (MH$^+$).

Example J23: Methyl 5-acetyl-2-cyclopropyl-6-methyl-4-(thieno[2,3-b]pyridin-3-yl)-1,4-dihydropyridine-3-carboxylate ¹H-NMR (400 MHz, DMSO-d$_6$) δ=8.51 (dd, 1H), 8.39 (dd, 1H), 7.95 (s, 1H), 7.44 (dd, 1H), 7.27 (s, 1H), 5.38 (s, 1H), 3.56 (s, 3H), 2.71 (dd, 1H), 2.34 (s, 3H), 2.14 (s, 3H), 0.84 (t, 4H).

A second reaction product was isolated by column chromatography:

Example J23-a: Dimethyl 2,6-dicyclopropyl-4-(thieno[2,3-b]pyridin-3-yl)-1,4-dihydropyridine-3,5-dicarboxylate ¹H-NMR (400 MHz, DMSO-d$_6$) δ=0.57 (q, 2H), 0.83 (m, 2H), 0.91 (t, 2H), 1.04 (q, 2H), 2.57 (td, 2H), 3.54 (s, 6H), 5.31 (s, 1H), 7.09 (s, 1H), 7.26 (s, 1H), 7.45 (dd, 1H), 8.30 (dd, 1H), 8.52 (m, 1H).
HPLC-MS: Rt 4.848; m/z 411.0 (MH$^+$).

Example J24: Methyl 5-acetyl-4-(benzo[b]thiophen-3-yl)-2,6-dicyclopropyl-1,4-dihydropyridine-3-carboxylate ¹H-NMR (400 MHz, DMSO-d$_6$) δ=0.81 (m, 7H), 1.07 (dt, 1H), 2.14 (m, 1H), 2.28 (s, 3H), 2.74 (m, 1H), 3.57 (s, 3H), 5.49 (s, 1H), 7.14 (s, 1H), 7.31 (t, 1H), 7.36 (t, 1H), 7.90 (m, 2H), 7.98 (d, 1H).
HPLC-MS: Rt 4.670; m/z 260.1 (MH$^+$).

Example J25: Methyl 5-acetyl-4-(5-chlorobenzo[b]thiophen-3-yl)-2-cyclopropyl-6-methyl-1,4-dihydropyridine-3-carboxylate ¹H-NMR (400 MHz, DMSO-d$_6$) δ=0.84 (m, 3H), 1.05 (m, 1H), 2.15 (s, 3H), 2.34 (s, 3H), 2.70 (ddd, 1H), 3.58 (s, 3H), 5.35 (s, 1H), 7.26 (s, 1H), 7.35 (dd, 1H), 7.94 (d, 1H), 7.97 (s, 1H), 8.08 (d, 1H).
HPLC-MS: Rt 5.312; m/z 402.9 (MH$^+$).

A second reaction product was isolated by column chromatography:

Example J25-a: Dimethyl 4-(5-chlorobenzo[b]thiophen-3-yl)-2,6-dicyclopropyl-1,4-dihydropyridine-3,5-dicarboxylate ¹H-NMR (400 MHz, DMSO-d$_6$) δ=2.28 (s, 6H), 3.50 (s, 6H), 5.26 (s, 1H), 7.33 (s, 2H), 7.93 (d, 1H), 8.00 (s, 1H), 9.10 (s, 1H).
HPLC-MS: Rt 4.773; m/z 224.1 (MH$^+$).

Example J26: Methyl 5-acetyl-4-(7-bromobenzo[b]thiophen-3-yl)-2-cyclopropyl-6-methyl-1,4-dihydropyridine-3-carboxylate ¹H-NMR (400 MHz, DMSO-d$_6$) δ=0.82 (m, 3H), 1.05 (dq, 1H), 2.13 (s, 3H), 2.33 (s, 3H), 2.69 (m, 1H), 3.56 (s, 3H), 5.38 (s, 1H), 7.28 (s, 1H), 7.37 (t, 1H), 7.57 (d, 1H), 7.93 (s, 1H), 8.10 (d, 1H).
HPLC-MS: Rt 5.355; m/z 448.8 (MH$^+$).

Example J27: Methyl 5-acetyl-2-cyclopropyl-4-(7-(cyclopropylcarbamoyl)benzo[b]thiophen-3-yl)-6-methyl-1,4-dihydropyridine-3-carboxylate ¹H-NMR (400 MHz, DMSO-d$_6$) δ=0.59 (m, 2H), 0.71 (m, 2H), 0.84 (dd, 4H), 2.10 (s, 3H), 2.33 (s, 3H), 2.68 (m, 1H), 2.88 (m, 1H), 3.55 (s, 3H), 5.40 (s, 1H), 7.21 (s, 1H), 7.47 (m, 1H), 7.86 (d, 1H), 7.89 (s, 1H), 8.23 (d, 1H), 8.63 (d, 1H).
HPLC-MS: Rt 4.354; m/z 451.0 (MH$^+$).

Example J28: Methyl 5-acetyl-4-(7-cyanobenzo[b]thiophen-3-yl)-2-cyclopropyl-6-methyl-1,4-dihydropyridine-3-carboxylate ¹H-NMR (400 MHz, DMSO-d$_6$) δ=0.85 (m, 3H), 1.06 (m, 1H), 2.14 (s, 2H), 2.34 (s, 3H), 2.70 (t, 1H), 3.54 (s, 3H), 5.42 (d, 1H), 7.60 (dd, 1H), 7.38 (s, 1H), 7.91 (d, 1H), 7.98 (s, 1H), 8.42 (dd, 1H).
HPLC-MS: Rt 4.848; m/z 393.0 (MH$^+$).

Example J28-a: Dimethyl 4-(7-cyanobenzo[b]thiophen-3-yl)-2,6-dicyclopropyl-1,4-dihydropyridine-3,5-dicarboxylate ¹H-NMR (400 MHz, DMSO-d$_6$) δ=0.58 (td, 2H), 0.88 (m, 4H), 1.03 (q, 2H), 2.56 (m, 2H), 3.53 (s, 6H), 5.36 (s, 1H), 7.10 (s, 1H), 7.38 (s, 1H), 7.62 (m, 1H), 7.92 (d, 1H), 8.32 (d, 1H).
HPLC-MS: Rt 5.493; m/z 435.0 (MH$^+$).

Example J29: Methyl 5-acetyl-2-cyclopropyl-4-(7-(methoxycarbonyl) benzo[b]thiophen-3-yl)-6-methyl-1,4-dihydropyridine-3-carboxylate ¹H-NMR (400 MHz, DMSO-d₆) δ=0.76 (m, 1H), 0.87 (m, 2H), 1.06 (dt, 1H), 2.12 (s, 3H), 2.34 (s, 3H), 2.69 (m, 1H), 3.55 (s, 3H), 3.93 (s, 3H), 5.43 (s, 1H), 7.28 (s, 1H), 7.57 (t, 1H), 7.92 (s, 1H), 8.04 (d, 1H), 8.39 (d, 1H).
HPLC-MS: Rt 4.875; m/z 426.1 (MH⁺).
A second reaction product was isolated by column chromatography:

Example J29-a: Dimethyl 2,6-dicyclopropyl-4-(7-(methoxycarbonyl)benzo[b]thiophen-3-yl)-1,4-dihydropyridine-3,5-dicarboxylate ¹H-NMR (400 MHz, DMSO-d₆) δ=0.56 (td, 2H), 0.87 (m, 4H), 1.05 (td, 2H), 2.57 (m, 2H), 3.53 (s, 6H), 3.93 (s, 3H), 5.38 (s, 1H), 7.06 (s, 1H), 7.27 (s, 1H), 7.58 (t, 1H), 8.05 (d, 1H), 8.30 (d, 1H).
HPLC-MS: Rt 5.520; m/z 468.1 (MH⁺).
The ester functionality on the benzothiophene ring of methyl 5-acetyl-2-cyclopropyl-4-(7-(methoxycarbonyl)benzo[b]thiophen-3-yl)-6-methyl-1,4-dihydropyridine-3-carboxylate (Example J29) was hydrolyzed as follows:

Example J30: 3-(3-Acetyl-6-cyclopropyl-5-(methoxycarbonyl)-2-methyl-1,4-dihydropyridin-4-yl)benzo[b]thiophene-7-carboxylicacid A mixture of methyl 5-acetyl-2-cyclopropyl-4-(7-(methoxycarbonyl)benzo[b]thiophen-3-yl)-6-methyl-1,4-dihydropyridine-3-carboxylate (0.004 g, 0.094 mmol) and 1M NaOH (0.47 mL, 0.470 mmol) in 1 mL THF was stirred at 40° C. over the weekend. The reaction mixture was diluted with 0.1 M NaOH and washed with DCM. The aqueous layer was cooled to 0° C. and 4M HCl were added until a solid started to precipitate. Then 1M HCl was dropwise added until the pH reached 2-3. The precipitate was filtered off, washed with water and purified by column chromatography (DCM/MeOH) to give the title compound (0.0116 g, 30%).
¹H-NMR (400 MHz, DMSO-d₆) δ=0.83 (m, 2H), 1.06 (m, 2H), 2.12 (s, 3H), 2.34 (s, 3H), 2.69 (m, 1H), 3.56 (s, 3H), 5.43 (s, 1H), 7.24 (s, 1H), 7.54 (t, 1H), 7.91 (s, 1H), 8.01 (d, 1H), 8.34 (d, 1H), 13.46 (s, 1H).
HPLC-MS: Rt 3.039; m/z 410.0 (MH⁺).

Example J31: Benzyl 5-acetyl-2-cyclopropyl-6-methyl-4-(thieno[2,3-b]pyridin-3-yl)-1,4-dihydropyridine-3-carboxylate The title compound was obtained following Method J.
¹H-NMR (400 MHz, DMSO-d₆) δ=0.81 (m, 3H), 1.08 (m, 1H), 2.15 (s, 3H), 2.34 (s, 3H), 2.72 (dt, 1H), 5.06 (d, 2H), 5.41 (s, 1H), 7.17 (dd, 2H), 7.24 (s, 1H), 7.27 (m, 2H), 7.30 (dd, 2H), 8.00 (s, 1H), 8.31 (d, 1H), 8.47 (d, 1H).
HPLC-MS: Rt 4.976; m/z 445.1 (MH⁺).

Example J32: Pyridin-4-ylmethyl 5-acetyl-4-(benzo[b]thiophen-3-yl)-2-cyclopropyl-6-methyl-1,4-dihydropyridine-3-carboxylate ¹H-NMR (400 MHz, DMSO-d₆) δ=0.83 (m, 3H), 1.09 (m, 1H), 2.16 (s, 3H), 2.33 (s, 3H), 2.73 (m, 1H), 5.11 (q, 2H), 5.51 (s, 1H), 7.08 (d, 2H), 7.18 (s, 1H), 7.28 (m, 2H), 7.90 (d, 1H), 8.02 (d, 2H), 8.41 (d, 2H).
HPLC-MS: Rt 4.673; m/z 445.1 (MH⁺).
A second reaction product was isolated by column chromatography:

Example J32-a: bis(pyridin-4-ylmethyl) 2,6-dicyclopropyl-4-(thieno[2,3-b]pyridin-3-yl)-1,4-dihydropyridine-3,5-dicarboxylate ¹H-NMR (400 MHz, DMSO-d₆) δ=0.62 (m, 2H), 0.86 (dd, 4H) 1.06 (dt, 2H), 2.57 (m, 2H), 5.08 (m, 4H), 5.42 (s, 1H), 7.06 (d, 4H), 7.19 (dd, 1H), 7.28 (s, 1H), 7.33 (s, 1H), 8.15 (dd, 1H), 8.40 (d, 4H), 8.46 (dd, 1H).
HPLC-MS: Rt 4.445; m/z 565.2 (MH⁺).

Example J33: Pyridin-4-ylmethyl 5-acetyl-4-(7-bromobenzo[b]thiophen-3-yl)-2,6-dimethyl-1,4-dihydropyridine-3-carboxylate ¹H-NMR (400 MHz, DMSO-d₆) δ=2.15 (s, 3H), 2.31 (d, 6H), 5.06 (dd, 2H), 5.43 (s, 1H), 7.00 (d, 2H), 7.24 (t, 1H), 7.39 (s, 1H), 7.53 (d, 1H), 8.08 (d, 1H), 8.38 (d, 2H), 9.18 (s, 1H).
HPLC-MS: Rt 4.799; m/z 497.0 (MH⁺).

Example J34: Pyridin-4-ylmethyl 5-acetyl-4-(5-chlorobenzo[b]thiophen-3-yl)-2-cyclopropyl-6-methyl-1,4-dihydropyridine-3-carboxylate ¹H-NMR (400 MHz, DMSO-d₆) δ=0.86 (m, 3H), 1.09 (dd, 1H), 2.18 (s, 3H), 2.34 (s, 3H), 2.75 (ddd, 1H), 5.11 (d, 2H), 5.44 (s, 1H), 7.05 (d, 2H), 7.30 (s, 1H) 7.32 (dd, 1H), 7.94 (d, 1H), 8.07 (s, 1H), 8.10 (d, 1H), 8.40 (d, 2H).
HPLC-MS: Rt 5.002; m/z 479.0 (MH⁺).

Example J35: Pyridin-4-ylmethyl 5-acetyl-4-(7-cyanobenzo[b]thiophen-3-yl)-2-cyclopropyl-6-methyl-1,4-dihydropyridine-3-carboxylate ¹H-NMR (400 MHz, DMSO-d₆) δ=0.86 (m, 3H), 1.10 (m, 1H), 2.18 (s, 3H), 2.35 (s, 3H), 2.75 (t, 1H), 5.08 (dd, 2H), 5.50 (s, 1H), 7.03 (d, 2H), 7.42 (s, 1H), 7.46 (t, 1H), 7.87 (d, 1H), 8.08 (s, 1H), 8.39 (dd, 3H).
HPLC-MS: Rt 4.603; m/z 470.1 (MH⁺).

Example J36: Pyridin-4-ylmethyl 5-acetyl-2-cyclopropyl-6-methyl-4-(thieno[2,3-b]pyridin-3-yl)-1,4-dihydropyridine-3-carboxylate ¹H-NMR (400 MHz, DMSO-d₆) δ=0.85 (dt, 3H), 1.10 (m, 1H), 2.18 (s, 2H), 2.34 (s, 2H), 2.75 (dd, 1H), 5.10 (dd, 2H), 5.45 (s, 1H), 7.06 (d, 2H), 7.32 (m, 2H), 8.06 (s, 1H), 8.36 (d, 1H), 8.40 (d, 2H), 8.48 (d, 1H).
HPLC-MS: Rt 3.943; m/z 446.1 (MH⁺).

Example J37: Benzyl 5-acetyl-2-cyclopropyl-4-(7-(methoxycarbonyl)benzo[b]thiophen-3-yl)-6-methyl-1,4-dihydropyridine-3-carboxylate ¹H-NMR (400 MHz, DMSO-d₆) δ=0.80 (dd, 3H), 1.08 (d, 1H), 2.13 (s, 3H), 2.34 (s, 3H), 2.71 (t, 1H), 3.93 (s, 3H), 5.05 (s, 2H), 5.47 (s, 1H), 7.18 (d, 2H), 7.26 (s, 4H), 7.42 (t, 1H), 8.00 (m, 2H), 8.32 (d, 1H).
HPLC-MS: Rt 5.546; m/z 502.2 (MH⁺).

A second reaction product was isolated by column chromatography:

Example J37-a: Dibenzyl 2,6-dicyclopropyl-4-(7-(methoxycarbonyl)benzo[b]thiophen-3-yl)-1,4-dihydropyridine-3,5-dicarboxylate ¹H-NMR (400 MHz, DMSO-d₆) δ=0.55 (dd, 2H), 0.82 (dd, 4H), 1.05 (m, 2H), 2.57 (m, 2H), 3.93 (s, 3H), 5.01 (q, 4H), 5.44 (s, 1H), 7.15 (d, 4H), 7.26 (m, 8H), 7.99 (d, 1H), 8.12 (d, 1H).
HPLC-MS: Rt 6.574; m/z 621.3 (MH⁺).

Example J38: Benzyl 5-acetyl-4-(7-(methoxycarbonyl)benzo[b]thiophen-3-yl)-2,6-dimethyl-1,4-dihydropyridine-3-carboxylate ¹H-NMR (400 MHz, DMSO-d₆) δ=2.11 (s, 3H), 2.28 (s, 3H), 2.32 (s, 3H), 3.92 (s, 3H), 5.00 (s, 2H), 5.44 (s, 1H), 7.14 (d, 2H), 7.24 (d, 3H), 7.33 (s, 1H), 7.41 (dd, 1H), 8.00 (d, 1H), 8.33 (d, 1H), 9.12 (s, 1H).
HPLC-MS: Rt 5.546; m/z 502.2 (MH⁺).

Example J39: Methyl 3-(3,5-diacetyl-2,6-dimethyl-1,4-dihydropyridin-4-yl)benzo[b]thiophene-7-carboxylate ¹H-NMR (400 MHz, DMSO-d₆) δ=2.16 (s, 6H), 2.31 (s, 6H), 3.92 (s, 3H), 5.52 (s, 1H), 7.34 (s, 1H), 7.55 (t, 1H), 8.03 (d, 1H), 8.50 (d, 1H), 9.13 (s, 1H).
HPLC-MS: Rt 4.224; m/z 384.1 (MH⁺).

Example J40: 3-(3,5-diacetyl-2,6-dimethyl-1,4-dihydropyridin-4-yl)benzo[b]thiophene-7-carbonitrile ¹H-NMR (400 MHz, DMSO-d₆) δ=2.17 (s, 5H), 2.32 (s, 5H), 5.52 (s, 1H), 7.43 (s, 1H), 7.59 (m, 1H), 7.90 (d, 1H), 8.54 (d, 1H), 9.19 (s, 1H).
HPLC-MS: Rt 4.212; m/z 351.1 (MH⁺).

Example J41: Pyridin-4-ylmethyl 5-acetyl-4-(7-bromobenzo[b]thiophen-3-yl)-2-cyclopropyl-6-methyl-1,4-dihydropyridine-3-carboxylate ¹H-NMR (400 MHz, DMSO-d₆) δ=0.85 (m, 3H) 1.09 (t, 1H), 2.16 (s, 3H), 2.34 (s, 3H), 2.73 (m, 1H), 5.10 (d, 2H), 5.45 (s, 1H), 7.05 (d, 2H), 7.24 (m, 1H), 7.31 (s, 1H), 7.54 (d, 1H), 8.06 (m, 2H), 8.40 (d, 2H).
HPLC-MS: Rt 5.143; m/z 523.1 (MH⁺).

Example J42: 4-fluorobenzyl 5-acetyl-2-cyclopropyl-6-methyl-4-(thieno[2,3-b]pyridin-3-yl)-1,4-dihydropyridine-3-carboxylate ¹H-NMR (400 MHz, DMSO-d₆) δ=0.80 (m, 8H), 1.05 (d, 3H), 2.15 (s, 7H), 2.33 (s, 8H), 5.04 (q, 5H), 5.39 (d, 2H), 7.08 (t, 4H), 7.24 (m, 7H), 7.30 (dd, 3H), 7.99 (s, 2H), 8.29 (dd, 2H), 8.48 (dd, 2H).
HPLC-MS: Rt 5.056; m/z 463.1 (MH⁺).

A second reaction product was isolated by column chromatography:

Example J42-a: bis(4-fluorobenzyl) 2,6-dicyclopropyl-4-(thieno[2,3-b]pyridin-3-yl)-1,4-dihydropyridine-3,5-dicarboxylate ¹H-NMR (400 MHz, DMSO-d₆) δ=0.57 (dd, 2H), 0.82 (m, 6H), 1.02 (d, 2H), 5.01 (d, 4H), 5.34 (d, 1H), 7.19 (m, 8H), 8.05 (dd, 2H), 8.46 (m, 2H).
HPLC-MS: Rt 6.223; m/z 599.2 (MH⁺).

Example J43: 4-cyanobenzyl 5-acetyl-2-cyclopropyl-6-methyl-4-(thieno[2,3-b]pyridin-3-yl)-1,4-dihydropyridine-3-carboxylate ¹H-NMR (400 MHz, DMSO-d₆) δ=0.83 (m, 3H), 1.09 (m, 1H), 2.16 (s, 3H), 2.34 (s, 3H), 2.73 (m, 1H), 5.14 (dd, 2H), 5.41 (s, 1H), 7.31 (m, 4H), 7.70 (d, 2H), 8.03 (s, 1H), 8.32 (d, 1H), 8.47 (d, 1H).
HPLC-MS: Rt 4.766; m/z 470.1 (MH⁺).

Method K

Example K1: Methyl 5-acetyl-2-amino-4-(benzo[b]thiophen-3-yl)-6-methyl-1,4-dihydropyridine-3-carboxylate hydrochloride

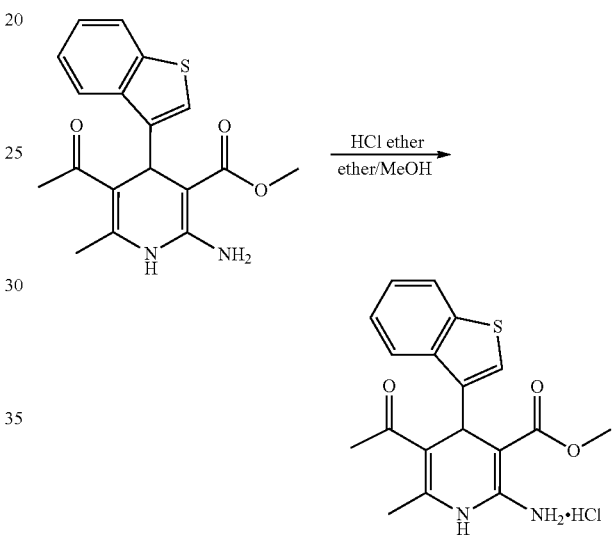

To a mixture of methyl 5-acetyl-2-amino-4-(benzo[b]thiophen-3-yl)-6-methyl-1,4-dihydropyridine-3-carboxylate (0.07 g, 0.20 mmol) in DCM/MeOH (1:1, 2 mL), 2M HCl in ether (0.21 mL, 0.40 mmol) was added dropwise at 0° C. The mixture was allowed to warm up to RT and stirred at RT overnight. The solvent was removed under reduced pressure, and the remaining solid was washed with ether and dichloromethane affording a white solid (0.055 g, 71%). Anal. calculated $C_{18}H_{19}ClN_2O_3S$ (378.08): C, 57.06; H, 5.06; N, 7.39; S, 8.46. Found: C, 56.14; H, 5.25; N, 7.05; S, 8.22.

¹H-NMR (300 MHz, DMSO-d₆) δ=12.36 (s, 1H), 10.27 (s, 1H), 9.60 (s, 1H), 8.06 (d, J=8.0 Hz, 1H), 7.90 (d, J=8.0 Hz, 1H), 7.63-7.40 (m, 2H), 7.40-7.14 (m, 1H), 4.98 (s, 1H), 4.34 (s, 1H), 3.81 (s, 3H), 2.44 (s, 3H), 2.17 (s, 3H).

Example K2: Methyl 5-acetyl-2-amino-4-(benzo[b]thiophen-3-yl)-6-methyl-1,4-dihydropyridine-3-carboxylate trifluoromethanesulfonate Method K yielded the title compound as a white solid (0.091 g, 89%). Anal. calculated $C_{19}H_{19}F_3N_2O_6S_2$ (492.06): C, 46.34; H, 3.89; N, 5.69; S, 13.02. Found: C, 46.28; H, 4.21; N, 5.53; S, 13.15.

¹H-NMR (300 MHz, DMSO-d₆) δ=11.67 (s, 1H), 10.04 (s, 1H), 9.34 (s, 1H), 8.06 (d, J=8.0 Hz, 1H), 7.92 (d, J=7.9

Hz, 1H), 7.65-7.46 (m, 2H), 7.41-7.17 (m, 1H), 4.99 (s, 1H), 4.24 (s, 1H), 3.81 (s, 3H), 2.42 (s, 3H), 2.17 (s, 3H).

Method L

Example L1: 4-(pyridin-4-yl)benzyl 5-acetyl-2,6-dimethyl-4-(thieno[2,3-b]pyridin-3-yl)-1,4 dihydropyridine-3-carboxylate

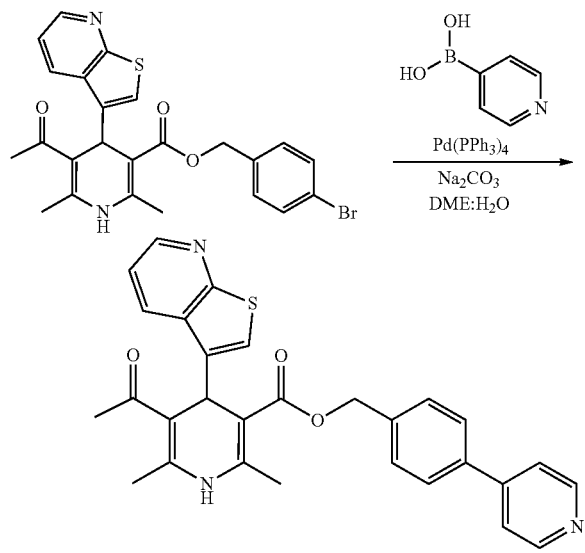

A mixture of 4-bromobenzyl 5-acetyl-2,6-dimethyl-4-(thieno[2,3-b]pyridin-3-yl)-1,4-dihydropyridine-3-carboxylate (0.030 g, 0.06 mmol), pyridin-4-ylboronic acid (0.011 g, 0.09 mmol), Palladium-tetrakis(triphenylphosphine) (0.003 g, 0.003 mmol) and potassium carbonate (0.019 g, 0.18 mmol) in DME:H$_2$O (3:1, 1 mL) was heated at 110° C. for 3 h. The mixture was allowed to cool to RT, filtered over Celite and the solvent was removed under reduced pressure. The residue was purified by column chromatography (dichloromethane: methanol 2%) affording a yellow solid (0.036 g, 61%).

$^1$H-NMR (300 MHz, CDCl$_3$) δ=8.67 (s, 2H), 8.45 (dd, J=4.5, 1.6 Hz, 1H), 8.32 (dd, J=8.2, 1.6 Hz, 1H), 7.54-7.47 (m, 4H), 7.25-7.17 (m, 3H), 7.13 (dd, J=8.2, 4.6 Hz, 1H), 6.48 (bs, 1H), 5.48 (s, 1H), 5.09 (q, J=15.0 Hz, 2H), 2.36 (s, 6H), 2.16 (s, 3H).

HRMS (IE) m/z calculated C$_{29}$H$_{25}$N$_3$O$_3$S [M$^+$]: 495.1617, found: 495.1636.

The following Examples were prepared following Method L.

Example L2: 4-(pyridin-3-yl)benzyl 5-acetyl-2,6-dimethyl-4-(thieno[2,3-b]pyridin-3-yl)-1,4-dihydropyridine-3-carboxylate Yellow solid (0.025 g, 51%).

$^1$H-NMR (300 MHz, CDCl$_3$) δ=8.83 (s, 1H), 8.65-8.54 (m, 1H), 8.45 (dd, J=4.6, 1.6 Hz, 1H), 8.33 (dd, J=8.2, 1.6 Hz, 1H), 7.87 (dt, J=8.0, 1.8 Hz, 1H), 7.50-7.43 (m, 2H), 7.38 (dd, J=7.9, 4.8 Hz, 1H), 7.26-7.20 (m, 2H), 7.18 (s, 1H), 7.15 (dd, J=8.2, 4.6 Hz, 1H), 6.61 (s, 1H), 5.48 (s, 1H), 5.12 (q, J=15.0 Hz, 2H), 2.36 (s, 3H), 2.36 (s, 3H), 2.16 (s, 3H).

HRMS (IE) m/z calculated C$_{29}$H$_{25}$N$_3$O$_3$S [M$^+$]: 495.1617, found: 495.1619.

Example L3: 3-(pyridin-4-yl)benzyl 5-acetyl-2,6-dimethyl-4-(thieno[2,3-b]pyridin-3-yl)-1,4-dihydropyridine-3-carboxylate Yellow solid (0.037 g, 78%).

$^1$H-NMR (300 MHz, CDCl$_3$) δ=8.65 (d, J=4.8 Hz, 2H), 8.42 (dd, J=4.8, 1.6 Hz, 1H), 8.31 (dd, J=8.2, 1.6 Hz, 1H), 7.55 (dt, J=7.7, 1.5 Hz, 1H), 7.46-7.33 (m, 4H), 7.22 (dt, J=7.7, 1.5 Hz, 1H), 7.17 (s, 1H), 7.14-7.05 (m, 1H), 6.76 (s, 1H), 5.48 (s, 1H), 5.23-5.04 (m, 2H), 2.36 (s, 3H), 2.35 (s, 3H), 2.15 (s, 3H).

HRMS (IE) m/z calculated C$_{29}$H$_{25}$N$_3$O$_3$S [M$^+$]: 495.1566, found: 495.1541.

Example L4: 3-(pyridin-3-yl)benzyl 5-acetyl-2,6-dimethyl-4-(thieno[2,3-b]pyridin-3-yl)-1,4-dihydropyridine-3-carboxylate Yellow solid, 0.26 g, 62%).

$^1$H-NMR (300 MHz, CDCl$_3$) δ=8.77 (s, 1H), 8.60 (d, J=4.9 Hz, 1H), 8.42 (dd, J=4.9, 1.6 Hz, 1H), 8.31 (dd, J=8.2, 1.6 Hz, 1H), 7.77 (dt, J=7.9, 1.9 Hz, 1H), 7.49 (dt, J=7.7, 1.5 Hz, 1H), 7.43-7.32 (m, 3H), 7.20 (dt, J=7.5, 1.5 Hz, 1H), 7.17 (s, 1H), 7.10 (dd, J=8.2, 4.5 Hz, 1H), 6.62 (s, 1H), 5.47 (s, 1H), 5.15 (q, J=12.5 Hz, 2H), 2.36 (s, 3H), 2.35 (s, 3H), 2.14 (s, 3H).

HRMS (IE) m/z calculated C$_{29}$H$_{25}$N$_3$O$_3$S [M$^+$]: 495.1566, found: 495.1565.

Example L5: 2-(pyridin-4-yl)benzyl 5-acetyl-2,6-dimethyl-4-(thieno[2,3-b]pyridin-3-yl)-1,4-dihydropyridine-3-carboxylate Yellow solid (0.023 g, 45%).

$^1$H-NMR (300 MHz, CDCl$_3$) δ=8.75 (s, 1H), 8.52 (s, 1H), 8.41 (dd, J=4.6, 1.6 Hz, 1H), 8.13 (dd, J=8.2, 1.6 Hz, 1H), 7.54 (d, J=5.3 Hz, 1H), 7.48-7.31 (m, 2H), 7.19 (dd, J=7.3, 1.6 Hz, 1H), 7.13 (s, 1H), 7.08-6.94 (m, 3H), 6.37 (s, 1H), 5.36 (s, 1H), 4.97 (q, J=7.3 Hz, 2H), 2.35 (s, 3H), 2.29 (s, 3H), 2.15 (s, 3H).

HRMS (IE) m/z calculated C$_{29}$H$_{26}$N$_3$O$_3$S [M$^+$]: 496.1689, found: 496.1689.

Example L6: 2-(pyridin-3-yl)benzyl 5-acetyl-2,6-dimethyl-4-(thieno[2,3-b]pyridin-3-yl)-1,4-dihydropyridine-3-carboxylate Yellow solid (0.018 g, 48%).

$^1$H-NMR (300 MHz, CDCl$_3$) δ=8.53 (s, 1H), 8.42 (dd, J=4.7, 1.6 Hz, 2H), 8.16 (dd, J=8.2, 1.6 Hz, 1H), 7.45-7.27 (m, 4H), 7.25-7.16 (m, 2H), 7.14 (s, 1H), 7.09-6.94 (m, 1H), 6.42 (s, 1H), 5.38 (s, 1H), 4.97 (q, J=12 Hz, 2H), 2.35 (s, 3H), 2.28 (s, 3H), 2.15 (s, 3H).

HRMS (IE) m/z calculated C$_{29}$H$_{26}$N$_3$O$_3$S [M$^+$]: 496.1689, found: 496.1687.

Example L7: [3,4'-bipyridin]-5-ylmethyl 5-acetyl-2,6-dimethyl-4-(thieno[2,3-b]pyridin-3-yl)-1,4-dihydropyridine-3-carboxylate Yellow solid (0.025 g, 64%).

$^1$H-NMR (300 MHz, CDCl$_3$) δ=8.81-8.68 (m, 3H), 8.58-8.52 (m, 1H), 8.42 (dd, J=4.6, 1.6 Hz, 1H), 8.32 (dd, J=8.2, 1.6 Hz, 1H), 7.60 (t, J=2.2 Hz, 1H), 7.37 (d, J=5.2 Hz, 2H), 7.17 (s, 1H), 7.14 (dd, J=8.2, 4.6 Hz, 1H), 6.38 (s, 1H), 5.46 (s, 1H), 5.17 (q, J=12 Hz, 2H), 2.36 (s, 6H), 2.16 (s, 3H).

HRMS (IE) m/z calculated $C_{28}H_{24}N_4O_3S$ [M$^+$]: 496.1569, found: 496.1556.

Example L8: [3,3'-bipyridin]-5-ylmethyl 5-acetyl-2,6-dimethyl-4-(thieno[2,3-b]pyridin-3-yl)-1,4-dihydropyridine-3-carboxylate Yellow solid (0.022 g, 57%).

$^1$H-NMR (300 MHz, CDCl$_3$) δ=8.77-8.62 (m, 3H), 8.55-8.50 (m, 1H), 8.41 (dd, J=4.6, 1.6 Hz, 1H), 8.33 (dd, J=8.2, 1.6 Hz, 1H), 7.73 (dt, J=8.1, 1.8 Hz, 1H), 7.56 (t, J=2.1 Hz, 1H), 7.43 (dd, J=8.0, 4.8 Hz, 1H), 7.17 (s, 1H), 7.14 (dd, J=8.2, 4.6 Hz, 1H), 6.54 (s, 1H), 5.45 (s, 1H), 5.26-5.04 (m, 2H), 2.36 (s, 6H), 2.15 (s, 3H).

HRMS (IE) m/z calculated $C_2H_{24}N_4O_3S$ [M$^+$]: 496.1569, found: 496.1580.

Example L9: [2,4'-bipyridin]-5-ylmethyl 5-acetyl-2,6-dimethyl-4-(thieno[2,3-b]pyridin-3-yl)-1,4-dihydropyridine-3-carboxylate Yellow solid (0.014 g, 23%).

$^1$H-NMR (300 MHz, CDCl$_3$) δ=8.73 (d, J=5.1 Hz, 2H), 8.59 (d, J=2.2 Hz, 1H), 8.44 (dd, J=4.6, 1.6 Hz, 1H), 8.31 (dd, J=8.2, 1.6 Hz, 1H), 7.92-7.86 (m, 2H), 7.61 (d, J=8.1 Hz, 1H), 7.40 (dd, J=8.1, 2.2 Hz, 1H), 7.18 (s, 1H), 7.14 (dd, J=8.2, 4.6 Hz, 1H), 6.38 (s, 1H), 5.45 (s, 1H), 5.26-5.01 (q, J=15 Hz, 2H), 2.36 (s, 6H), 2.16 (s, 3H).

HRMS (IE) m/z calculated $C_{28}H_{24}N_4O_3S$ [M$^+$]: 496.1569, found: 496.1563.

Example L10: [2,3'-bipyridin]-5-ylmethyl 5-acetyl-2,6-dimethyl-4-(thieno[2,3-b]pyridin-3-yl)-1,4-dihydropyridine-3-carboxylate Yellow solid (0.032 g, 72%).

$^1$H-NMR (300 MHz, CDCl$_3$) δ=9.19 (s, 1H), 8.78-8.63 (m, 1H), 8.59 (d, J=2.3 Hz, 1H), 8.45 (dd, J=4.6, 1.6 Hz, 1H), 8.31 (dt, J=8.0, 1.6 Hz, 2H), 7.59 (dd, J=8.0, 0.9 Hz, 1H), 7.47-7.36 (m, 2H), 7.18 (s, 1H), 7.17-7.11 (m, 1H), 6.31 (s, 1H), 5.45 (s, 1H), 5.22-5.04 (q, J=12 Hz, 2H), 2.36 (s, 6H), 2.15 (s, 3H).

HRMS (IE) m/z calculated $C_{28}H_{24}N_4O_3S$ [M$^+$]: 496.1569, found: 496.1563.

Example L11: [2,3'-bipyridin]-4-ylmethyl 5-acetyl-2,6-dimethyl-4-(thieno[2,3-b]pyridin-3-yl)-1,4-dihydropyridine-3-carboxylate Yellow solid (0.040 g, 82%).

$^1$H-NMR (300 MHz, CDCl$_3$) δ=9.11-9.01 (m, 1H), 8.64 (dd, J=5.0, 1.5 Hz, 1H), 8.56 (dd, J=5.0, 0.9 Hz, 1H), 8.43 (dt, J=4.6, 1.2 Hz, 1H), 8.36 (dt, J=8.2, 1.2 Hz, 1H), 8.16 (dq, J=8.0, 1.5, 1.0 Hz, 1H), 7.46-7.37 (m, 2H), 7.21 (s, 1H), 7.15 (ddd, J=8.2, 4.6, 0.9 Hz, 1H), 6.96 (dt, J=5.1, 1.2 Hz, 1H), 6.76 (s, 1H), 5.51 (s, 1H), 5.27-5.03 (q, J=15 Hz, 2H), 2.38 (d, J=0.9 Hz, 3H), 2.37-2.35 (m, 3H), 2.17 (d, J=1.0 Hz, 3H).

HRMS (IE) m/z calculated $C_{28}H_{24}N_4O_3S$ [M$^+$]: 496.1569, found: 496.1570.

Example L12: [2,4'-bipyridin]-4-ylmethyl 5-acetyl-2,6-dimethyl-4-(thieno[2,3-b]pyridin-3-yl)-1,4-dihydropyridine-3-carboxylate Yellow solid (0.024 g, 50%).

$^1$H-NMR (300 MHz, CDCl$_3$) δ=8.78-8.62 (m, 2H), 8.57 (d, J=5.0 Hz, 1H), 8.44 (dd, J=4.6, 1.6 Hz, 1H), 8.36 (dd, J=8.2, 1.6 Hz, 1H), 7.84-7.66 (m, 2H), 7.45 (s, 1H), 7.21 (s, 1H), 7.15 (dd, J=8.2, 4.6 Hz, 1H), 7.00 (dd, J=5.0, 1.5 Hz, 1H), 6.60 (s, 1H), 5.52 (s, 1H), 5.12 (q, J=12 Hz, 2H), 2.39 (s, 3H), 2.37 (s, 3H), 2.19 (s, 3H).

HRMS (IE) m/z calculated $C_{28}H_{24}N_4O_3S$ [M$^+$]: 496.1569, found: 496.1545.

Example L13: Methyl 5-acetyl-2-cyclopropyl-6-methyl-4-(7-(pyridin-4-yl)benzo[b]thiophen-3-yl)-1,4-dihydropyridine-3-carboxylate Method L in dioxane/water 3:1 gave the title compound as a yellow solid (0.018 g, 64%).

$^1$H-NMR (300 MHz, CDCl$_3$) δ=8.72 (bs, 2H), 8.21 (dd, J=8.2, 1.1 Hz, 1H), 7.69-7.59 (m, 2H), 7.53 (t, J=7.7 Hz, 1H), 7.42-7.35 (m, 1H), 7.15 (s, 1H), 5.72 (bs, 1H), 5.52 (s, 1H), 3.69 (s, 3H), 2.61 (tt, J=8.6, 5.7 Hz, 1H), 2.37 (s, 3H), 2.16 (s, 3H), 0.98 (dtq, J=17.6, 8.6, 4.1 Hz, 2H), 0.79-0.56 (m, 2H).

HRMS (IE) m/z calculated $C_{26}H_{24}N_2O_3S$ [M$^+$]: 444.1508, found: 444.1526.

Example L14: Methyl 5-acetyl-2-cyclopropyl-4-(7-cyclopropylbenzo[b]thiophen-3-yl)-6-methyl-1,4-dihydropyridine-3-carboxylate Method L in toluene/water 19:1 gave the title compound as a yellow solid (0.030 g, 66%).

$^1$H-NMR (300 MHz, CDCl$_3$) δ=7.92 (d, J=8.1 Hz, 1H), 7.32 (t, J=7.7 Hz, 1H), 7.11 (s, 1H), 6.96 (d, J=7.7 Hz, 1H), 5.63 (bs, 1H), 5.47 (s, 1H), 3.67 (d, J=1.4 Hz, 3H), 2.59 (tt, J=8.6, 5.7 Hz, 1H), 2.36 (s, 3H), 2.13 (s, 3H), 2.11-2.03 (m, 1H), 1.07-0.86 (m, 4H), 0.85-0.75 (m, 2H), 0.73-0.57 (m, 2H).

HRMS (IE) m/z calculated $C_{24}H_{25}NO_3S$ [M$^+$]: 407.1555, found: 407.1551.

Example L15: 3-(pyridin-4-yl)benzyl 5-acetyl-2-cyclopropyl-6-methyl-4-(thieno[2,3-b]pyridin-3-yl)-1,4-dihydropyridine-3-carboxylate Method L gave the title compound as a yellow solid (0.018 g, 42%).

$^1$H-NMR (300 MHz, CDCl$_3$) δ (ppm): 8.66 (d, J=4.7 Hz, 2H), 8.44 (dd, J=4.7, 1.4 Hz, 1H), 8.29 (dd, J=8.2, 1.4 Hz, 1H), 7.56 (d, J=7.8 Hz, 1H), 7.46 (s, 1H), 7.44-7.35 (m, 3H), 7.23 (d, J=1.4 Hz, 1H), 7.14-7.06 (m, 2H), 5.79 (bs, 1H), 5.49 (s, 1H), 5.24-5.10 (m, 2H), 2.71-2.55 (m, 1H), 2.35 (s, 3H), 2.14 (s, 3H), 1.01-0.84 (m, 2H), 0.80-0.55 (m, 2H).

HRMS (IE) m/z calculated $C_{31}H_{27}N_3O_3S$ [M$^+$]: 521.1773, found: 521.1783.

HPLC (95.0%): Rt 31.35 min

Method M

Example M1: 1,1'-(2,6-dimethyl-4-(5-(pyridin-3-yl)benzo[b]thiophen-3-yl)-1,4-dihydro-pyridine-3,5-diyl)diethanone

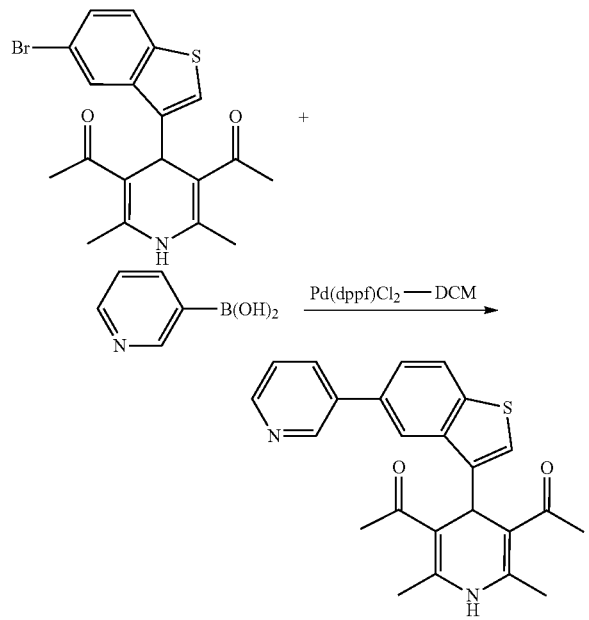

To a mixture of 1,1'-(4-(5-bromobenzo[b]thiophen-3-yl)-2,6-dimethyl-1,4-dihydropyridine-3,5-diyl)diethanone (53 mg, 0.13 mmol), 3-pyridylboronic acid (24.8 mg, 0.20 mmol) and [1,1'-bis(diphenylphosphino)ferrocene]dichloropalladium(II) complex with dichloromethane (4.6 mg, 0.0056 mmol) in dry DCM (3 mL) under nitrogen atmosphere at RT, aq 2M $Cs_2CO_3$ (0.40 mmol) was added dropwise. The mixture was then refluxed for 24 h under a $N_2$ stream, cooled to RT, filtered to remove the catalyst and concentrated in vacuum. Column chromatography afforded the title compound.

$^1$H-NMR (400 MHz, DMSO-$d_6$) δ=2.20 (s, 6H), 2.32 (s, 6H), 5.60 (s, 1H), 7.30 (s, 1H), 7.56 (dd, 1H), 7.68 (dd, 1H), 8.02 (d, 1H), 8.13 (dd, 1H), 8.52 (d, 1H), 8.61 (s, 1H), 8.97 (s, 1H), 9.17 (s, 1H).

HPLC-MS: Rt 3.645 min, m/z 403.1 (MH$^+$).

Method N

Example N1: Methyl 5-acetyl-2-cyclopropyl-6-methyl-4-(7-phenylbenzo[b]thiophen-3-yl)-1,4-dihydropyridine-3-carboxylate

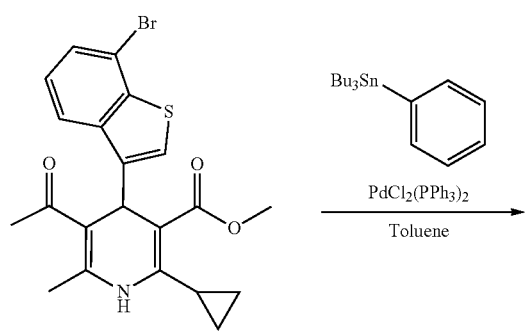

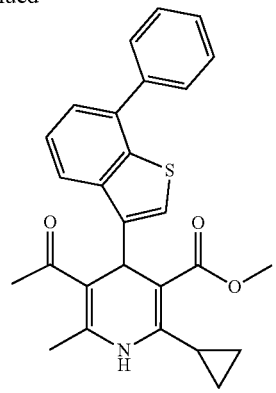

A mixture of methyl 5-acetyl-4-(7-bromobenzo[b]thiophen-3-yl)-2-cyclopropyl-6-methyl-1,4-dihydropyridine-3-carboxylate (0.050 g, 0.11 mmol), tributyl(phenyl) stannane (0.073 mL, 0.22 mmol) and palladium(II)bis(triphenylphosphine)dichloride (0.008 g, 0.011 mmol) in toluene (2 mL) was heated at 90° C. for 12 h. The mixture was allowed to cool to RT, filtered over Celite, concentrated and purified by column chromatography (5:1 hexane:ethyl acetate) affording a yellow solid (0.025 g, 50%).

$^1$H-NMR (300 MHz, CDCl$_3$) δ=8.15-8.06 (m, 1H), 7.72-7.64 (m, 2H), 7.53-7.29 (m, 5H), 7.12 (s, 1H), 5.62 (s, 1H), 5.51 (s, 1H), 3.70 (s, 3H), 2.61 (tt, J=8.7, 5.7 Hz, 1H), 2.37 (s, 3H), 2.17 (s, 3H), 1.03-0.84 (m, 2H), 0.74-0.57 (m, 2H).

HRMS (IE) m/z calculated $C_{27}H_{25}NO_3S$ [M$^+$]: 443.1555, found: 443.1557.

ABBREVIATIONS

The following abbreviations have been used along the present specification:
ACN: Acetonitrile
Ac: Acetyl
Dba: dibenzylideneacetone
DCM: Dichloromethane
DIBAL: Diisobutylaluminium hydride
DIPEA: N,N-Diisopropylethylamine
DMAP: 4-Dimethylaminopyridine
DME: 1,2-Dimethoxyethane
DMEM: Dulbecco's Modified Eagle's Medium
DMF: Dimethylformamide
DMSO: Dimethylsulfoxide
dppf: 1,1'-bis(diphenylphosphino)ferrocene
EDTA: Ethylenediaminetetraacetic acid
ESI: Electrosprayionization
EtOH: Ethanol
FBS: Fetal bovine serum
HBSS: Hank's Balanced Solution
HOBT: Benzotriazol-1-ol
HPLC: High performance liquid chromatography
HRMS: High ressolution mass spectrometry
IE: Electronionization
i-PrOH: Isopropanol
MeOH: Methanol
MS4 Å: 4 Å Molecular sieves
MW: molecular weight
NMP: N-methylpyrrolidone
NMR: Nuclear magnetic resonance
PEI: Polyethyleneimine
Ph: Phenyl
PPA: Polyphosphoric acid RT: Room temperature
Rt: Retention time
tBut: ter-butyl
TES: N-[tris(hydroxymethyl)methyl]-2-aminoethanesulfonic acid
TFA: Trifluoroacetic acid
THF: Tetrahydrofurane The following are particular embodiments of the present invention:

Embodiment 1

A compound of formula (I):

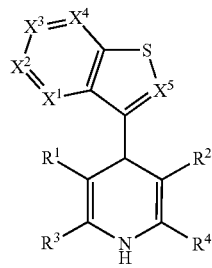

wherein:
R$^1$ is a group selected from:
  a) —COR$^5$,
  b) —COOR$^5$,
  c) —CN,
  d) —CHO
R$^5$ is a group selected from:
  a) linear or branched C$_1$-C$_6$ alkyl optionally substituted by 1, 2 or 3 substituents selected from —N(R$^6$)R$^7$ and —OR$^6$,
  b) C$_3$-C$_6$ cycloalkyl,
R$^2$ is a group selected from:
  a) —COOR$^8$,
  b) —COR$^8$,
  c) —C(O)N(R$^8$)R$^9$,
  d) —CN,
  e) —S(O)$_n$R$^8$, wherein n is an integer from 1 to 2,
R$^8$ and R$^9$ are independently selected from:
  a) linear or branched C$_1$-C$_6$ alkyl optionally substituted by 1, 2 or 3 substituents selected from A$^1$ or B$^2$,
  b) A$^1$ group,
  c) hydrogen atom,
  or
R$^8$ and R$^9$ together with the nitrogen atom to which they are attached form a 5-6 membered heterocycle which optionally comprises 1 heteroatom selected from O and N, and said heterocycle being optionally substituted by 1 or 2 groups independently selected from linear or branched C$_1$-C$_4$ alkyl
R$^3$ is a group selected from:
  a) linear or branched C$_1$-C$_6$ alkyl optionally substituted by 1, 2 or 3 substituents selected from halogen atom, —N(R$^6$)R$^7$, and —OR$^6$,
  b) C$_3$-C$_6$ cycloalkyl optionally substituted by halogen atom,
  c) hydrogen atom,
  d) —NH$_2$,
  e) —CN,
R$^4$ is a group selected from:
  a) A$^1$ group,
  b) linear or branched C$_1$-C$_6$ alkyl optionally substituted by 1, 2 or 3 substituents selected from A$^1$ or B$^2$,
  c) —N(R$^6$)R$^7$,
  d) —CN,
  f) hydrogen atom,
R$^1$ and R$^3$ form together a group —(CR$^{10}$R$^{11}$)$_n$— wherein n is an integer from 3 to 4 wherein 1, 2 or 3 of the —CR$^{10}$R$^{11}$— moieties may be independently replaced by a group selected from —O—, —NR$^{12}$—, —S— and —C(=O)— and wherein R$^{10}$, R$^{11}$ and R$^{12}$ are independently selected from hydrogen, R$^6$, —C(=O)R$^6$, phenyl or 5 to 6 membered heteroaryl group, said phenyl or heteroaryl group being optionally substituted by —R$^6$ or halogen atom;
R$^2$ and R$^4$ form together a group —(CR$^{10}$R$^{11}$)$_n$— wherein n is an integer from 3 to 4 wherein 1, 2 or 3 of the —CR$^{10}$R$^{11}$— moieties may be independently replaced by a group selected from —O—, —NR$^{12}$—, —S— and —C(=O) and wherein R$^{10}$, R and R$^{12}$ are independently selected from hydrogen, —R$^6$, —C(=O)R$^6$, phenyl or 5 to 6 membered heteroaryl group, said phenyl or heteroaryl group being optionally substituted by —R$^6$ or halogen atom;
X$^1$, X$^2$, X$^3$, X$^4$, and X$^5$ are independently selected from C—B$^1$, N and C—H,
A$^1$ is selected from:
  a) C$_3$-C$_6$ cycloalkyl which ring is optionally substituted by 1, 2 or 3 substituents selected from =O and B$^3$;
  b) a 3 to 6 membered saturated heterocyclyl ring comprising 1, 2 or 3 heteroatoms selected from O, S and N, and which ring is optionally substituted by 1, 2 or 3 substituents selected from =O and B$^3$;
  c) phenyl or 5 to 6 membered heteroaryl group, either ones are optionally substituted by 1, 2 or 3 substituents selected from B$^1$;
each B$^1$ is independently selected from halogen atom, 5 to 6 membered heteroaryl, linear or branched C$_1$-C$_6$ alkyl, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$ and —S(O)$_2$R$^6$,
each B$^2$ is independently selected from halogen atom, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$, —S(O)$_2$R$^6$,
each B$^3$ is independently selected from halogen atom, linear or branched C$_1$-C$_6$ alkyl, —CN, —N(R$^6$)R$^7$, —OR$^6$, —C(=O)R$^6$, —C(=O)OR$^6$, —C(=O)N(R$^6$)R$^7$, —OC(=O)—R$^6$, —N(R$^6$)C(=O)R$^7$, —NR$^7$SO$_2$R$^6$, —SO$_2$N(R$^6$)R$^7$, —SR$^6$, —S(O)R$^6$, —S(O)$_2$R$^6$,
each R$^6$ and R$^7$ independently represents:
hydrogen atom,
linear or branched C$_1$-C$_{12}$ alkyl, C$_3$-C$_6$ cycloalkyl and C$_4$-C heterocycloalkyl, which are optionally substituted by 1, 2 or 3 substituents selected from =O (oxo), halogen atom, hydroxy, phenyl, C$_3$-C$_6$ cycloalkyl, linear or branched C$_1$-C$_6$ alkoxy, amino, alkylamino, dialkylamino, linear or branched C$_1$-C$_6$ alkylcarbonyl,
phenyl or 5 to 6 membered heteroaryl group, which are optionally substituted by 1, 2 or 3 substituents selected from halogen atom, cyano group, linear or branched C$_1$-C$_6$ alkyl, linear or branched C$_1$-C$_6$ haloalkyl, hydroxy, linear or branched C$_1$-C$_6$ alkoxy, amino, alkylamino, dialkylamino;

R⁶ and R⁷ form together with the nitrogen atom to which they are attached, a 3- to 8 membered ring which optionally contains a further heteroatom selected from O, N and S, and which ring is optionally substituted by 1, 2 or 3 substituents selected from =O (oxo), linear or branched $C_1$-$C_6$ alkyl, linear or branched $C_1$-$C_6$ haloalkyl, linear or branched $C_1$-$C_6$ alkylcarbonyl;

with the proviso that when $R^1$ is —COOR⁵ and $R^2$ is —COOR⁸ then $R^4$ is not a methyl group, and pharmaceutically acceptable salts thereof.

Embodiment 2

Compound according to Embodiment 1 wherein $X^1$, $X^2$, $X^3$ and $X^5$ represent C—H or C—$B^1$, wherein $B^1$ represents halogen atom.

Embodiment 3

Compound according to Embodiment 2 wherein $X^4$ is a group selected from C—$B^1$ and N.

Embodiment 4

Compound according to Embodiment 3 wherein $B^1$ is selected from —CN group and halogen atom.

Embodiment 5

Compound according to any one of Embodiments 2 to 4 wherein $R^1$ is a group selected from —COR⁵, —COOR⁵ and —CN group.

Embodiment 6

Compound according to Embodiment 5 wherein $R^5$ is selected from:
$C_1$-$C_3$ alkyl, and
$C_3$-$C_6$ cycloalkyl, Embodiment 7

Compound according to any one of Embodiments 2 to 6 wherein $R^2$ represents —COOR⁸.

Embodiment 8

Compound according to Embodiment 7 wherein R⁸ represents independently:
linear or branched $C_1$-$C_6$ alkyl optionally substituted by 1, 2 or 3 substituents selected from $A^1$, or
$A^1$ group, which represents $C_3$-$C_6$ cycloalkyl which is optionally substituted by 1, 2 or 3 substituents selected from the group consisting of fluorine atoms and $C_1$-$C_3$ alkyl groups.
$A^1$ group, which represents a 3 to 6 membered saturated heterocyclyl ring comprising 1, 2 or 3 heteroatoms selected from O, S and N, and which ring is optionally substituted by 1, 2 or 3 $C_1$-$C_3$ alkyl groups.

Embodiment 9

Compound according to any one of Embodiments 2 to 8 wherein $R^3$ is a group selected from linear or branched $C_1$-$C_4$ alkyl and $C_3$-$C_6$ cycloalkyl.

Embodiment 10

Compound according to any one of Embodiments 2 to 9 wherein $R^4$ is a group selected from:
linear or branched $C_1$-$C_3$ alkyl optionally substituted by 1, 2 or 3 substituents selected from $A^1$ or $B^2$,
$A^1$ group, which represents $C_3$-$C_6$ cycloalkyl,
—N(R⁶)R⁷, wherein R⁶ and R⁷ are independently selected from a hydrogen atom and a linear or branched $C_1$-$C_3$ alkyl,
A cyano group.

Embodiment 11

Compound according to Embodiment 1 wherein $X^1$, $X^2$, $X^3$ and $X^5$ represent —CH, $X^4$ represents C—$B^1$, wherein $B^1$ represents —CN group or bromine atom, $R^1$ is a group selected from —C(O)CH₃, —C(O)OCH₃ and CN, $R^2$ is a group selected from —C(O)OCH₃ and C(O)OCH₂-cyclopropyl, $R^3$ is a group selected from linear or branched $C_1$-$C_3$ alkyl and $C_3$-$C_4$ cycloalkyl and $R^4$ is a group selected from a linear or branched $C_1$-$C_3$ alkyl, $C_3$-$C_4$ cycloalkyl and —NH₂.

Embodiment 12

Compound according to Embodiment 1 wherein $X^1$, $X^2$, $X^3$ and $X^5$ represent a —CH, $X^4$ represents a nitrogen atom, $R^1$ is a group selected from —C(O)CH₃, —C(O)OCH₃ and CN, $R^2$ is a group selected from —C(O)OCH₃ and C(O)OCH₂-cyclopropyl, $R^3$ is a group selected from linear or branched $C_1$-$C_3$ alkyl and $C_3$-$C_4$ cycloalkyl and $R^4$ is a group selected from a linear or branched $C_1$-$C_3$ alkyl, $C_3$-$C_4$ cycloalkyl and —NH₂.

Embodiment 13

A compound according to Embodiment 1, which is selected from the group consisting of:
Methyl 5-acetyl-4-(benzo[b]thiophen-3-yl)-2,6-dimethyl-1,4-dihydro-pyridine-3-carboxylate
Methyl 5-acetyl-4-(benzo[b]thiophen-3-yl)-2,6-dimethyl-1,4-dihydro-pyridine-3-carboxylate (Enantiomer 1)
Methyl 5-acetyl-4-(benzo[b]thiophen-3-yl)-2,6-dimethyl-1,4-dihydro-pyridine-3-carboxylate (Enantiomer 2)
5-acetyl-4-(benzo[b]thiophen-3-yl)-2,6-dimethyl-1,4-dihydropyridine-3-carboxamide
1-(4-(benzo[b]thiophen-3-yl)-5-benzoyl-2,6-dimethyl-1,4-dihydropyridin-3-yl)ethan-1-one
Methyl 5-acetyl-4-(benzo[b]thiophen-3-yl)-6-methyl-2-phenyl-1,4-dihydropyridine-3-carboxylate
3-Acetyl-4-(benzo[b]thiophen-3-yl)-2,7,7-trimethyl-4,6,7,8-tetrahydro-quinolin-5(1H)-one
1-(4-(benzo[b]thiophen-3-yl)-2,6-dimethyl-5-nicotinoyl-1,4-dihydro pyridin-3-yl)ethan-1-one
Methyl 5-acetyl-4-(benzo[b]thiophen-3-yl)-6-methyl-1,4-dihydro-[2,3'-bipyridine]-3-carboxylate
2,2,2-trifluoroethyl 5-acetyl-4-(benzo[b]thiophen-3-yl)-2,6-dimethyl-1,4-dihydropyridine-3-carboxylate
5-Acetyl-4-(benzo[b]thiophen-3-yl)-2,6-dimethyl-1,4-dihydropyridine-3-carboxylic acid
1-(4-(Benzo[b]thiophen-3-yl)-2,6-dimethyl-5-(4-methylpiperazine-1-carbonyl)-1,4-dihydropyridin-3-yl)ethan-1-one
5-Acetyl-4-(benzo[b]thiophen-3-yl)-N,N-diethyl-2,6-dimethyl-1,4-dihydropyridine-3-carboxamide
1-(4-(Benzo[b]thiophen-3-yl)-2,6-dimethyl-5-(morpholine-4-carbonyl)-1,4-dihydropyridin-3-yl)ethan-1-one
2-Methoxyethyl 5-acetyl-4-(benzo[b]thiophen-3-yl)-2,6-dimethyl-1,4-dihydropyridine-3-carboxylate 3-Acetamidopropyl 5-acetyl-4-(benzo[b]thiophen-3-yl)-2,6-dimethyl-1,4-dihydropyridine-3-carboxylate Benzyl 5-acetyl-4-(benzo[b]thiophen-3-yl)-2,6-dimethyl-1,4-dihydro-pyridine-3-carboxylate 2-Morpholinoethyl 5-acetyl-4-(benzo[b]thiophen-3-yl)-2,6-dimethyl-1,4-dihydropyridine-3-carboxylate 2-(Dimethylamino)ethyl 5-acetyl-4-(benzo[b]thiophen-3-yl)-2,6-dimethyl-1,4-dihydropyridine-3-carboxylate 2-Acetamidoethyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-2-(methoxymethyl)-6-methyl-1,4-dihydropyridine-3-carboxylate Methyl 5-acetyl-4-(benzo[b]thiophen-3-yl)-2-((dimethylamino)methyl)-6-methyl-1,4-dihydropyridine-3-carboxylate Pyridin-4-ylmethyl 5-acetyl-4-(benzo[b]thiophen-3-yl)-2,6-dimethyl-1,4-dihydropyridine-3-carboxylate 4-Methoxybenzyl 5-acetyl-4-(benzo[b]thiophen-3-yl)-2,6-dimethyl-1,4-dihydropyridine-3-carboxylate 5-(Benzo[b]thiophen-3-yl)-5,10-dihydro-1H,3H-dipyrano[3,4-b:4',3'-e]pyridine-4,6(7H,9H)-dione Pyridin-2-ylmethyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-6-methyl-2-(morpholino-methyl)-1,4-dihydropyridine-3-carboxylate Dimethyl 4-(benzo[b]thiophen-3-yl)-2,6-bis(morpholinomethyl)-1,4-dihydropyridine-3,5-dicarboxylate 2-Hydroxyethyl 5-acetyl-4-(benzo[b]thiophen-3-yl)-2,6-dimethyl-1,4-dihydropyridine-3-carboxylate 1-(4-(Benzo[b]thiophen-3-yl)-5-(cyclopropanecarbonyl)-6-cyclopropyl-2-methyl-1,4-dihydropyridin-3-yl)ethan-1-one Methyl 5-acetyl-4-(benzo[b]thiophen-3-yl)-2-(1-(tert-butoxycarbonyl) azetidin-3-yl)-6-methyl-1,4-dihydropyridine-3-carboxylate 3-Acetyl-4-(benzo[b]thiophen-3-yl)-2-methyl-1,4,7,8-tetrahydro-5H-6,8-methano-1,6-naphthyridin-5-one (1-(tert-Butoxycarbonyl)piperidin-4-yl)methyl 5-acetyl-4-(benzo[b] thiophen-3-yl)-2,6-dimethyl-1,4-dihydropyridine-3-carboxylate Cyclohexylmethyl 5-acetyl-4-(benzo[b]thiophen-3-yl)-2,6-dimethyl-1,4-dihydropyridine-3-carboxylate Methyl 4-(benzo[b]thiophen-3-yl)-5-(cyclopropanecarbonyl)-2,6-dicyclopropyl-1,4-dihydropyridine-3-carboxylate 5-acetyl-4-(benzo[b]thiophen-3-yl)-2,6-dimethyl-N-phenyl-1,4-dihydropyridine-3-carboxamide Tetrahydro-2H-pyran-4-yl 5-acetyl-4-(benzo[b]thiophen-3-yl)-2,6-dimethyl-1,4-dihydropyridine-3-carboxylate (Tetrahydro-2H-pyran-4-yl)methyl 5-acetyl-4-(benzo[b]thiophen-3-yl)-2,6-dimethyl-1,4-dihydropyridine-3-carboxylate Cyclohexyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-2-(2-methoxy-2-oxoethyl)-6-methyl-1,4-dihydropyridine-3-carboxylate Methyl 5-acetyl-2,6-dimethyl-4-(2-methylbenzo[b]thiophen-3-yl)-1,4-dihydropyridine-3-carboxylate Cyclopropylmethyl 5-acetyl-4-(benzo[b]thiophen-3-yl)-2,6-dimethyl-1,4-dihydropyridine-3-carboxylate Methyl 5-acetyl-4-(benzo[b]thiophen-3-yl)-2-(2-methoxyethyl)-6-methyl-1,4-dihydropyridine-3-carboxylate Methyl 5-acetyl-4-(benzo[b]thiophen-3-yl)-2-((benzyloxy)methyl)-6-methyl-1,4-dihydropyridine-3-carboxylate Methyl 5-acetyl-4-(benzo[b]thiophen-3-yl)-6-methyl-2-(phenoxymethyl)-1,4-dihydropyridine-3-carboxylate Phenethyl 5-acetyl-4-(benzo[b]thiophen-3-yl)-2,6-dimethyl-1,4-dihydropyridine-3-carboxylate Methyl 4-(benzo[b]thiophen-3-yl)-5-(cyclopropanecarbonyl)-6-cyclopropyl-2-methyl-1,4-dihydropyridine-3-carboxylate 3-acetyl-4-(benzo[b]thiophen-3-yl)-2-methyl-4,8-dihydro-1H-pyrano[3,4-b]pyridin-5(6H)-one Methyl 4-(benzo[b]thiophen-3-yl)-2-methyl-5-oxo-4,5,6,8-tetrahydro-1H-pyrano[3,4-b]pyridine-3-carboxylate Methyl 5-acetyl-4-(benzo[b]thiophen-3-yl)-6-methyl-2-(trifluoromethyl)-1,4-dihydropyridine-3-carboxylate Methyl 5-acetyl-4-(benzo[b]thiophen-3-yl)-6-benzyl-2-methyl-1,4-dihydropyridine-3-carboxylate Methyl 4-(benzo[b]thiophen-3-yl)-2,6-dimethyl-5-(2-phenylacetyl)-1,4-dihydropyridine-3-carboxylate 3-acetyl-4-(benzo[b]thiophen-3-yl)-2-methyl-4,8-dihydro-1H-thiopyrano[3,4-b]pyridin-5(6H)-one Methyl 4-(benzo[b]thiophen-3-yl)-5-(2-methoxyacetyl)-2,6-dimethyl-1,4-dihydropyridine-3-carboxylate Methyl 5-acetyl-4-(benzo[b]thiophen-3-yl)-6-(methoxymethyl)-2-methyl-1,4-dihydropyridine-3-carboxylate Methyl 5-acetyl-4-(benzo[b]thiophen-3-yl)-2-(fluoromethyl)-6-methyl-1,4-dihydropyridine-3-carboxylate Cyclopropylmethyl 5-acetyl-4-(5-fluorobenzo[b]thiophen-3-yl)-2,6-dimethyl-1,4-dihydropyridine-3-carboxylate 1-(tert-Butoxycarbonyl)piperidin-4-yl 5-acetyl-4-(benzo[b]thiophen-3-yl)-2,6-dimethyl-1,4-dihydropyridine-3-carboxylate Cyclopentylmethyl 5-acetyl-4-(benzo[b]thiophen-3-yl)-2,6-dimethyl-1,4-dihydropyridine-3-carboxylate Cyclopropylmethyl 5-acetyl-2,6-dimethyl-4-(thieno[2,3-b]pyridin-3-yl)-1,4-dihydropyridine-3-carboxylate 1-methylpiperidin-4-yl 5-acetyl-4-(benzo[b]thiophen-3-yl)-2,6-dimethyl-1,4-dihydropyridine-3-carboxylate Cyclopentyl 5-acetyl-4-(benzo[b]thiophen-3-yl)-2,6-dimethyl-1,4-dihydropyridine-3-carboxylate 4,4-dimethylcyclohexyl 5-acetyl-4-(benzo[b]thiophen-3-yl)-2,6-dimethyl-1,4-dihydropyridine-3-carboxylate Cyclobutyl 5-acetyl-4-(benzo[b]thiophen-3-yl)-2,6-dimethyl-1,4-dihydropyridine-3-carboxylate Methyl 5-acetyl-4-(5-fluorobenzo[b]thiophen-3-yl)-6-methyl-2-(trifluoromethyl)-1,4-dihydropyridine-3-carboxylate Methyl 5-acetyl-2,6-dimethyl-4-(thieno[3,2-b]pyridin-3-yl)-1,4-dihydropyridine-3-carboxylate Methyl 5-acetyl-4-(benzo[b]thiophen-3-yl)-2-methyl-6-(trifluoromethyl)-1,4-dihydropyridine-3-carboxylate Cyclopropylmethyl 5-acetyl-4-(5-chlorobenzo[b]thiophen-3-yl)-2,6-dimethyl-1,4-dihydropyridine-3-carboxylate Cyclohexylmethyl 5-acetyl-4-(5-chlorobenzo[b]thiophen-3-yl)-2,6-dimethyl-1,4-dihydropyridine-3-carboxylate Cyclohexylmethyl 5-acetyl-2,6-dimethyl-4-(thieno[2,3-b]pyridin-3-yl)-1,4-dihydropyridine-3-carboxylate Cyclopentylmethyl 5-acetyl-2,6-dimethyl-4-(thieno[2,3-b]pyridin-3-yl)-1,4-dihydropyridine-3-carboxylate Cyclohexyl 5-acetyl-2,6-dimethyl-4-(thieno[2,3-b]pyridin-3-yl)-1,4-dihydropyridine-3-carboxylate Cyclopentyl 5-acetyl-2,6-dimethyl-4-(thieno[2,3-b]pyridin-3-yl)-1,4-dihydropyridine-3-carboxylate Methyl 5-acetyl-4-(5-chlorobenzo[b]thiophen-3-yl)-6-methyl-2-(trifluoromethyl)-1,4-dihydropyridine-3-carboxylate Benzyl 5-acetyl-2,6-dimethyl-4-(thieno[2,3-b]pyridin-3-yl)-1,4-dihydropyridine-3-carboxylate (Tetrahydro-2H-pyran-4-yl)methyl 5-acetyl-2,6-dimethyl-4-(thieno[2,3-b]pyridin-3-yl)-1,4-dihydropyridine-3-carboxylate Benzyl 5-acetyl-4-(5-fluorobenzo[b]thiophen-3-yl)-2,6-dimethyl-1,4-dihydropyridine-3-carboxylate
Benzyl 5-acetyl-4-(5-chlorobenzo[b]thiophen-3-yl)-2,6-dimethyl-1,4-dihydropyridine-3-carboxylate
(Tetrahydro-2H-pyran-4-yl)methyl 5-acetyl-4-(5-chlorobenzo[b]thiophen-3-yl)-2,6-dimethyl-1,4-dihydropyridine-3-carboxylate
(Tetrahydro-2H-pyran-4-yl)methyl 5-acetyl-4-(5-fluorobenzo[b]thiophen-3-yl)-2,6-dimethyl-1,4-dihydropyridine-3-carboxylate
Benzyl 5-acetyl-4-(benzo[b]thiophen-3-yl)-6-methyl-2-(trifluoromethyl)-1,4-dihydropyridine-3-carboxylate
Pyridin-4-ylmethyl 5-acetyl-4-(5-fluorobenzo[b]thiophen-3-yl)-2,6-dimethyl-1,4-dihydropyridine-3-carboxylate
4-Fluorobenzyl 5-acetyl-2,6-dimethyl-4-(thieno[2,3-b]pyridin-3-yl)-1,4-dihydropyridine-3-carboxylate
Pyridin-3-ylmethyl 5-acetyl-4-(benzo[b]thiophen-3-yl)-2,6-dimethyl-1,4-dihydropyridine-3-carboxylate
6-Acetyl-5-(benzo[b]thiophen-3-yl)-1,3,7-trimethyl-5,8-dihydro-pyrido[2,3-d]pyrimidine-2,4(1H,3H)-dione
3-Acetyl-4-(benzo[b]thiophen-3-yl)-2-methyl-4,7-dihydrofuro[3,4-b]pyridin-5(1H)-one
1,1'-(4-(benzo[b]thiophen-3-yl)-2-benzyl-6-methyl-1,4-dihydropyridine-3,5-diyl)bis(ethan-1-one)
1-(5-acetyl-4-(benzo[b]thiophen-3-yl)-2,6-dimethyl-1,4-dihydropyridin-3-yl)-2-phenylethan-1-one
Methyl 5-acetyl-6-methyl-4-(thieno[2,3-b]pyridin-3-yl)-2-(trifluoromethyl)-1,4-dihydropyridine-3-carboxylate
1-(2-methyl-5-(piperidine-1-carbonyl)-4-(thieno[2,3-b]pyridin-3-yl)-6-(trifluoromethyl)-1,4-dihydropyridin-3-yl)ethan-1-one
4-(((5-acetyl-4-(benzo[b]thiophen-3-yl)-2,6-dimethyl-1,4-dihydro-pyridine-3-carbonyl)oxy)methyl)benzoic acid
Benzyl 5-acetyl-6-methyl-4-(thieno[2,3-b]pyridin-3-yl)-2-(trifluoromethyl)-1,4-dihydropyridine-3-carboxylate
Pyridin-3-ylmethyl 5-acetyl-4-(5-fluorobenzo[b]thiophen-3-yl)-2,6-dimethyl-1,4-dihydropyridine-3-carboxylate
Pyridin-3-ylmethyl 5-acetyl-4-(7-bromobenzo[b]thiophen-3-yl)-2,6-dimethyl-1,4-dihydropyridine-3-carboxylate
Pyridin-3-ylmethyl 5-acetyl-4-(7-cyanobenzo[b]thiophen-3-yl)-2,6-dimethyl-1,4-dihydropyridine-3-carboxylate
Pyridin-3-ylmethyl 5-acetyl-4-(5-chlorobenzo[b]thiophen-3-yl)-2,6-dimethyl-1,4-dihydropyridine-3-carboxylate
Pyridin-3-ylmethyl 5-acetyl-2,6-dimethyl-4-(thieno[2,3-b]pyridin-3-yl)-1,4-dihydropyridine-3-carboxylate
Pyridin-4-ylmethyl 5-acetyl-4-(5-chlorobenzo[b]thiophen-3-yl)-2,6-dimethyl-1,4-dihydropyridine-3-carboxylate
4-(Cyclopropylcarbamoyl)benzyl 5-acetyl-4-(benzo[b]thiophen-3-yl)-2,6-dimethyl-1,4-dihydropyridine-3-carboxylate
Pyridin-4-ylmethyl 5-acetyl-2,6-dimethyl-4-(thieno[2,3-b]pyridin-3-yl)-1,4dihydropyridine-3-carboxylate
4-Bromobenzyl 5-acetyl-2,6-dimethyl-4-(thieno[2,3-b]pyridin-3-yl)-1,4-dihydropyridine-3-carboxylate
3-Bromobenzyl 5-acetyl-2,6-dimethyl-4-(thieno[2,3-b]pyridin-3-yl)-1,4-dihydropyridine-3-carboxylate
2-Bromobenzyl 5-acetyl-2,6-dimethyl-4-(thieno[2,3-b]pyridin-3-yl)-1,4-dihydropyridine-3-carboxylate
(3-Fluoropyridin-4-yl)methyl 5-acetyl-2,6-dimethyl-4-(thieno[2,3-b]pyridin-3-yl)-1,4-dihydropyridine-3-carboxylate
Pyrimidin-5-ylmethyl 5-acetyl-2,6-dimethyl-4-(thieno[2,3-b]pyridin-3-yl)-1,4-dihydropyridine-3-carboxylate
(5-Bromopyridin-3-yl)methyl 5-acetyl-2,6-dimethyl-4-(thieno[2,3-b]pyridin-3-yl)-1,4-dihydropyridine-3-carboxylate
2-Phenylpropan-2-yl 5-acetyl-2,6-dimethyl-4-(thieno[2,3-b]pyridin-3-yl)-1,4-dihydropyridine-3-carboxylate
3-cyanobenzyl 5-acetyl-2,6-dimethyl-4-(thieno[2,3-b]pyridin-3-yl)-1,4-dihydropyridine-3-carboxylate
4-cyanobenzyl 5-acetyl-2,6-dimethyl-4-(thieno[2,3-b]pyridin-3-yl)-1,4-dihydropyridine-3-carboxylate
(6-Chloropyridin-3-yl)methyl 5-acetyl-2,6-dimethyl-4-(thieno[2,3-b]pyridin-3-yl)-1,4-dihydropyridine-3-carboxylate
3-Morpholinobenzyl 5-acetyl-2,6-dimethyl-4-(thieno[2,3-b]pyridin-3-yl)-1,4-dihydropyridine-3-carboxylate
4,4-Dimethylcyclohexyl 5-acetyl-2,6-dimethyl-4-(thieno[2,3-b]pyridin-3-yl)-1,4-dihydropyridine-3-carboxylate
(2-Chloropyridin-4-yl)methyl 5-acetyl-2,6-dimethyl-4-(thieno[2,3-b]pyridin-3-yl)-1,4-dihydropyridine-3-carboxylate
Tetrahydro-2H-pyran-4-yl 5-acetyl-2,6-dimethyl-4-(thieno[2,3-b]pyridin-3-yl)-1,4-dihydropyridine-3-carboxylate
4,4-Difluorocyclohexyl 5-acetyl-2,6-dimethyl-4-(thieno[2,3-b]pyridin-3-yl)-1,4-dihydropyridine-3-carboxylate
5-Acetyl-N-benzyl-N,2,6-trimethyl-4-(thieno[2,3-b]pyridin-3-yl)-1,4-dihydropyridine-3-carboxamide
Oxetan-3-yl 5-acetyl-4-(7-bromobenzo[b]thiophen-3-yl)-2-cyclopropyl-6-methyl-1,4-dihydropyridine-3-carboxylate
Isopropyl 5-acetyl-4-(7-bromobenzo[b]thiophen-3-yl)-2-cyclopropyl-6-methyl-1,4-dihydropyridine-3-carboxylate
Methyl 5-acetyl-4-(7-bromobenzo[b]thiophen-3-yl)-6-methyl-2-(trifluoromethyl)-1,4-dihydropyridine-3-carboxylate
Cyclopropylmethyl 5-acetyl-4-(7-bromobenzo[b]thiophen-3-yl)-2-cyclopropyl-6-methyl-1,4-dihydropyridine-3-carboxylate
Methyl 5-acetyl-2-cyclopropyl-6-methyl-4-(7-(2,2,2-trifluoroacetyl) benzo[b]thiophen-3-yl)-1,4-dihydropyridine-3-carboxylate
2-Phenylpropan-2-yl 5-acetyl-4-(7-bromobenzo[b]thiophen-3-yl)-2,6-dimethyl-1,4-dihydropyridine-3-carboxylate
Methyl 5-acetyl-2-amino-4-(benzo[b]thiophen-3-yl)-6-methyl-1,4-dihydropyridine-3-carboxylate
Methyl 2-amino-4-(benzo[b]thiophen-3-yl)-5-(cyclopropanecarbonyl)-6-methyl-1,4-dihydropyridine-3-carboxylate
Methyl 5-acetyl-2-amino-4-(5-fluorobenzo[b]thiophen-3-yl)-6-methyl-1,4-dihydropyridine-3-carboxylate
Methyl 5-acetyl-2-amino-4-(7-bromobenzo[b]thiophen-3-yl)-6-methyl-1,4-dihydropyridine-3-carboxylate
Methyl 5-acetyl-2-amino-4-(7-cyanobenzo[b]thiophen-3-yl)-6-methyl-1,4-dihydropyridine-3-carboxylate
Cyclopentyl 5-acetyl-2-amino-4-(7-bromobenzo[b]thiophen-3-yl)-6-methyl-1,4-dihydropyridine-3-carboxylate
Dimethyl 2-amino-4-(7-cyanobenzo[b]thiophen-3-yl)-6-methyl-1,4-dihydropyridine-3,5-dicarboxylate
Cyclopentyl 5-acetyl-2-amino-4-(7-cyanobenzo[b]thiophen-3-yl)-6-methyl-1,4-dihydropyridine-3-carboxylate
Dimethyl 2,6-diamino-4-(benzo[b]thiophen-3-yl)-1,4-dihydropyridine-3,5-dicarboxylate cyclopropylmethyl 5-acetyl-2-amino-4-(7-cyanobenzo[b]thiophen-3-yl)-6-methyl-1,4-dihydropyridine-3-carboxylate
4,4-difluorocyclohexyl 5-acetyl-2-amino-4-(7-cyanobenzo[b]thiophen-3-yl)-6-methyl-1,4-dihydropyridine-3-carboxylate
methyl 2-amino-5-cyano-4-(7-cyanobenzo[b]thiophen-3-yl)-6-methyl-1,4-dihydropyridine-3-carboxylate
4-fluorobenzyl 5-acetyl-2-amino-4-(7-cyanobenzo[b]thiophen-3-yl)-6-methyl-1,4-dihydropyridine-3-carboxylate methyl 5-acetyl-2-amino-4-(5-fluorothieno[2,3-b]pyridin-3-yl)-6-methyl-1,4-dihydropyridine-3-carboxylate methyl 2-acetamido-5-acetyl-4-(5-fluorothieno[2,3-b]pyridin-3-yl)-6-methyl-1,4-dihydropyridine-3-carboxylate cyclopentylmethyl 5-acetyl-2-amino-4-(7-cyanobenzo[b]thiophen-3-yl)-6-methyl-1,4-dihydropyridine-3-carboxylate 3-(cyclopropylmethyl) 5-methyl 2-amino-4-(7-cyanobenzo[b]thiophen-3-yl)-6-methyl-1,4-dihydropyridine-3,5-dicarboxylate dimethyl 2-amino-4-(7-cyanobenzo[b]thiophen-3-yl)-6-cyclopropyl-1,4-dihydropyridine-3,5-dicarboxylate 3-(cyclopropylmethyl) 5-methyl 2-amino-4-(7-cyanobenzo[b]thiophen-3-yl)-6-cyclopropyl-1,4-dihydropyridine-3,5-dicarboxylate dimethyl 2,6-diamino-4-(7-cyanobenzo[b]thiophen-3-yl)-1,4-dihydropyridine-3,5-dicarboxylate 5-(cyclopropylmethyl) 3-methyl 2-amino-4-(7-cyanobenzo[b]thiophen-3-yl)-6-cyclopropyl-1,4-dihydropyridine-3,5-dicarboxylate 3-(4-fluorobenzyl) 5-methyl 2-amino-4-(7-cyanobenzo[b]thiophen-3-yl)-6-methyl-1,4-dihydropyridine-3,5-dicarboxylate 3-(4-fluorobenzyl) 5-methyl 2-amino-4-(7-cyanobenzo[b]thiophen-3-yl)-6-cyclopropyl-1,4-dihydropyridine-3,5-dicarboxylate 4-(Benzo[b]thiophen-3-yl)-2,6-dimethyl-1,4-dihydropyridine-3,5-dicarbonitrile 4-(6-hydroxybenzo[b]thiophen-3-yl)-2,6-dimethyl-1,4-dihydropyridine-3,5-dicarbonitrile 4-(6-methoxybenzo[b]thiophen-3-yl)-2,6-dimethyl-1,4-dihydropyridine-3,5-dicarbonitrile 2,6-dimethyl-4-(thieno[2,3-b]pyridin-3-yl)-1,4-dihydropyridine-3,5-dicarbonitrile 4-(benzo[b]thiophen-3-yl)-2-methyl-6-phenyl-1,4-dihydropyridine-3,5-dicarbonitrile 4-(benzo[b]thiophen-3-yl)-2-cyclopropyl-6-methyl-1,4-dihydropyridine-3,5-dicarbonitrile 5-acetyl-4-(benzo[b]thiophen-3-yl)-2,6-dimethyl-1,4-dihydropyridine-3-carbonitrile Ethyl 4-(benzo[b]thiophen-3-yl)-5-cyano-2,6-dimethyl-1,4-dihydropyridine-3-carboxylate Ethyl 4-(benzo[b]thiophen-3-yl)-5-cyano-2-methyl-6-phenyl-1,4-dihydropyridine-3-carboxylate Ethyl 4-(benzo[b]thiophen-3-yl)-5-cyano-2-cyclopropyl-6-methyl-1,4-dihydropyridine-3-carboxylate Methyl 4-(benzo[b]thiophen-3-yl)-5-cyano-2-cyclopropyl-6-methyl-1,4-dihydropyridine-3-carboxylate 1,1'-(4-(benzo[b]thiophen-3-yl)-2,6-dimethyl-1,4-dihydropyridine-3,5-diyl)diethanone 1,1'-(4-(6-hydroxybenzo[b]thiophen-3-yl)-2,6-dimethyl-1,4-dihydropyridine-3,5-diyl)bis(ethan-1-one)

1,1'-(4-(6-Methoxybenzo[b]thiophen-3-yl)-2,6-dimethyl-1,4-dihydropyridine-3,5-diyl)diethanone 1,1'-(4-(Benzo[b]thiophen-3-yl)-2,6-dicyclopropyl-1,4-dihydropyridine-3,5-diyl)diethanone 9-(benzo[b]thiophen-3-yl)-3,4,6,7,9,10-hexahydroacridine-1,8(2H,5H)-dione 1,1'-(4-(5-chlorobenzo[b]thiophen-3-yl)-2,6-dimethyl-1,4-dihydropyridine-3,5-diyl)diethanone 1,1'-(4-(5-bromobenzo[b]thiophen-3-yl)-2,6-dimethyl-1,4-dihydropyridine-3,5-diyl)diethanone 1,1'-(4-(5-fluorobenzo[b]thiophen-3-yl)-2,6-dimethyl-1,4-dihydropyridine-3,5-diyl)bis(ethan-1-one)

1,1'-(2,6-dimethyl-4-(5-morpholinobenzo[b]thiophen-3-yl)-1,4-dihydropyridine-3,5-diyl)bis(ethan-1-one)

1,1'-(2,6-dimethyl-4-(5-(4-methylpiperazin-1-yl)benzo[b]thiophen-3-yl)-1,4-dihydropyridine-3,5-diyl)bis(ethan-1-one)

1,1'-(4-(5-(benzylamino)benzo[b]thiophen-3-yl)-2,6-dimethyl-1,4-dihydropyridine-3,5-diyl)bis(ethan-1-one)

3-(3,5-diacetyl-2,6-dimethyl-1,4-dihydropyridin-4-yl)benzo[b]thiophene-5-carbonitrile 3-(3,5-diacetyl-2,6-dimethyl-1,4-dihydropyridin-4-yl)benzo[b]thiophene-5-carboxylic acid N-cyclopropyl-3-(3,5-diacetyl-2,6-dimethyl-1,4-dihydropyridin-4-yl)benzo[b]thiophene-5-carboxamide N-(cyclopropylmethyl)-3-(3,5-diacetyl-2,6-dimethyl-1,4-dihydropyridin-4-yl)benzo[b]thiophene-5-carboxamide 1,1'-(2,6-Dimethyl-4-(5-(4-methylpiperazine-1-carbonyl)benzo[b]thiophen-3-yl)-1,4-dihydropyridine-3,5-diyl)bis(ethan-1-one)

1,1'-(2,6-Dimethyl-4-(5-(morpholine-4-carbonyl)benzo[b]thiophen-3-yl)-1,4-dihydropyridine-3,5-diyl)bis(ethan-1-one)

1,1'-(2,6-Dimethyl-4-(thieno[3,2-c]pyridin-3-yl)-1,4-dihydropyridine-3,5-diyl)bis(ethan-1-one)

1,1'-(2,6-Dimethyl-4-(thieno[2,3-c]pyridin-3-yl)-1,4-dihydropyridine-3,5-diyl)bis(ethan-1-one)

1,1'-(2,6-Dimethyl-4-(thieno[2,3-b]pyridin-3-yl)-1,4-dihydropyridine-3,5-diyl)bis(ethan-1-one)

Methyl 5-acetyl-4-(benzo[b]thiophen-3-yl)-2-cyclopropyl-6-methyl-1,4-dihydropyridine-3-carboxylate Dimethyl 4-(benzo[b]thiophen-3-yl)-2,6-dicyclopropyl-1,4-dihydropyridine-3,5-dicarboxylate Ethyl 5-acetyl-4-(benzo[b]thiophen-3-yl)-2,6-dimethyl-1,4-dihydropyridine-3-carboxylate Methyl 5-acetyl-4-(5-chlorobenzo[b]thiophen-3-yl)-2,6-dimethyl-1,4-dihydropyridine-3-carboxylate 3-acetyl-4-(benzo[b]thiophen-3-yl)-2-methyl-4,6,7,8-tetrahydroquinolin-5(1H)-one Methyl 4-(benzo[b]thiophen-3-yl)-2-methyl-5-oxo-1,4,5,6,7,8-hexahydro-quinoline-3-carboxylate 1,1'-(4-(benzo[b]thiophen-3-yl)-2-cyclopropyl-6-methyl-1,4-dihydro-pyridine-3,5-diyl)diethanone 3-acetyl-4-(benzo[b]thiophen-3-yl)-1,4,6,7-tetrahydro-2-methylcyclopenta[b]pyridin-5-one 3-acetyl-4-(benzo[b]thiophen-3-yl)-1,4,6,7,8-pentahydro-2-methyl-7-phenylcyclohexa[b]pyridin-5-one 3-acetyl-4-(benzo[b]thiophen-3-yl)-7-(4-fluorophenyl)-2-methyl-4,6,7,8-tetrahydroquinolin-5(1H)-one 1-(4-(benzo[b]thiophen-3-yl)-2,6-dimethyl-5-(methylsulfonyl)-1,4-dihydro-pyridin-3-yl)ethanone Methyl 5-acetyl-4-(5-fluorobenzo[b]thiophen-3-yl)-2,6-dimethyl-1,4-dihydropyridine-3-carboxylate Methyl 5-acetyl-4-(5-bromobenzo[b]thiophen-3-yl)-2,6-dimethyl-1,4-dihydropyridine-3-carboxylate methyl 5-acetyl-4-(5-cyanobenzo[b]thiophen-3-yl)-2,6-dimethyl-1,4-dihydropyridine-3-carboxylate 3-(3-acetyl-5-(methoxycarbonyl)-2,6-dimethyl-1,4-dihydropyridin-4-yl)benzo[b]thiophene-5-carboxylic acid methyl 5-acetyl-4-(5-(cyclopropylcarbamoyl)benzo[b]thiophen-3-yl)-2,6-dimethyl-1,4-dihydropyridine-3-carboxylate Methyl 5-acetyl-4-(5-((cyclopropylmethyl)carbamoyl)benzo[b]thiophen-3-yl)-2,6-dimethyl-1,4-dihydropyridine-3-carboxylate Methyl 5-acetyl-2,6-dimethyl-4-(5-(4-methylpiperazine-1-carbonyl)benzo[b]thiophen-3-yl)-1,4-dihydropyridine-3-carboxylate Methyl 5-acetyl-2,6-dimethyl-4-(5-(morpholine-4-carbonyl)benzo[b]thiophen-3-yl)-1,4-dihydropyridine-3-carboxylate Methyl 5-acetyl-2,6-dimethyl-4-(thieno[3,2-c]pyridin-3-yl)-1,4-dihydropyridine-3-carboxylate Methyl 5-acetyl-2,6-dimethyl-4-(thieno[2,3-c]pyridin-3-yl)-1,4-dihydropyridine-3-carboxylate Methyl 5-acetyl-2,6-dimethyl-4-(thieno[2,3-b]pyridin-3-yl)-1,4-dihydropyridine-3-carboxylate Methyl 5-acetyl-2-cyclopropyl-4-(5-fluorobenzo[b]thiophen-3-yl)-6-methyl-1,4-dihydropyridine-3-carboxylate Dimethyl 2,6-dicyclopropyl-4-(5-fluorobenzo[b]thiophen-3-yl)-1,4-dihydropyridine-3,5-dicarboxylate Methyl 5-acetyl-2-cyclopropyl-6-methyl-4-(thieno[2,3-b]pyridin-3-yl)-1,4-dihydropyridine-3-carboxylate Dimethyl 2,6-dicyclopropyl-4-(thieno[2,3-b]pyridin-3-yl)-1,4-dihydropyridine-3,5-dicarboxylate Methyl 5-acetyl-4-(benzo[b]thiophen-3-yl)-2,6-dicyclopropyl-1,4-dihydropyridine-3-carboxylate Methyl 5-acetyl-4-(5-chlorobenzo[b]thiophen-3-yl)-2-cyclopropyl-6-methyl-1,4-dihydropyridine-3-carboxylate Dimethyl 4-(5-chlorobenzo[b]thiophen-3-yl)-2,6-dicyclopropyl-1,4-dihydropyridine-3,5-dicarboxylate Methyl 5-acetyl-4-(7-bromobenzo[b]thiophen-3-yl)-2-cyclopropyl-6-methyl-1,4-dihydropyridine-3-carboxylate Methyl 5-acetyl-2-cyclopropyl-4-(7-(cyclopropylcarbamoyl)benzo[b]thiophen-3-yl)-6-methyl-1,4-dihydropyridine-3-carboxylate Methyl 5-acetyl-4-(7-cyanobenzo[b]thiophen-3-yl)-2-cyclopropyl-6-methyl-1,4-dihydropyridine-3-carboxylate Dimethyl 4-(7-cyanobenzo[b]thiophen-3-yl)-2,6-dicyclopropyl-1,4-dihydropyridine-3,5-dicarboxylate Methyl 5-acetyl-2-cyclopropyl-4-(7-(methoxycarbonyl)benzo[b]thiophen-3-yl)-6-methyl-1,4-dihydropyridine-3-carboxylate Dimethyl 2,6-dicyclopropyl-4-(7-(methoxycarbonyl)benzo[b]thiophen-3-yl)-1,4-dihydropyridine-3,5-dicarboxylate 3-(3-Acetyl-6-cyclopropyl-5-(methoxycarbonyl)-2-methyl-1,4-dihydropyridin-4-yl)benzo[b]thiophene-7-carboxylic acid Benzyl 5-acetyl-2-cyclopropyl-6-methyl-4-(thieno[2,3-b]pyridin-3-yl)-1,4-dihydropyridine-3-carboxylate Pyridin-4-ylmethyl 5-acetyl-4-(benzo[b]thiophen-3-yl)-2-cyclopropyl-6-methyl-1,4-dihydropyridine-3-carboxylate bis(pyridin-4-ylmethyl) 2,6-dicyclopropyl-4-(thieno[2,3-b]pyridin-3-yl)-1,4-dihydropyridine-3,5-dicarboxylate Pyridin-4-ylmethyl 5-acetyl-4-(7-bromobenzo[b]thiophen-3-yl)-2,6-dimethyl-1,4-dihydropyridine-3-carboxylate Pyridin-4-ylmethyl 5-acetyl-4-(5-chlorobenzo[b]thiophen-3-yl)-2-cyclopropyl-6-methyl-1,4-dihydropyridine-3-carboxylate Pyridin-4-ylmethyl 5-acetyl-4-(7-cyanobenzo[b]thiophen-3-yl)-2-cyclopropyl-6-methyl-1,4-dihydropyridine-3-carboxylate Pyridin-4-ylmethyl 5-acetyl-2-cyclopropyl-6-methyl-4-(thieno[2,3-b]pyridin-3-yl)-1,4-dihydropyridine-3-carboxylate Benzyl 5-acetyl-2-cyclopropyl-4-(7-(methoxycarbonyl)benzo[b]thiophen-3-yl)-6-methyl-1,4-dihydropyridine-3-carboxylate Dibenzyl 2,6-dicyclopropyl-4-(7-(methoxycarbonyl)benzo[b]thiophen-3-yl)-1,4-dihydropyridine-3,5-dicarboxylate Benzyl 5-acetyl-4-(7-(methoxycarbonyl)benzo[b]thiophen-3-yl)-2,6-dimethyl-1,4-dihydropyridine-3-carboxylate Methyl 3-(3,5-diacetyl-2,6-dimethyl-1,4-dihydropyridin-4-yl)benzo[b]thiophene-7-carboxylate 3-(3,5-Diacetyl-2,6-dimethyl-1,4-dihydropyridin-4-yl)benzo[b]thiophene-7-carbonitrile Pyridin-4-ylmethyl 5-acetyl-4-(7-bromobenzo[b]thiophen-3-yl)-2-cyclopropyl-6-methyl-1,4-dihydropyridine-3-carboxylate 4-Fluorobenzyl 5-acetyl-2-cyclopropyl-6-methyl-4-(thieno[2,3-b]pyridin-3-yl)-1,4-dihydropyridine-3-carboxylate bis(4-fluorobenzyl) 2,6-dicyclopropyl-4-(thieno[2,3-b]pyridin-3-yl)-1,4-dihydropyridine-3,5-dicarboxylate 4-cyanobenzyl 5-acetyl-2-cyclopropyl-6-methyl-4-(thieno[2,3-b]pyridin-3-yl)-1,4-dihydropyridine-3-carboxylate Methyl 5-acetyl-4-(7-chlorobenzo[b]thiophen-3-yl)-2-cyclopropyl-6-methyl-1,4-dihydropyridine-3-carboxylate methyl 5-acetyl-2-cyclopropyl-6-methyl-4-(7-(trifluoromethyl)benzo[b]thiophen-3-yl)-1,4-dihydropyridine-3-carboxylate 3-chlorobenzyl 5-acetyl-2,6-dimethyl-4-(thieno[2,3-b]pyridin-3-yl)-1,4-dihydropyridine-3-carboxylate 2-phenylpropan-2-yl 5-acetyl-4-(7-bromobenzo[b]thiophen-3-yl)-2-cyclopropyl-6-methyl-1,4-dihydropyridine-3-carboxylate Cyclohexyl 5-acetyl-2-cyclopropyl-6-methyl-4-(thieno[2,3-b]pyridin-3-yl)-1,4-dihydropyridine-3-carboxylate 2-Phenylpropan-2-yl 5-acetyl-2-cyclopropyl-6-methyl-4-(thieno[2,3-b]pyridin-3-yl)-1,4-dihydropyridine-3-carboxylate 1-(4-(7-Bromobenzo[b]thiophen-3-yl)-5-(cyclopropanecarbonyl)-6-cyclopropyl-2-methyl-1,4-dihydropyridin-3-yl)ethan-1-one 3-chlorobenzyl 5-acetyl-2-cyclopropyl-6-methyl-4-(thieno[2,3-b]pyridin-3-yl)-1,4-dihydropyridine-3-carboxylate 2-(4-Fluorophenyl)propan-2-yl 5-acetyl-2,6-dimethyl-4-(thieno[2,3-b]pyridin-3-yl)-1,4-dihydropyridine-3-carboxylate 2-(4-fluorophenyl)propan-2-yl 5-acetyl-4-(7-bromobenzo[b]thiophen-3-yl)-2-cyclopropyl-6-methyl-1,4-dihydropyridine-3-carboxylate 2-(4-fluorophenyl)propan-2-yl 5-acetyl-2-cyclopropyl-6-methyl-4-(thieno[2,3-b]pyridin-3-yl)-1,4-dihydropyridine-3-carboxylate Methyl 5-acetyl-2-cyclopropyl-4-(7-fluorobenzo[b]thiophen-3-yl)-6-methyl-1,4-dihydropyridine-3-carboxylate Cyclopropylmethyl 5-acetyl-2-cyclopropyl-6-methyl-4-(thieno[2,3-b]pyridin-3-yl)-1,4-dihydropyridine-3-carboxylate Cyclopentyl 5-acetyl-2-cyclopropyl-6-methyl-4-(thieno[2,3-b]pyridin-3-yl)-1,4-dihydropyridine-3-carboxylate Cyclopropylmethyl 5-acetyl-4-(7-cyanobenzo[b]thiophen-3-yl)-2-cyclopropyl-6-methyl-1,4-dihydropyridine-3-carboxylate Methyl 5-acetyl-4-(7-bromobenzo[b]thiophen-3-yl)-2-cyclobutyl-6-methyl-1,4-dihydropyridine-3-carboxylate Dimethyl 4-(7-cyanobenzo[b]thiophen-3-yl)-2-cyclopropyl-6-methyl-1,4-dihydropyridine-3,5-dicarboxylate Methyl 5-cyano-4-(7-cyanobenzo[b]thiophen-3-yl)-2-cyclopropyl-6-methyl-1,4-dihydropyridine-3-carboxylate Methyl 5-acetyl-4-(7-bromobenzo[b]thiophen-3-yl)-2-cyclopentyl-6-methyl-1,4-dihydropyridine-3-carboxylate Methyl 5-acetyl-4-(7-bromobenzo[b]thiophen-3-yl)-2-cyclohexyl-6-methyl-1,4-dihydropyridine-3-carboxylate Methyl 5-cyano-4-(7-cyanobenzo[b]thiophen-3-yl)-2,6-dicyclopropyl-1,4-dihydropyridine-3-carboxylate 3-((4-Methylpiperazin-1-yl)methyl)benzyl 5-acetyl-4-(7-bromobenzo[b]thiophen-3-yl)-2,6-dimethyl-1,4-dihydropyridine-3-carboxylate 3-(cyclopropylmethyl) 5-methyl 4-(7-cyanobenzo[b]thiophen-3-yl)-2-cyclopropyl-6-methyl-1,4-dihydropyridine-3,5-dicarboxylate 3-(cyclopropylmethyl) 5-methyl 4-(7-cyanobenzo[b]thiophen-3-yl)-2,6-dicyclopropyl-1,4-dihydropyridine-3,5-dicarboxylate cyclopropylmethyl 5-cyano-4-(7-cyanobenzo[b]thiophen-3-yl)-2-cyclopropyl-6-methyl-1,4-dihydropyridine-3-carboxylate dimethyl 2-cyano-4-(7-cyanobenzo[b]thiophen-3-yl)-6-cyclopropyl-1,4-dihydropyridine-3,5-dicarboxylate dimethyl 2-cyano-4-(7-cyanobenzo[b]thiophen-3-yl)-6-methyl-1,4-dihydropyridine-3,5-dicarboxylate methyl 5-acetyl-2-((2-aminoethoxy)methyl)-4-(benzo[b]thiophen-3-yl)-6-methyl-1,4-dihydropyridine-3-carboxylate methyl 5-acetyl-2-((2-aminoethoxy)methyl)-4-(7-bromobenzo[b]thiophen-3-yl)-6-methyl-1,4-dihydropyridine-3-carboxylate methyl 5-acetyl-2-((2-aminoethoxy)methyl)-4-(7-cyanobenzo[b]thiophen-3-yl)-6-methyl-1,4-dihydropyridine-3-carboxylate Methyl 5-acetyl-2-amino-4-(benzo[b]thiophen-3-yl)-6-methyl-1,4-dihydropyridine-3-carboxylate hydrochloride Methyl 5-acetyl-2-amino-4-(benzo[b]thiophen-3-yl)-6-methyl-1,4-dihydropyridine-3-carboxylate trifluoromethanesulfonate 4-(Pyridin-4-yl)benzyl 5-acetyl-2,6-dimethyl-4-(thieno[2,3-b]pyridin-3-yl)-1,4 dihydropyridine-3-carboxylate 4-(Pyridin-3-yl)benzyl 5-acetyl-2,6-dimethyl-4-(thieno[2,3-b]pyridin-3-yl)-1,4-dihydropyridine-3-carboxylate 3-(Pyridin-4-yl)benzyl 5-acetyl-2,6-dimethyl-4-(thieno[2,3-b]pyridin-3-yl)-1,4-dihydropyridine-3-carboxylate 3-(Pyridin-3-yl)benzyl 5-acetyl-2,6-dimethyl-4-(thieno[2,3-b]pyridin-3-yl)-1,4-dihydropyridine-3-carboxylate 2-(Pyridin-4-yl)benzyl 5-acetyl-2,6-dimethyl-4-(thieno[2,3-b]pyridin-3-yl)-1,4-dihydropyridine-3-carboxylate 2-(pyridin-3-yl)benzyl 5-acetyl-2,6-dimethyl-4-(thieno[2,3-b]pyridin-3-yl)-1,4-dihydropyridine-3-carboxylate

[3,4'-Bipyridin]-5-ylmethyl 5-acetyl-2,6-dimethyl-4-(thieno[2,3-b]pyridin-3-yl)-1,4-dihydropyridine-3-carboxylate

[3,3'-Bipyridin]-5-ylmethyl 5-acetyl-2,6-dimethyl-4-(thieno[2,3-b]pyridin-3-yl)-1,4-dihydropyridine-3-carboxylate

[2,4'-Bipyridin]-5-ylmethyl 5-acetyl-2,6-dimethyl-4-(thieno[2,3-b]pyridin-3-yl)-1,4-dihydropyridine-3-carboxylate

[2,3'-Bipyridin]-5-ylmethyl 5-acetyl-2,6-dimethyl-4-(thieno[2,3-b]pyridin-3-yl)-1,4-dihydropyridine-3-carboxylate

[2,3'-Bipyridin]-4-ylmethyl 5-acetyl-2,6-dimethyl-4-(thieno[2,3-b]pyridin-3-yl)-1,4-dihydropyridine-3-carboxylate

[2,4'-Bipyridin]-4-ylmethyl 5-acetyl-2,6-dimethyl-4-(thieno[2,3-b]pyridin-3-yl)-1,4-dihydropyridine-3-carboxylate Methyl 5-acetyl-2-cyclopropyl-6-methyl-4-(7-(pyridin-4-yl)benzo[b]thiophen-3-yl)-1,4-dihydropyridine-3-carboxylate Methyl 5-acetyl-2-cyclopropyl-4-(7-cyclopropylbenzo[b]thiophen-3-yl)-6-methyl-1,4-dihydropyridine-3-carboxylate 3-(Pyridin-4-yl)benzyl 5-acetyl-2-cyclopropyl-6-methyl-4-(thieno[2,3-b]pyridin-3-yl)-1,4-dihydropyridine-3-carboxylate 1,1'-(2,6-Dimethyl-4-(5-(pyridin-3-yl)benzo[b]thiophen-3-yl)-1,4-dihydro-pyridine-3,5-diyl)diethanone Methyl 5-acetyl-2-cyclopropyl-6-methyl-4-(7-phenylbenzo[b]thiophen-3-yl)-1,4-dihydropyridine-3-carboxylate.

Embodiment 14

Compound as defined in any one of Embodiments 1 to 13 for use in the treatment of a disease or pathological condition susceptible of improvement by antagonism of androgen receptor and/or glucocorticoid receptor.

Embodiment 15

Compound for use according to Embodiment 14, wherein the disease or pathological condition susceptible of improvement by antagonism of androgen receptor and/or glucocorticoid receptor is selected from prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

Embodiment 16

A pharmaceutical composition comprising a compound as defined in any one of Embodiments 1 to 13 and a pharmaceutically acceptable diluent or carrier.

Embodiment 17

A pharmaceutical composition according to Embodiment 16 further comprising a therapeutically effective amount of a therapeutic agent selected from agents for treating prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

Embodiment 18

A combination product comprising a compound according to any one Embodiments 1 to 13 and a therapeutic agent used for the treatment of prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

Embodiment 19

A combination product according to Embodiment 18 wherein the therapeutic agent is selected from gonadotropin-releasing hormone (GnRH) receptor agonist or antagonist, androgen receptor antagonist, CYP17 inhibitor, VEGF inhibitor, EGFR inhibitor, PI3K inhibitor, AKT inhibitor, mTOR inhibitor, c-Met inhibitor, Src, inhibitor, PARP inhibitor, angiopoietin, ALK inhibitor, ROS-1 inhibitor, anti-(IGF) antibodies, taxane anti-neoplastic agent, topoisomerase II inhibitor, anti-tumor antibiotic, HSP90 inhibitor, aurora kinase inhibitor, PSA-directed vaccine, GR antagonists, 11-beta HSD inhibitors, one or more immunotherapeutic agent selected from the group consisting of antibodies anti-CTLA4, antibodies anti-PD1 and antibodies anti-PDL1.

Embodiment 20

A combination product according to Embodiment 19 wherein the immunotherapeutic agent is selected from the group consisting of ipilimumab, tremelimumab, nivolumab, pembrolizumab, CT-011, AMP-224, MPDL3280A, MEDI4736 and MDX-1105.

The invention claimed is:
1. A compound of formula (I):

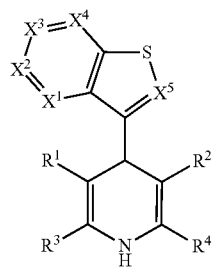

wherein:
$R^1$ is a group selected from:
a) —$COR^5$,
b) —$COOR^5$,
c) —CN, and
d) —$C(O)NH_2$,
$R^5$ is a group selected from:
a) linear or branched $C_1$-$C_6$ alkyl optionally substituted by 1, 2 or 3 substituents selected from —$N(R^6)R^7$ and —$OR^6$, halogen atom, $C_3$-$C_6$ cycloalkyl and alkynyl group, and
b) $C_3$-$C_6$ cycloalkyl,
$R^2$ is a group selected from:
a) —$COOR^8$,
b) —$COR^8$,
c) —$C(O)N(R^8)R^9$,
d) —CN, and
e) —$S(O)_nR^8$, wherein n is an integer from 1 to 2,
$R^8$ and $R^9$ are independently selected from:
a) linear or branched $C_1$-$C_6$ alkyl optionally substituted by 1, 2 or 3 substituents selected from $A^1$ or $B^2$,
b) $A^1$ group, and
c) hydrogen atom,
or
$R^8$ and $R^9$ together with the nitrogen atom to which they are attached form a 5-6 membered heterocycle which optionally comprises 1 heteroatom selected from O and N, and said heterocycle being optionally substituted by 1 or 2 groups independently selected from linear or branched $C_1$-$C_4$ alkyl,
$R^3$ is a group selected from:
a) linear or branched $C_1$-$C_6$ alkyl optionally substituted by 1, 2 or 3 substituents selected from halogen atom, —$N(R^6)R^7$, and —$OR^6$, $R^4$ is a group selected from:
a) $A^1$ group,
b) linear or branched $C_1$-$C_6$ alkyl optionally substituted by 1, 2 or 3 substituents selected from $A^1$ or $B^2$,
c) —$N(R^6)R^7$,
d) —CN,
e) —CO—H;
f) —CO-Me, and
g) CO—OMe
$X^1$ and $X^4$ are independently selected from C—$B^1$, N and C—H,
$X^2$, $X^3$, and $X^5$ are independently selected from C—$B^1$ and C—H,
$A^1$ is selected from:
a) $C_3$-$C_6$ cycloalkyl which ring is optionally substituted by 1, 2, 3 or 4 substituents selected from =O and $B^3$;
b) a 3 to 6 membered saturated heterocyclyl ring comprising 1, 2 or 3 heteroatoms selected from O, S and N, and which ring is optionally substituted by 1, 2 or 3 substituents selected from =O and $B^3$; and
c) phenyl or 5 to 6 membered heteroaryl group, either ones are optionally substituted by 1, 2 or 3 substituents selected from $B^1$;
each $B^1$ is independently selected from halogen atom, —$CF_3$ group, 5 to 6 membered heteroaryl, linear or branched $C_1$-$C_6$ alkyl, —CN, —$N(R^6)R^7$, —$OR^6$, —$C(=O)R^6$, —$C(=O)OR^6$, —$C(=O)N(R^6)R^7$, —$OC(=O)$—$R^6$, —$N(R^6)C(=O)R^7$, —$NR^7SO_2R^6$, —$SO_2N(R^6)R^7$, —$SR^6$, —$S(O)R^6$ and —$S(O)_2R^6$,
each $B^2$ is independently selected from halogen atom, —CN, —$N(R^6)R^7$, —$OR^6$, —$C(=O)R^6$, —$C(=O)OR^6$, —$C(=O)N(R^6)R^7$, —$OC(=O)$—$R^6$, —$N(R^6)C(=O)R^7$, —$NR^7SO_2R^6$, —$SO_2N(R^6)R^7$, —$SR^6$, —$S(O)R^6$, —$S(O)_2R^6$, and alkynyl group,
each $B^3$ is independently selected from halogen atom, linear or branched $C_1$-$C_6$ alkyl, —CN, —$N(R^6)R^7$, —$OR^6$, —$C(=O)R^6$, —$C(=O)OR^6$, —$C(=O)N(R^6)R^7$, —$OC(=O)$—$R^6$, —$N(R^6)C(=O)R^7$, —$NR^7SO_2R^6$, —$SO_2N(R^6)R^7$, —$SR^6$, —$S(O)R^6$, and —$S(O)_2R^6$,
each $R^6$ and $R^7$ independently represents:
hydrogen atom,
linear or branched $C_1$-$C_{12}$ alkyl, $C_3$-$C_6$ cycloalkyl and $C_4$-$C_6$ heterocycloalkyl, which are optionally substituted by 1, 2 or 3 substituents selected from =O (oxo), halogen atom, hydroxy, phenyl, $C_3$-$C_6$ cycloalkyl, linear or branched $C_1$-$C_6$ alkoxy, amino, alkylamino, dialkylamino, and linear or branched $C_1$-$C_6$ alkylcarbonyl,
phenyl or 5 to 6 membered heteroaryl group, which are optionally substituted by 1, 2 or 3 substituents selected from halogen atom, cyano group, linear or branched $C_1$-$C_6$ alkyl, linear or branched $C_1$-$C_6$ haloalkyl, hydroxy, linear or branched $C_1$-$C_6$ alkoxy, amino, alkylamino, and dialkylamino;
$R^6$ and $R^7$ form together with the nitrogen atom to which they are attached, a 3- to 8 membered ring which optionally contains a further heteroatom selected from O, N and S, and which ring is optionally substituted by 1, 2 or 3 substituents selected from =O (oxo), linear or branched $C_1$-$C_6$ alkyl, linear or branched $C_1$-$C_6$ haloalkyl, and linear or branched $C_1$-$C_6$ alkylcarbonyl;

with the proviso that when $R^1$ is —COOR$^5$ and $R^2$ is —COOR$^8$ then $R^4$ is not a methyl group, and pharmaceutically acceptable salts thereof.

2. The compound according to claim 1 wherein $X^1$, $X^2$, $X^3$ and $X^5$ represent C—H or C—B$^1$, wherein B$^1$ represents halogen atom.

3. The compound according to claim 2 wherein $X^4$ is a group selected from C—B$^1$ and N.

4. The compound according to claim 3 wherein B$^1$ is selected from —CN group and halogen atom.

5. The compound according to claim 2 wherein $R^1$ is a group selected from —COR$^5$, —COOR$^5$ and —CN group.

6. The compound according to claim 5 wherein R$^5$ is selected from:
   $C_1$-$C_4$ alkyl wherein the terminal methyl is unsubstituted or substituted by three fluorine atoms (—CF$_3$);
   $C_1$-$C_3$ alkyl optionally substituted at any position by an alkynyl group; and
   $C_3$-$C_5$ cycloalkyl.

7. The compound according to claim 2 wherein $R^2$ represents —COOR$^8$.

8. The compound according to claim 7 wherein R$^8$ represents independently:
   linear or branched $C_1$-$C_6$ alkyl optionally substituted by 1, 2 or 3 substituents selected from fluorine atoms and $C_3$-$C_5$ cycloalkyl optionally substituted by 1, 2 or 3 fluorine atoms; or
   A$^1$ group, which represents $C_3$-$C_6$ cycloalkyl which is optionally substituted by 1, 2 or 3 substituents selected from the group consisting of fluorine atoms and $C_1$-$C_3$ alkyl groups.

9. The compound according to claim 2 wherein $R^3$ is a linear or branched $C_1$-$C_4$ alkyl optionally substituted by 1, 2 or 3 fluorine atoms.

10. The compound according to claim 2 wherein R$^4$ is a group selected from:
    N(R$^6$)R$^7$, wherein R$^6$ and R$^7$ are independently selected from a hydrogen atom and a linear or branched $C_1$-$C_3$ alkyl;
    A$^1$ group, which represents $C_3$-$C_6$ cycloalkyl; or
    linear or branched $C_1$-$C_3$ alkyl optionally substituted by 1, 2 or 3 substituents selected from 1, 2 or 3 fluorine atoms or 1 hydroxyl group.

11. The compound according to claim 1 wherein $X^1$, $X^2$, $X^3$ and $X^5$ represent —CH, $X^4$ represents C—B$^1$, wherein B$^1$ represents —CN group or bromine atom, $R^1$ is a group selected from —C(O)CH$_3$, —C(O)OCH$_3$, —C(O)OCH$_2$-alkynyl and CN, $R^2$ is a group selected from —C(O)O—linear or branched $C_1$-$C_5$ alkyl group optionally substituted by 1, 2 or 3 fluorine atoms and C(O)OCH$_2$-cyclopropyl optionally substituted by 1, 2 or 3 fluorine atoms, $R^3$ is a linear or branched $C_1$-$C_3$ alkyl and $R^4$ is a group selected from a linear or branched $C_1$-$C_3$ alkyl, $C_3$-$C_4$ cycloalkyl and —NH$_2$.

12. The compound according to claim 1 wherein $X^1$, $X^2$, $X^3$ and $X^5$ represent a —CH, $X^4$ represents C—B$^1$, wherein B$^1$ represents —CN group, $R^1$ is a group selected from —C(O)CH$_3$, —C(O)OCH$_3$, $R^2$ is a group selected from —C(O)OCH$_2$-cyclopropyl optionally substituted by 1, 2 or 3 fluorine atoms, and —C(O)OCH$_2$—CF$_3$, $R^3$ is methyl and $R^4$ is a group selected from cyclopropyl and —NH$_2$.

13. The compound according to claim 1, which is selected from the group consisting of:
Methyl 5-acetyl-4-(benzo[b]thiophen-3-yl)-2,6-dimethyl-1,4-dihydro-pyridine-3-carboxylate;
Methyl 5-acetyl-4-(benzo[b]thiophen-3-yl)-2,6-dimethyl-1,4-dihydro-pyridine-3-carboxylate (Enantiomer 1);
Methyl 5-acetyl-4-(benzo[b]thiophen-3-yl)-2,6-dimethyl-1,4-dihydro-pyridine-3-carboxylate (Enantiomer 2);
5-acetyl-4-(benzo[b]thiophen-3-yl)-2,6-dimethyl-1,4-dihydropyridine-3-carboxamide;
1-(4-(benzo[b]thiophen-3-yl)-5-benzoyl-2,6-dimethyl-1,4-dihydropyridin-3-yl)ethan-1-one;
Methyl 5-acetyl-4-(benzo[b]thiophen-3-yl)-6-methyl-2-phenyl-1,4-dihydropyridine-3-carboxylate;
1-(4-(benzo[b]thiophen-3-yl)-2,6-dimethyl-5-nicotinoyl-1,4-dihydro pyridin-3-yl)ethan-1-one;
Methyl 5-acetyl-4-(benzo[b]thiophen-3-yl)-6-methyl-1,4-dihydro-[2,3'-bipyridine]-3-carboxylate;
2,2,2-trifluoroethyl 5-acetyl-4-(benzo[b]thiophen-3-yl)-2,6-dimethyl-1,4-dihydropyridine-3-carboxylate;
5-Acetyl-4-(benzo[b]thiophen-3-yl)-2,6-dimethyl-1,4-dihydropyridine-3-carboxylic acid;
1-(4-(Benzo[b]thiophen-3-yl)-2,6-dimethyl-5-(4-methylpiperazine-1-carbonyl)-1,4-dihydropyridin-3-yl)ethan-1-one;
5-Acetyl-4-(benzo[b]thiophen-3-yl)-N,N-diethyl-2,6-dimethyl-1,4-dihydropyridine-3-carboxamide;
1-(4-(Benzo[b]thiophen-3-yl)-2,6-dimethyl-5-(morpholine-4-carbonyl)-1,4-dihydropyridin-3-yl)ethan-1-one;
2-Methoxyethyl 5-acetyl-4-(benzo[b]thiophen-3-yl)-2,6-dimethyl-1,4-dihydropyridine-3-carboxylate;
3-Acetamidopropyl 5-acetyl-4-(benzo[b]thiophen-3-yl)-2,6-dimethyl-1,4-dihydropyridine-3-carboxylate;
Benzyl 5-acetyl-4-(benzo[b]thiophen-3-yl)-2,6-dimethyl-1,4-dihydro-pyridine-3-carboxylate;
2-Morpholinoethyl 5-acetyl-4-(benzo[b]thiophen-3-yl)-2,6-dimethyl-1,4-dihydropyridine-3-carboxylate;
2-(Dimethylamino)ethyl 5-acetyl-4-(benzo[b]thiophen-3-yl)-2,6-dimethyl-1,4-dihydropyridine-3-carboxylate;
2-Acetamidoethyl 5-acetyl-4-(benzo[b]thiophen-3-yl)-2,6-dimethyl-1,4-dihydropyridine-3-carboxylate;
Methyl 5-acetyl-4-(benzo[b]thiophen-3-yl)-2-(methoxymethyl)-6-methyl-1,4-dihydropyridine-3-carboxylate;
Methyl 5-acetyl-4-(benzo[b]thiophen-3-yl)-2-((dimethylamino)methyl)-6-methyl-1,4-dihydropyridine-3-carboxylate;
Pyridin-4-ylmethyl 5-acetyl-4-(benzo[b]thiophen-3-yl)-2,6-dimethyl-1,4-dihydropyridine-3-carboxylate;
4-Methoxybenzyl 5-acetyl-4-(benzo[b]thiophen-3-yl)-2,6-dimethyl-1,4-dihydropyridine-3-carboxylate;
Pyridin-2-ylmethyl 5-acetyl-4-(benzo[b]thiophen-3-yl)-2,6-dimethyl-1,4-dihydropyridine-3-carboxylate;
Methyl 5-acetyl-4-(benzo[b]thiophen-3-yl)-6-methyl-2-(morpholino-methyl)-1,4-dihydropyridine-3-carboxylate;
Dimethyl 4-(benzo[b]thiophen-3-yl)-2,6-bis(morpholinomethyl)-1,4-dihydropyridine-3,5-dicarboxylate;
2-Hydroxyethyl 5-acetyl-4-(benzo[b]thiophen-3-yl)-2,6-dimethyl-1,4-dihydropyridine-3-carboxylate;
1-(4-(Benzo[b]thiophen-3-yl)-5-(cyclopropanecarbonyl)-6-cyclopropyl-2-methyl-1,4-dihydropyridin-3-yl)ethan-1-one;
Methyl 5-acetyl-4-(benzo[b]thiophen-3-yl)-2-(1-(tert-butoxycarbonyl) azetidin-3-yl)-6-methyl-1,4-dihydropyridine-3-carboxylate;
(1-(tert-Butoxycarbonyl)piperidin-4-yl)methyl 5-acetyl-4-(benzo[b] thiophen-3-yl)-2,6-dimethyl-1,4-dihydropyridine-3-carboxylate;
Cyclohexylmethyl 5-acetyl-4-(benzo[b]thiophen-3-yl)-2,6-dimethyl-1,4-dihydropyridine-3-carboxylate;
5-acetyl-4-(benzo[b]thiophen-3-yl)-2,6-dimethyl-N-phenyl-1,4-dihydropyridine-3-carboxamide;

Tetrahydro-2H-pyran-4-yl 5-acetyl-4-(benzo[b]thiophen-3-yl)-2,6-dimethyl-1,4-dihydropyridine-3-carboxylate;
(Tetrahydro-2H-pyran-4-yl)methyl 5-acetyl-4-(benzo[b]thiophen-3-yl)-2,6-dimethyl-1,4-dihydropyridine-3-carboxylate;
Cyclohexyl 5-acetyl-4-(benzo[b]thiophen-3-yl)-2,6-dimethyl-1,4-dihydropyridine-3-carboxylate;
Methyl 5-acetyl-4-(benzo[b]thiophen-3-yl)-2-(2-methoxy-2-oxoethyl)-6-methyl-1,4-dihydropyridine-3-carboxylate;
Methyl 5-acetyl-2,6-dimethyl-4-(2-methylbenzo[b]thiophen-3-yl)-1,4-dihydropyridine-3-carboxylate;
Cyclopropylmethyl 5-acetyl-4-(benzo[b]thiophen-3-yl)-2,6-dimethyl-1,4-dihydropyridine-3-carboxylate;
Methyl 5-acetyl-4-(benzo[b]thiophen-3-yl)-2-(2-methoxyethyl)-6-methyl-1,4-dihydropyridine-3-carboxylate;
Methyl 5-acetyl-4-(benzo[b]thiophen-3-yl)-2-((benzyloxy)methyl)-6-methyl-1,4-dihydropyridine-3-carboxylate;
Methyl 5-acetyl-4-(benzo[b]thiophen-3-yl)-6-methyl-2-(phenoxymethyl)-1,4-dihydropyridine-3-carboxylate;
Phenethyl 5-acetyl-4-(benzo[b]thiophen-3-yl)-2,6-dimethyl-1,4-dihydropyridine-3-carboxylate;
Methyl 4-(benzo[b]thiophen-3-yl)-5-(cyclopropanecarbonyl)-6-cyclopropyl-2-methyl-1,4-dihydropyridine-3-carboxylate;
Methyl 5-acetyl-4-(benzo[b]thiophen-3-yl)-6-methyl-2-(trifluoromethyl)-1,4-dihydropyridine-3-carboxylate;
Methyl 5-acetyl-4-(benzo[b]thiophen-3-yl)-6-benzyl-2-methyl-1,4-dihydropyridine-3-carboxylate;
Methyl 4-(benzo[b]thiophen-3-yl)-2,6-dimethyl-5-(2-phenylacetyl)-1,4-dihydropyridine-3-carboxylate;
Methyl 4-(benzo[b]thiophen-3-yl)-5-(2-methoxyacetyl)-2,6-dimethyl-1,4-dihydropyridine-3-carboxylate;
Methyl 5-acetyl-4-(benzo[b]thiophen-3-yl)-6-(methoxymethyl)-2-methyl-1,4-dihydropyridine-3-carboxylate;
Methyl 5-acetyl-4-(benzo[b]thiophen-3-yl)-2-(fluoromethyl)-6-methyl-1,4-dihydropyridine-3-carboxylate;
Cyclopropylmethyl 5-acetyl-4-(5-fluorobenzo[b]thiophen-3-yl)-2,6-dimethyl-1,4-dihydropyridine-3-carboxylate;
1-(tert-Butoxycarbonyl)piperidin-4-yl 5-acetyl-4-(benzo[b]thiophen-3-yl)-2,6-dimethyl-1,4-dihydropyridine-3-carboxylate;
Cyclopentylmethyl 5-acetyl-4-(benzo[b]thiophen-3-yl)-2,6-dimethyl-1,4-dihydropyridine-3-carboxylate;
Cyclopropylmethyl 5-acetyl-2,6-dimethyl-4-(thieno[2,3-b]pyridin-3-yl)-1,4-dihydropyridine-3-carboxylate;
1-methylpiperidin-4-yl 5-acetyl-4-(benzo[b]thiophen-3-yl)-2,6-dimethyl-1,4-dihydropyridine-3-carboxylate;
Cyclopentyl 5-acetyl-4-(benzo[b]thiophen-3-yl)-2,6-dimethyl-1,4-dihydropyridine-3-carboxylate;
4,4-dimethylcyclohexyl 5-acetyl-4-(benzo[b]thiophen-3-yl)-2,6-dimethyl-1,4-dihydropyridine-3-carboxylate;
Cyclobutyl 5-acetyl-4-(benzo[b]thiophen-3-yl)-2,6-dimethyl-1,4-dihydropyridine-3-carboxylate;
Methyl 5-acetyl-4-(5-fluorobenzo[b]thiophen-3-yl)-6-methyl-2-(trifluoromethyl)-1,4-dihydropyridine-3-carboxylate;
Methyl 5-acetyl-2,6-dimethyl-4-(thieno[3,2-b]pyridin-3-yl)-1,4-dihydropyridine-3-carboxylate;
Methyl 5-acetyl-4-(benzo[b]thiophen-3-yl)-2-methyl-6-(trifluoromethyl)-1,4-dihydropyridine-3-carboxylate;
Cyclopropylmethyl 5-acetyl-4-(5-chlorobenzo[b]thiophen-3-yl)-2,6-dimethyl-1,4-dihydropyridine-3-carboxylate;
Cyclohexylmethyl 5-acetyl-4-(5-chlorobenzo[b]thiophen-3-yl)-2,6-dimethyl-1,4-dihydropyridine-3-carboxylate;
Cyclohexylmethyl 5-acetyl-2,6-dimethyl-4-(thieno[2,3-b]pyridin-3-yl)-1,4-dihydropyridine-3-carboxylate;
Cyclopentylmethyl 5-acetyl-2,6-dimethyl-4-(thieno[2,3-b]pyridin-3-yl)-1,4-dihydropyridine-3-carboxylate;
Cyclohexyl 5-acetyl-2,6-dimethyl-4-(thieno[2,3-b]pyridin-3-yl)-1,4-dihydropyridine-3-carboxylate;
Cyclopentyl 5-acetyl-2,6-dimethyl-4-(thieno[2,3-b]pyridin-3-yl)-1,4-dihydropyridine-3-carboxylate;
Methyl 5-acetyl-4-(5-chlorobenzo[b]thiophen-3-yl)-6-methyl-2-(trifluoromethyl)-1,4-dihydropyridine-3-carboxylate;
Benzyl 5-acetyl-2,6-dimethyl-4-(thieno[2,3-b]pyridin-3-yl)-1,4-dihydropyridine-3-carboxylate;
(Tetrahydro-2H-pyran-4-yl)methyl 5-acetyl-2,6-dimethyl-4-(thieno[2,3-b]pyridin-3-yl)-1,4-dihydropyridine-3-carboxylate;
Benzyl 5-acetyl-4-(5-fluorobenzo[b]thiophen-3-yl)-2,6-dimethyl-1,4-dihydropyridine-3-carboxylate;
Benzyl 5-acetyl-4-(5-chlorobenzo[b]thiophen-3-yl)-2,6-dimethyl-1,4-dihydropyridine-3-carboxylate;
(Tetrahydro-2H-pyran-4-yl)methyl 5-acetyl-4-(5-chlorobenzo[b]thiophen-3-yl)-2,6-dimethyl-1,4-dihydropyridine-3-carboxylate;
(Tetrahydro-2H-pyran-4-yl)methyl 5-acetyl-4-(5-fluorobenzo[b]thiophen-3-yl)-2,6-dimethyl-1,4-dihydropyridine-3-carboxylate;
Benzyl 5-acetyl-4-(benzo[b]thiophen-3-yl)-6-methyl-2-(trifluoromethyl)-1,4-dihydropyridine-3-carboxylate;
Pyridin-4-ylmethyl 5-acetyl-4-(5-fluorobenzo[b]thiophen-3-yl)-2,6-dimethyl-1,4-dihydropyridine-3-carboxylate;
4-Fluorobenzyl 5-acetyl-2,6-dimethyl-4-(thieno[2,3-b]pyridin-3-yl)-1,4-dihydropyridine-3-carboxylate;
Pyridin-3-ylmethyl 5-acetyl-4-(benzo[b]thiophen-3-yl)-2,6-dimethyl-1,4-dihydropyridine-3-carboxylate;
1,1'-(4-(benzo[b]thiophen-3-yl)-2-benzyl-6-methyl-1,4-dihydropyridine-3,5-diyl)bis(ethan-1-one);
1-(5-acetyl-4-(benzo[b]thiophen-3-yl)-2,6-dimethyl-1,4-dihydropyridin-3-yl)-2-phenylethan-1-one;
Methyl 5-acetyl-6-methyl-4-(thieno[2,3-b]pyridin-3-yl)-2-(trifluoromethyl)-1,4-dihydropyridine-3-carboxylate;
1-(2-methyl-5-(piperidine-1-carbonyl)-4-(thieno[2,3-b]pyridin-3-yl)-6-(trifluoromethyl)-1,4-dihydropyridin-3-yl)ethan-1-one;
4-(((5-acetyl-4-(benzo[b]thiophen-3-yl)-2,6-dimethyl-1,4-dihydro-pyridine-3-carbonyl)oxy)methyl)benzoic acid;
Benzyl 5-acetyl-6-methyl-4-(thieno[2,3-b]pyridin-3-yl)-2-(trifluoromethyl)-1,4-dihydropyridine-3-carboxylate;
Pyridin-3-ylmethyl 5-acetyl-4-(5-fluorobenzo[b]thiophen-3-yl)-2,6-dimethyl-1,4-dihydropyridine-3-carboxylate;
Pyridin-3-ylmethyl 5-acetyl-4-(7-bromobenzo[b]thiophen-3-yl)-2,6-dimethyl-1,4-dihydropyridine-3-carboxylate;
Pyridin-3-ylmethyl 5-acetyl-4-(7-cyanobenzo[b]thiophen-3-yl)-2,6-dimethyl-1,4-dihydropyridine-3-carboxylate;

Pyridin-3-ylmethyl 5-acetyl-4-(5-chlorobenzo[b]thiophen-3-yl)-2,6-dimethyl-1,4-dihydropyridine-3-carboxylate;
Pyridin-3-ylmethyl 5-acetyl-2,6-dimethyl-4-(thieno[2,3-b]pyridin-3-yl)-1,4-dihydropyridine-3-carboxylate;
Pyridin-4-ylmethyl 5-acetyl-4-(5-chlorobenzo[b]thiophen-3-yl)-2,6-dimethyl-1,4-dihydropyridine-3-carboxylate;
4-(Cyclopropylcarbamoyl)benzyl 5-acetyl-4-(benzo[b]thiophen-3-yl)-2,6-dimethyl-1,4-dihydropyridine-3-carboxylate;
Pyridin-4-ylmethyl 5-acetyl-2,6-dimethyl-4-(thieno[2,3-b]pyridin-3-yl)-1,4dihydropyridine-3-carboxylate;
4-Bromobenzyl 5-acetyl-2,6-dimethyl-4-(thieno[2,3-b]pyridin-3-yl)-1,4-dihydropyridine-3-carboxylate;
3-Bromobenzyl 5-acetyl-2,6-dimethyl-4-(thieno[2,3-b]pyridin-3-yl)-1,4-dihydropyridine-3-carboxylate;
2-Bromobenzyl 5-acetyl-2,6-dimethyl-4-(thieno[2,3-b]pyridin-3-yl)-1,4-dihydropyridine-3-carboxylate;
(3-Fluoropyridin-4-yl)methyl 5-acetyl-2,6-dimethyl-4-(thieno[2,3-b]pyridin-3-yl)-1,4-dihydropyridine-3-carboxylate;
Pyrimidin-5-ylmethyl 5-acetyl-2,6-dimethyl-4-(thieno[2,3-b]pyridin-3-yl)-1,4-dihydropyridine-3-carboxylate;
(5-Bromopyridin-3-yl)methyl 5-acetyl-2,6-dimethyl-4-(thieno[2,3-b]pyridin-3-yl)-1,4-dihydropyridine-3-carboxylate;
2-Phenylpropan-2-yl 5-acetyl-2,6-dimethyl-4-(thieno[2,3-b]pyridin-3-yl)-1,4-dihydropyridine-3-carboxylate;
3-cyanobenzyl 5-acetyl-2,6-dimethyl-4-(thieno[2,3-b]pyridin-3-yl)-1,4-dihydropyridine-3-carboxylate;
4-cyanobenzyl 5-acetyl-2,6-dimethyl-4-(thieno[2,3-b]pyridin-3-yl)-1,4-dihydropyridine-3-carboxylate;
(6-Chloropyridin-3-yl)methyl 5-acetyl-2,6-dimethyl-4-(thieno[2,3-b]pyridin-3-yl)-1,4-dihydropyridine-3-carboxylate;
3-Morpholinobenzyl 5-acetyl-2,6-dimethyl-4-(thieno[2,3-b]pyridin-3-yl)-1,4-dihydropyridine-3-carboxylate;
4,4-Dimethylcyclohexyl 5-acetyl-2,6-dimethyl-4-(thieno[2,3-b]pyridin-3-yl)-1,4-dihydropyridine-3-carboxylate;
(2-Chloropyridin-4-yl)methyl 5-acetyl-2,6-dimethyl-4-(thieno[2,3-b]pyridin-3-yl)-1,4-dihydropyridine-3-carboxylate;
Tetrahydro-2H-pyran-4-yl 5-acetyl-2,6-dimethyl-4-(thieno[2,3-b]pyridin-3-yl)-1,4-dihydropyridine-3-carboxylate;
4,4-Difluorocyclohexyl 5-acetyl-2,6-dimethyl-4-(thieno[2,3-b]pyridin-3-yl)-1,4-dihydropyridine-3-carboxylate;
5-Acetyl-N-benzyl-N,2,6-trimethyl-4-(thieno[2,3-b]pyridin-3-yl)-1,4-dihydropyridine-3-carboxamide;
Oxetan-3-yl 5-acetyl-4-(7-bromobenzo[b]thiophen-3-yl)-2-cyclopropyl-6-methyl-1,4-dihydropyridine-3-carboxylate;
Isopropyl 5-acetyl-4-(7-bromobenzo[b]thiophen-3-yl)-2-cyclopropyl-6-methyl-1,4-dihydropyridine-3-carboxylate;
Methyl 5-acetyl-4-(7-bromobenzo[b]thiophen-3-yl)-6-methyl-2-(trifluoromethyl)-1,4-dihydropyridine-3-carboxylate;
Cyclopropylmethyl 5-acetyl-4-(7-bromobenzo[b]thiophen-3-yl)-2-cyclopropyl-6-methyl-1,4-dihydropyridine-3-carboxylate;
Methyl 5-acetyl-2-cyclopropyl-6-methyl-4-(7-(2,2,2-trifluoroacetyl) benzo[b]thiophen-3-yl)-1,4-dihydropyridine-3-carboxylate;
2-Phenylpropan-2-yl 5-acetyl-4-(7-bromobenzo[b]thiophen-3-yl)-2,6-dimethyl-1,4-dihydropyridine-3-carboxylate;
Methyl 5-acetyl-2-amino-4-(benzo[b]thiophen-3-yl)-6-methyl-1,4-dihydropyridine-3-carboxylate;
Methyl 2-amino-4-(benzo[b]thiophen-3-yl)-5-(cyclopropanecarbonyl)-6-methyl-1,4-dihydropyridine-3-carboxylate;
Methyl 5-acetyl-2-amino-4-(5-fluorobenzo[b]thiophen-3-yl)-6-methyl-1,4-dihydropyridine-3-carboxylate;
Methyl 5-acetyl-2-amino-4-(7-bromobenzo[b]thiophen-3-yl)-6-methyl-1,4-dihydropyridine-3-carboxylate;
Methyl 5-acetyl-2-amino-4-(7-cyanobenzo[b]thiophen-3-yl)-6-methyl-1,4-dihydropyridine-3-carboxylate;
Cyclopentyl 5-acetyl-2-amino-4-(7-bromobenzo[b]thiophen-3-yl)-6-methyl-1,4-dihydropyridine-3-carboxylate;
Dimethyl 2-amino-4-(7-cyanobenzo[b]thiophen-3-yl)-6-methyl-1,4-dihydropyridine-3,5-dicarboxylate;
Cyclopentyl 5-acetyl-2-amino-4-(7-cyanobenzo[b]thiophen-3-yl)-6-methyl-1,4-dihydropyridine-3-carboxylate;
cyclopropylmethyl 5-acetyl-2-amino-4-(7-cyanobenzo[b]thiophen-3-yl)-6-methyl-1,4-dihydropyridine-3-carboxylate;
4,4-difluorocyclohexyl 5-acetyl-2-amino-4-(7-cyanobenzo[b]thiophen-3-yl)-6-methyl-1,4-dihydropyridine-3-carboxylate;
methyl 2-amino-5-cyano-4-(7-cyanobenzo[b]thiophen-3-yl)-6-methyl-1,4-dihydropyridine-3-carboxylate;
4-fluorobenzyl 5-acetyl-2-amino-4-(7-cyanobenzo[b]thiophen-3-yl)-6-methyl-1,4-dihydropyridine-3-carboxylate;
methyl 5-acetyl-2-amino-4-(5-fluorothieno[2,3-b]pyridin-3-yl)-6-methyl-1,4-dihydropyridine-3-carboxylate;
methyl 2-acetamido-5-acetyl-4-(5-fluorothieno[2,3-b]pyridin-3-yl)-6-methyl-1,4-dihydropyridine-3-carboxylate;
cyclopentylmethyl 5-acetyl-2-amino-4-(7-cyanobenzo[b]thiophen-3-yl)-6-methyl-1,4-dihydropyridine-3-carboxylate;
3-(cyclopropylmethyl) 5-methyl 2-amino-4-(7-cyanobenzo[b]thiophen-3-yl)-6-methyl-1,4-dihydropyridine-3,5-dicarboxylate;
3-(4-fluorobenzyl) 5-methyl 2-amino-4-(7-cyanobenzo[b]thiophen-3-yl)-6-methyl-1,4-dihydropyridine-3,5-dicarboxylate;
Cyclopropylmethyl 2-amino-5-cyano-4-(7-cyanobenzo[b]thiophen-3-yl)-6-methyl-1,4-dihydropyridine-3-carboxylate;
4-Fluorobenzyl 2-amino-5-cyano-4-(7-cyanobenzo[b]thiophen-3-yl)-6-methyl-1,4-dihydropyridine-3-carboxylate;
3-Cyclopentyl 5-methyl 2-amino-4-(7-cyanobenzo[b]thiophen-3-yl)-6-methyl-1,4-dihydropyridine-3,5-dicarboxylate;
Cyclopropylmethyl 5-acetyl-2-amino-4-(6-cyanobenzo[b]thiophen-3-yl)-6-methyl-1,4-dihydropyridine-3-carboxylate;
Cyclohexyl 5-acetyl-2-amino-4-(7-cyanobenzo[b]thiophen-3-yl)-6-methyl-1,4-dihydropyridine-3-carboxylate;
Cyclohexylmethyl 5-acetyl-2-amino-4-(7-cyanobenzo[b]thiophen-3-yl)-6-methyl-1,4-dihydropyridine-3-carboxylate;

Cyclopropylmethyl 2-amino-4-(7-cyanobenzo[b]thiophen-3-yl)-5-(cyclopropanecarbonyl)-6-methyl-1,4-dihydropyridine-3-carboxylate;

3-Fluorobenzyl 5-acetyl-2-amino-4-(7-cyanobenzo[b]thiophen-3-yl)-6-methyl-1,4-dihydropyridine-3-carboxylate;

3-(Cyclobutylmethyl) 5-methyl 2-amino-4-(7-cyanobenzo[b]thiophen-3-yl)-6-methyl-1,4-dihydropyridine-3,5-dicarboxylate;

3-((3,3-Difluorocyclobutyl)methyl) 5-methyl 2-amino-4-(7-cyanobenzo[b]thiophen-3-yl)-6-methyl-1,4-dihydropyridine-3,5-dicarboxylate;

Cyclopropylmethyl 2-amino-5-carbamoyl-4-(7-cyanobenzo[b]thiophen-3-yl)-6-methyl-1,4-dihydropyridine-3-carboxylate;

3-((2,2-Difluorocyclopropyl)methyl) 5-methyl 2-amino-4-(7-cyanobenzo[b]thiophen-3-yl)-6-methyl-1,4-dihydropyridine-3,5-dicarboxylate;

5-Cyclopropyl 3-(cyclopropylmethyl) 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(7-cyano-5-fluorobenzo[b]thiophen-3-yl)-6-methyl-1,4-dihydropyridine-3,5-dicarboxylate;

3-(cyclopropylmethyl) 5-methyl 2-amino-4-(7-cyano-4-fluorobenzo[b]thiophen-3-yl)-6-methyl-1,4-dihydropyridine-3,5-dicarboxylate;

3-Isopropyl 5-methyl 2-amino-4-(7-cyanobenzo[b]thiophen-3-yl)-6-methyl-1,4-dihydropyridine-3,5-dicarboxylate;

3-((2,2-Difluoro-3,3-dimethylcyclopropyl)methyl) 5-methyl 2-amino-4-(7-cyanobenzo[b]thiophen-3-yl)-6-methyl-1,4-dihydropyridine-3,5-dicarboxylate;

5-Methyl 3-neopentyl 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(7-cyanothieno[3,2-b]pyridin-3-yl)-6-methyl-1,4-dihydropyridine-3,5-dicarboxylate;

Bis(cyclopropylmethyl) 2-amino-4-(7-cyanobenzo[b]thiophen-3-yl)-6-methyl-1,4-dihydropyridine-3,5-dicarboxylate;

3-(Cyclopropylmethyl) 5-(prop-2-yn-1-yl) 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(5,7-dicyanobenzo[b]thiophen-3-yl)-6-methyl-1,4-dihydropyridine-3,5-dicarboxylate;

5-(But-2-yn-1-yl) 3-(cyclopropylmethyl) 2-amino-4-(7-cyanobenzo[b]thiophen-3-yl)-6-methyl-1,4-dihydropyridine-3,5-dicarboxylate;

5-Methyl 3-(2,2,2-trifluoroethyl) 2-amino-4-(7-cyanobenzo[b]thiophen-3-yl)-6-methyl-1,4-dihydropyridine-3,5-dicarboxylate;

3-(Cyclopropylmethyl) 5-(2,2,2-trifluoroethyl) 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(6-chloro-7-cyanobenzo[b]thiophen-3-yl)-6-methyl-1,4-dihydropyridine-3,5-dicarboxylate;

3-(2-Fluoro-2-methylpropyl) 5-methyl 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(7-cyano-6-(trifluoromethyl)benzo[b]thiophen-3-yl)-6-methyl-1,4-dihydropyridine-3,5-dicarboxylate;

5-Methyl 3-prop-2-yn-1-yl 2-amino-4-(7-cyanobenzo[b]thiophen-3-yl)-6-methyl-1,4-dihydropyridine-3,5-dicarboxylate;

3-(Cyclopropylmethyl) 5-methyl 2-amino-4-(7-cyanobenzo[b]thiophen-3-yl)-6-(trifluoromethyl)-1,4-dihydropyridine-3,5-dicarboxylate;

4-(Benzo[b]thiophen-3-yl)-2,6-dimethyl-1,4-dihydropyridine-3,5-dicarbonitrile;

4-(6-hydroxybenzo[b]thiophen-3-yl)-2,6-dimethyl-1,4-dihydropyridine-3,5-dicarbonitrile;

4-(6-methoxybenzo[b]thiophen-3-yl)-2,6-dimethyl-1,4-dihydropyridine-3,5-dicarbonitrile;

2,6-dimethyl-4-(thieno[2,3-b]pyridin-3-yl)-1,4-dihydropyridine-3,5-dicarbonitrile;

4-(benzo[b]thiophen-3-yl)-2-methyl-6-phenyl-1,4-dihydropyridine-3,5-dicarbonitrile;

4-(benzo[b]thiophen-3-yl)-2-cyclopropyl-6-methyl-1,4-dihydropyridine-3,5-dicarbonitrile;

5-acetyl-4-(benzo[b]thiophen-3-yl)-2,6-dimethyl-1,4-dihydropyridine-3-carbonitrile;

Ethyl 4-(benzo[b]thiophen-3-yl)-5-cyano-2,6-dimethyl-1,4-dihydropyridine-3-carboxylate;

Ethyl 4-(benzo[b]thiophen-3-yl)-5-cyano-2-methyl-6-phenyl-1,4-dihydropyridine-3-carboxylate;

Ethyl 4-(benzo[b]thiophen-3-yl)-5-cyano-2-cyclopropyl-6-methyl-1,4-dihydropyridine-3-carboxylate;

Methyl 4-(benzo[b]thiophen-3-yl)-5-cyano-2-cyclopropyl-6-methyl-1,4-dihydropyridine-3-carboxylate;

1,1'-(4-(benzo[b]thiophen-3-yl)-2,6-dimethyl-1,4-dihydropyridine-3,5-diyl)diethanone;

1,1'-(4-(6-hydroxybenzo[b]thiophen-3-yl)-2,6-dimethyl-1,4-dihydropyridine-3,5-diyl)bis(ethan-1-one);

1,1'-(4-(6-Methoxybenzo[b]thiophen-3-yl)-2,6-dimethyl-1,4-dihydropyridine-3,5-diyl)diethanone;

1,1'-(4-(5-chlorobenzo[b]thiophen-3-yl)-2,6-dimethyl-1,4-dihydropyridine-3,5-diyl)diethanone;

1,1'-(4-(5-bromobenzo[b]thiophen-3-yl)-2,6-dimethyl-1,4-dihydropyridine-3,5-diyl)diethanone;

1,1'-(4-(5-fluorobenzo[b]thiophen-3-yl)-2,6-dimethyl-1,4-dihydropyridine-3,5-diyl)bis(ethan-1-one);

1,1'-(2,6-dimethyl-4-(5-morpholinobenzo[b]thiophen-3-yl)-1,4-dihydropyridine-3,5-diyl)bis(ethan-1-one);

1,1'-(2,6-dimethyl-4-(5-(4-methylpiperazin-1-yl)benzo[b]thiophen-3-yl)-1,4-dihydropyridine-3,5-diyl)bis(ethan-1-one);

1,1'-(4-(5-(benzylamino)benzo[b]thiophen-3-yl)-2,6-dimethyl-1,4-dihydropyridine-3,5-diyl)bis(ethan-1-one);

3-(3,5-diacetyl-2,6-dimethyl-1,4-dihydropyridin-4-yl)benzo[b]thiophene-5-carbonitrile;

3-(3,5-diacetyl-2,6-dimethyl-1,4-dihydropyridin-4-yl)benzo[b]thiophene-5-carboxylic acid;

N-cyclopropyl-3-(3,5-diacetyl-2,6-dimethyl-1,4-dihydropyridin-4-yl)benzo[b]thiophene-5-carboxamide;

N-(cyclopropylmethyl)-3-(3,5-diacetyl-2,6-dimethyl-1,4-dihydropyridin-4-yl)benzo[b]thiophene-5-carboxamide;

1,1'-(2,6-Dimethyl-4-(5-(4-methylpiperazine-1-carbonyl)benzo[b]thiophen-3-yl)-1,4-dihydropyridine-3,5-diyl)bis(ethan-1-one);

1,1'-(2,6-Dimethyl-4-(5-(morpholine-4-carbonyl)benzo[b]thiophen-3-yl)-1,4-dihydropyridine-3,5-diyl)bis(ethan-1-one);

1,1'-(2,6-Dimethyl-4-(thieno[2,3-b]pyridin-3-yl)-1,4-dihydropyridine-3,5-diyl)bis(ethan-1-one);

Dimethyl 5-acetyl-4-(benzo[b]thiophen-3-yl)-6-methyl-1,4-dihydropyridine-2,3-dicarboxylate;

Dimethyl 5-acetyl-4-(7-cyanobenzo[b]thiophen-3-yl)-6-methyl-1,4-dihydropyridine-2,3-dicarboxylate;
Methyl 5-acetyl-4-(benzo[b]thiophen-3-yl)-2-cyclopropyl-6-methyl-1,4-dihydropyridine-3-carboxylate;
Ethyl 5-acetyl-4-(benzo[b]thiophen-3-yl)-2,6-dimethyl-1,4-dihydropyridine-3-carboxylate;
Methyl 5-acetyl-4-(5-chlorobenzo[b]thiophen-3-yl)-2,6-dimethyl-1,4-dihydropyridine-3-carboxylate;
1,1'-(4-(benzo[b]thiophen-3-yl)-2-cyclopropyl-6-methyl-1,4-dihydro-pyridine-3,5-diyl)diethanone;
1-(4-(benzo[b]thiophen-3-yl)-2,6-dimethyl-5-(methylsulfonyl)-1,4-dihydro-pyridin-3-yl)ethanone;
Methyl 5-acetyl-4-(5-fluorobenzo[b]thiophen-3-yl)-2,6-dimethyl-1,4-dihydropyridine-3-carboxylate;
Methyl 5-acetyl-4-(5-bromobenzo[b]thiophen-3-yl)-2,6-dimethyl-1,4-dihydropyridine-3-carboxylate;
methyl 5-acetyl-4-(5-cyanobenzo[b]thiophen-3-yl)-2,6-dimethyl-1,4-dihydropyridine-3-carboxylate;
3-(3-acetyl-5-(methoxycarbonyl)-2,6-dimethyl-1,4-dihydropyridin-4-yl)benzo[b]thiophene-5-carboxylic acid;
methyl 5-acetyl-4-(5-(cyclopropylcarbamoyl)benzo[b]thiophen-3-yl)-2,6-dimethyl-1,4-dihydropyridine-3-carboxylate;
Methyl 5-acetyl-4-(5-((cyclopropylmethyl)carbamoyl)benzo[b]thiophen-3-yl)-2,6-dimethyl-1,4-dihydropyridine-3-carboxylate;
Methyl 5-acetyl-2,6-dimethyl-4-(5-(4-methylpiperazine-1-carbonyl)benzo[b]thiophen-3-yl)-1,4-dihydropyridine-3-carboxylate;
Methyl 5-acetyl-2,6-dimethyl-4-(5-(morpholine-4-carbonyl)benzo[b]thiophen-3-yl)-1,4-dihydropyridine-3-carboxylate;
Methyl 5-acetyl-2,6-dimethyl-4-(thieno[2,3-b]pyridin-3-yl)-1,4-dihydropyridine-3-carboxylate;
Methyl 5-acetyl-2-cyclopropyl-4-(5-fluorobenzo[b]thiophen-3-yl)-6-methyl-1,4-dihydropyridine-3-carboxylate;
Methyl 5-acetyl-2-cyclopropyl-6-methyl-4-(thieno[2,3-b]pyridin-3-yl)-1,4-dihydropyridine-3-carboxylate;
Methyl 5-acetyl-4-(5-chlorobenzo[b]thiophen-3-yl)-2-cyclopropyl-6-methyl-1,4-dihydropyridine-3-carboxylate;
Methyl 5-acetyl-4-(7-bromobenzo[b]thiophen-3-yl)-2-cyclopropyl-6-methyl-1,4-dihydropyridine-3-carboxylate;
Methyl 5-acetyl-2-cyclopropyl-4-(7-(cyclopropylcarbamoyl)benzo[b] thiophen-3-yl)-6-methyl-1,4-dihydropyridine-3-carboxylate;
Methyl 5-acetyl-4-(7-cyanobenzo[b]thiophen-3-yl)-2-cyclopropyl-6-methyl-1,4-dihydropyridine-3-carboxylate;
Methyl 5-acetyl-2-cyclopropyl-4-(7-(methoxycarbonyl)benzo[b]thiophen-3-yl)-6-methyl-1,4-dihydropyridine-3-carboxylate;
3-(3-Acetyl-6-cyclopropyl-5-(methoxycarbonyl)-2-methyl-1,4-dihydropyridin-4-yl)benzo[b]thiophene-7-carboxylic acid;
Benzyl 5-acetyl-2-cyclopropyl-6-methyl-4-(thieno[2,3-b]pyridin-3-yl)-1,4-dihydropyridine-3-carboxylate;
Pyridin-4-ylmethyl 5-acetyl-4-(benzo[b]thiophen-3-yl)-2-cyclopropyl-6-methyl-1,4-dihydropyridine-3-carboxylate;
bis(pyridin-4-ylmethyl) 2,6-dicyclopropyl-4-(thieno[2,3-b]pyridin-3-yl)-1,4-dihydropyridine-3,5-dicarboxylate;
Pyridin-4-ylmethyl 5-acetyl-4-(7-bromobenzo[b]thiophen-3-yl)-2,6-dimethyl-1,4-dihydropyridine-3-carboxylate;
Pyridin-4-ylmethyl 5-acetyl-4-(5-chlorobenzo[b]thiophen-3-yl)-2-cyclopropyl-6-methyl-1,4-dihydropyridine-3-carboxylate;
Pyridin-4-ylmethyl 5-acetyl-4-(7-cyanobenzo[b]thiophen-3-yl)-2-cyclopropyl-6-methyl-1,4-dihydropyridine-3-carboxylate;
Pyridin-4-ylmethyl 5-acetyl-2-cyclopropyl-6-methyl-4-(thieno[2,3-b]pyridin-3-yl)-1,4-dihydropyridine-3-carboxylate;
Benzyl 5-acetyl-2-cyclopropyl-4-(7-(methoxycarbonyl)benzo[b]thiophen-3-yl)-6-methyl-1,4-dihydropyridine-3-carboxylate;
Benzyl 5-acetyl-4-(7-(methoxycarbonyl)benzo[b]thiophen-3-yl)-2,6-dimethyl-1,4-dihydropyridine-3-carboxylate;
Methyl 3-(3,5-diacetyl-2,6-dimethyl-1,4-dihydropyridin-4-yl)benzo[b]thiophene-7-carboxylate;
3-(3,5-Diacetyl-2,6-dimethyl-1,4-dihydropyridin-4-yl)benzo[b]thiophene-7-carbonitrile;
Pyridin-4-ylmethyl 5-acetyl-4-(7-bromobenzo[b]thiophen-3-yl)-2-cyclopropyl-6-methyl-1,4-dihydropyridine-3-carboxylate;
4-Fluorobenzyl 5-acetyl-2-cyclopropyl-6-methyl-4-(thieno[2,3-b]pyridin-3-yl)-1,4-dihydropyridine-3-carboxylate;
4-cyanobenzyl 5-acetyl-2-cyclopropyl-6-methyl-4-(thieno[2,3-b]pyridin-3-yl)-1,4-dihydropyridine-3-carboxylate;
Methyl 5-acetyl-4-(7-chlorobenzo[b]thiophen-3-yl)-2-cyclopropyl-6-methyl-1,4-dihydropyridine-3-carboxylate;
methyl 5-acetyl-2-cyclopropyl-6-methyl-4-(7-(trifluoromethyl)benzo[b]thiophen-3-yl)-1,4-dihydropyridine-3-carboxylate;
3-chlorobenzyl 5-acetyl-2,6-dimethyl-4-(thieno[2,3-b]pyridin-3-yl)-1,4-dihydropyridine-3-carboxylate;
2-phenylpropan-2-yl 5-acetyl-4-(7-bromobenzo[b]thiophen-3-yl)-2-cyclopropyl-6-methyl-1,4-dihydropyridine-3-carboxylate;
Cyclohexyl 5-acetyl-2-cyclopropyl-6-methyl-4-(thieno[2,3-b]pyridin-3-yl)-1,4-dihydropyridine-3-carboxylate;
2-Phenylpropan-2-yl 5-acetyl-2-cyclopropyl-6-methyl-4-(thieno[2,3-b]pyridin-3-yl)-1,4-dihydropyridine-3-carboxylate;
1-(4-(7-Bromobenzo[b]thiophen-3-yl)-5-(cyclopropanecarbonyl)-6-cyclopropyl-2-methyl-1,4-dihydropyridin-3-yl)ethan-1-one;
3-chlorobenzyl 5-acetyl-2-cyclopropyl-6-methyl-4-(thieno[2,3-b]pyridin-3-yl)-1,4-dihydropyridine-3-carboxylate;
2-(4-Fluorophenyl)propan-2-yl 5-acetyl-2,6-dimethyl-4-(thieno[2,3-b]pyridin-3-yl)-1,4-dihydropyridine-3-carboxylate;
2-(4-fluorophenyl)propan-2-yl 5-acetyl-4-(7-bromobenzo[b]thiophen-3-yl)-2-cyclopropyl-6-methyl-1,4-dihydropyridine-3-carboxylate;
2-(4-fluorophenyl)propan-2-yl 5-acetyl-2-cyclopropyl-6-methyl-4-(thieno[2,3-b]pyridin-3-yl)-1,4-dihydropyridine-3-carboxylate;
Methyl 5-acetyl-2-cyclopropyl-4-(7-fluorobenzo[b]thiophen-3-yl)-6-methyl-1,4-dihydropyridine-3-carboxylate;
Cyclopropylmethyl 5-acetyl-2-cyclopropyl-6-methyl-4-(thieno[2,3-b]pyridin-3-yl)-1,4-dihydropyridine-3-carboxylate;

Cyclopentyl 5-acetyl-2-cyclopropyl-6-methyl-4-(thieno[2,3-b]pyridin-3-yl)-1,4-dihydropyridine-3-carboxylate;
Cyclopropylmethyl 5-acetyl-4-(7-cyanobenzo[b]thiophen-3-yl)-2-cyclopropyl-6-methyl-1,4-dihydropyridine-3-carboxylate;
Methyl 5-acetyl-4-(7-bromobenzo[b]thiophen-3-yl)-2-cyclobutyl-6-methyl-1,4-dihydropyridine-3-carboxylate;
Dimethyl 4-(7-cyanobenzo[b]thiophen-3-yl)-2-cyclopropyl-6-methyl-1,4-dihydropyridine-3,5-dicarboxylate;
Methyl 5-cyano-4-(7-cyanobenzo[b]thiophen-3-yl)-2-cyclopropyl-6-methyl-1,4-dihydropyridine-3-carboxylate;
Methyl 5-acetyl-4-(7-bromobenzo[b]thiophen-3-yl)-2-cyclopentyl-6-methyl-1,4-dihydropyridine-3-carboxylate;
Methyl 5-acetyl-4-(7-bromobenzo[b]thiophen-3-yl)-2-cyclohexyl-6-methyl-1,4-dihydropyridine-3-carboxylate;
3-((4-Methylpiperazin-1-yl)methyl)benzyl 5-acetyl-4-(7-bromobenzo[b]thiophen-3-yl)-2,6-dimethyl-1,4-dihydropyridine-3-carboxylate;
3-(cyclopropylmethyl) 5-methyl 4-(7-cyanobenzo[b]thiophen-3-yl)-2-cyclopropyl-6-methyl-1,4-dihydropyridine-3,5-dicarboxylate;
cyclopropylmethyl 5-cyano-4-(7-cyanobenzo[b]thiophen-3-yl)-2-cyclopropyl-6-methyl-1,4-dihydropyridine-3-carboxylate;
dimethyl 2-cyano-4-(7-cyanobenzo[b]thiophen-3-yl)-6-methyl-1,4-dihydropyridine-3,5-dicarboxylate;
methyl 5-acetyl-2-((2-aminoethoxy)methyl)-4-(benzo[b]thiophen-3-yl)-6-methyl-1,4-dihydropyridine-3-carboxylate;
methyl 5-acetyl-2-((2-aminoethoxy)methyl)-4-(7-bromobenzo[b]thiophen-3-yl)-6-methyl-1,4-dihydropyridine-3-carboxylate;
methyl 5-acetyl-2-((2-aminoethoxy)methyl)-4-(7-cyanobenzo[b]thiophen-3-yl)-6-methyl-1,4-dihydropyridine-3-carboxylate;
Dimethyl 4-(7-cyanobenzo[b]thiophen-3-yl)-2-cyclopropyl-6-(hydroxymethyl)-1,4-dihydropyridine-3,5-dicarboxylate;
Dimethyl 4-(7-cyanobenzo[b]thiophen-3-yl)-2-formyl-6-methyl-1,4-dihydropyridine-3,5-dicarboxylate;
Dimethyl 2-cyano-6-methyl-4-(thieno[2,3-b]pyridin-3-yl)-1,4-dihydropyridine-3,5-dicarboxylate;
Cyclopropylmethyl 5-acetyl-4-(6-cyanobenzo[b]thiophen-3-yl)-2-cyclopropyl-6-methyl-1,4-dihydropyridine-3-carboxylate;
Cyclopropylmethyl 2,5-diacetyl-4-(7-cyanobenzo[b]thiophen-3-yl)-6-methyl-1,4-dihydropyridine-3-carboxylate;
Methyl 5-acetyl-2-amino-4-(benzo[b]thiophen-3-yl)-6-methyl-1,4-dihydropyridine-3-carboxylate hydrochloride;
Methyl 5-acetyl-2-amino-4-(benzo[b]thiophen-3-yl)-6-methyl-1,4-dihydropyridine-3-carboxylate trifluoromethanesulfonate;
4-(Pyridin-4-yl)benzyl 5-acetyl-2,6-dimethyl-4-(thieno[2,3-b]pyridin-3-yl)-1,4 dihydropyridine-3-carboxylate;
4-(Pyridin-3-yl)benzyl 5-acetyl-2,6-dimethyl-4-(thieno[2,3-b]pyridin-3-yl)-1,4-dihydropyridine-3-carboxylate;
3-(Pyridin-4-yl)benzyl 5-acetyl-2,6-dimethyl-4-(thieno[2,3-b]pyridin-3-yl)-1,4-dihydropyridine-3-carboxylate;
3-(Pyridin-3-yl)benzyl 5-acetyl-2,6-dimethyl-4-(thieno[2,3-b]pyridin-3-yl)-1,4-dihydropyridine-3-carboxylate;
2-(Pyridin-4-yl)benzyl 5-acetyl-2,6-dimethyl-4-(thieno[2,3-b]pyridin-3-yl)-1,4-dihydropyridine-3-carboxylate;
2-(pyridin-3-yl)benzyl 5-acetyl-2,6-dimethyl-4-(thieno[2,3-b]pyridin-3-yl)-1,4-dihydropyridine-3-carboxylate;
[3,4'-Bipyridin]-5-ylmethyl 5-acetyl-2,6-dimethyl-4-(thieno[2,3-b]pyridin-3-yl)-1,4-dihydropyridine-3-carboxylate;
[3,3'-Bipyridin]-5-ylmethyl 5-acetyl-2,6-dimethyl-4-(thieno[2,3-b]pyridin-3-yl)-1,4-dihydropyridine-3-carboxylate;
[2,4'-Bipyridin]-5-ylmethyl 5-acetyl-2,6-dimethyl-4-(thieno[2,3-b]pyridin-3-yl)-1,4-dihydropyridine-3-carboxylate;
[2,3'-Bipyridin]-5-ylmethyl 5-acetyl-2,6-dimethyl-4-(thieno[2,3-b]pyridin-3-yl)-1,4-dihydropyridine-3-carboxylate;
[2,3'-Bipyridin]-4-ylmethyl 5-acetyl-2,6-dimethyl-4-(thieno[2,3-b]pyridin-3-yl)-1,4-dihydropyridine-3-carboxylate;
[2,4'-Bipyridin]-4-ylmethyl 5-acetyl-2,6-dimethyl-4-(thieno[2,3-b]pyridin-3-yl)-1,4-dihydropyridine-3-carboxylate;
Methyl 5-acetyl-2-cyclopropyl-6-methyl-4-(7-(pyridin-4-yl)benzo[b]thiophen-3-yl)-1,4-dihydropyridine-3-carboxylate;
Methyl 5-acetyl-2-cyclopropyl-4-(7-cyclopropylbenzo[b]thiophen-3-yl)-6-methyl-1,4-dihydropyridine-3-carboxylate;
3-(Pyridin-4-yl)benzyl 5-acetyl-2-cyclopropyl-6-methyl-4-(thieno[2,3-b]pyridin-3-yl)-1,4-dihydropyridine-3-carboxylate;
1,1'-(2,6-Dimethyl-4-(5-(pyridin-3-yl)benzo[b]thiophen-3-yl)-1,4-dihydro-pyridine-3,5-diyl)diethanone; and
Methyl 5-acetyl-2-cyclopropyl-6-methyl-4-(7-phenylbenzo[b]thiophen-3-yl)-1,4-dihydropyridine-3-carboxylate.

14. A pharmaceutical composition comprising a compound as defined in claim 1 and a pharmaceutically acceptable diluent or carrier.

15. The pharmaceutical composition according to claim 14 further comprising a therapeutically effective amount of a therapeutic agent selected from agents for treating prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

16. A combination product comprising a compound according to claim 1 and a therapeutic agent used for the treatment of prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

17. The combination product according to claim 16 wherein the therapeutic agent is selected from gonadotropin-releasing hormone (GnRH) receptor agonist or antagonist, androgen receptor antagonist, CYP17 inhibitor, VEGF inhibitor, EGFR inhibitor, PI3K inhibitor, AKT inhibitor, mTOR inhibitor, c-Met inhibitor, Src, inhibitor, PARP inhibitor, angiopoietin, ALK inhibitor, ROS-1 inhibitor, anti-(IGF) antibodies, taxane anti-neoplastic agent, topoisomerase II inhibitor, anti-tumor antibiotic, HSP90 inhibitor, aurora kinase inhibitor, PSA-directed vaccine, GR antagonists, 11-beta HSD inhibitors, one or more immunotherapeutic agent selected from the group consisting of antibodies anti-CTLA4, antibodies anti-PD1 and antibodies anti-PDL1.

18. The combination product according to claim 17 wherein the immunotherapeutic agent is selected from the group consisting of ipilimumab, tremelimumab, nivolumab, pembrolizumab, CT-011, AMP-224, MPDL3280A, MEDI4736 and MDX-1105.

19. A method of treating a disease or pathological condition susceptible of improvement by antagonism of androgen receptor and/or glucocorticoid receptor comprising the administration to a subject in need thereof of a compound as defined in claim 1.

20. The method according to claim 19, wherein the disease or pathological condition susceptible of improvement by antagonism of androgen receptor and/or glucocorticoid receptor is selected from prostate cancer, castration-resistant prostate cancer, pancreatic cancer, bladder cancer, renal cancer, gastric cancer, lung cancer, breast cancer, colon cancer, colorectal cancer, ovarian cancer, and other solid tumours, melanoma, metastasizing cancers, benign prostate hyperplasia, polycystic ovary syndrome (PCOS), hair loss, hirsutism, acne, hypogonadism, muscle wasting diseases and cachexia, and Cushing's syndrome, anti-psychotic drug induced weight gain, obesity, post-traumatic stress disorder and alcoholism.

* * * * *